US010865246B2

(12) United States Patent
Konnai et al.

(10) Patent No.: US 10,865,246 B2
(45) Date of Patent: Dec. 15, 2020

(54) ANTI-PD-L1 ANTIBODY FOR DETECTING PD-L1

(71) Applicants: Fuso Pharmaceutical Industries, Ltd., Osaka (JP); National University Corporation Hokkaido University, Hokkaido (JP)

(72) Inventors: Satoru Konnai, Hokkaido (JP); Kazuhiko Ohashi, Hokkaido (JP); Shiro Murata, Hokkaido (JP); Tomohiro Okagawa, Hokkaido (JP); Asami Nishimori, Hokkaido (JP); Naoya Maekawa, Hokkaido (JP); Satoshi Takagi, Hokkaido (JP); Yumiko Kagawa, Hokkaido (JP); Yasuhiko Suzuki, Hokkaido (JP); Chie Nakajima, Hokkaido (JP)

(73) Assignees: Fuso Pharmaceutical Industries, Ltd., Osaka (JP); National University Corporation Hokkaido University, Hokkaido (JP)

( * ) Notice: Subject to any disclaimer, the term of this patent is extended or adjusted under 35 U.S.C. 154(b) by 0 days.

(21) Appl. No.: 16/491,145

(22) PCT Filed: Mar. 23, 2018

(86) PCT No.: PCT/JP2018/011895

§ 371 (c)(1),
(2) Date: Sep. 4, 2019

(87) PCT Pub. No.: WO2018/181064

PCT Pub. Date: Oct. 4, 2018

(65) Prior Publication Data

US 2020/0031932 A1 Jan. 30, 2020

(30) Foreign Application Priority Data

Mar. 27, 2017 (JP) ................................ 2017-061389

(51) Int. Cl.
*C07K 16/28* (2006.01)
*C12N 15/85* (2006.01)
*G01N 33/574* (2006.01)
*G01N 33/569* (2006.01)

(52) U.S. Cl.
CPC .......... *C07K 16/2827* (2013.01); *C12N 15/85* (2013.01); *G01N 33/5695* (2013.01); *G01N 33/57492* (2013.01); *C07K 2317/52* (2013.01); *C07K 2317/565* (2013.01); *G01N 2800/26* (2013.01)

(58) Field of Classification Search
None
See application file for complete search history.

(56) References Cited

FOREIGN PATENT DOCUMENTS

WO WO-2016006241 A1 1/2016
WO WO-2016050721 A1 4/2016

OTHER PUBLICATIONS

"International Application Serial No. PCT/JP2018/011895, International Search Report dated Jun. 19, 2018", w/ English Translation, (Jun. 19, 2018), 6 pgs.
"International Application Serial No. PCT/JP2018/011895, Written Opinion dated Jun. 19, 2018", (Jun. 19, 2018), 6 pgs.
Ikebuchi, Ryoyo, et al., "Influence of PD-L 1 cross-linking on cell death in PD-L 1-expressing cell lines and bovine lymphocytes", Immunology 142.4, (2014), 551-561.
Maekawa, Naoya, et al., "Expression of PD-L1 on canine tumor cells and enhancement of IFN-? production from tumor-infiltrating cells by PD-L1 blockade", PLoS One 9.6, (2014), e98415.
Okagawa, Tomohiro, et al., "Bovine immunoinhibitory receptors contribute to suppression of *Mycobacterium avium* subsp. paratuberculosis-specific T-cell responses", Infection and immunity 84.1, (2016), 77-89.
"International Application Serial No. PCT JP2018 011895 International Preliminary Report on Patentability dated Oct. 3, 2019", 7 pgs.
Koenig, A., "Expression of S100a, vimentin, NSE, and Melan A MART-1 in seven canine melanoma cell lines and twenty-nine retrospective cases of canine melanoma", Veterinary pathology 38.4, (2001), 427-435.
Ramos-Vara, J.A., "Retrospective study of 338 canine oral melanomas with clinical, histologic, and immunohistochemical review of 129 cases", Veterinary Pathology 37.6, (2000), 597-608.
Todoroff, R. J., "Oral and pharyngeal neoplasia in the dog: a retrospective survey of 361 cases", Journal of the American Veterinary Medical Association 175.6, (1979), 567-571.
Koenig, A., et al., "Expression of S100a, vimentin, NSE, and Melan A/MART-1 in seven canine melanoma cell lines and twenty-nine retrospective cases of canine melanoma", Veterinary pathology 38.4, (2001), 427-435.
Ramos-Vara, J.A., et al., "Retrospective study of 338 canine oral melanomas with clinical, histologic, and immunohistochemical review of 129 cases", Veterinary Pathology 37.6, (2000), 597-608.
Todoroff, R. J., et al., "Oral and pharyngeal neoplasia in the dog: a retrospective survey of 361 cases", Journal of the American Veterinary Medical Association 175.6, (1979), 567-571.

*Primary Examiner* — Padmavathi Baskar
(74) *Attorney, Agent, or Firm* — Schwegman Lundberg & Woessner, P.A.

(57) ABSTRACT

The present invention provides an anti-PD-L1 antibody capable of staining tumor cells such as melanoma cells. An anti-PD-L1 antibody comprising (a) a light chain comprising CDR1 having the amino acid sequence of KSISKY (SEQ ID NO: 1), CDR2 having the amino acid sequence of SGS and CDR3 having the amino acid sequence of QQHNEYPLT (SEQ ID NO: 2) and (b) a heavy chain comprising CDR1 having the amino acid sequence of GYTFTDYI (SEQ ID NO: 3), CDR2 having the amino acid sequence of INPDSGGN (SEQ ID NO: 4) and CDR3 having the amino acid sequence of ARGITMMVVISHWKFDF (SEQ ID NO: 5). A composition for detecting PD-L1, comprising the above antibody as an active ingredient. A method for preparing the above antibody is also provided.

10 Claims, 17 Drawing Sheets
(12 of 17 Drawing Sheet(s) Filed in Color)

Specification includes a Sequence Listing.

Fig. 2

CDR1
CDR2
CDR3

Light chain variable region
MRVQIQFWGLLLLWTSGIQCDVQMTQSPSNLAASPGESVSINCKASKSISKYLAWYQ
QKPGKANKLLIYSGSTLQSGTPSRFSGSGSGTDFTLTIRNLEPEDFGLYYCQQHNEY
PLTFGSGTKLEIK Heavy chain variable region
MGWICIIFLVAIATGAHSQVKLLQSGAALVKPGDSVKMSCKASGYTFTDYIIHWVKQ
SHGKSLEWIGYINPDSGGNNYNEKFKSKATLTVDKSSSTAYMEFSRLTSEDSAIYYC
ARGITMMVVISHWKFDFWGPGTMVTVSS Rat Anti-Bovine PD-L1 Antibody Commercial Antibody (MelanA Antibody)

Case of Canine Melanoma

Case of Canine Osteosarcoma
Case 2 of Canine Renal Cell Carcinoma
Case of Canine Lymphoma
Case 1 of Canine Renal Cell Carcinoma Case of Canine Squamous Cell Carcinoma Case of Canine Fibrosarcoma Case of Ovine Listeriosis Enlarged Photo of the Left Micrograph Porcine Circovirus Type 2 Infection Porcine Mycoplasma Pneumonia

Fig. 9

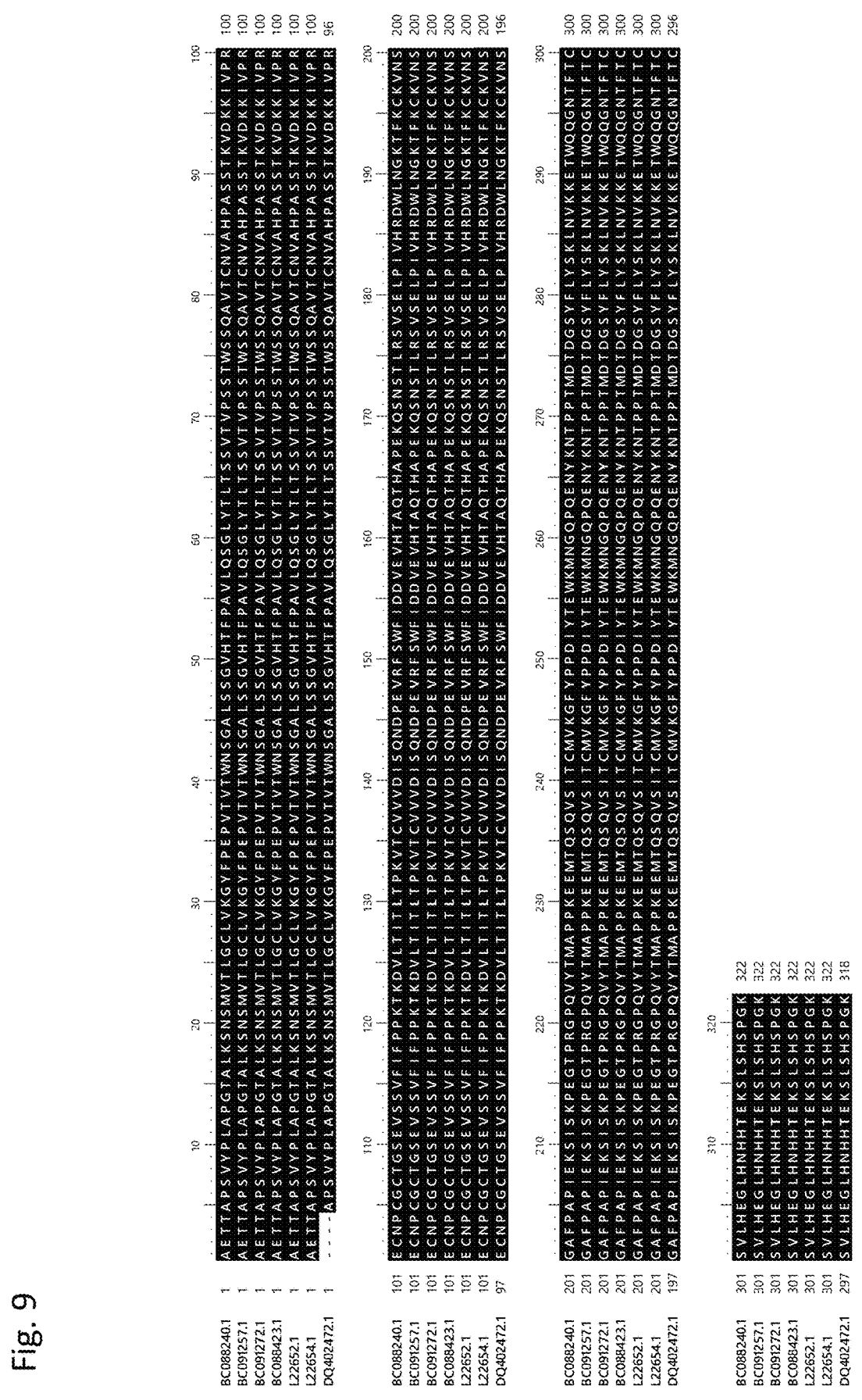

```
                 10        20        30        40        50        60        70        80        90        100
BC088240.1  1    AETTAPSVYPLAPGTALKSNSMVTLGCLVKGYFPEPVTVTWNSGALSSGVHTFPAVLQSGLYTLTSSVTVPSSTWSSQAVTCNVAHPASSTKVDKKIVPR  100
BC091257.1  1    AETTAPSVYPLAPGTALKSNSMVTLGCLVKGYFPEPVTVTWNSGALSSGVHTFPAVLQSGLYTLTSSVTVPSSTWSSQAVTCNVAHPASSTKVDKKIVPR  100
BC091272.1  1    AETTAPSVYPLAPGTALKSNSMVTLGCLVKGYFPEPVTVTWNSGALSSGVHTFPAVLQSGLYTLTSSVTVPSSTWSSQAVTCNVAHPASSTKVDKKIVPR  100
BC088423.1  1    AETTAPSVYPLAPGTALKSNSMVTLGCLVKGYFPEPVTVTWNSGALSSGVHTFPAVLQSGLYTLTSSVTVPSSTWSSQAVTCNVAHPASSTKVDKKIVPR  100
L22652.1    1    AETTAPSVYPLAPGTALKSNSMVTLGCLVKGYFPEPVTVTWNSGALSSGVHTFPAVLQSGLYTLTSSVTVPSSTWSSQAVTCNVAHPASSTKVDKKIVPR  100
L22654.1    1    AETTAPSVYPLAPGTALKSNSMVTLGCLVKGYFPEPVTVTWNSGALSSGVHTFPAVLQSGLYTLTSSVTVPSSTWSSQAVTCNVAHPASSTKVDKKIVPR  100
DQ402472.1  1    ----APSVYPLAPGTALKSNSMVTLGCLVKGYFPEPVTVTWNSGALSSGVHTFPAVLQSGLYTLTSSVTVPSSTWSSQAVTCNVAHPASSTKVDKKIVPR  96

                 110       120       130       140       150       160       170       180       190       200
BC088240.1  101  ECNPCGCTGSEVSSVFIFPPKTKDVLTITLTPKVTCVVVDISQNDPEVRFSWFIDDVEVHTAQTHAPEKQSNSTLRSVSELPIVHRDWLNGKTFKCKVNS  200
BC091257.1  101  ECNPCGCTGSEVSSVFIFPPKTKDVLTITLTPKVTCVVVDISQNDPEVRFSWFIDDVEVHTAQTHAPEKQSNSTLRSVSELPIVHRDWLNGKTFKCKVNS  200
BC091272.1  101  ECNPCGCTGSEVSSVFIFPPKTKDVLTITLTPKVTCVVVDISQNDPEVRFSWFIDDVEVHTAQTHAPEKQSNSTLRSVSELPIVHRDWLNGKTFKCKVNS  200
BC088423.1  101  ECNPCGCTGSEVSSVFIFPPKTKDVLTITLTPKVTCVVVDISQNDPEVRFSWFIDDVEVHTAQTHAPEKQSNSTLRSVSELPIVHRDWLNGKTFKCKVNS  200
L22652.1    101  ECNPCGCTGSEVSSVFIFPPKTKDVLTITLTPKVTCVVVDISQNDPEVRFSWFIDDVEVHTAQTHAPEKQSNSTLRSVSELPIVHRDWLNGKTFKCKVNS  200
L22654.1    101  ECNPCGCTGSEVSSVFIFPPKTKDVLTITLTPKVTCVVVDISQNDPEVRFSWFIDDVEVHTAQTHAPEKQSNSTLRSVSELPIVHRDWLNGKTFKCKVNS  200
DQ402472.1  97   ECNPCGCTGSEVSSVFIFPPKTKDVLTITLTPKVTCVVVDISQNDPEVRFSWFIDDVEVHTAQTHAPEKQSNSTLRSVSELPIVHRDWLNGKTFKCKVNS  196

                 210       220       230       240       250       260       270       280       290       300
BC088240.1  201  GAFPAPIEKSISKPEGTPRGPQVYTMAPPKEEMTQSQVSITCMVKGFYPPDIYTEWKMNGQPQENYKNTPPTMDTDGSYFLYSKLNVKKETWQQGNTFTC  300
BC091257.1  201  GAFPAPIEKSISKPEGTPRGPQVYTMAPPKEEMTQSQVSITCMVKGFYPPDIYTEWKMNGQPQENYKNTPPTMDTDGSYFLYSKLNVKKETWQQGNTFTC  300
BC091272.1  201  GAFPAPIEKSISKPEGTPRGPQVYTMAPPKEEMTQSQVSITCMVKGFYPPDIYTEWKMNGQPQENYKNTPPTMDTDGSYFLYSKLNVKKETWQQGNTFTC  300
BC088423.1  201  GAFPAPIEKSISKPEGTPRGPQVYTMAPPKEEMTQSQVSITCMVKGFYPPDIYTEWKMNGQPQENYKNTPPTMDTDGSYFLYSKLNVKKETWQQGNTFTC  300
L22652.1    201  GAFPAPIEKSISKPEGTPRGPQVYTMAPPKEEMTQSQVSITCMVKGFYPPDIYTEWKMNGQPQENYKNTPPTMDTDGSYFLYSKLNVKKETWQQGNTFTC  300
L22654.1    201  GAFPAPIEKSISKPEGTPRGPQVYTMAPPKEEMTQSQVSITCMVKGFYPPDIYTEWKMNGQPQENYKNTPPTMDTDGSYFLYSKLNVKKETWQQGNTFTC  300
DQ402472.1  197  GAFPAPIEKSISKPEGTPRGPQVYTMAPPKEEMTQSQVSITCMVKGFYPPDIYTEWKMNGQPQENYKNTPPTMDTDGSYFLYSKLNVKKETWQQGNTFTC  296

                 310       320
BC088240.1  301  SVLHEGLHNHHTEKSLSHSPGK  322
BC091257.1  301  SVLHEGLHNHHTEKSLSHSPGK  322
BC091272.1  301  SVLHEGLHNHHTEKSLSHSPGK  322
BC088423.1  301  SVLHEGLHNHHTEKSLSHSPGK  322
L22652.1    301  SVLHEGLHNHHTEKSLSHSPGK  322
L22654.1    301  SVLHEGLHNHHTEKSLSHSPGK  322
DQ402472.1  297  SVLHEGLHNHHTEKSLSHSPGK  318
```

Anal Sac Gland carcinoma
Soft Tissue Sarcoma
Osteosarcoma

6G7-E1
6C11-3A11

ANTI-PD-L1 ANTIBODY FOR DETECTING PD-L1

PRIORITY APPLICATIONS

This application is a U.S. National Stage Filing under 35 U.S.C. 371 from International Application No. PCT/JP2018/011895, filed on Mar. 23, 2018, and published as WO2018/181064 on Oct. 4, 2018, which claims the benefit of priority to Japanese Application No. 2017-061389, filed on Mar. 27, 2017; the benefit of priority of each of which is hereby claimed herein, and which applications and publication are hereby incorporated herein by reference in their entirety.

TECHNICAL FIELD

The present invention relates to an anti-PD-L1 antibody for detecting PD-L1.

BACKGROUND ART

Malignant melanoma originating from melanocytes is one of the most commonly observed malignant tumors in the canine oral cavity (Non-Patent Document No. 1: Todoroff et al., J Am Vet Med Assoc. 1979 Sep. 15: 175(6):567-71). Since this type of melanoma generally tends to be highly invasive and metastatic, early diagnosis and treatment are desired. On the other hand, malignant melanoma has a wide tissue variation, presenting various morphologies such as epithelial-like, round cell-like or fibrosarcoma-like morphology. Thus, malignant melanoma is one of those tumors which involve difficulty in tissue diagnosis. Although confirmation of melanin pigment is important for their diagnosis, a large number of malignant melanomas do not have melanin pigment and, sometimes, diagnosis cannot be made with histological observations alone. This has led to searches for diagnostic markers that can be used in immunohistochemical techniques. Among such markers, Melan A/MART-1, vimentin, S100, neuron-specific enolase and the like have been reported to be useful (Non-Patent Document No. 2: Ramos-Vara et al., Vet Pathol. 2000 November; 37(6):597-608). However, even Melan A/MART-1, the most widely used diagnostic marker, has a positive rate not higher than about 60% which varies among reports (Non-Patent Document No. 3: Koenig et al., Vet Pathol. 2001 July; 38(4):427-35). Because of this sensitivity problem, the utility of Melan A/MART-1 in actual diagnosis is still arguable. Further. Melan A/MART-1 is not stained in amelanotic melanoma (Non-Patent Document No. 3: Koenig et al., Vet Pathol. 2001 July; 38(4):427-35), so its application to diagnosis is limited. Under these circumstances, it is desired to develop highly sensitive, novel diagnostic markers to malignant melanoma.

PRIOR ART LITERATURE

Non-Patent Documents

Non-Patent Document No. 1: Todoroff et al., J Am Vet Med Assoc. 1979 Sep. 15; 175(6):567-71

Non-Patent Document No. 2: Ramos-Vara et al., Vet Pathol. 2000 November; 37(6):597-608

Non-Patent Document No. 3: Koenig et al., Vet Pathol. 2001 July; 38(4):427-35

DISCLOSURE OF THE INVENTION

Problem for Solution by the Invention

It is an object of the present invention to provide a PD-L1 antibody capable of staining tumor cells such as melanoma cells.

Means to Solve the Problem

The present inventors have established a number of monoclonal antibodies which react with the PD-L1 protein of various animals. It has been revealed that, among those monoclonal antibodies, a rat anti-bovine PD-L1 monoclonal antibody (6C11-3A11) is capable of staining melanoma tumor cells very strongly. Currently, this monoclonal antibody is used for selecting candidate dogs for therapy with chimeric antibodies. The subject PD-L1 antibody (6C11-3A11) is also capable of immunohistochemically staining ovine, porcine and bovine PD-L1 proteins. Further, the present inventors have determined the CDRs (complementarity-determining regions) of the variable regions of the subject PD-L1 antibody (6C11-3A11). The present invention has been achieved based on these findings.

A summary of the present invention is as described below.

(1) An anti-PD-L1 antibody comprising (a) a light chain comprising CDR1 having the amino acid sequence of KSISKY (SEQ ID NO: 1), CDR2 having the amino acid sequence of SGS and CDR3 having the amino acid sequence of QQHNEYPLT (SEQ ID NO: 2) and (b) a heavy chain comprising CDR1 having the amino acid sequence of GYTFTDYI (SEQ ID NO: 3), CDR2 having the amino acid sequence of INPDSGGN (SEQ ID NO: 4) and CDR3 having the amino acid sequence of ARGITMMVVISHWKFDF (SEQ ID NO: 5).

(2) The antibody of (1) above, which is derived from rat.

(3) The antibody of (2) above, which is a rat anti-bovine PD-L1 antibody.

(4) The antibody of (3) above, wherein the light chain variable region has the amino acid sequence as show in SEQ ID NO. 6 and the heavy chain variable region has the amino acid sequence as shown in SEQ ID NO: 7.

(5) The antibody of any one of (1) to (4) above, wherein the light chain constant region has the amino acid sequence of the constant region of kappa chain.

(6) The antibody of any one of (1) to (5) above, wherein the heavy chain constant region has the amino acid sequence of the constant region of IgG2a.

(7) The antibody of (5) or (6) above, wherein the light chain constant region has the amino acid sequence as shown in any one of SEQ ID NOS: 8, 10 to 12 and the heavy chain constant region has the amino acid sequence as shown in SEQ ID NO: 9 or 13.

(8) The antibody of anyone of (1) to (7) above which has a four-chain structure comprising two light chains and two heavy chains.

(9) A composition for detecting PD-L1, comprising the antibody of any one of (1) to (8) above as an active ingredient.

(10) The composition of (9) above for use in diagnosis of cancers and/or inflammations.

(11) The composition of (10) above, wherein the cancers and/or inflammations are selected from the group consisting of neoplastic diseases, leukemia, Johne's disease, anaplasmosis, bacterial mastitis, mycotic mastitis, mycoplasma infections (such as mycoplasma mastitis, mycoplasma pneumonia or the like), tuberculosis, *Theileria*

*orientalis* infection, cryptosporidiosis, coccidiosis, trypanosomiasis and leishmaniasis.

(12) The composition of (9) above for use in selecting subject animals suitable for therapy with anti-PD-L1 antibodies.

(13) A DNA encoding the anti-PD-L1 antibody of (1) above.

(14) A vector comprising the DNA of (13) above.

(15) A host cell transformed with the vector of (14) above.

(16) A method of preparing an antibody, comprising culturing the host cell of (15) above and collecting an anti-PD-L1 antibody from the resultant culture.

(17) A DNA encoding the light chain of an anti-PD-L1 antibody, said light chain comprising CDR1 having the amino acid sequence of KSISKY (SEQ ID NO: 1), CDR2 having the amino acid sequence of SGS and CDR3 having the amino acid sequence of QQHNEYPLT (SEQ ID NO: 2).

(18) A DNA encoding the heavy chain of an anti-PD-L1 antibody, said heavy chain comprising CDR1 having the amino acid sequence of GYTFTDYI (SEQ ID NO: 3), CDR2 having the amino acid sequence of INPDSGGN (SEQ ID NO: 4) and CDR3 having the amino acid sequence of ARGTMMVVISHWKFDF (SEQ ID NO: 5).

Effect of the Invention

According to the present invention, a novel anti-PD-L1 antibody capable of staining tumor cells, such as melanoma cells, has been obtained.

The present specification encompasses the contents disclosed in the specification and/or the drawings of Japanese Patent Application No. 2017-61389 based on which the present patent application claims priority.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

FIG. 2 Predicted CDR regions of rat anti-bovine PD-L1 antibody 6C11-3A11. The regions of CDR1. CDR2 and CDR3 in the light chain variable region and the heavy chain variable region of rat anti-bovine PD-L1 antibody 6C1-3A11 are shown.

FIG. 5-1 Immunohistochemical staining images of other tumors. Upper left: case of canine lymphoma. Upper right: case of canine osteosarcoma. Lower left: case 1 of canine renal cell carcinoma. Lower right: case 2 of canine renal cell carcinoma.

FIG. 5-2 Immunohistochemical staining images of other tumors. Left: case of canine squamous cell carcinoma. Right: case of canine fibrosarcoma.

FIG. 9 Alignment of amino acid sequences of the constant region of rat IgG2a chain (heavy chain).

BEST MODES FOR CARRYING OUT THE INVENTION

Hereinbelow, the present invention will be described in detail.

The present invention provides an anti-PD-L1 antibody comprising (a) a light chain comprising CDR1 having the amino acid sequence of KSISKY (SEQ ID NO: 1), CDR2 having the amino acid sequence of SGS and CDR3 having the amino acid sequence of QQHNEYPLT (SEQ ID NO: 2) and (b) a heavy chain comprising CDR1 having the amino acid sequence of GYTFTDYI (SEQ ID NO: 3), CDR2 having the amino acid sequence of INPDSGGN (SEQ ID NO: 4) and CDR3 having the amino acid sequence of ARGITMMVVISHWKFDF (SEQ ID NO: 5).

Figures 1, 5:
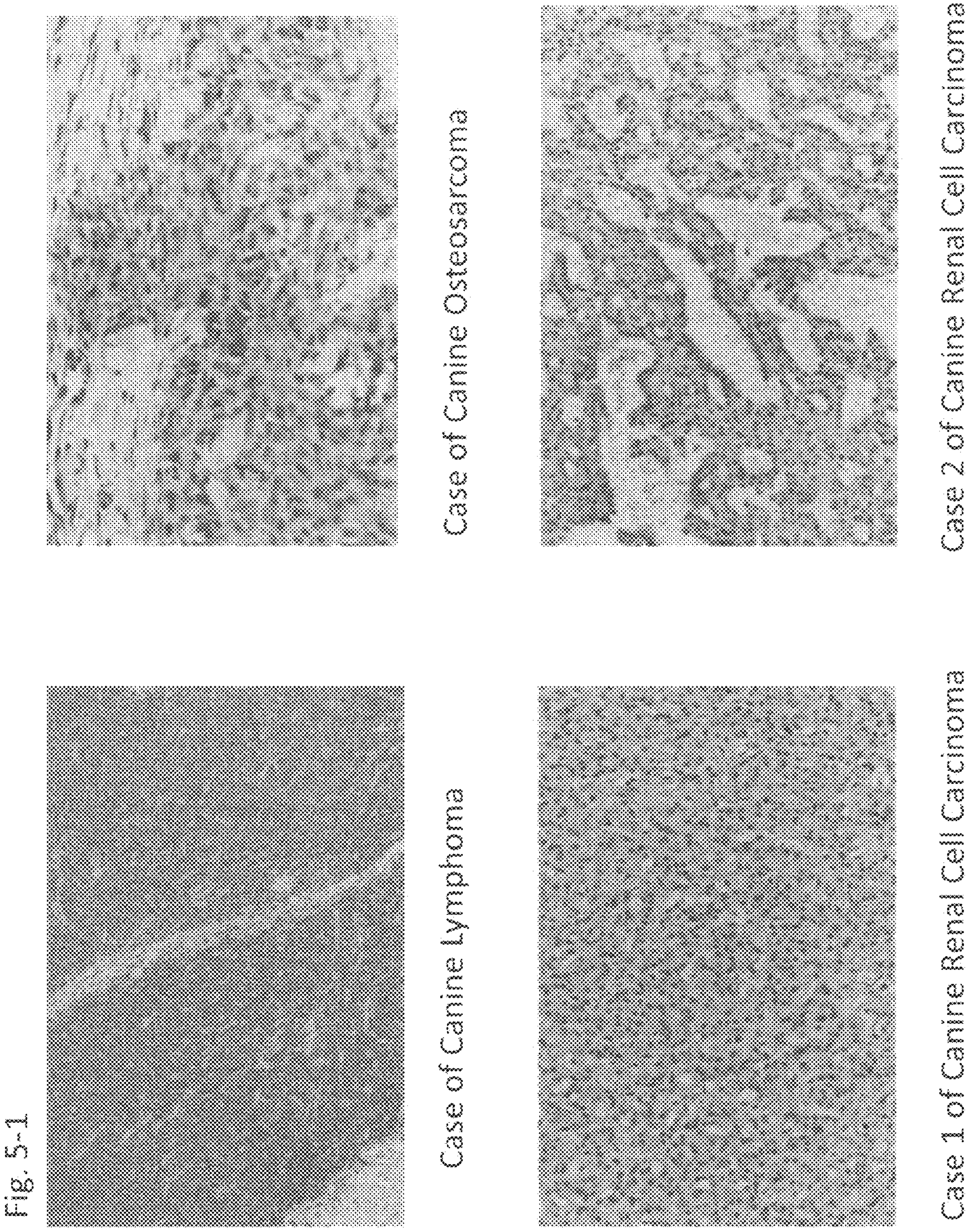
Figures 2, 5:
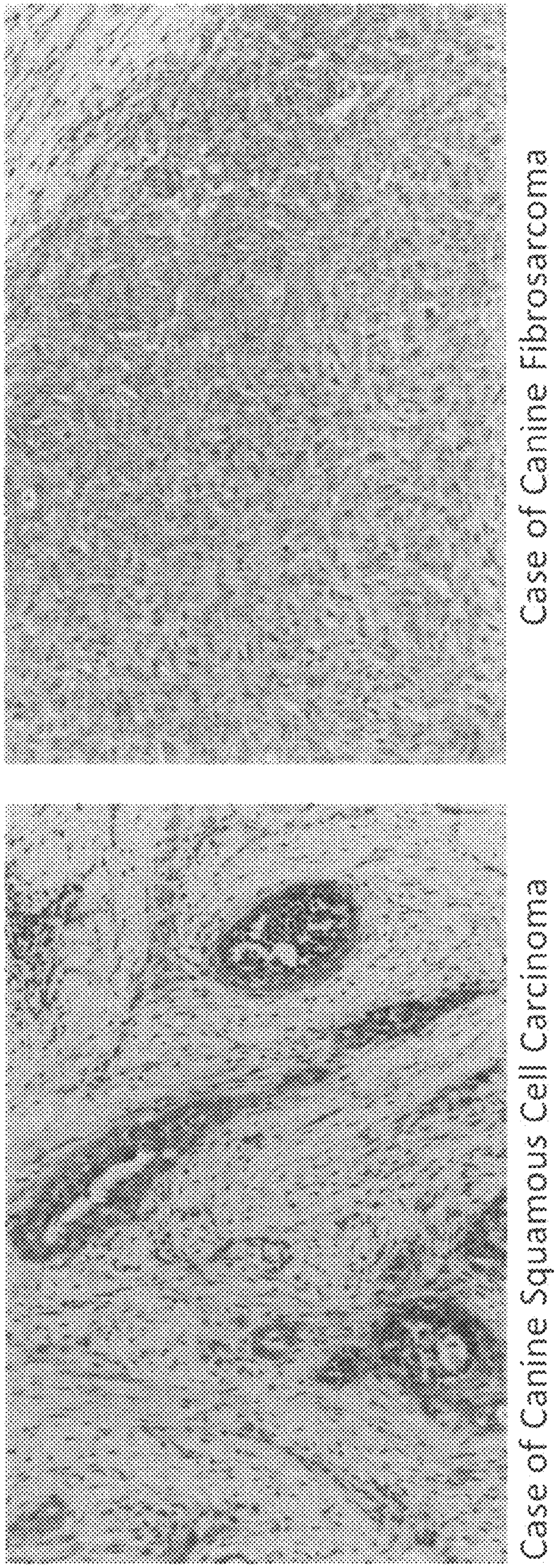

CDR1, CDR2 and CDR3 in the light chain variable region (VL) of rat anti-bovine PD-L1 antibody 6C11-3A11 (monoclonal antibody) established by the present inventors are a region consisting of the amino acid sequence of KSISKY (SEQ ID NO: 1), a region consisting of the amino acid sequence of SGS and a region consisting of the amino acid sequence of QQHNEYPLT (SEQ ID NO: 2), respectively (see FIG. 2).

Further. CDR1, CDR2 and CDR3 in the heavy chain variable region (VH) of rat anti-bovine PD-L1 antibody 6C1-3A1 are a region consisting of the amino acid sequence of GYTFTDYI (SEQ ID NO: 3), a region consisting of the amino acid sequence of INPDSGGN (SEQ ID NO: 4) and a region consisting of the amino acid sequence of ARGITMMVVISHWKFDF (SEQ ID NO: 5), respectively (see FIG. 2).

In the amino acid sequences of KSISKY (SEQ ID NO: 1), SGS and QQHNEYPLT (SEQ ID NO: 2), as well as the amino acid sequences of GYTFTDYI (SEQ ID NO: 3), INPDSGGN (SEQ ID NO: 4) and ARGITMMVVISH-WKFDF (SEQ ID NO: 5), one, two, three, four or five amino acids may be deleted, substituted or added. Even when such mutations have been introduced, the resulting amino acid sequences are capable of having the function as CDR of VL or CDR of VH of the PD-L1 antibody.

As used herein, the term "antibody" is a concept encompassing not only full-length antibodies but also antibodies of smaller molecular sizes such as Fab, F(ab)'$_2$. ScFv, Diabody, $V_H$, $V_L$. Sc(Fv)$_2$, Bispecific sc(Fv)$_2$, Minibody, scFv-Fc monomer and scFv-Fc dimer.

The anti-PD-L1 antibody of the present invention may be derived from rat. For example, the anti-PD-L1 antibody may be a rat anti-bovine PD-L1 antibody.

The amino acid sequence of the VL and the amino acid sequence of the VH of rat anti-bovine PD-L1 antibody 6C11-3A11 (monoclonal antibody) are shown in SEQ ID NOS: 6 and 7, respectively. The amino acid sequences as shown in SEQ ID NOS: 6 and 7 may have deletion(s), substitution(s) or addition(s) of one or several (e.g., up to five, about 10 at the most) amino acids. Even when such mutations have been introduced, the resulting amino acid sequences are capable of having the function as VL or VH of the PD-L1 antibody.

There are two types of immunoglobulin light chain, which are called Kappa chain (κ) and Lambda chain (λ). In the anti-PD-L1 antibody of the present invention, the light chain constant region (CL) may have the amino acid sequence of the constant region of either Kappa chain or Lambda chain. However, the relative abundance of Lambda chain is higher in ovine, feline, canine and equine, and that of Kappa chain is higher in mouse, rat, human and porcine. Rat anti-bovine PD-L1 antibody 6C11-3A11 (monoclonal antibody) is a rat-derived IgG2a, and the CL thereof has the amino acid sequence of the constant region of Kappa chain.

The heavy chain constant region (CH) of the anti-PD-L1 antibody of the present invention may have the amino acid sequence of the constant region of rat IgG2a. Immunoglobulin heavy chain is classified into γ chain, μ chain, α chain, δ chain and ε chain depending on the difference in constant region. According to the type of heavy chain present, five classes (isotypes) of immunoglobulin are formed, they are IgG, IgM, IgA, IgD and IgE.

Immunoglobulin G (IgG) accounts for 70-75% of human immunoglobulins and is the most abundantly found monomeric antibody in plasma. IgG has a four-chain structure consisting of two light chains and two heavy chains. Human IgG1, IgG2 and IgG4 have molecular weights of about 146,000, whereas human IgG3 has a long hinge region that connects Fab region and Fc region and has a larger molecular weight of 170,000. Human IgG1 accounts for about 65%, human IgG2 about 25%, human IgG3 about 7%, and human IgG4 about 3% of human IgG. They are uniformly distributed inside and outside of blood vessels. Having a strong affinity for Fc receptors and complement factors on effector cell surfaces, human IgG1 induces antibody-dependent cell cytotoxicity (ADCC) and also activates complements to induce complement-dependent cell cytotoxicity (CDC). Human IgG2 and IgG4 are low at ADCC and CDC activities because their affinity for Fc receptors and complement factors is low.

Immunoglobulin M (IgM), which accounts for about 10% of human immunoglobulins, is a pentameric antibody consisting of five basic four-chain structures joined together. It has a molecular weight of 970,000. Usually occurring only in blood, IgM is produced against infectious microorganisms and takes charge of early stage immunity.

Immunoglobulin A (IgA) accounts for 10-15% of human immunoglobulins. It has a molecular weight of 160,000. Secreted IgA is a dimeric antibody consisting of two IgA molecules joined together. IgA1 is found in serum, nasal discharge, saliva and breast milk. In intestinal juice, IgA2 is found abundantly.

Immunoglobulin D (IgD) is a monomeric antibody accounting for no more than 1% of human immunoglobulins. IgD is found on B cell surfaces and involved in induction of antibody production.

Immunoglobulin E (IgE) is a monomeric antibody that occurs in an extremely small amount, accounting for only 0.001% or less of human immunoglobulins. Immunoglobulin E is considered to be involved in immune response to parasites but in advanced countries where parasites are rare. IgE is largely involved in bronchial asthma and allergy among other things.

With respect to rat, sequences of IgG1, IgG2a, IgG2b and IgG2c have been identified as the heavy chain of IgG. Rat anti-bovine PD-L1 antibody 6C11-3A11 has the amino acid sequence of the CH of IgG2a.

In the antibody of the present invention, it is more preferable that the CL has the amino acid sequence of the constant region of Kappa chain and that the CH has the amino acid sequence of the constant region of IgG2a.

The amino acid sequence and the nucleotide sequence of the VL of rat anti-bovine PD-L1 antibody 6C11-3A1 identified by the present inventors are shown in SEQ ID NOS: 6 and 14, respectively.

The amino acid sequence and the nucleotide sequence of the VH of rat anti-bovine PD-L1 antibody 6C11-3A11 identified by the present inventors are shown in SEQ ID NOS: 7 and 15, respectively.

The amino acid sequence and the nucleotide sequence of the CL (Kappa chain) of rat anti-bovine PD-L1 antibody 6C11-3A11 identified by the present inventors are shown in SEQ ID NOS: 8 and 16, respectively. These sequences are identical with the sequences registered at GenBank (a nucleotide sequence database provided by National Center for Biotechnology Information (NCBI)) under accession numbers #XM_008775358.2. #BC062802.1, #3C088255.1, #L22653.1. #L22655.1 and #M14434.1.

The amino acid sequence and the nucleotide sequence of the CH (IgG2a) of rat anti-bovine PD-L1 antibody 6C11-3A11 identified by the present inventors are shown in SEQ ID NOS: 9 and 17, respectively. These sequences are identical with the sequences registered at GenBank under accession numbers #BC088240.1. #BC091257.1. #BC091272.1. #BC088423.1, #L22652.1 and #L22654.1.

Amino acid sequences and nucleotide sequences of CLs and CHs for rat antibodies other than the above may be obtained from known databases for use in the present invention.

As an amino acid sequence and a nucleotide sequence of rat Ig Kappa chain, the sequence registered at GenBank under accession number #V01241.1 is shown in SEQ ID NOS: 10 and 18.

As an amino acid sequence and a nucleotide sequence of rat Ig Kappa chain, the sequence registered at GenBank under accession number #X16129.1 is shown in SEQ ID NOS: 11 and 19.

As an amino acid sequence and a nucleotide sequence of rat Ig Kappa chain, the sequence registered at GenBank under accession number #DQ402471.1 is shown in SEQ ID NOS: 12 and 20.

As the CH of rat IgG2a, the sequence registered at GenBank under accession number #DQ402472.1 is shown in SEQ ID NOS: 13 and 21.

The anti-PD-L1 antibody of the present invention may be an anti-PD-L1 antibody in which the CL has the amino acid sequence as shown in any one of SEQ ID NOS: 8 and 10 to 12 and the CH has the amino acid sequence as shown in SEQ ID NO: 9 or 13.

The amino acid sequences as shown in SEQ ID NOS: 8 to 13 may have deletion(s), substitution(s) or addition(s) of one or several (e.g., up to five, about 10 at the most) amino acids. Even when such mutations have been introduced, the resulting amino acid sequences are capable of having the function as CL or CH of the PD-L antibody.

Figure 8:
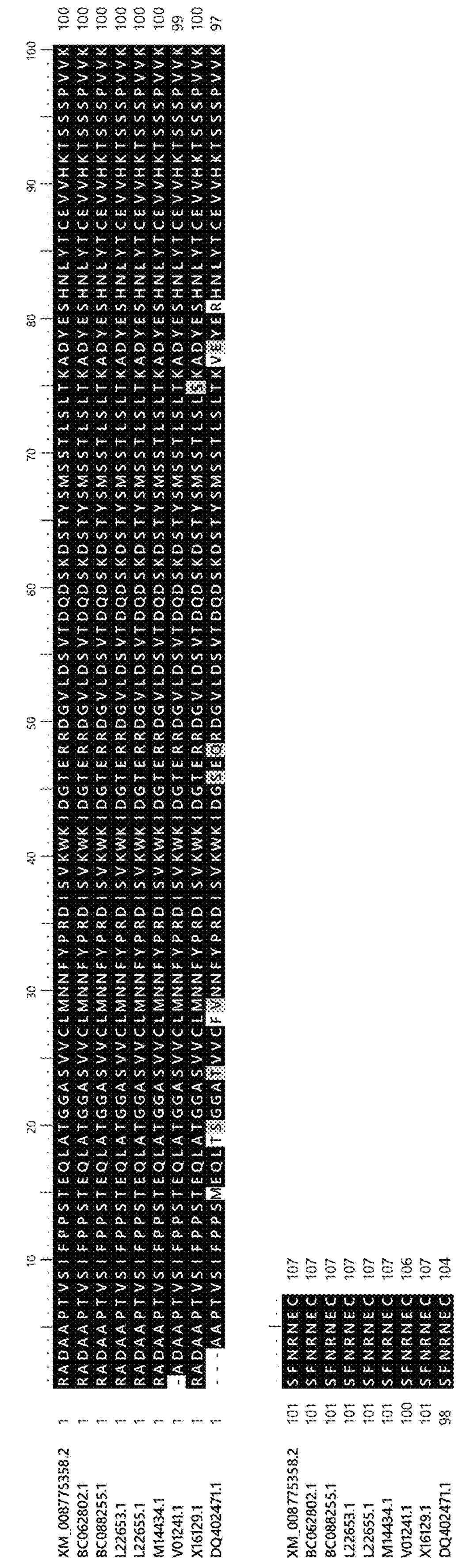
FIG. 8 Alignment of amino acid sequences of the constant region of rat Ig kappa chain (light chain).

Alignments of amino acid sequences of the CL and the CH of a rat anti-PD-L1 antibody are shown in FIG. 8 and FIG. 9, respectively. The above-described mutations such as deletion, substitution or addition of amino acids may suitably have occurred at the mutation sites as shown in FIGS. 8 and 9 or at the vicinity thereof.

The anti-PD-L1 antibody of the present invention may be a chimeric antibody. The VL and the VH of the antibody may be suitably derived from rat. For example, the VL may be the VL of a rat anti-PD-L1 antibody (e.g., 6C11-3A11); the VH may be the VH of a rat anti-PD-L1 antibody, and the CL and the CH may be derived from an animal other than rat. For example, when a rat antibody is chimerized using the constant regions of a mouse antibody, the resulting chimeric antibody will be useful for testing and diagnosis because various secondary antibodies to mouse antibodies are commercially available. Amino acid sequences and nucleotide sequences of the CLs and the CHs of antibodies of animals other than rat may be obtained from known databases for use in the present invention.

Amino acid sequences and nucleotide sequences of CLs and CHs for human, mouse, bovine, canine, ovine, porcine and water buffalo are summarized in the table below.

TABLE

| Species | Ig | Domain | Nucleotide Sequence | Amino Acid Sequence | GenBank Accession No. | IMGT Database | Reference |
|---|---|---|---|---|---|---|---|
| Human (Scientific Name: *Homo sapiens*) | Human Ig heavy chain re-gion (CH1 CH3) | IgG4 variant 1 | GCACCTGAGTTCCTGGCGGGAOCATCAGTCTTCCTC<br>TTCCCCCCAAAACCCAAGGACACTCTCATGATCTCC<br>GGGACCGCTGAGGTCACGTGCGTGGTGGTGGACGTG<br>AGGCAGGAAGACCCCGAGGTCCAGTTCAACTGGTAC<br>GTGGATGGCGTGGAGGTGCATAATGCCAAGACAAAG<br>CCGCGGGAGGAGCAGTTCAACAGCACGTACCGTGTG<br>GTCAGCGTCCTCACCGTCCTGCACCAGGACTGGCTG<br>AACGGCAAGGAGTACAAGTGCAAGGTCTCCAACAAA<br>GGCCTCCCGTCCTCCATCGAGAAAACCATCTCCAAA<br>GCCAAAGGGCAGCCCCGAGAGCCACAGGTGTACACC<br>CTGCCCCCATCCCAGGAGGAGATGACCAAGAACCAG<br>GTCAGCCTGACCTGCCTGGTCAAAGGCTTCTACCCC<br>AGCGACATCGCCGTGGAGTGGGAGAGCAATGGGCAG<br>CCGGAGAACAACTACAAGACCACGCCTCCCGTGCTG<br>GACTCCGACGGCTCCTTCTTCCTCTACAGCAGGCTA<br>ACCGTGGACAAGAGCAGGTGGCAGGAGGGGAATGTC<br>TTCTCATGCTCCGTGARGCATGAGGCTCTGCACAAC<br>CACTACACACAGAAGAGCCTCTCCCTGTCTCTGGGT<br>AAATGA<br>(SEQ ID NO: 31) | KPKDTLMISRTPEVTCVCCDVSQEDPE<br>VQFNWYVDCVEVHNAKTKPREEGFNS<br>TYRWSVLTVLHQDWLNGKEYKCKVS<br>NKGLPSSIEKTISKAKGQPREPQVYTLP<br>PSGEEMTKNQVSLTCLVKGFYPSDIAV<br>EWESNGQPENNYKTTPPVLDSDGSFFL<br>YSRLTVDKSRWQEGNVFSCSVMHEAL<br>HNHYTQKSLSLSLGK*<br>(SEQ ID NO: 30) | K01316 | http://www.<br>imgt.org/<br>IMGT<br>reportoire/<br>index.<br>ghp?section<br>=locus<br>Genes&<br>reportoire=<br>genetable&<br>species=<br>human&<br>gcf=IGHC | Ellison J. et al DNA, 1 11-16 (1981) PMID: 6299662 |
| | | IgG4 variant 2 | GAGTCCAAATATGGTCCCCCGTGGCCATCATGGCCA<br>GCACCTGAGTTCCTGGGGGGACCATCAGTCTTCCTG<br>TTCCCCCCAAAACCCAAGGACACTCTGATGATCTCC<br>CGGACCCCTGAGGTCACGTGCGTGGTGGTGGACGTG<br>AGCCAGGAAGACCCCGAGGTCCAGTTCAACTGGTAC<br>GTGGATGGCGTGGAGGTGCATAATGCCAAGACAAAG<br>CCGCGGGAGGAGCAGTTCAACAGCACGTACCGTGTG<br>GTCAGCGTGCTCACGGTCGTGCACCAGGACTGGCTG<br>AACGGCAAGGAGTACAAGTGCAAGGTCTCCAACAAA<br>GGCCTCCCGTCCTCCATCGAGAAAACCATCTCCAAA<br>GCCAAAGGCCACCCCCGAGAGCCACAGCTGTACACC<br>CTGCCCCCATCCCAGGAGGAGATGACCAAGAACCAG<br>GTCAGCCTGACCTGCCTGGTCAAAGGCTTCTACCCC<br>AGCGACATCGCCGTGGAGTGGGAGAGCAATGGGCAG<br>CCGGAGAACAACTACAAGACCACGCCTCCCGTGOTG<br>GACTCCGACGGCTCCTTCTTCCTCTACAGCAGGCTA<br>ACGGTGGACAAGAGCAGGTGGCAGGAGGGGAATGTC<br>TTCTCATGCTCCGTGATGCATGAGGCTCTGCACAAC<br>CACTACACGCAGAAGAGCCTCTCCCTGTCTCTGGGT<br>AAATGA<br>(SEQ ID NO: 33) | ESKYGPPCPSCPAPEFLGGPSVFLFPP<br>KPKDTLMISRTPEVTCVVVDVSGEDPE<br>VQFNWYVDGVEVHNAKTKPREEQFNS<br>TYRVVSVLTVVHQDWLNGKEYKCKVS<br>NKGLPSSIEKTISKAKGQPREPQVYTLP<br>PSQEEMTKNQVSLTCLVKGFYPSDIAV<br>EWESNGQPENNYKTTPPVLDSDGSFFL<br>YSRLTVDKSRWQEGNVFSCSVMHEAL<br>HNHYTQKSLSLSLGK*<br>(SEQ ID NO: 32) | AJ001583 | | Brusco A. et al. Eur. J. Immuno genol., 25, 348-355 (1998). PMID: 9805657 |
| | | IgG4 variant 3 | GCACCTGAGTTCCTGGGGGGACCATCAGTCTTCCTG<br>TTCCCCCCAAAACCCAAGGACACTCTCATGATCTCC<br>CGGACCCCTGAGGTCACGTCCGTGGTGGTGGACGTG<br>AGCCAGGAAGACCCCGAGGTCCAGTTCAACTGGTAC<br>GTGGATGGCGTGGAGGTGCATAATGCCAAGACAAAG<br>CCGCGGGAGGAGCAGTTCAACAGCACGTACCGTGTG<br>GTCAGCGTCCTCACCGTCCTGCACCAGGACTGGCTG<br>AACGGCAAGGAGTACAAGTGCAAGGTCTCCAACAAA | APEFLGGPSVFLFPPKPKDTLMISRTPE<br>VTCVVVDVSQEDPEVQFNWYVDGVEV<br>HNAKTKPREEQFNSTYRVVSVLTVLHQ<br>DWLNGKEYKCKVSNKGLPSSIEKTISKA<br>KGQPREPQVYTIPPSQEEMTKNQVSL<br>TCLVKGFYPSDIAVEWESNGQPENNYK<br>TTPPVLDSDGSFFLYSKLTVDKSRWQE<br>GNVFSCSVMHEALHNHYTQKSLSLSLG | AJ001564 | | |

TABLE-continued

| Species | Ig Domain | Nucleotide Sequence | Amino Acid Sequence | GenBank Accession No. | IMGT Database | Reference |
|---|---|---|---|---|---|---|
| | | GGCCTCCCGTCCTCCATCGAGAAAACCATCTCCAAA<br>GCCAAAGGGCAGCCCCGAGAGCCACAGGTGTACACC<br>CTGCCCCCATCCCAGGAGGAGATGACCAAGAACCAG<br>GTCAGCCTGACCTGCGTGGTCAAAGGCTTCTACCCC<br>AGCGACATCGCGGTGGAGTGGGAGAGCAATGGGCAG<br>CCGGAGAACAACTACAAGACCACGCCTCCCGTGCTG<br>GACTCCGACGGCTCCTTCTTCCTCTACAGCAAGCTC<br>ACCGTGGACAAGAGCAGGTGGCAGGAGGGGAACGTC<br>TTCTCATGCTCCGTGATGCATGAGGCTCTGCACAAC<br>CACTACACGCAGAAGAGCCTCTCCCTGTCTCTGGGT<br>AAATGA<br>(SEQ ID NO: 33) | K*<br>(SEQ ID NO 34) | | | |
| | Human Ig light con-stant region Ig kappa (CK) | ACTGTGGCTGCACCATCTGTCTTCATCTTCCCGCCA<br>TCTGATGAGCAGTTGAAATCTGGAACTGCCTCTGTT<br>GTGTGCCTGCTGAATAACTTCTATCCCAGAGAGGCC<br>AAAGTACAGTGGAAGGTGGATAACGCCCTCCAATCG<br>GGTAACTCCCAGGAGAGTGTCACAGAGCAGGACAGG<br>AAGGACAGCACCTACAGCCTCAGCAGGACCCTGACG<br>CTGAGCAAAGCAGACTACGAGAAACACAAAGTCTAC<br>GCCTGCGAAGTCACCCATCAGGGCCTGAGCTCGCCC<br>GTCACAAAGAGCTTCAACAGGGGAGAGTGTTAG<br>(SEQ ID NO: 29) | TVAAPSVFIFPPSDEQLKSGTASVVCL<br>LNNFYPRCAKVQWKVDNALQSGNSQE<br>SVTEQDSKDSTYSLSSTLTLSKAQYEK<br>HKVYACEVTHQCLSSPVTKSFNRGEC*<br>(SEQ ID NO: 28) | X96754 | http://www.<br>imgt.org/<br>IMGT<br>reportoire/<br>index.<br>ghp?section<br>=locus<br>Genes&<br>reportoire=<br>genetable&<br>species=<br>human&<br>gcf=IGHC | GL |
| Mouse (Scientific Name: *Mus Musculus*) | Mouse Ig heavy chain region (CH1 CH3) IgG1 variant 1 | GCCAAAACGACACCCCCATCTGTCTATCCACTGGCCC<br>CTGGATCTGCTGCCCAAACTAACTCCATGGTGACCCT<br>GGGATGCCTGGTCAAGGGCTATTTCCCTGAGCCAGT<br>GACAGTGACCTGGAACTCTGGATCCCTGTCCAGCGG<br>TGTGCACACCTTCCCAGCTGTCCTGGAGTCTGACCTC<br>TACACTCTGAGCAGCTCAGTGACTGTCCCCTCCAGCC<br>CTCGGCCCAGCGAGACCGTCACCTGCAACGTTGCCC<br>ACCCGGCGACCAGCACCAAGGTGGACAAGAAAATTG<br>TGCCCAGGGATTGTGGTTGTAAGCCTTGCATATGTAC<br>AGTCCCAGAAGTATCATCTGTCTTCATCTTCCCCCCA<br>AAGCCCAAGGATGTGCTCACCATTACTCTCACTCCTA<br>AGGTCACGTGTGTTGTGGTAGACATCAGCAAGGATGA<br>TCCCGAGGTCCAGTTCAGCTGGTTTGTAGATGATGTG<br>GAGGTGCACAGAGCTCAGACGCAAGCGCGGGAGGAG<br>GAGTTCAACAGCACTTTGGGCTCAGTCAGTGAACTTC<br>CCATCATGCACCACGACTGCCTCAATCGCAAGCAGTT<br>CAAATGCAGGGTCAACAGTCCAGCTTTCCCTGCCCCC<br>ATCGAGAAAACCATCTCCAAAACCAAAGGCAGACCG<br>AAGGCTCCACAGGTGTACAGCATTCCACCTCCCAAGG<br>AGCAGATGGCCAAGGATAAAGTCAGTCTGACCTGCAT<br>GATAACAGACTTCTTCCCTGAAGACATTACTGTGGAG<br>TCGCACTGGAATGCGCAGCCAGCCGAGAACTACAAG<br>AACACTCAGCCCATCATGAACACGAATGGCTCTTACT | AKTTPPSVYPLAPGSAAQTNSMVTLG<br>CLVKGYFPEPVTVTWNSGSLSSGVHTF<br>PAVLESDLYTLSSSVTVPSSPRPSETV<br>TCNVAHPASSTKVDKKIVPRDCGCKPC<br>ICTVPEVSSVFIFPPKPKDVLTITLTPK<br>VTCVVVDISKDDPEVQFSWFVDDVEVHT<br>AQTQPREEQFNSTFRSVSELPIMHQDW<br>LNGKEFKCRVNSAAFPAPIEKTISKTKG<br>RPKAPQVYTIPPPKEQMAKDKVSLTCM<br>ITDFFPEDITVEWQWNGQPAENYKNTQ<br>PIMNTNGSYFVYSKLNVQKSNWEAGNT<br>FTCSVLHEGLHNHHTEKSLSHSPGK<br>(SEQ ID NO: 44) | J00453<br>AH005309<br>V00793<br>D78344 | http://www.<br>imgt.org/<br>IMGT<br>reportoire/<br>index.<br>ghp?section<br>=locus<br>Genes&<br>reportoire=<br>genetable&<br>species=<br>human&<br>gcf=IGHC | Honjo T. et al. Ceit 18, 558-568 (1979) PMID: 115593 Akohoni Y. and Kursawa Y. Genomes, 41, 100-104 (1997) PMID: 9126488 |

TABLE-continued

| Species | Ig Domain | Nucleotide Sequence | Amino Acid Sequence | GenBank Accession No. | IMGT Database | Reference |
|---|---|---|---|---|---|---|
| | | TCGTCTACAGCAAGCTCAATGTGCAGAAGAGCAACTG<br>GGAGGCAGGAAATACTTTCACCTGCTCTGTGTTACAT<br>GAGGGCCTGCACAACCACCATACTGAGAAGAGCCTC<br>TCCCACTCTCCTGGTAAATGA<br>(SEQ ID NO: 45) | | | | |
| | IgG1 variant 2 | GCCAAAAGGACACCCCCATCTGTCTATCCACTGGCCC<br>CTGGATCTGCTGCCCAAACTAACTCCATGGTGACCCT<br>GGCATGCCTGGTCAAGGGCTATTTCCCTGACCCAGT<br>GACACTGACCTGGAACTCTGGATCCCTGTCCAGCGG<br>TGTGCACACCTTCCCAGCTGTCCTGCAGTCTGACCTC<br>TACACTCTGAGCAGCTCAGTGACTGTCCCCTCCAGCA<br>CCTGGCCCAGCCAGACCGTCACCTGCAACGTTGCCC<br>ACCCGGCCAGCAGCACCAAGGTCGACAAGAAAATTG<br>TGCCCAGGGATTGTGGTTGTAAGCCTTGCATATGTAC<br>AGTCCCAGAAGTATCATCTGTCTTCATCTTCCCCCCA<br>AAGCCCAAGGATGTGCTCACCATTACTCTGACTCCTA<br>AGGTCACGTGTGTTGTGGTAGACATCAGCAAGGATGA<br>TCCCGAGGTCCAGTTCAGCTGGTTTGTAGATGATGTG<br>GAGGTGCACACAGCTCAGACGAAACCCCGGGAGGAG<br>CAGATCAACAGCACTTTCCGTTCAGTCAGTGAACTTC<br>CCATCATGCACCAGGACTGGCTCAATGGCAAGGAGTT<br>CAAATGCAGGGTCAACAGTGCAGCTTTCCCTGCCCCC<br>ATCGAGAAAACCATCTCCAAAACCAAAGGCAGACCG<br>AAGGCTCCACAGGTGTACACCATTCCACCTCCCAAGG<br>AGCAGATGGCCAAGGATAAAGTGAGTGTGACCTGCAT<br>GATAACAAACTTGTTCCCTGAAGAGATTACTGTGGAG<br>TGGCAGTGGAATGGGCAGCCAGCGGAGAACTACAAG<br>AACACTCAGCCCATCATGGACACAGATGGCTCTTACT<br>TTCGTCTACAGCAAGCTCAATGTGCAGAAGAGCAACTG<br>GGAGGCAGGAAATACTTTCACCTCCTCTGTGTTACAT<br>TGAGGGCCTGCACAACCACCATACTGAGAAGAGCCTC<br>TCCCACTCTCCTGGTAAATGA<br>(SEQ ID NO: 47) | AKTTPPSVYPLAPGSAAQTNSMVTLG<br>CLVKGYFPEPVTVTWNSGSLSSGVHTF<br>PAVLQSDLYTLSSSVTVPSSTWSQTV<br>TCNVAHPASSTKVDKKIVPRDCGCKPC<br>ICTVPEVSSVFIFPPKPKDVLTITLTPK<br>VTCVVVDISKDDPEVQFSWFVDDVEVHT<br>AQTKPREEQINSTFRSVSELPIMHQDWL<br>NGKEFKCRVNSAAFPAPIEKTISKTKGR<br>PKAPQVYTIPPPKEQMAKDKVSLTCMI<br>TNFFPEDITVEWQNGQPAENYKNTQP<br>IMDTDGSYFVYSKLNVQKSNWEAGNTF<br>TCSVLHEGLHNHHTEKSLSHSPGK<br>(SEQ ID NO: 46) | L35252 | | Honjo T. et al, Ceit, 18 558-568 (1979) PMID: 115593 |
| | IgG2a variant 1 | GCCAAAACAACAGCCCCATCGGTCTATCCACTGGCC<br>CCTGTGTGTGGAGATACAACTGGCTCCTCGGTGACTC<br>TAGGATGCCTGGTCAAGGGTTATTTCCCTGAGCCAGT<br>GACCTTGACCTGGAACTCTGGATCCCTGTCCAGTGGT<br>GTGCACACCTTCCCAGCTGTCCTGCAGTCTGACCTCT<br>ACACCCTCAGCAGCTCAGTGACTGTAAGCTCGAGCAC<br>CTCGCCCAGCCAGTCCATCACCTGCAATGTGGCCCA<br>CCCGGCAAGCAGCACCAAGGTGGACAAGAAAATTGA<br>GCCCAGAGGGCCCACAATCAAGCCCTGTCCTCCATG<br>CAAATGCCCAGCACCTAACCTCTTGGGTGGACCATCC<br>GTCTTCATCTTCCCTCCAAAGATCAAGGATGTACTCA<br>TGATCTCCCTGAGCCCCATAGTCACATCTGTGGTGGT<br>GGATGTGAGCGAGGATGACCCAGATGTCCAGATGAG<br>CTGGTTTGTGAACAACGTGGAAGTACACACAGCTCAG<br>ACACAAACCCATAGAGAGGATTACAACAGTACTCTCC<br>GGGTGGTCAGTGCCCTCCCCATCCAGCACCAGGACT | AKTTAPSVYPLAPVCGDTTGSSVTLGC<br>LVKGYFPEPVTLTWNSGSLSSGVHTFP<br>AVLQSDLYTLSSSVTVTSSTWPSQSIT<br>CNVAHPASSTKVDKKIEPRGPTIKPCPP<br>CKCPAPNLLGGPSVFFPPKIKDVLMISL<br>SPIVTCVVVDVSEDDPDVQISWFVNNV<br>EVHTAQTQTHREDYNSTLRVVSALPIQ<br>HQDWMSGKEFKCKVNNKDLPAPIERTI<br>SKPKGSVRAPQVYVLPPPEEEMTKKQV<br>TLTCMVTDFMPEDIYVEWTNNGKTELN<br>YKNTEPVLDSDGSYFMYSKLRVEKKNE<br>VERNSYSCSVVHEGLHNHHTTKSFSRT<br>PGK<br>(SEQ ID NO: 48) | J00470<br>AH003509<br>V00825<br>V00766<br>D78344 | | Yamawaki Kataska Y. et al, Nucleic Acids Res. 9, 1365-1381 (1981). PMID: 6262729 Oto F. et al, Proc Natl. Acad Sci. U.S.A, 78, 2442-2446 |

TABLE-continued

| Species | Ig Domain | Nucleotide Sequence | Amino Acid Sequence | GenBank Accession No. | IMGT Database | Reference |
|---|---|---|---|---|---|---|
| | | GGATGAGTGGCAAGGAGTTCAAATGCAAGGTCAACA<br>ACAAAGACCTCCCAGCGCCCATGGAGAGAACCATCT<br>CAAAACCCAAAGGGTGAGTAAGAGGTCCACAGGTATA<br>TGTCTTGCCTCCACCAGAAGAAGAGATGACTAAGAAA<br>CAGGTCACTCTGACCTGCATGGTCACAGACTTCATGC<br>CTGAAGACATTTACGTGGAGTGGACCAACAACGGGA<br>AAACAGAGCTAAACTACAAGAACACTGAACCAGTCCT<br>GGACTCTGATGGTTCTTACTTCAFGTACAGCAAGCTG<br>AGAGTGGAAAAGAAGAACTGGGTGGAAAGAAATAGC<br>TACTCCTGTTCAGTGGTCCACGAGGGTCTGCACAATC<br>ACCACACGACTAAGAGCTTCTCCCGGACTCCGGGTA<br>AATGA<br>(SEQ ID NO: 49) | | | | (1981),<br>PMID:<br>0787604<br>Sikorev J.<br>et al,<br>Nucleic<br>Acids Res.<br>8, 3143-<br>3155 (1980)<br>PMID:<br>6777755<br>Akahon Y.<br>and<br>Kurwaska<br>Y.<br>Genomic,<br>41, 100-<br>104 (1997)<br>PMID:<br>9128488 |
| | IgG2a variant 2 | GCCAAAACAACAGCCCCATCGGTCTATCCACTGGCC<br>CCTGTGTGTGGAGATACAACTGGCTCCTCGGTGACTC<br>TAGGATGCCTGGTCAAGGGTTATTTCCCTGAGCCAGT<br>GACCTTGACCTGGAACTCTGCATCCCTGTCCAGTGGT<br>GTACACACCTTCCCAGCTGTCCTGCAGTCTGACCTCT<br>ACACCCTCAGCAGCTCAGTGACTGTAACCTCGAGCAC<br>CTGGCCGACCCAGTCGATCACCTGCAATGTGGCCCA<br>CCGGGCAAGCAGCACCAAGGTGGACAAGAAAATTGA<br>GCCCAGAGGGCCCACAATCAAGCCCTGTCCTCCATG<br>CAAATGCCCAGCACCTAACCTCTTGGGTGGACCATCC<br>GTCTTCATCTTCCCTCCAAAGATCAAGGATGTACTCA<br>TGATCTCCCTGACTCCCATGCTCACATGTGTGGTGGT<br>GGATGTGAGCGAGGATGACCCAGATGTCCAGATCAG<br>CTGGTTCGTGAACAACGTGGAAGTACTCACAGCTCAG<br>ACACAAACCCATAGAGAGGATTACAACAGTACTCTCC<br>GGGTGGTCAGTGCCCTCCCCATCCAGCACCAGGACT<br>TGGATGAGTGGCAAGGAGTTCAAATGCAAGGTCAACA<br>ACAAAGCCCTCCCAGCGCCCATCGAGAGAACCATCT<br>TCAAAACCCAAAGGGTCAGTAAGAGCTCCACAGGTATA<br>TGTCTTGCCTCCACCAGAAGAAGAGATGACTAAGAAA<br>CAGGTCACTCTGACCTGCATGGTCACAGACTTCATGC<br>CTGAAGACATTTACGTGGAGTGGACCAACAACGGGA<br>AAACAGAGCTAAACTACAAGAACACTCAACCAGTCCT<br>GGACTCTGATGGTTCTTACTTCATGTACACCAAGCTG<br>AGAGTGGAAAAGAAGAACTGGGTGGAAAGAAATAGC<br>TACTCCTGTTCAGTGGTCCACGAGGGTCTGCACAATC<br>ACCACACGACTAAGAGCTTCTCCCGGACTCCGGGTA<br>AATGA<br>(SEQ ID NO: 51) | AKTTAPSVYPLAPVCGDTTGSSVTLGC<br>LVKGYFPEPVTLTWNSGSLSSGVHTFP<br>AVLQSDLYTLSSSVTVTSSTWPSQSIT<br>CNVAHPASSTKVDKKIEPRGPTIKPCPP<br>CKCPAPNLLGGPSVFIFPPKIKDVLMIS<br>LSPMVTCVVVDVSEDDPDVQISWFVNN<br>VEVLTAQTQTHREDYNSTLRVVSALPI<br>QHQDWMSGKEFKCKVNNKALPAPIERT<br>ISKPKGSVRAPQVYVLPPPEEEMTKKQ<br>VTLTCMVTDFMPEDIYVEWTNNGKTEL<br>NYKNTEPVLDSDGSYFMYSKLRVEKKN<br>WVERNSYSCSVVHEGLHNHHTTKSFSR<br>TPGK<br>(SEQ ID NO: 50) | X16997 | | Morgado<br>M.G. et<br>al, EMBO<br>J. S.<br>3245-<br>3251<br>(1989)<br>PMID:<br>2510996 |

TABLE-continued

| Species | Ig Domain | Nucleotide Sequence | Amino Acid Sequence | GenBank Accession No. | IMGT Database | Reference |
|---|---|---|---|---|---|---|
| | IgG2b variant 1 | GCCAAAACAACACCCCCATCAGTCTATCGACTGGCCCCTGGGTGTGGAGATACAACTGGTTCCTCCGTGACTCTGGGATGCCTGGTCAAGGGCTACTTCGCTGAGTCAGTGACTGTGACTTGGAACTCTGGATCCCTGTCCAGCAGTGTGCACACCTTCCGAGCTCTCCTGCAGTCTGGACTCTACACTATGAGCAGCTCAGTGACTGTCCCCTCCAGCACTTTGGCCAAGTCAGACCGTCACCTGCAGCGTTGCTCACCGAGGCAGCAGCACCACGGTGGACAAAAAACTTGAGCCCAGCGGGCCCATTTCAAGAATCAACGCCTGTCCTCGATCCAAGGAGTGTCACAAATGCCCAGCTCCTAACCTCGAGGGTGGACCATCCGTCTTCATCTTCCCTCCAAATATCAAGGATGTACTCATGATCTCCCTGACACCCAAGGTCACGTGTGTGGTGGTGGATGTGAGCGAGGATGACCCAGACGTCCAGATCAGCTGGTTTGTGAACAACGTGGAAGTACACACAGCTCAGACACAAACCCATAGAGAGGATTACAACAGTACTATCCGGGTGGTCAGCACCCTCCGCATCCAGCACCAGGACTGGATGAGTGGCAAGGAGTTCAAATGCAAGGTCAACAACAAAGACCTCCCATCACCCATCGAGAGAACCATCTCAAAAATTAAAGGGCTAGTCAGAGCTCCACAAGTATACATCTTGCCGCCACCAGCAGAGCAGTTGTCCAGGAAAGATGTCAGTCTCACTTGCCTGGTCGTGGGCTTCAACCCTGGAGACATCAGTGTGGAGTGGACCAGCAATGGGCATACAGAGGAGAACTACAAGGACACCGCACCAGTCCTAGACTCTGACGGTTCTTACTTCATATATAGCAAGCTCAATATGAAAACAAGCAAGTGGGAGAAAACAGATTCCTTCTCATGCAACGTGAGACACGAGGGTCTGAAAAATTACTACCTGAAGAAGACCATCTCCCGGTCTCCGGGTAAATGA (SEQ ID NO: 53) | AKTTPPSVYPLAPGCGDTTGSSVYLGGLVKGYFPESVTVTVWSGSLSSSVHTFPALLQSGLYTMSSSVTVPSSTWPSQTVTCSVAHPASSTTVDKKLEPSGPISTINPCPPCKECHKCPAPNLEGGPSVFIFPPNIKDVLMISLTPKVTCVVVDVSEDDPDVQISWFVNNVEVHTAQTQTHREDYMSTIRVVSTLPIQHQDWMSGKEFKCKVNNKDLPSPIERTISKIKGLVRAPQVYILPPPAEQLSRKDVSLTCLVVGFNPGDISVEWTSNGHTEENYKDTAPVLDSDGSYFIYSKLNMKTSKWEKTDSFSCNVRHEGLKNYYLKKTISRSPGK (SEQ ID NO: 52) | J00461 AH005300 V00801 D78344 | | Yamawaki Kataoka Y. et al, Nature, 283, 786-789 (1980) PMID: 6766534 Oilo R. and Raugeon F. Nature, 298, 761-763 (1982) PMID: 6803173 Akahon Y and Kurosawa Y Genomics, 41, 100-104 (1997) PMID: 9126488 |
| | IgG2b variant 2 | GCCAAAACAACACCCCCATCAGTCTATCCACTGGCCCCTGGGTGTGGAGATAGAACTGGTTCCTCCGTGACCTCTGGGTGCCTGGTCAAGGGGTACTTCCCTGAGCCAGTGACTGTGACTTGGAACTCTGGATCCCTGTCCAGCAGTGTGCACACCTTCCCAGCTCTCCTGCAGTCTGGACTCTACACTATGAGCAGCTCAGTGACTGTCCCCTCCAGCACCTGGCCAAGTCAGACCGTCACCTGCAGCGTTGGTCACCCAGCCAGCAGCACCACGGTGGACAAAAAACTTGAGCCCAGCGGGCCCATTTCAACAATCAACCCCTGTCCTCCATGCAAGGAGTGTCACAAATGCCCAGCTCCTAACCTCGAGGGTGGACCATCCGTCTTCATCTTCCCTCCAAATATCAAGGATGTACTCATGATCTCCCTGACACCCAAGGTCACGTGTGTGGTGGTGGATGTGAGCGAGGATGACCCAGACGTCCAGATCAGCTGGTTTGTGAAGAACGTGGAAGTACACACAGCTCAGACACAAACCCATAGAGAGGATTACAACAGTACTATCCGGGTGGTGAGCACCCTCCCCATCCAGCACCAGGACTGCATGAGTGGCAAGGAGTTCAAATGCAAGGTGAACAACAAAGACCTCCCATCACCCATCGAGAGAACCATCTCAAAAATTAAAGGGCTAGTCAGAGCTCCACAAGTATACACTTTGCCGCCACCAGCAGA | AKTTPPSVYPLAPGCGDTTGSSVTSGCLVKGYFPEPVTVTWNSGSISSSVHTFPALLQSGLYTMSSSVTVPSSTWPSQTVTCSVAHPASSTTVDKKLEPSGPISTINPCPPCKECHKCPAPNLEGGPSVFIFPPNIKDVLMISLTPKVTCVVVDVSEDDPDVQISWFVNNVEVHTAQTQTHREDYNSTIRVVSTLPIQHQDWMSGKEFKCKVNNKDLPSPIERTISKIKGLVRAPQVYTLPPPAEQLSRKDVSLTCLVVGFNPGDISVEWTSNGHTEENYKDTAPVLDSDGSYFIYSKLNMKTSKWEKTDSFSCNVRHEGLKNYYLKKTISRSPGK (SEQ ID NO: 54) | V00763 | | Tuckor P.W. et al, Science 206 1303-1306 (1979) PMID 117549 |

TABLE-continued

| Species | Ig Domain | Nucleotide Sequence | Amino Acid Sequence | GenBank Accession No. | IMGT Database | Reference |
|---|---|---|---|---|---|---|
| | | GCAGTTGTCCAGGAAAGATGTCAGTCTCACTTGCCTG<br>GTCGTGGGCTTCAACCCTGGAGACATCAGTGTGGAGT<br>GGACCACCAATGGGCATACAGAGGAGAACTACAAGG<br>ACACCGCACCAGTTCTTGACTCTGACGGTTCTTACTT<br>CATATATAGCAAGCTCAATATGAAAACAAGCAAGTGG<br>GAGAAAAGAGATTCCTTCTCATGCAACGTGAGACACG<br>AGGGTCTGAAAAATTACTACCTGAAGAAGACCATCTC<br>CCGGTCTCCGGGTAAATGA<br>(SEQ ID NO: 55) | | | | |
| | IgG2c variant 1 | GCCAAAACAACAGCCCCATCGGTCTATCCACTGGCC<br>CCTGTGTGTGGAGGTACAACTGGCTCCTCGGTCACTC<br>TAGGATGCCTGGTCAAGGGTTATTTCCCTGAGCCAGT<br>GACCTTGACCTGGAACTCTGGATCCCTGTCCAGTGGT<br>GTGCACACCTTCCCAGCTCTCCTGCAGTCTGGCGTCT<br>ACACCCTCAGCAGCTCAGTGACTGTAACCTCGAACAC<br>CTGGCCCAGCCAGACCATCACCTGCAATGTGGCCCA<br>CCCGGCAAGCAGCACCAAAGTGGACAAGAAAATTGA<br>GCCCAGAGTGCCCATAACACAGAACCGGTGTCCTCC<br>ACTCAAAGAGTGTCCCCCATGCGCAGCTCCAGACCT<br>CTTGGGTGGACCATCCGTCTTCATCTTCCCTCCAAAG<br>ATCAAGGATGTACTCATGATCTCCCTGAGCCCCATGG<br>TCACATGTGTGGTGGTGGATGTGAGCGAGGATGACC<br>CAGACGTCCAGATCAGCTGGTTTGTGAACAACGTGGA<br>AGTACACACAGCTCAGACACAAACCCATAGAGAGGAT<br>TACAACAGTACTCTCCGGGTGGTGAGTGCCCTCCCCA<br>TCCAGCACCAGGACTGGATGAGTGGCAAGGAGTTCA<br>AATGCAAGGTCAACAACAGAGCCCTCCCATCCCCCAT<br>CGAGAAAACCATCTCAAAACCCAGAGGGCCAGTAAG<br>AGCTCCACAGGTATATGTCTTGGCTCCACCAGCAGAA<br>GAGATGACTAAGAAAGAGTTCAGTCTGACCTGCATGA<br>TCACAGGCTTCTTACCTGCCGAAATTGCTGTGGACTG<br>GACCAGCAATGGGCGTACAGAGGAAAACTACAAGAA<br>CACCGCAACAGTCCTGGACTCTGATGGTTCTTACTTC<br>ATGTACAGCAAGCTCAGAGTACAAAAGAGCACTTGGG<br>AAAGAGGAAGTCTTTTCGCCTGCTCAGTGGTCCACGA<br>GGTGCTGCACAATCACCTTACGACTAAGACCATCTCC<br>CGGTCTCTGGGTAAATGA<br>(SEQ ID NO: 57) | AKTTAPSVYPLAPVCGGTTGSSVTLGC<br>LVKGYFPEPVTLTWNSGSLSSGVHTFP<br>ALLQSGLYTLSSSVTVTSNTWPSQTIT<br>CNVAHPASSTKVDKKIEPRVPITQNPCP<br>PLKECPPCAAPDLLGGPSVFIFPPKIKD<br>VLMISLSPMVTCVVVDVSEDDPDVQIS<br>WFVNNVEVHTAQTQTHREDYNSTLRV<br>VSALPIQHQDWMSGKEFKCKVNNRALP<br>SPIEKTISKPRGPVRAPQVYVLPPPAEE<br>MTKKEFSLTCMITGFLPAEIAVDWTSNG<br>RTEQNYKNTATVLDSDGSYFMYSKLRV<br>QKSTWERGSLFACSVVHEVLHNHLTTK<br>TISRSLGK<br>(SEQ ID NO: 56) | J00479 | | Olio R. and Rougeon F. Cell, 32 515-523 (1983). PMID: 6297797 |
| | IgG2c variant 2 | GCCAAAACAACAGCCCCATCGGTCTATCCACTGGCC<br>CCTGTGTGTGGAGGTACAACTGGCTCCTCGGTGACTC<br>TAGGATGCCTGGTCAACGGTTATTTCCCTGAGCCAGT<br>GACCTTGACCTGGAACTCTGGATCGCTGTCCAGTGGT<br>GTGCACACCTTCCCAGCTCTCCTGCAGTCTGGCCTCT<br>ACACCCTGAGCAGCTCAGTGACTGTAACCTCGAACAC<br>CTGGCCCAGCCAGACCATCACCTGCAATGTGGCGCA<br>CCCGGCAAGCAGCACCAAAGTGGACAAGAAAATTGA<br>ATCCAGAAGGCCCATACCACCCAACTCCTGTCCTCCA<br>TGCAAAGAGTGTTCCATATTCCCAGCTGCTGACCTCT<br>TGGGTGGACCATCCGTCTTCATCTTCCCTCCAAAGAT | AKTTAPSVYPLAPVCGGTTGSSVTLGC<br>LVKGYFPEPVTLTWNSGSLSSGVHTFP<br>ALLGSGLYTLSSSVTVTSNTWPSQTIT<br>CNVAHPASSTKVDKKIESRRPIPPNSCP<br>PCKECSIFPAPDLLGGPSVFIFPPKIKD<br>VLMISLSPIVTCVVVDVSEDDPDVQISW<br>FVNNVEVHTAQTQTHREDYNSTLRVVS<br>ALPIQHQDWMSGKEFKCKVNNRALPSP<br>IEKTISKPRGPVRAPQVYVLPPPAEEMT<br>KKEFSLTCMITDFLPAEIAVDWTSMGHK<br>ELNYKNTAPVLDTDGSYFMYSKLRVQK | X16998 | | Morgado M.G. et al., EMBO J. 8, 3245-3251 (1989). PMID: 2510996 |

TABLE-continued

| Species | Ig Domain | Nucleotide Sequence | Amino Acid Sequence | GenBank Accession No. | IMGT Database | Reference |
|---|---|---|---|---|---|---|
| | | CAAGGATGTACTCATGATCTCCCTGAGCCCCATAGTC<br>ACATGTGTGGTGGTGGATGTGAGCGAGGATGACCCA<br>GATGTCCAGATCAGCTGGTTTGTGAACAACGTGGAAG<br>TACACACAGCTCAGACACAAACCCATAGAGAGGATTA<br>CAACAGTACTCTCCCGGTGGTCAGTGCCCTCCCCATC<br>CAGCACCAGGACTGGATGAGTGGCAAGGAGTTCAAA<br>TGCAAGGTCAACAACAGAGCCCTCCCATCCCCCATC<br>GAGAAAACCATCTCAAAACCCAGAGGGCCAGTAAGA<br>GCTCCACAGGTATATGTCTTGCGTCGACGAGCAGAAG<br>AGATGACTAAGAAAGAGTTCAGTCTGAGCTGCATGAT<br>CACAGACTTCTTACCTGCCGAAATTGCTGTGGACTGG<br>ACCAGCAATGGGCATAAAGAGCTGAACTACAAGAACA<br>CCGCACCAGTCCTGGACACTGATGGTTCTTACTTCAT<br>GTACAGCAAGCTCAGAGTGCAAAAGAGCACTTGGGA<br>AAAAGGAAGTCTTTTCGCCTGCTCAGTGGTCCACGAG<br>GGTCTGCACAATCACCATACGACTAAGACCATCTCCG<br>GGTCTCTGGGTAAATGA<br>(SEQ ID NO: 59) | STWEKGSLFACSVVHEGLHNHHTTKTI<br>SRSLGK<br>(SEQ ID NO: 58) | | | |
| | IgG2c variant 3 | GCCAAAACAACAGCCCCATCGGTCTATCCACTGGCC<br>CCTGTGTGTCGAGGTACAACTGGCTCCTCGGTGACTC<br>TAGGATGCCTGGTCAAGGGTTATTTCGCTGAGCCAGT<br>GACCTTGACCTGGAACTCTGGATCCCTGTCCAGTGGT<br>GTGCACACCTTCCCAGCTCTCCTGCAGTCTGGCCTCT<br>ACAGGCTCAGCAGCTCAGTGACTGTAACCTCGAACAC<br>CTGGCCCAGCCAGACCATCACCTGCAATGTGGCCCA<br>CCCGGCAAGCAGCACCAAAGTGGACAAGAAAATTGA<br>GGCCAGAGTGCCCATAACACAGAACCCCTGTCCTCC<br>ACTCAAAGAGTGTCCCCCATGCGCAGCTCCAGACCT<br>CTTGGGTGGACCATCCGTCTTCATCTTCCCTCCAAAG<br>ATCAAGGATGTACTCATGATCTCCCTGAGCCCCATGG<br>TCACATGTGTGCTGCTGGATGTGAGCGAGGATGACC<br>CAGACGTCCAGATCAGCTGGTTTGTGAACAACGTGGA<br>AGTACACACAGCTCAGACAGAAACCCATAGAGAGGAT<br>TACAACAGTACTCTCCGGGTGGTCAGTGCCCTCCCCA<br>TCCAGCACCAGGACTGGATGAGTGGCAAGGAGTTCA<br>AATGCAAGGTCAACAACAGAGCCCTCCCATCCCGCAT<br>CGAGAAAACCATCTCAAAACCCAGAGGGCCAGTAAG<br>AGCTCCACAGGTATATGTCTTGGCTCCACCAGCAGAA<br>GAGATGACTAAGAAAGAGTTCAGTCTGACCTGCATGA<br>TCACAGGCTTCTTACCTGCCGAAATTGCTGTGGACTG<br>GACCAGCAATGCGCGTACAGAGCAAAACTACAAGAA<br>CACCGCAACAGTCCTGGACTCTGATGGTTCTTACTTC<br>ATGTACAGCAAGCTCAGAGTACAAAAGAGCACTTGGG<br>AAAGAGGAAGTCTTTTCGCCTGCTCAGTGGTCCACGA<br>GGGTCTGCACAATCACCTTACGACTAAGACCATCTCC<br>CGGTCTCTGGGTAAATGA<br>(SEQ ID NO: 61) | AKTTAPSVYPLAPVCGGTTGSSVTLGC<br>LVKGYFPEPVTLTWNSGSLSSGVHTFP<br>ALLQSGLYTLSSSVTVTSNTWPSQTIT<br>CNVAHPASSTKVDKKIEPRVPITGNPCP<br>PLKECPPCAAPDLLGGPSVFIFPPKIKD<br>VLMISLSPMVTCVVVDVSEDDPDVQIS<br>WFVNNVEVHTAQTQTHREDYNSTLRV<br>VSALPIQHQDWMSGKEFKCKVNNRALP<br>SPIEKTISKPRGPVRAPQVYVLPPPAEE<br>MTKKEFSLTQMITGFLPAEIAVDWTSNG<br>RTEQNVKNTATVLDSDGSYFMYSKLRV<br>QKSTWERGSLFACSVVHEGLHNHLTTK<br>TISRSLGK<br>(SEQ ID NO: 60) | Y10606 | | Martin R.M et al, Immuno-genics, 46, 157-168 (1997). PMID: 9162106 |
| | IgG3 | GCTACAACAACAGCCCCATCTGTCTATCCCTTGGTCC<br>CTGGCTGCAGTGACACATCTGGATGCTCGGTGACACT | ATTTAPSVYPLVPGCSDTSGSSVTLGC<br>LVKGYFPEPVTVKVNWYGALSSGVRTVS | J00451<br>AH005309 | | Stanton L.W. |

TABLE-continued

| Species | Ig Domain | Nucleotide Sequence | Amino Acid Sequence | GenBank Accession No. | IMGT Database | Reference |
|---|---|---|---|---|---|---|
| | | GGGATGCCTTGTCAAAGGCTACTTCCCTGAGCCGGTA<br>ACTGTAAAATGGAACTATGGAGCCCTGTCCAGCGGTG<br>TGCGCACAGTCTCATCTGTCCTGCAGTCTGGGTTCTA<br>TTGCGTCAGCAGCTTGGTGACTGTACCCTCCAGCACC<br>TGGCCCAGCCAGACTGTCATCTGCAACGTAGCCCAC<br>CCAGCGAGCAAGACTGAGTTGATCAAGAGAATCGAG<br>CCTAGAATACCCAAGCCCAGTACGCCCCCAGGTTCTT<br>CATGCCCACCTGGTAACATCTTGGGTGGACCATCCGT<br>CTTCATCTTCCCCCCAAAGCCCAAGGATGCACTCATG<br>ATCTCCCTAACCCCCAAGGTTACGTGTGTGGTGGTGG<br>ATGTGAGCGAGGATGACCCAGATGTCCATGTCAGCTG<br>GTTTGTGGACAACAAAGAAGTACACACAGCCTGGACA<br>CAGCCGCGTGAAGGTCAGTACAACAGTACCTTCCGA<br>GTGGTCAGTGCCCTCCCCATCCAGCACCAGGACTGG<br>ATCAGGGGCAAGGAGTTCAAATGCAAGGTCAACAAC<br>AAAGCCCTCCCAGCCCCCATCGAGAGAACCATCTCA<br>AAACCCAAAGGAAGAGCCCAGACACCTCAAGTATAC<br>ACCATACCCCCACCTCGTGAACAAATGTCCAAGAAGA<br>AGGTTAGTCTGACCTGCCTGGTCACCAACTTCTTCTC<br>TGAAGCCATCAGTGTGGAGTGGGAAAGGAACGGAGA<br>ACTGGAGCAGGATTACAAGAACAGTCCAGCCATCCTG<br>GACTCAGATGGGACCTACTTCCTCTACAGCAACCTCA<br>CTGTGGATACAGACAGTTGGTTGCAAGGAGAAATTTT<br>TACCTGCTCCGTGGTGCATGAGGCTCTCCATAACCAC<br>CACACACAGAAGAACCTGTCTCGCTGCCCTGGTAAAT<br>GA<br>(SEQ ID NO: 63) | SVLQSGFYSLSSLVTVPSSTWPSQTVI<br>CNVAHPASKTELIKRIEPRIPKPSTPPG<br>SSCPPGNILGGPSVFIFPPKPKDALMIS<br>LTPKVTCVVVDVSEDDPDVHVSWFVDN<br>KEVHTAWTQPREAQYNSTFRVVSALPI<br>QHQDWMRGKFFKCKVNNKALPAPIERT<br>ISKPKGRAQTPQVYTIPPPREQMSKKK<br>VSLTCLVTNFFSEAISVEWWRNGELEQD<br>YKNTPPILDSDGTYFLYSKLTVDTDSWL<br>QGEIFTCSVVHEALHNHHTQKNLSRSP<br>GK<br>(SEQ ID NO: 62) | X00915<br>D78343 | | and Marcus<br>K.B.<br>Nucleic<br>Acids Res.<br>10, 5993-<br>6006 (1982)<br>PMID:<br>629864<br>Wels J.A.<br>et al,<br>EMBO J.<br>2041-2046<br>(1984)<br>PMID:<br>6092053<br>Akahoni Y.<br>and<br>Kurosawa<br>Y.<br>Genomics,<br>41, 100-<br>10 (1997)<br>PMID:<br>9126498 |
| Mouse Ig light con-stant region | Ig kappa (CK) | GCTGATGCTGGACCAACTGTATCCATCTTCCCACCAT<br>CCAGTGACCAGTTAACATCTGCACGTGCCTCAGTCGT<br>GTGCTTCTTGAAGAACTTCTACCCCAAAGACATCAAT<br>GTCAAGTGGAAGATTGATGGCAGTGAACGACAAAATG<br>GCGTCCTGAACAGTTGGACTGATCAGGACAGCAAAG<br>ACAGCACCTACAGCATGAGCAGCACCCTCACGTTGA<br>CCAAGGACGAGTATGAACGAGATAACAGCTATACCTG<br>TGAGGCCACTCACAAGACATCAACTTCACCCATTGTC<br>AAGAGCTTCAACAGGAATGAGTGTTAC<br>(SEQ ID NO: 37) | ADAAPTVSIFPPSSEQLTSGGASVVCF<br>LNNFYPKDINVKWKIDGSERQNGVLNS<br>WTDQDSKDSTYSMSSTLTLTKDEYERH<br>NSYTCEATHKTSTSPIVKSFNRNEC<br>(SEQ ID NO: 36) | V00807<br>V00777<br>V01569<br>V00806<br>X67002<br>X67003<br>X67004<br>X67005<br>X67006<br>X67007<br>X67008<br>X67009<br>X670010<br>X670011<br>X670012 | http://www.<br>imgt.org/<br>IMGT<br>reportoire/<br>index.<br>ghp?section<br>=locus<br>Genes&<br>reportoire=<br>genetable&<br>species=<br>*mus musculus*&<br>group=IGKC | Hieter<br>P.A. et<br>al. Cell,<br>22, 197-<br>207 (1980)<br>PMID:<br>6775818<br>Max E.E<br>et al. J.<br>Bio. Chem,<br>256, 5116-<br>5120 (1981)<br>PMID:<br>6262318<br>Seidman<br>J.G. et al,<br>Nature,<br>280, 370-<br>375 (1979)<br>PMID:<br>111146<br>Solin M.L. |

TABLE-continued

| Species | Ig Domain | Nucleotide Sequence | Amino Acid Sequence | GenBank Accession No. | IMGT Database | Reference |
|---|---|---|---|---|---|---|
| | | | | | | and Kaartnen M. Immuno-genics, 37 401-407 (1983) PMID: 8436414 |
| | Ig lambda 1 (CL) | GGCCAGCCCAAGTCTTCGCCATCAGTCACCCTGTTTC CACCTTCCTCTGAAGAGCTCGAGACTAACAAGGCCAC ACTGCTGTGTACGATCACTCATTTCTACCCAGGTGTG GTGACAGTGGACTGGAAGGTACATCCTACCCCTGTC ACTCAGGGTATGGAGACAACCCAGCCTTGCAAACAG AGCAACAAGAAGTACATGGCTAGCAGCTACCTGACCC TGACAGCAAGACCATGGGAAAGGCATAGCAGTTACA GCTGCCAGGTCACTCATGAAGGTCACACTGTGGAGA AGAGTTTGTGCCGTGCTGACTGTTCCTAG (SEQ ID NO: 39) | GQPKSSPSVTLFPFSSEELETNKATLV CTITDFYPGVVTVDWKVDGTPVTQGME TTQPSKQSNNKYMASSYLTLTARAWER HSSYSCQVTHEGHTVEKSLSRADCS (SEQ ID NO: 38) | J00587 AH005311 X58411 V00814 | http://www.imgt.org/IMGT reportoire/index.ghp?section=locus Genes&reportoire=genetable&species=*mus musculus*&group=IGKC | Selsing E. et al. Proc Natl. Acad Sci USA. 79, 4681-4685 (1982) PMID: 8812053 Weiss S. and W GE. EMBO J. 6, 927-937 (1987) PMID: 3105891 Bernard O. et al. Cell, 15, 1133-144 (1978) PMID: 103630 |
| | | GGTCAGCCCAAGTCCACTCCCACTCTCACGGTGTTTC CACCTTCCTCTGAGGAGCTCAAGGAAAAGAAAGCCAC ACTGGTGTGTCTGATTTCCAACTTTTCCCCGAGTGGT GTGACAGTGGCCTGGAAGGCAAATGGTACACCTATCA CCCAGGGTGTGGACACTTCAAATCCCACCAAAGAGG GCAACAAGTTCATGGCCACCAGCTTCCTACATTTGAC ATCGCACCAGTGGAGATCTCACAACAGTTTTACCTGT CAAGTTACACATGAAGCGGACAGTGTCGAGAAGAGT CTGTCTCCTGGAGAATGTCTGTAA (SEQ ID NO: 41) | GQPKSTPTLTVTPPSSEELKENKATLV CLISNFSPSGVTVAWKANGTPITQGVD TSNPTKEDNKYMASSFLHLTSDQWRSH NSFTCQVTHEGDTVEKSLSPAECL (SEQ ID NO: 40) | J00595 AH001968 J00592 AH001967 X58414 | | Selsing E. et al. Proc Natl. Acad Sci USA. 79, 4681-4685 (1982) PMID: 8812053 Wu G. et al, Cell 33, 77-83 (1983) PMID: 3109691 |
| | | GGTCAGGCCAAGTGCACTCCCACACTGAGCATGTTTG CACCTTCCCCTGAGGAGCTCCAGGAAAACAAAGCCA CACTCCTGTGTCTGATTTCCAATTTTTCCCCAAGTGG TGTGACAGTGGCCTGGAAGGCAAATGGTACACCTATC ACCCAGGGTGTGGACAGTTCAAATCCCACCAAAGAG | GQPKSTPTLTMFPPSSEELQENKATLV CLISNFSPSGVTVAWKANGTPITQGVD TSNPTKEDNKYMASSFLHLTSDQWRSH NSFTCQVTHEGDTVEKSLSPAECL (SEQ ID NO: 42) | J00585 AH005311 X58415 X58411 | | Selsing E. et al. Proc Natl. Acad Sci USA. 79, 4681- |

TABLE-continued

| Species | Ig Domain | Nucleotide Sequence | Amino Acid Sequence | GenBank Accession No. | IMGT Database | Reference |
|---|---|---|---|---|---|---|
| | | GACAACAAGTACATGGGCAGCAGGTTCTTACATTTGA<br>CATCGGAGCAGTGGAGATCTCACAACAGTTTTAGCTG<br>CCAAGTTACACATGAAGGGGACACTGTGGAGAAGAG<br>TCTGTCTCCTGCAGAATGTCTGTAA<br>(SEQ ID NO: 43) | | | | 4685 (1982)<br>PMID:<br>8812053<br>Weiss S.<br>and W GE.<br>EMBO J.<br>6, 927-<br>937 (1987)<br>PMID:<br>3105891 |
| Bovine<br>(Scientific<br>Name: *Bos*<br>*taurus*) | Bovine IgG1<br>Ig variant<br>heavy 1<br>chain<br>con-<br>stant<br>region<br>(CH1<br>CH3) | GCCTCCACCACAGCCCCGAAAGTCTACCCTCTGAGTTC<br>TTGCTGCGGGGACAAGTCCAGCTCCACCGTGACCCTGG<br>GCTGCCTGGTCTCCAGCTACATGCCCGAGCCGGTGACC<br>GTGACCTGGAACTCGGGTGCCCTGAAGAGCGGGGTGCA<br>CACCTTCCCGGCTGTCCTTCAGTCCTCCGGGCTGTACT<br>CTCTCAGCAGCATGGTGACCGTGCCCGGCAGCACCTCA<br>GGACAGACCTTCACCTGCAACGTAGCCCACCCGGCCAG<br>CAGCACCAAGGTGGACAAGGCTGTTGATCCCACATGCA<br>AACCATCACCCTGTGACTGTTGCCCACCCCCTGAGCTC<br>GCCGGAGGACCCTCTGTCTTCATCTTCCCACCGAAACC<br>CAAGGACACCCTCAGAATCTCGGGAACGCCCGAGGTCA<br>CGTGTGTGGTGGTGGAGGTGGGCCACGATGACCCCGAG<br>GTGAAGTTCTCCTGGTTCGTGGACGACGTGGAGGTAAA<br>CACAGCCACGACGAAGCCCAGAGAGGAGCAGTTCAACA<br>GCACCTACCGCGTGGTCAGCGCCCTGCGCATCCAGCAC<br>CAGGACTGGACTGGAGGAAAGGAGTTCAAGTGCAAGGT<br>CCACAACGAAGGCCTCCCGGCCCCCATCGTGAGGACGA<br>TCTCCAGGACCAAAGGGCCGGGCCGCGAGCCGCAGGT<br>GTATGTCCTGGCCCCACCCCAGGAAGAGCTCAGCAAAA<br>GCACGGTCAGCCTCACCTGCATGGTCACCAGCTTCTAC<br>CCAGACTACATCGCCGTGGAGTGGCAGAGAAAGGGGCA<br>GCCTGAGTCGGAGGACAAGTACGGCACCACCCCCGCC<br>CAGCTGGACGCCGACAGCTCCTACTTCCTCTACAGCAA<br>GCTCAGGGTGGACAGGAACAGCTGGCAGGAAGGAGAC<br>ACCTACACGTGTGTGGTGATGCACGAGGCCCTGCACAA<br>TCACTACACGCAGAAGTCCACCTCTAAGTCTGCGGGTA<br>AATGA<br>(SEQ ID NO: 67) | ASTTAPKVYPLSSCCGDKSSSTVTLGC<br>LVSSYMPEPVTVTWNSGALKSGVHTFP<br>AVLQSSGLYSLSSMVTVPGSTSGQTFT<br>CNVAHPASSTKVDKAVDPTCKPSPCD<br>CCPPPELPGGPSVFIFPPKPKDTLTISG<br>TPEVTCVVVDVGHDDPEVKFSWFVDD<br>VEVNTATTKPREEQFNSTYRVVSALRI<br>QHQDWTGGKEFKCKVHNEGLPAPIVRT<br>ISRTKGPAREPQVYVLAPPQEELSKST<br>VSLTCMVTSFYPDYIAVEWQRNGQPES<br>EDKYGTTPPQLDADSSYFLYSKLRVDR<br>NSWQEGDTYTCVVMHEALHNHYTQKS<br>TSKSAGK*<br>(SEQ ID NO: 66) | X62916 | http://www.<br>imgt.org/<br>IMGT<br>reportoire/<br>index.<br>ghp?section<br>=locus<br>Genes&<br>reportoire=<br>genetable&<br>species=<br>*bovine taurus*<br>&group=IGKC | Symons D.B<br>et a;. J.<br>Immuno-<br>genes, 14,<br>273-283<br>(1987)<br>PMID:<br>341517<br>Symons D.B<br>et al, Mol.<br>Immno., 26<br>341-350<br>(1989)<br>PMID:<br>2513487<br>Kacksovics<br>I. and<br>Butler J.E.<br>Mol.<br>Immunol, 33<br>189-195<br>(1999)<br>PMID:<br>8849440<br>Rabbani H.<br>et al.<br>Immuno-<br>genetics,<br>46, 328-<br>331 (1997)<br>PMID:<br>9218535<br>Saini S.S.<br>et al<br>Searol J.<br>Immunol.<br>65, 32-8<br>(2007) |

TABLE-continued

| Species | Ig Domain | Nucleotide Sequence | Amino Acid Sequence | GenBank Accession No. | IMGT Database | Reference |
|---|---|---|---|---|---|---|
| | | | | | | PMID:<br>17212754 |
| | IgG1<br>variant<br>2 | GGCTCCAGGACAGGCGCGAAAGTCTAGCCTGTGAGTTC<br>TTGCTGCGGGGACAAGTCCAGCTCCACCGTGACCCTGG<br>GCTGCCTGGTCTCCAGCTACATGCCCGAGCCGGTCACC<br>GTGACCTGGAACTCGGGTGCCCTGAAGAGCGGGGTGCA<br>CACCTTCCCCGCCGTCCTTCAGTCCTCCGGGCTGTACT<br>CTCTCAGGAGCATGGTGACCGTGCCCGGCAGCACCTCA<br>GGACAGAGCTTCACGTGCAACGTAGCCCACCCGGCCAG<br>CAGCACCAAGGTGGACAAGGCTGTTGATCCCACATGCA<br>AACCATCACCCTGTGACTGTTGCCCACCCCCTGAGCTC<br>CGCGGAGGACCCTCTGTCTTCATCTTCCCACCGAAACC<br>CAAGCACACCCTCACAATCTCCGCAACGCCCGAGGTCA<br>CGTGTGTGCTGCTGGACGTGGGCCACCATGACCCCGAG<br>GTGAAGTTCTCCTGGTTCGTGGACGACGTGGAGGTAAA<br>CACAGCCACGACGAAGCCGAGAGAGGAGCAGTTCAACA<br>GCACCTACCGCGTGGTCAGCGCCCTGCGCATCCACCAC<br>CAGGACTGGACTGGAGGAAAGGAGTTCAAGTGCAAGGT<br>CCACAACGAAGGCCTCCCGGCCCCCATCGTGAGGACCA<br>TCTCCAGGACCAAAGGGCCGGCCCGGGAGCCCCAGGT<br>GTATGTCCTGGCCCCACCCCAGGAAGAGCTCAGCAAAA<br>GCACCGTCAGCCTCACCTGCATGGTCACCACCTTCTAC<br>CCAGACTACATCGCCGTGGACTGGCAGACAAACGGGCA<br>GCCTGAGTCGGAGGACAAGTACGGCACGACCCCGGGC<br>CAGCTGGACGCCGACAGCTCCTACTTCCTGTACAGCAA<br>GCTCAGGGTGGACAGGAACAGCTGGCAGGAAGGAGAC<br>ACCTACACGTCTGTGGTGATGCACGAGGCCCTCCACAA<br>TCACTACACGCAGAAGTCCACCTCTAAGTCTGCGGGTA<br>AATGA<br>(SEQ ID NO: 69) | ASTTAPKVYPLSSCCGDKSSSTVTLGC<br>LVSSYMPEPVVTVWNSGALKSGVHTFP<br>AVLQSSGLYSLSSMVTVPGSTSGQTFT<br>CNVAHPASSTKVDKAVDPTCKPSPCD<br>CCPPPELPGCPSVFIFPPKPKDTLTISG<br>TPEVTCVVVDVGHDDPEVKFSWFVDD<br>VEVNTATTKPREEQFNSTYRVVSALRI<br>QHQDWTGGKEFKCKVHNEGLPAPIVRT<br>ISRTKGPAREPQVYVLAPPQEELSKST<br>VSLTCMVTSFYPDYIAVEWQRNGQPES<br>EDKYGTTPPQLDADSSYFLYSKLRVDR<br>NSWQEGDTYTCVVMHEALHNHYTQKS<br>TSKSAGK*<br>(SEQ ID NO: 68) | X16701<br>(M25278) | | |
| | IgG1<br>variant<br>3 | GCCTCCACCACAGCCCCGAAAGTCTACCCTCTGAGTTC<br>TTGCTGCGGGGACAAGTCCAGCTCCACCGTGACCCTGG<br>GCTGCCTGGTCTCCAGCTACATGCCCGAGCCGGTGACC<br>GTGACCTGGAACTCGGGTGCCCTGAACAGCGGCGTGCA<br>CACCTTCCCGGCCGTCCTTCAGTCCTCCGGGCTCTACT<br>CTCTCAGCAGCATGGTGACCGTGCCCGGCAGCACCTCA<br>GGAACCCAGACCTTCACCTGCAACGTAGCCCACCCGGC<br>CAGCAGCACCAAGGTGGACAAGGCTGTTGATCCCAGAT<br>GCAAAACAACCTGTGACTGTTCCCCACCGCCTGAGCTC<br>CCTGGAGGACCCTCTGTCTTCATCTTCCCACCGAAACC<br>CAAGGACACGCTCACAATCTCGGGAACGCCCGAGGTCA<br>CGTGTGTGGTGGTGGACGTGGGCCACGATGACCCCGAG<br>GTGAAGTTCTCCTGGTTCGTGGACGACGTGGAGCTAAA<br>CACAGCCACGACGAAGCCGAGAGAGGAGCAGTTCAACA<br>GCACCTACCGCGTGGTCAGCGCCCTGCGCATCCAGCAC<br>CAGGACTGGACTGGAGGAAAGGAGTTCAAGTGCAAGGT<br>CCACAACGAAGGCCTCCCAGCCCCCATCGTGAGGACCA<br>TCTCCACGACCAAAGGGCCGGCCCGGGACGCGGAGGT<br>GTATGTGCTGGCCCCAGCCCAGGAAGAGGTCAGCAAAA | ASTTAPKVYPLSSCCGDKSSSTVTLGC<br>LVSSYMPEPVTVTWNSGALKSGVHTFP<br>AVLQSSGLYSLSSMVTVPGSTSGTQTF<br>TCNVAHPASSTKVDKAVDPRCKTTGD<br>CCPPPELPGGPSVFIFPPKPKDTLTISG<br>TPEVTCVVVDVGHDDPEVKFSWFVDD<br>VEVNTATTKPREEQFNSTYRVVSALRI<br>QHQDWTGGKEFKCKVHNEGLPAPIVRT<br>ISRTKGPAREPQVYVLAPPQEELSKST<br>VSLTCMVTSFYPDYIAVEWQRNGQPES<br>EDKYGTTPPQLDADGSYFLYSRLRVDR<br>NSWQEGDTYTCVVMHEALHNHYTQKS<br>TSKSAGK*<br>(SEQ ID NO: 70) | S82407 | | |

TABLE-continued

| Species | Ig Domain | Nucleotide Sequence | Amino Acid Sequence | GenBank Accession No. | IMGT Database | Reference |
|---|---|---|---|---|---|---|
| | | GCACGGTCAGCCTCACGTGCATGGTCACCAGCTTCTAC<br>CCAGACTACATCGCCGTGGAGTGGCAGAGAAATGCGCA<br>GCCTGAGTCAGAGGACAAGTACGGCACGACCCCTCCCC<br>AGCTGGACGCCGACCGCTCCTACTTCCTGTACACCAGG<br>CTCAGGGTGGACAGGAACAGCTGGCAGGAAGGAGACA<br>CCTACACGTGTGTGGTGATGGACGAGGCCCTGCACAAT<br>CACTACACGCAGAAGTCCACCTCTAAGTCTGCGGGTAA<br>ATGA<br>(SEQ ID NO: 71) | | | | |
| | IgG2 variant 1 | GCCTCCACCACAGCCCCGAAAGTCTACCCTCTGGCATC<br>CAGCTGCGCAGACACATCCAGCTCCACCGTGACCCTGG<br>GCTGCCTGGTGTCCAGCTACATGCCCGAGCCGGTGACC<br>GTGACCTGGAACTCGGGTGCCCTGAAGAGCGGCGTGCA<br>CACCTTCCCGGCTGTCCTTCAGTCCTCCGGGCTCTACT<br>CTCTCAGCAGCATGGTGACCGTGCCCGCCAGCAGCTCA<br>GGACAGACCTTCACCTGCAACGTAGCCCACCCGGCCAG<br>CAGCACCAAGGTGGACAAGGCTGTTGGGGTCTCCATTG<br>ACTGCTCCAAGTGTCATAACCAGCCTTGCGTGAGGGAA<br>CCATCTGTCTTCATCTTCCCACCGAAACCCAAAGACAC<br>CCTGATGATCACAGGAACCCCCCACCTCACGTGTGTCG<br>TGGTGAACGTGGGCCACGATAACCCCGAGGTGCAGTTC<br>TCCTGGTTCGTGGATGACGTGGAGGTGCACACGGCCAG<br>GTCGAAGCCAAGAGAGGAGCAGTTCAACAGCACGTACC<br>GCGTGGTCACCGCCCTGCGCATCCAGCACCAGGACTGG<br>ACTGGAGGAAAGGAGTTCAAGTGCAAGGTCAACAACAA<br>AGGCCTCTCGGCCCCCATCGTGAGGATCATCTCCAGGA<br>GCAAAGGGCCGGCCCGGGAGCCGCAGGTGTATGTCCT<br>GGACCCACCCAAGGAAGAGCTCAGCAAAAGCACGCTCA<br>GCGTCACCTGCATGGTCACCCGCTTCTACCCAGAAGAT<br>GTAGCCGTGGAGTGGCAGAGAAACCGGCAGACTGAGTC<br>GGAGGACAAGTACCGCACGACCCCGCCCCAGCTGGAC<br>ACCGACCGCTCCTACTTCCTGTACAGCAAGCTCAGGGT<br>GGACAGGAACAGCTGCCACGAAGGAGACGCCTACACG<br>TGTGTGGTGATGCACGAGGCCCTGCACAATCACTACAT<br>GCAGAAGTCCACCTCTAAGTCTGCGGGTAAATGA<br>(SEQ ID NO: 73) | ASTTAPKVYPLASSCGDTSSSTVTLGC<br>LVSSYMPEPVTVTWNSGALKSGVHTFP<br>AVLQSSGLYSLSSMVTVPASSSGQTFT<br>CNVAHPASSTKVDKAVGVSIDCSKCHN<br>QPCVREPSVFIFPPKPKDTLMITGTPEV<br>TCVVVNVGHDNPEVQFSWFVDDVEVH<br>TARSKPREEQFNSTYRVVSALPIQHQD<br>WTGGKEFKCKVNNKGLSAPIVRIISRSK<br>GPAREPQVYVLDPPKEELSKSTLSVTC<br>MVTGFYPEDVAVEWQRNRQTESEDKY<br>RTTPPQLDTDRSYFLYSKLRVDRNSWQ<br>EGDAYTCVVMHEALHNHYMQKSTSKS<br>AGK*<br>(SEQ ID NO: 72) | S82407 | | |
| | IgG2 variant 2 | GCCTCCACCACAGCCCCGAAAGTCTACCCTCTGACTTC<br>TTGCTGCGGGGACAAGTCCAGCTCCACCGTGACCCTGG<br>GCTGCCTGGTGTCCAGCTACATGCCCGAGCCGGTGACC<br>GTGACCTGGAACTCGGGTGCCCTGAAGAGCGGCGTGCA<br>CACCTTCCCGGCCGTCCTTCAGTCCTCCGGGCTCTACT<br>CTCTCAGCAGCATGGTGACCGTGCCCGGCAGCACCTCA<br>GGACAGACCTTCACCTGCAACGTAGCCCACCCGGCCAG<br>CAGCACCAAGGTGGACAAGGCTGTTGGGGTCTCCAGTG<br>ACTGGTCCAAGCCTAATAACCAGCATTGCGTGACGGAA<br>CCATCTGTCTTCATCTTCCCACCGAAACCCAAAGACAC<br>CCTGATGATCACAGGAACCCCCGAGGTCACGTGTGTGG<br>TGGTGAACGTGGGCCACGATAACCCCGAGGTGCAGTTC<br>TCCTGGTTCGTGGACGACGTGGAGGTGCACACGGCCAG | ASTTAPKVYPLSSCCGDKSSSTVTLGC<br>LVSSYMPEPVTVTWNSGALKSGVHTFP<br>AVLQSSGLYSLSSMVTVPGSTSGQTFT<br>CNVAHPASSTKVDKAVGVSSDCSKPN<br>NQHCVREPSVFIFPPKPKDTLMITGTPE<br>VTCVVVNVGHDNPEVQFSWFVDDVEV<br>HTARTKPREEQFNSTYRVVSALPIQHQ<br>DWTGGKEFKCKVNIKGLSASIVRIISRS<br>KGPAREPQVYVLDPPKEELSKSTVSVTC<br>MVIGFYPEDVDVEWQRDRQTESEDKYR<br>TTPPQLDADRSYFLYSKLRVDRNSWQR<br>GDTYTCVVMHEALHNHYMQKSTSKSA<br>GK* | M36946<br>(X08703) | | |

TABLE-continued

| Species | Ig Domain | Nucleotide Sequence | Amino Acid Sequence | GenBank Accession No. | IMGT Database | Reference |
|---|---|---|---|---|---|---|
| | | GACGAAGCCGAGAGAGGACCAGTTCAACAGCACGTACC | (SEQ ID NO: 74) | | | |
| | | GCGTGGTCAGCGCCCTGCCCATCCAGCACCAGGACTGG | | | | |
| | | ACTGGAGGAAAGGAGTTCAAGTGCAAGGTCAACATCAA | | | | |
| | | AGGCCTCTCGGCCTCCATCGTGAGGATCATCTCCAGGA | | | | |
| | | GCAAAGGGCCGGCCCGGGAGCCGCAGGTGTATGTCCT | | | | |
| | | GCACCCACCCAAGGAACAGCTCAGCAAAAGCACGGTCA | | | | |
| | | GCGTCACCTGCATGGTCATCGGCTTCTACCCAGAAGAT | | | | |
| | | GTAGACGTGGAGTGGCAGAGAGACCGGCAGACTGAGTC | | | | |
| | | GGAGGACAAGTACCGCACGACCCCGCCCCAGCTGGAC | | | | |
| | | GCCGACCGCTGGTACTTCCTGTACAGCAAGCTCAGGGT | | | | |
| | | GGACAGGAACAGCTGGCAGAGAGGAGACACCTACACGT | | | | |
| | | GTGTGGTGATGCACGAGGCCCTGCACAATCACTACATG | | | | |
| | | CAGAAGTCCACCTCTAAGTCTGCGGGTAAATGA | | | | |
| | | (SEQ ID NO: 75) | | | | |
| | IgG2 | GCCTCCACCACAGCCCCGAAAGTCTACCCTCTGAGTTC | ASTTAPKVYPLSSCCGDKSSSGVTLGC | X16702 | | |
| | variant | TTGCTGCGGGGACAAGTCCAGCTCGGGGGTGACCCTGG | LVSSYMPFPVTVTWNSGALKSGVHTFP | (M25278) | | |
| | 3 | GCTGCCTGGTCTCCAGCTACATGCCCGAGCCGGTGACC | AVLQSSGLYSLSSMVTVPASSSGTQTF | | | |
| | | GTGACCTGGAAGTCGGGTGCCCTGAAGAGCGGCGTGCA | TCNVAHPASSTKVDKAVGVSSDCSKP | | | |
| | | CACCTTCCCGGCCGTCCTTCAGTCCTCCGGGCTCTACT | NNQHCVREPSVFIFPPKPKDTLMITGTP | | | |
| | | CTCTCAGCACCATCGTCACCGTGCCCGCCAGCAGCTCA | EVTCVVVNVGHDNPEVQFSWFVDDVE | | | |
| | | GGAACCCAGACCTTCACCTGCAACGTAGCCCACCCGGC | VHTARTKPREEQFNSTYRVVSALPIQH | | | |
| | | CAGCAGCACCAAGGTGGACAAGGCTGTTGGGGTCTCCA | QDWTGGKEFKCKVNIKGLSASIVRIISR | | | |
| | | GTGACTGCTCCAAGCCTAATAACCAGCATTGCGTGAGG | SKGPAREPQVYVLDPPKEELSKSTVSLT | | | |
| | | GAACCATCTGTCTTCATCTTCCCACCGAAACCCAAAGA | CMVIGFYPEDVDVEWQRDRQTESEDKY | | | |
| | | CACCCTGATGATCACAGGAACGCCGGAGGTCACGTGTG | RTTPPQLDADRSYFLYSKLRVDRNSWQ | | | |
| | | TGCTGCTGAACGTGGGCCACGATAACCCCGAGGTGCAG | RGDTYTCVVMHEALHNHYMQKSTSKS | | | |
| | | TTCTCCTGGTTCGTGGACGACGTGGAGGTGCACACGGC | AGK* | | | |
| | | CAGGACGAAGCCGAGAGAGGAGCAGTTCAACAGCACGT | (SEQ ID NO: 76) | | | |
| | | ACCGCGTGGTCAGCGCCCTGCCCATCCAGCACCAGGAC | | | | |
| | | TGGACTGGAGGAAAGGAGTTCAAGTGCAAGGTCAACAT | | | | |
| | | CAAAGGCCTCTCGGCCTCCATCGTGAGGATCATCTCCA | | | | |
| | | GGAGCAAAGGGCCGGCCCGGGAGCCGCAGGTGTATGT | | | | |
| | | CCTGGACCCACCCAAGGAAGAGCTCAGCAAAAGCACGG | | | | |
| | | TCAGCCTCACCTGGATGGTCATCGGCTTCTACCCAGAA | | | | |
| | | GATGTAGACGTGGAGTGGCAGAGAGACCGGCAGACTGA | | | | |
| | | GTCGGAGGACAAGTACCGCACGACCCCCCCCCAGCTG | | | | |
| | | GACGCCGAGGGCTCCTACTTCCTGTACAGCAAGCTGAG | | | | |
| | | GGTGGACAGGAACAGCTGCCAGAGAGGAGACACCTAC | | | | |
| | | ACGTGTGTGGTGATGCAGGAGGCCCTGCACAATCACTA | | | | |
| | | CATGCAGAAGTCCACCTCTAAGTCTGCGGGTAAATGA | | | | |
| | | (SEQ ID NO: 77) | | U63638 | | |
| | IgG3 | GCCTCCACCACAGCCCCGAAAGTCTACCCTCTGGCATC | AKTTAPKVYPLASSCGDTSSSTVTLGC | | | |
| | variant | CAGCTGCGGAGACACATGCAGCTCCACCGTGACCCTGG | LVSSYMPEPVTVTWNSGALKSGVHTFP | | | |
| | 1 | GCTGCCTGGTCTCCAGCTACATGCCCGAGCCGGTGACC | AVRQSSGLYSLSSMVTVPASSSETQTF | | | |
| | | GTGACCTGGAACTCGGGTGCCCTGAAGAGCGGCGTGCA | TCNVAHPASSTKVKDAVTARRPVPTTP | | | |
| | | CACCTTCCCGGCCGTCCGGCAGTGCTCTGGGCTGTACT | KTTIPPGKPTTPKSEVEKTPCQCSKCP | | | |
| | | CTCTCAGCAGCATGGTCACTGTGCGGGCCAGCAGCTCA | EPLGGLSVFIFPPKPKDTLTISGTPEVT | | | |
| | | GAAACCCAGACCTTCACCTGCAACGTAGCCCACCCGGC | CVVVDVGQDDPEVQFSWFVDDEVHT | | | |
| | | CAGCAGCACCAAGGTGGACAAGGCTGTCACTGCAAGGC | ARTKPREEQFNSTYRVVSALRIQHQDW | | | |

TABLE-continued

| Species | Ig Domain | Nucleotide Sequence | Amino Acid Sequence | GenBank Accession No. | IMGT Database | Reference |
|---|---|---|---|---|---|---|
| | | GTCCAGTCCCGACGACGCCAAAGAGAACTATCCCTCCT<br>GGAAAACCGACAACCCCAAAGTGTGAAGTTGAAAAGAC<br>ACCCTGCCAGTGTTCCAAATGCCCAGAACCTCTGGGAG<br>GACTGTCTGTCTTCATCTTCCCACCGAAACCCAAGCAC<br>ACCCTCACAATCTCGGGAACGCCCGAGGTCACGTGTGT<br>GGTGGTGGACGTGGGCCAGGATGACCCCGAGGTGCAG<br>TTCTCCTGGTTGGTGGACGACGTGGAGGTGCACACGGC<br>CAGGACGAAGCCGACAGAGGACCAGTTCAACAGCACCT<br>ACCGCGTGGTCAGCGCCCTGCGCATCCAGCACCAGGA<br>CTGGCTGCAGGGAAAGGAGTTCAAGTGCAAGGTCAACA<br>ACAAAGGCCTCCCGGCCCCCATTGTGAGGACCATCTCC<br>AGGACCAAAGGGCAGGCCCGGGAGCCGCAGGTGTATG<br>TCCTGGCCCCACCCCGGGAAGAGCTCAGGAAAAGCACG<br>CTCAGCCTCACCTGCCTGATCACCGGTTTCTACCCAGA<br>AGAGATAGACGTGGAGTGGCAGAGAAATGGGCAGCCTG<br>AGTCGGAGGACAAGTACCACACGACCGCACCCCAGCTG<br>GATGCTGACGGCTCCTACTTCCTGTACAGCAAGCTCAC<br>GGTGAACAAGAGCAGCTGGCAGGAAGGAGACCACTACA<br>CGTGTGCAGTGATGCACGAAGCTTTACGGAATCACTAC<br>AAAGAGAAGTCCATCTCGAGGTCTCCGGGTAAATGA<br>(SEQ ID NO: 79) | LQGKEKCKVNNKGLPAPIVRTISRTKG<br>QAREPQVYVLAPPREELSKSTLSLTCLI<br>TGFYPEEIDVEWQRNGQPESEDKYHTT<br>APQLDADGSYFLYSKLRVNKSSWQEG<br>DHYTCAVMHEALRNHYKEKSISRSPGK<br>*<br>(SEQ ID NO: 78) | | | |
| | IgG3 variant 2 | GCCTCCACCACAGCCCCGAAAGTCTACCCTCTGGCATC<br>CCGCTGCGGAGACACATCCAGCTCCACCGTGACCCTGG<br>GCTGCCTGGTCTCCAGCTACATCCCCGACCCCGTGACC<br>GTGACCTGGAACTCGGGTGCCCTGAAGACTCCCGTGCA<br>CAGCTTCCCGGCCGTCGTTGAGTCCTCCGGGCTGTACT<br>CTCTCAGCAGGATGGTGACCGTGCCCGCCAGCACCTCA<br>GAAACCCAGACCTTCACCTGCAAGGTAGCCCACCCGGC<br>CAGCAGCACCAAGGTGGACAAGGCTGTCACTGCAAGGC<br>GTCCAGTCCCGACGACGCCAAAGAGAACCATCCCGCCT<br>GGAAAACCCACAACCCAGGAGTCTGAAGTTGAAAAGAC<br>ACCCTGCCAGTGTTGCAAATGCCCAGAACCTCTGGGAG<br>GACTGTCTGTCTTCATCTTCCCACCGAAACCCAAGGAC<br>ACCCTCACAATCTCGGGAACGCCCGAGGTCACGTGTGT<br>GGTGGTGGACGTGGGCCAGGATGACCCCGAGGTGCAG<br>TGCTCCTGGTTCGTGGACGACGTGGAGGTGCACACGGC<br>CAGGACGAAGCCGAGAGAGGAGCAGTTCAAGAGCAGCT<br>ACCCCGTGGTCAGGGCCCTGCGCATCCAGCACCAGGA<br>CTCGCTGCAGGGAAAGGAGTTCAAGTGCAAGGTCAACA<br>ACAAAGGCCTCCCGGCCCCCATTGTGAGGAGCATCTCC<br>AGGACCAAAGGGCAGGCCCGGGAGCCGCAGGTGTATG<br>TCCTGGCCCCACCCCGGGAAGAGCTCAGCAAAAGCACG<br>CTCAGCCTCACCTGCCTGATCACCGGTTTCTACCCAGA<br>AGAGATAGACGTGGAGTGGCAGAGAAATGGGCAGCCTC<br>AGTCGGAGGACAAGTACCACACGACCGCACCCCAGCTG<br>GATGCTGACGGCTGCTACTTCCTGTACAGCAGGCTCAG<br>GGTGAACAAGAGCAGCTGGCAGGAAGGAGACCACTACA<br>CGTGTGCAGTGATGCATGAAGCTTTACGGAATCACTAC<br>AAAGAGAAGTCCATCTCGAGGTCTCCGGGTAAATGA | ASTTAPKVYPLASRCGDTSSSTVTLGC<br>LVSSYMPEPVTVTVWNSGALKSGVHTFP<br>AVLQSSGLYSLSSMVTVPASTSETQTF<br>TCNVAHPASSTKVDKAVTARRPVPTTP<br>KTTIPPGKPTTQESEVEKTPCQCSKGP<br>EPLGGLSVFIFPPKPKDTLTISGTPEVT<br>CVVVDVGQDDPEVQFSWFVDDVEVHT<br>ARTKPREEQFNSTYRVVSALRIQHQDW<br>LQKKEFKCKVNNKGLPAPIVRTISRTKG<br>QAREPQVYVLAPPREELSKSTLSLTCLI<br>TGFYPEEIDVEWQRNGQPESEDKYHTT<br>APQLDADGSYFLYSRLRVNKSSWQEG<br>DHYTCAVMHEALRNHYKEKSISRSPGK<br>*<br>(SEQ ID NO 80) | U63639 | | |

TABLE-continued

| Species | Ig Domain | Nucleotide Sequence | Amino Acid Sequence | GenBank Accession No. | IMGT Database | Reference |
|---|---|---|---|---|---|---|
| | | (SEQ ID NO: 81) | | | | |
| | Bovine Ig Ig lambda light chain con-stant region (CL) | CAGCCCAAGTCCCCACCCTCGGTCACCCTGTTCCCGCC<br>CTCCAGGGAGGAGCTCAACGGCAACAAGGCCACCCTG<br>GTGTGTCTCATCAGCGACTTCTACCCGGGTAGCGTCTAC<br>CGTGGTCTCGAAGGCAGACGGCACCACCATCACCCGCA<br>ACGTGGAGACCACCCGGGCCTCCAAACAGAGCAACAG<br>CAAGTAGGCGGCCAGCAGCTACCTGAGGCTGACGAGCA<br>GCGACTGGAAATCGAAAGGCAGTTACAGCTGCGAGGTC<br>ACGCACGAGGGGAGCACCGTGACGAAGACAGTGAAGC<br>CCTCAGAGTGTTCTTAG<br>(SEQ ID NO: 65) | QPKSPPSVTLFPPSTEELNGNKATLVC<br>LISDFYPGSVTVVWKADGSTITRNVETT<br>RASKQSNSKYAASSYLSLTSSDWKSKG<br>SYSCEVTHEGSTVTKTVKPSECS*<br>(SEQ ID NO: 64) | X62917 | Not registerd | Chen L. et al., Vet. Immunol. Immuno-pathol, 124, 284-294 (2008) PMID: 18538861 |
| Canine (Specific Name: *Canis Lupus familiaris*) | Canine IgG-D Ig heavy chain con-stant region (CH1 CH3) | GCCTGCACCACGGCCGCCTCGGTTTTCCCACTGGCC<br>CCCAGCTGCGGGTCCACTTCCGGCTCCACGGTGGCC<br>CTGGCCTGCCTGGTGTCAGGCTACTTCCCCGAGCCT<br>GTAACTGTGTCCTGGAATTCCGGCTCCTTGACCAGC<br>GGTGTGCACACCTTCCCGTCCGTCGTGCAGTCCTCA<br>GGGCTCTACTCCCTCAGCAGGACGGTGACAGTGCCC<br>TCCAGCAGGTGGCCCAGCGAGACCTTCACCTGCAAC<br>GTGGTCCACCCGGCCAGCAACACTAAAGTAGACAAG<br>CCAGTGCCCAAAGAGTCCACCTGCAAGTGTATATCC<br>CCATGCCCAGTCCCTGAATCACTGGGAGGGGCTTCG<br>GTCTTCATCTTTCCCCCGAAACCCAAGGACATCCTC<br>AGGATTACCCGAACACCCGAGATCACCTGTGTGGTG<br>TTAGATGTGGGCGGTGAGGAGCCTGAGGTGCAGATC<br>AGCTGGTTCGTGGATGGTAAGGAGGTGCACACAGCC<br>AAGACGCAGCCTCGTGAGCAGCAGTTCAACAGCACC<br>TACCGTGTGGTCAGCGTCCTCCCCATTGAGCACCAG<br>GACTGGCTCACCGGAAAGGAGTTCAAGTGCAGAGTC<br>AACCACATAGGCCTCCCGTCCCCCATCGAGAGGACT<br>ATCTCCAAAGCCAGAGGGCAAGCCCATCAGCCCAGT<br>GTGTATGTCCTGCCACCATCCCCAAAGGAGTTGTCA<br>TCCAGTGACACGGTCACCCTGACCTGCCTGATCAAA<br>GACTTCTTCCCACCTGACATTGATGTGGAGTGGCAG<br>AGCAATGGACAGCCGGAGCCCGAGAGCAAGTACCAC<br>ACGACTGCGCCCCAGCTGGACGAGGACGGGTCCTAC<br>TTCCTGTACAGCAATTCTCTCTGTGGACAAGAGCCGC<br>TGGCAGCAGGGAGACACCTTCACATGTGCGGTGATG<br>CATGAAGCTCTACAGAACCACTACACAGATCTATCCC<br>TCTCCCATTCTCCGGGTAAATGA<br>(SEQ ID NO: 85) | ASTTAPSVFPLAPSCGSTSGSTVALAC<br>LVSGYFPEPVTVSWNSGSLTSGVHTFP<br>SVLQSSGLYSLSSTVTVPSSRWPSETF<br>TCNVVHPASNTKVDKPVPKESTCKCIS<br>PCPVPESLGGPSVFIFPPKPKDILRITR<br>TPEITCVVLDLGREDPEVQISWFVDGKE<br>VHTAKTQPREQQFNSTYRVVSVLPIEHQ<br>DWLTGKEFKCRVNHIGLPSPIERTISKA<br>RGQAHQPSVYVLPPSPKELSSSDTVTL<br>TCLIKDFFPPEIDVEWQSNGQPEPESKY<br>HTTAPQLDEDGSYFLYSKLSVDKSRWQI<br>QGDTFTCAVMHEALGNHYTDLSLSHS<br>PGK*<br>(SEQ ID NO 84) | AF354267 | http://www.imgt.org/IMGT reportoire/index.ghp?section=locus Genes&reportoire=genetable&species=*dog*&group=IGHC | Tang L. et al., Vet Immuno-pathol 80 (3-4), 259-270 (2001) PMID: 11457479 |
| | Canine Ig Ig lambda light (CL) chain con-stant region | CAGCCCAAGGCGTCCCCCTCGGTCACACTCTTCCCG<br>CCCTCCTCTGACGAGCTCGGCCCCAACAAGGCCACC<br>CTGGTGTGCCTCATCAGCGACTTCTACCCCAGCGGC<br>GTGACGGTGGCCGGAAGGCAAGCGGCAGCCCCGT<br>CACCCAGGGCGTGGAGACGACCAAGCCCTCCAAGCA<br>GAGCAACAACAAGTACGCGGCCAGCAGCTACCTGAG<br>CCTGACGCCTGACAAGTGGAAATCTCACAGCAGCTT<br>CAGCTGCCTGGTCACGCACGAGGGGAGCACCGTGG | QPKASPSVTLFPPSSEELGANKATLVC<br>LISDFYPSGVTVAWKASGSPVTQGVET<br>TKPSKQSNNKYAASSYLSLTPDKWKSHI<br>SSFSCLVTHEGSTVEKKVAPAECS*<br>(SEQ ID NO: 82) | E02824 | not registered | None |

TABLE-continued

| Species | Ig Domain | Nucleotide Sequence | Amino Acid Sequence | GenBank Accession No. | IMGT Database | Reference |
|---|---|---|---|---|---|---|
| | | AGAAGAAGGTGGCCCCCGCAGAGTGCTCTTAG<br>(SEQ ID NO: 83) | | | | |
| Ovian (Scientific Name: *Ovis aries*) | Ovine Ig chain light con-stant region CH1 CH3) IgG1 | GCCTCAACAACACCCCCGAAAGTGTACCCTCTGACT<br>TCTTGCTGCGGGGACACGTCCAGCTCCATCGTGACC<br>CTGGGCTGCCTGGTCTGCAGCTATATGCCCGAGCCG<br>GTGACCGTGACCTGGAACTCTGGTGCCCTGACCAGG<br>GGCGTGCACACCTTCCCGGCCATCCTGCAGTCCTCC<br>GGGCTCTACTCTCTCAGCAGCGTGGTGACCGTGCCG<br>GCCAGCACCTCAGGAGCCCAGACCTTCATCTGCAAC<br>GTAGCCCACCCGGCCAGCAGCACCAAGGTGGACAAG<br>CGTGTTGAGCCCGGATGCCCGGACCCATGCAAACAT<br>TGCCGATGCCCACCCCCTGAGCTCCCCGGAGGACC<br>GTCTGTCTTCATCTTCCCACCGAAACCCAAGGACAC<br>CCTTACAATCTCTGGAACGCCCGAGGTCACGTGTGT<br>GGTGGTGGACGTGGGCCAGGATGACCCCGAGGTGC<br>ACTTCTCCTGGTTCGTGGACAACGTGGACGTGCCCA<br>CGGCCAGGACAAAGCCGAGAGAGGAGCAGTTCAACA<br>GCACCTTCCGCGTGGTCAGCGCCGTGCCCATCCAGC<br>ACCAAGACTGGACTGGAGGAAAGGAGTTCAAGTGCA<br>AGGTCCACAACGAAGCCCTCCCGGCCCCCATCGTGA<br>GGACCATCTCCAGGACCAAAGGGCAGGCCCGGGAG<br>CCGGAGGTGTACGTCCTGGCCCCACCCCAGGAAGAG<br>CTCAGCAAAAGCACGCTCAGCGTCACCTGCCTGGTC<br>ACCGGCTTCTACCCAGACTACATCGCCGTGGAGTGG<br>CAGAAAAATGGGCAGCCTGAGTCGGAGGACAAGTAC<br>GGCACGACCACATCCCAGCTGGACGCCGACGGCTCC<br>TACTTGCTGTACAGCAGGCTCAGGGTGGAGAAGAAC<br>AGCTGGCAAGAAGGAGACACCTACGCGTGTGTGGTG<br>ATGCACGAGGCTCTGCACAACCACTACACACAGAAG<br>TCGATCTCTAAGCCTCCGGGTAAATGA<br>(SEQ ID NO: 91) | ASTTPPKVYPLTSCCGDTSSSIVTLGC<br>LVSSYMPEPVTVTWNSGALTSGVHTF<br>PAILQSSGLYSLSSVVTVPASTSGAQT<br>FICNVAHPASSTKVDKRVEPGCPDPCK<br>HCRCPPPELPGGPSVFIFPPKPKDTLTI<br>SGTPEVTCVVVDVGQDDPEVQFSWFV<br>DNVEVRTARTKPREEQFNSTFRVVSAL<br>PIQHQDWTGGKEFKCKVHNEALPAPIV<br>RTISRTKGQAREPQVYVLAPPQEELSK<br>STLSVTCLVTGFYPDYIAVEWQKNGQP<br>ESEDKYGTTTSQLDADGSYFLYSRLRV<br>DKNSWQEGDTYACVVMHEALHNHYTQ<br>KSISKPPGK*<br>(SEQ ID NO: 90) | X69797 | http://www.<br>imgt.org/<br>IMGT<br>reportoire/<br>index.<br>ghp?section<br>=locus<br>Genes&<br>reportoire=<br>genetable&<br>species=<br>*sheep*<br>&group=IGHC | Dufour V. et al. J. Immunol, 156, 2163-2170 (1996) PMID: 8690905 |
| | IgG2 | GCCTCCACCACAGCCCCGAAAGTCTACCCTCTCACT<br>TCTTGCTGCGGGGACACGTCCAGCTCCAGCTCCATC<br>GTGACCCTGGGCTGCCTGGTCTCCAGCTATATGCCC<br>GAGCCGGTGACCGTGACCTGGAACTCTGGTGCCCTG<br>ACCAGCGGCGTGCACACCTTCCCGGCCATCCTGCAG<br>TCCTCCGGGCTCTACTCTCTCAGCAGCGTGGTGACC<br>GTGCCGGCCAGCAGCTCAGGAGCCCAGACCTTCATC<br>TGCAACGTACCCCACCCCCCCAGCACCGCGAACGTG<br>GACAAGCGTGTTGGGATCTCCAGTGACTACTCCAAG<br>TGTTCTAAACCGCCTTGCGTGAGCCGACCGTCTGTC<br>TTCATCTTCCCCCCGAAACCCAAGGACAGCCTCATG<br>ATCACAGGAACGCCCGAGGTCACGTGTGTCGTGGTG<br>GACGTGGGCCAGGGTGACCCCGAGGTGCAGTTCTCC<br>TGGTTCGTGGACAACGTGGAGGTGCGCACGGCCAGG<br>ACAAAGCCGAGAGAGGAGCAGTTCAACAGCACCTTC<br>CGCGTGGTCAGCGCCCTGCCCATCCAGCACGACCAC<br>TGGACTCGAGGAAAGGAGTTCAAGTGCAAGGTCCAC | ASTTAPKVYPLTSCCGDTSSSSSIVTL<br>GCLVSSYMPEPVTVTWNSGALTSGVH<br>TFPAILQSSGLYSLSSVVTVPASTSGA<br>QTFICNVAHPASSAKVDKRVGISSDYS<br>KCSKPPCVSRPSVFIFPPKPKDSLMITG<br>TPEVTCVVVDVGQGDPEVGFSWFVDN<br>VEVRTARTKPREEQFNSTFRVVSALPI<br>QHDHWTGGKEFKCKVHSKGLPAIVRT<br>ISRAKGQAREPQVYVLAPPQEELSKST<br>LSVTCLVTGFYPDYIAVEWQRARQPES<br>EDKYGTTTSQLDADGSYFLYSRLRVGK<br>SSWQRGDTYACVVMHEALHNHYTGKS<br>ISKPPGK*<br>(SEQ ID NO: 92) | X70983 | | Clarkson C.A. et al, Mol. Immunol, 20 1195-1204 (1993) PMID: 8413324 |

TABLE-continued

| Species | Ig Domain | | Nucleotide Sequence | Amino Acid Sequence | GenBank Accession No. | IMGT Database | Reference |
|---|---|---|---|---|---|---|---|
| | | | AGCAAAGCCCTCCCGGCCCCCATCGTGAGGACCATC<br>TCCAGGGCCAAAGGGCAGGCCCGGGAGCCGCAGGT<br>GTAGGTCCTGGCCCCACCCCAGGAAGAGCTCAGCAA<br>AAGCACGCTCAGCGTCACCTGCCTGGTCACCGGCTT<br>CTACCCAGACTACATCGCCGTGGAGTGGCAGAGAGC<br>GCGGCAGCCTCAGTCCGAGGAGAAGTACGCCACGAC<br>CACATCCCAGCTGGACGCCGACGGCTCCTACTTCCT<br>GTACAGCAGGCTCAGGGTGGACAAGAGCAGCTGGCA<br>AAGAGGAGACACCTAGGCGTGTGTGGTGATGCACGA<br>GGCTCTGCACAACCACTACACACAGAAGTCGATCTC<br>TAAGCCTCCGGGTAAATGA<br>(SEQ ID NO: 93) | | | | |
| | Ovine Ig light chain con- stant region | Ig kappa (CL) | CCATCCGTCTTCCTCTTCAAACCATCTGAGGAACAG<br>CTGAGGACCGGAACTGTCTCTGTCGTCTGCTTCGTG<br>AATGATTTCTACCCCAAAGATATCAATGTCAAGGTGA<br>AAGTGGATGGGGTTACCCAGAACAGCAACTTCCAGA<br>ACAGCTTCACAGACCAGGACAGRAAGAAAAGCACCT<br>ACAGCCTCAGCAGCACCCTGAGACTGTCCAGCTCAG<br>AGTACCAGAGCCATAACGCCTATGCGTGTGAGGTCA<br>GCCACAAGAGCCTGCCCACCGCCCTCGTCAAGAGCT<br>TCAATAAGAATGAATGTTAG<br>(SEQ ID NO: 87) | PSVFLFKPSEEQLRTGTVSVVCLVNDF<br>YPKDINVKVKVDGVTQNSNFQNSFTDQ<br>DSKKSTYSLSSTLTLSSSEYQSHNAYA<br>CEVSHKSLPTALVKSFNKNEC*<br>(SEQ ID NO: 86) | X54110 | Not registered | Jenne C.N. et al. Dev Comp. Immunol. 30 (1-2), 165-174 (2006) PMID: 16083958 |
| | | Ig lambda (CL) | GGTCAGCCCAACTCCGCACCCTCGGTCACCCTGTTC<br>CCGCCTTCCACGGAGGAGCTCAGTAGCAAGAAGGCC<br>ACCGTGGTGTGTCTCATCAACGACTTCTACCCGGGT<br>AGCGTGAACGTGGTCTGGAAGGCAGATGGCAGCACC<br>ATCAATCAGAACGTGAAGACCACCCAGGCCTCCAAA<br>CAGAGCAACAGCAAGTACGCGGCCAGCAGCTACCTG<br>ACCCTGACGGGCAGCGAGTGGAAGTCTAAGAGCAGT<br>TAGACCTGCGAGGTCACGCACGAGGGGAGCACCGTG<br>ACGAAGACAGTGAAGCCCTCAGAGTGTTCTTAG<br>(SEQ ID NO: 89) | GQPKSAPSVTLFPPSTEELSTNKATVV<br>CLINDFYPGSVNVVWKADGSTINQNVK<br>TTQASKQSNSKYAASSYLTLTGSEWKS<br>KSSYTCEVTHEGSTVTKTVKPSECS*<br>(SEQ ID NO: 88) | AY734681 | | |
| Porcine (Scientific Name: *Sus serpa*) | Por- cine Ig heavy chain con- stant region (CH1 CH3) | IgG3 | GCCCCCAAGACGGCCCCATCGGTCTACCCTCTGGCCCCCTGCGGCAC<br>CGACACGTCTC<br>GCCCTAACGTGGCCTTGGGGTGCCTGGCCTCAAGCTACTTCCCCGAG<br>CCAGTGACCATG<br>ACCTGGAACTGGGGCGCCCTGACCAGTGGCGTGCATACCTTCCCATC<br>CGTCCTCCAGCC<br>CTCAGGGCTCTACTCCCTCAGCAGCATGGTCACCGTGCCCGCCAGCA<br>GCCTGTCGAGCA<br>AGAGCTACACCTGCAATGTCACCACCCGGCCACCACCACCAAGGTGG<br>ACAAGCGTGTT<br>GGAACAAAGACCAAACCACCATGTCCCATATGCCCAGGCTGTGAAGT<br>GCCCGGGCCCTC<br>GGTCTTCATCTTCCCTCCAAAACCCAAGGACACCCTCATGATCTCCC<br>AGACCCCCGAGG<br>TCACGTGCGTGGTGGTGGACGTCAGCAAGGAGCACGCCGAGCTCCAG<br>TTCTCCTGGTAC | APKTAPSVYPLAPCGRDTSGPNVALG<br>CLASSYFPEPVTMTWNSGALTSGVHT<br>FPSVLQPSGLYSLSSMVTVPASSLSS<br>KSYTCNVNHPATTTKVDKRVGTKTKP<br>PCPICPGCEVAGPSVFIFPPKPKDTLMI<br>SQTPEVTCVVVDVSKEHAEVQFSWYV<br>DGVEVHTAETRPKEEQFNSTYRVVSV<br>LPIQHQDWLKGKEFKCKVNNVDLPAP<br>TRTISKAIGQSREPQVYTLPPPAEELS<br>RSKVTVTCLVIGIFYPPDIHVEWKSNGQ<br>PEPEGNYRTTPPQDDVDGTFFLYSKL<br>AVDKARWDHGETFECAVMHEALHNHY<br>TQKSISKTGGK*<br>(SEQ ID NO: 94) | U03781 | http://www. imgt.org/ IMGT reportoire/ index. ghp?section =locus Genes& reportoire= genetable& species= *sheep* &group=IGHC | Butler J.E. et al. Immuno- genetics 61(3) 209-230 PMID: 19028748 Kaeskoves I et al. J. Immunol 153(8) 3585-3573 (1994) PMID: 7930579 |

TABLE-continued

| Species | Ig Domain | Nucleotide Sequence | Amino Acid Sequence | GenBank Accession No. | IMGT Database | Reference |
|---|---|---|---|---|---|---|
| | | GTGGACGGCGTAGAGGTGCACACGCCCGACACGAGACCAAAGGAGGA<br>GCAGTTCAACAG<br>CACCTACCGTGTCCTCAGCGTCCTGCCCATCCAGCACCACGACTGGC<br>TGAAGGGGAAGG<br>AGTTCAAGTGCAAGGTCAACAACGTAGACCTCCCAGCCCCCATCACG<br>AGGACCATCTCC<br>AAGGCTATAGGGCAGAGCCGGGAGCGGCAGGTGTACACCCTGCCCCC<br>ACCCGCCGAGG<br>ACCTGTCCAGGAGCAAAGTCACCGTAACCTGCCTGGTCATTGGCTTC<br>TACCCACCTGAC<br>ATCCATGTTGAGTGGAAGAGCAACGGACAGCCGGAGCCAGAGGGCAA<br>TTACCGCACCAC<br>CCCGCCCCAGCAGGACGTGGACGGGACCTTCTTCCTGTACAGCAAGC<br>TCGCGGTGGACA<br>AGGCAAGATGGGACCATGGAGAAACATTTGAGTGTGCCGTGATGCAC<br>GAGGCTCTGGAC<br>AACCACTACAGCCAGAAGTCCATCTCCAAGACTCAGGGTAAATGA<br>(SEQ ID NO: 95) | | | | |
| | IgG3 | GCCCCCAAGACGGCCCCATCGGTCTACCCTCTGGCCCCCTGCCGCAG<br>GGACGTCTCTG<br>GCCCTAACGTGGCCTTGGGCTGCCTGGCCTCAAGCTACTTCCCCGAG<br>CCAGTGACCGTG<br>ACCTGGAACTCGGGCGCCCTGACCACTGGCGTGCACACCTTCCCATC<br>CGTCCTGCAGCC<br>GTCAGGGCTCTACTCCCTCACCAGCATGCTCACCGTGCCGGCCAGCA<br>GCCTGTCCAGCA<br>AGAGCTACACCTGCAATGTCAACCACCCGGCCAGCACCACCAAGGTG<br>GACAAGCGTGTT<br>GGAATACACCAGCCGCAAACATGTCCCATATGCCCAGGCTGTGAAGT<br>GGCCGGGCCCTC<br>GGTCTTCATCTTCCCTCCAAAACCCAACGACACCCTCATGATCTCCC<br>AGACCCCCGAGG<br>TCACGTGCGTGGTGGTGGACGTCAGCAAGGAGCACGCCGAGGTCCAG<br>TTCTCCTGGTAC<br>GTGGACGGCGTAGAGGTGCACACGGCCGAGACGAGACCAAAGGAGGA<br>GCAGTTCAACAG<br>CACCTACCGTGTGGTCAGCGTCGTGCCCATCCAGCACGAGGACTGGC<br>TGAAGGGGAACG<br>AGTTCAAGTGCAAGGTCAACAACGTAGACCTCCCACCCCCCATCACC<br>AGGACCATCTCC<br>AAGGCTATAGGGCAGAGCCGGGAGCCGCAGGTGTACACCCTGCCCCC<br>ACCCGCCGAGG<br>AGCTGTCCAGGAGCAAAGTCACGCTAAGCGCCTCCCCATTGCCTTCT<br>ACCCACCTGAC<br>ATCCATGTTGAGTGGAAGAGCAACGGACAGCCGGAGCCAGAGAACAC<br>ATACCGCACCAC<br>CCCGCCCCAGCAGGACGTGGACGGGACCTTCTTCCTGTACAGCAAAC<br>TCGCGGTGGACA<br>AGGCAACATCGGAOCATGGAGACAAATTTGAGTGTCCGCGGAGGGAC | APKTAPSVYPLAPCGRDVSGPNVALG<br>CLASSYFPEPVTVTWNSGALTSGVHT<br>FPSVLQPSGLYSLSSMVTVPASSLSS<br>KSYTCNVNHPATTTKVDKRVGIHQPQ<br>TCPICPGCEVAGPSVFIFPPKPKDTLMI<br>SQTPEVTCVVVDVSKEHAEVQFSWYV<br>DGVEVHTAETRPKEEQFNSTYRVVSV<br>LPIQHQDWLKGKEFKCKVNNVKLPAPI<br>TRTISKAIGQSREPQVYTLPPPAEELS<br>RSKVTLTCLVIGFYPPDIHVEWKSNGQ<br>PEPENTYRTTPPQQDVDGTFLYSKL<br>AVDKARWDHGDKFECAVMHEALHNH<br>YTQKSISKTQGK*<br>(SEQ ID NO: 96) | U003718 | | |

TABLE-continued

| Species | Ig Domain | Nucleotide Sequence | Amino Acid Sequence | GenBank Accession No. | IMGT Database | Reference |
|---|---|---|---|---|---|---|
| | | CACGCGCTGCAC<br>AACCACTACACCCAGAAGACCATCTCCAAGACTCAGGGTAAATGA<br>(SEQ ID NO: 97) | | | | |
| | IgG2 | GCCCCCCAAGACGCCCCCATCGGTCTACCCTCTGGCCCCCTGCAGCA<br>GGGACACGTCTG<br>GCCCTAACGTGGCGTTGGGCTGCCTGGCCTCAAGCTACTTCCCCGAG<br>CCAGTGACCGTG<br>ACCTGGAACTCGGGCGCCCTGTCCAGTGGCGTGCATACCTTCCCATC<br>CGTCCTGCAGCC<br>GTCAGGGCTCTACTCCCTCAGCAGCATGGTGACCGTGCCGGCCAGCA<br>GCCTGTCCAGCA<br>AGAGCTACACCTGCAATGTCAACCACCCGGCCACCACCACCAAGGTG<br>GACAAGCGTGTT<br>TGGAACAAAGACCAAACCACCATGTCCCATATGCCCAGCCTGTGAAT<br>CACCAGGGCCCTC<br>TGGTCTTCATCTTCCCTCCAAAACCCAAGGACACCCTCATGATCTCC<br>CCGACACCCCAGG<br>TCACGTGCGTGGTGGTTGATGTGAGCCAGGAGAACCGGCAGGTCCAG<br>TTCTGCTGGTAC<br>GTGGACGGCGTAGAGGTGCACACGGCCCAGACGAGGCCAAAGGAGGA<br>GCAGTTCAACAG<br>CACCTACCGCGTGGTCAGCGTCCTACCCATCCAGCACCAGGACTCGC<br>TGAACGGGAAGG<br>AGTTCAAGTCCAAGGTCAACAACAAAGACCTCCCAGCCCCCATCACA<br>AGGATCATCTCC<br>AAGGCCAAAGGGCAGACCCGGGAGCCGCAGGTGTACACCCTGCCCCC<br>ACACGCCGAGG<br>TACCTCTCCACGAGCAAAGTCACCATAACCTGCCTGGTCATTCGCTT<br>GTACCCACCTCAC<br>ATCGATGTCGAGTGCCAAAGAAACGGACAGCCGGAGCCAGAGGGCAA<br>TTACCGCACCAC<br>CCCGCCCCAGCAGGACGTGGACGGGACCTACTTCCTGTACAGCAAGT<br>TCTCGGTGGACA<br>AGCCCAGCTGGGAGGGTGGAGGCATATTCCAGTGTGCGGTGATCGAC<br>GAGGGTCTGCAC<br>AACCACTACACCCAGAAGTCTATCTCCAAGACTCCGGGTAAATGA<br>(SEQ ID NO: 99) | APKTAPSVYPLAPCSRDTSGPNVALG<br>CLASSYFPEPVTVTWNSGALSSGVHT<br>FPSVLQPSGLYSLSSMVTVPASSLSS<br>KSYTCNVNHPATTTKVDKRVGTKTKP<br>PCPICPACESPGPSVFIFPPKPKDTLMI<br>SRTPQVTCVVVDVSQENPEVQFSWYV<br>GDVEVHTAQTRPKEEQFNSTYRVVSV<br>LIIQHQDWLNGKEFKCKVNNKDLPAPI<br>TRISKAKGQTREPQVYTLPPHAEELS<br>RSKVSITCLVIGFYPPDIDVEWQRNGQ<br>PEPGNYRTTPPQQDVDGTYFLYSKF<br>SVDKASWQGGGIFQCAVMHEALHNHY<br>TQKSISKTPGK*<br>(SEQ ID NO: 98) | U03779 | | |
| | IgG2 | GCCCCCAAGACCGCCCCATTGCTCTACCCTCTCCCCCGCTGCCCCAG<br>GGAACGTCTG<br>GCCCTAACGTGGCCTTGGGCTGCCTGGCCTCAAGCTACTTCCCCGAG<br>CCAGTGACCGTG<br>ACCTGGAACTCGGGCGCCCTGACCACTGGGGTCCATACCTTCCCATC<br>CGTCCTCCACCG<br>GTCAGGGCTCTACTCCCTCAGCAGCATGGTGACCGTGCCGGCCAGCA<br>GCCTCTCCACCA<br>AGAGCTACACCTGCAATGTCAACCACCCGGCCAGCACCACCAAGGTG<br>GACAAGCCTCTT<br>GGAACAAAGACCAAAGCACCATGTCCCATATGCCCAGCCTGTCAATCG<br>CCAGGGCCCTC | APKTAPLVYPLAPCGRDTSGPNVALG<br>CLASSYFPEPVTVTWNSGALTSGVHT<br>FPSVLQPSGLYSLSSMVTVPASSLSS<br>KSYTCNVNHPATTTKVDKRVGTKTKP<br>PCPICPACESPGPSVFIFPPKPKDTLMI<br>SRTPQVTCVVVDVSQENPEVQFSWYV<br>DGVEVHTAQTRPKEEQFNSTYRVVSV<br>LIIQHQDWLNGKEFKCKVNNKDLPAPI<br>TRISKAKGQTREPQVYTLPPHEELS<br>RSKVSITCLVIGFYPPDIDVEWQRNGQ<br>PEPEGNYRTTPPQQDVDGTYFLYSKF<br>SVDKASWQGGGIFQCAVMHEALHNHY | U03780 | | |

TABLE-continued

| Species | Ig Domain | Nucleotide Sequence | Amino Acid Sequence | GenBank Accession No. | IMGT Database | Reference |
|---|---|---|---|---|---|---|
| | | GGTCTTCATCTTCCCTCCAAAACCCAACGACACCCTCATGATCTCCC<br>CCACACCCCAGG<br>TTCAGGTGCGTGGTAGTTGATGTGAGCCAGGAGAAGGCGGAGGTCCA<br>GTTCTCCTGGTAC<br>GTGGACGGCCTAGAGGTGCACACCGCCCAGACGAGGCCAAAGGAGGA<br>GCAGTTCAACAC<br>CAGCTACCGCCTGGTCAGCGTCCTGCCCATCCAGCACGAGGACTGGCT<br>GAACGGGAAGG<br>AGTTCAAGTGCAAGGTCAACAACAAAGACCTCCCAGCCCCCATCACAA<br>GGATCATCTCC<br>AAGGCCAAAGGGCAGACCCGGGAGCCGCACGTGTACACCCTGCCCCCA<br>CACCCCGAGG<br>AGCTCTCCAGGACCAAAGTCACCATAACCTGCCTGCTCATTGCCTTCT<br>ACCCACCTGAC<br>ATCGATGTCGAGTGGCAAAGAAACGGACAGCCGGAGCCAGAGGGCAAT<br>TACCGCACCAC<br>CCCCCCCCAGCAGCACCTGGACGTGACCTACAACCTGTACAGCAAGT<br>TCTCGGCGACA<br>TAGGCCACCTGGCACGGTGGACGCATATTGGAGTGTTCCGGTGATGC<br>ACGAGGCTCTGCAC<br>AACCACTACACCCAGAAGTCTATCTCCAAGACTCCGGGTAAATGA<br>(SEQ ID NO: 101) | TQKSISTPGK*<br>(SEQ ID NO: 100) | | | |
| | IgG3 | GCCTACAACACACCTCCATCCGTCTACCCTCTGGCCCCCTGTGGCAGC<br>CGGCGTCTCTCA<br>TCATAACGTGGCCTTGGGCTGCCTTGTCTCAAGCTACTTCCCCGAGC<br>CAGTGACCGTGA<br>CCTGGAACTCGGGTGCCCTGTCCAGAGTCGTGCATACCTTCCCATCC<br>GTCCTGCAGCCG<br>TCAGGCCTCTACTCCCTGAGCAGCATCGTGATCGTCCCGCCCACCAGC<br>CTGTCCACCCT<br>GAGCTACACGTGCAACGTCTACCACCCGGCCACCAACACCAAGGTGGA<br>CAAGCGTCTTG<br>ACATCGAACCGCCCACACCCATCTGTCCCGAAATTTGCTCATGCCCAG<br>CTGCAGAGGTC<br>CTCGGAGCACCGTCGGTCTTCCTCTTCCCTCCAAAACCCAAGGACATC<br>CTCATGATCTC<br>CCGGACACCCAAGGTCACGTGCGTCGTCGTGGACGTGAGCCAGGAGGA<br>GGCTGAAGTCC<br>AGTTCTCCTGGTACGTGGACGGCGTACAGTTGTACACGGCCCAGACG<br>AGGCCAATGGAG<br>GAGCAGTTGAACAGCACCTACCGCGTGGTCAGCGTCCTGCCCATCCAG<br>CACCAGGACTG<br>GCTGAAGGGGAACGAGTTCAAGTCCAAGGTCAACAACAAAGACCTCCT<br>TTCCCCCATCA<br>CGAGGACCATCTCCAAGGCTACAGGGCCGAGCCGGGTGCCGCAGGTGT<br>ACACCCTGCC<br>CCCAGCCTCCGAACACCTGTCCAACAGCAAAGTCACCATAACCTGCCT<br>GGTCACTGGGT<br>TCTACCCACCTGACATCGATGTCGAGTGGCAGAGCAACCGACAACAAG | AYNTAPSVYPLAPCGRDVSDHNVALG<br>CLVSSYFPEPVTVTWNSGALSRVVHT<br>FPSVLQPSGLYSLSSMVIVAASSLSTL<br>SYTCNVYHPATNTKVDKRVDIEPPTPI<br>CPEICSCPAAEVLGAPSVFLFPPKPKD<br>ILMISRTPKVTCVVVDVSQEEAEVQFS<br>WYVDGVQLYTAQTRPMEEQFNSTYRV<br>VSVLPIQHQDWLKGKEFKCKVNNKDLL<br>SPITRTISKATGPSRVPQVYTLPPAWE<br>ELSKSKVSITCLVTGFYPPDIDVEQWS<br>NGQQEPEGNYRTTPPQQDVDGTYFLY<br>SKLAVDKVRWQRGDLFQCAVMHEALH<br>NHYTQKSISKTQGK<br>(SEQ ID NO: 102) | EU372858 | | |

TABLE-continued

| Species | Ig Domain | Nucleotide Sequence | Amino Acid Sequence | GenBank Accession No. | IMGT Database | Reference |
|---|---|---|---|---|---|---|
| | | AGCCAGAGGGC<br>AATTACCGCACCACCCCGCCCCAGCAGGAGGTGGATGGGACGTACTTC<br>CTGTACAGCAA<br>GCTCGCGGTGGACAAGGTCAGGTGGCAGCGFGGAGACCTATTCCAGTG<br>TGCGGTGACGC<br>ACGAGGCTCTGCACAACCACTACACCCAGAAGTCCATCTCCAAGACT<br>CAGGGTAAATGA<br>(SEQ ID NO: 103) | | | | |
| | IgG4 | ACCTTCCCATCCGTCGTGCAGCCGTCAGGCCTCTACTCCCTCAGCAGC<br>ATGGTGACCGT<br>GCCGGCCAGCAGCCTGTCCAGCAAGAGCTACACCTGCAATGTCAACC<br>ACCCGGCCACCA<br>CCACCAAGGTGGACAAGCGTGTTGGAACAAAGACCAAACCACCATGTC<br>CCATATGCCCA<br>GCCTGTGAAGGGCCCGGGCCCTCGGCCTTCATCTTCCCTCCAAAACCC<br>AAGGACACCCT<br>CATGATCTCCCGGACCCCCAAGGTCACGTGCGTGGTGGTAGATGTGAG<br>CCAGGAGAACC<br>CGGAGGTCCAGTTCTCCTGGTACGTGGACGGCGTAGAGGTGCACACG<br>GCCCAGACGAGG<br>CCAAAGGACGAGCACTTCAACAGCACCTACCCCGTGGTCAGCGTCCTC<br>CCCATCCACCA<br>CCAGGACTGGCTGAACGGGAAGGAGTTCAAGTGCAAGGTCAACAACA<br>AAGACCTCCCAG<br>CCCCCATCACAAGGATCATCTCCAAGGCCAAAGGGCAGACCCGGGAGC<br>CGCAGGTGTAC<br>ACCCTGCCCCGACCCACCGAGGAGCTCTCCAGGTCCAAAGTCACGCTA<br>ACCTGCCTGGT<br>CACTGGCTTCTACCCACCTGACATCGATGTCGAGTGGCAAAGAAACGG<br>ACAGCCGGAGC<br>CAGAGGGCAATTACCGCACCACCCCGCCCCAGCAGGACGTGGACGGGA<br>CCTACTTCCTG<br>TACAGCAAGCTCGCCGTCCACAAGGCCACCTGCCAGCCTGGACACACA<br>TTCCAGTGTCC<br>GGTGATGCACGAGGCTCTGCACAACCACTACACCCAGAAGTCCATCTT<br>CAAGACTCCGG<br>GTAAATGA<br>(SEQ ID NO: 105) | TFPSVLQPSGLYSLSSMVTVPASSLS<br>SKSYTCNVNHPATTTKVDKRVGTKTK<br>PPCPICPACEGPGPSAFIFPPKPKDTL<br>MISTRPKVTCVVVDVSQENPEVQFSW<br>YVDGVEVHTAQTRPKEEQFNSTYRVV<br>SVLPIQHQDWLNGKEFKCKVNNKDLP<br>APITRISKAKGQTREPQVYTLPPPTEE<br>LSRSKVTLTCLVTGFYPPDIDVEWQRN<br>GQPEPEGNYRTTPPQQDVDGTYFLYS<br>KLAVDKASWQRGDTFQCAVMHEALH<br>NHYTQKSIFKTPGK*<br>(SEQ ID NO: 104) | U03782 | | |
| | IgG4 | GCCCCCAAGACGGCCCCATCGGTCTACCCTCTGGCCCCCTGCGGCAGG<br>GACGTGTCTG<br>GCCCTAACGTGGCCTTGGGGTGCCTGGCCTCAAGCTACTTCCCCGAGC<br>CAGTGACCGTG<br>ACCTGGAACTCGGGCGCCCTGACCAGTGGCGTGCACACCTTCCCATCC<br>GTCCTGCAGCC<br>GTCAGGGCTCTACTCCCTCAGCAGCATGGTGACCGTGCCGGCCAGCAG<br>CCTGTCCAGCA<br>AGAGCTACACCTGCAATGTCTAACCAGCCGGCCACCACCACCAAGGTG<br>GACAAGCGTGTT<br>GGAATACACCAGCCGCAAACATGTCCCATATGCCGAGCCTGTGAAGGG | APKTAPSVYPLAPCGRDVSGPNVALG<br>CLASSYFPEPVTVTWNSGALTSGVHT<br>FPSVLQPSGLYSLSSMVTVPASSLSS<br>KSYTCNVNHPATTKVDKRVGIHQPQ<br>TCPICPACEGPGPSAFIFPPKPKDTLMI<br>SRTPKVTCVVVDVSQENPEVQFSWYV<br>GHVEVHTAQTRPKEEQFNSTYRVVSV<br>LLIQHQDWLNGKEFKCKVNNKDLPAPI<br>TRISKAKGQTREPQVYTLPPPTEELSF<br>SKVTLTCLVTGFYPPDIDVEWQRNGQ<br>PEPEGNYRTTPPQQDVDGTYFLYSKL | EU372654 | | |

TABLE-continued

| Species | Ig Domain | Nucleotide Sequence | Amino Acid Sequence | GenBank Accession No. | IMGT Database | Reference |
|---|---|---|---|---|---|---|
| | | CCCCGGCCCTC<br>GGCCTTCATCTTCCCTCCAAAACCCAAGGACACCCTCATGATCTCCCG<br>GACCCCCAAGG<br>TCACGTGCGTGGTGGTTGATGTGAGGCAGGAGAACCCGGAGGTCCAGT<br>TGTCCTGGTAC<br>GTGGACGGCGTAGAGGTGCACACGGCCCAGACGAGGCCAAAGGAGGAG<br>CAGTTCAACAG<br>CACCTACCGCGTGGTCAGCGTCCTGCTCATCCAGCACCAGGACTGGCT<br>GAAGGGGAAGG<br>AGTTCAAGTGCAAGCTCAAGAACAAAGACCTCCCAGCCCCCATCACAA<br>GGATCATCTCC<br>AAGGCCAAAGGGCAGACCCGGGAGCCGCAGGTGTACACCCTGCCCCCA<br>CCCACCGAGG<br>AGCTGTCCAGGAGCAAAGTCACGCTAACCTGCCTGGTCACTGGCTTCT<br>ACCCACCTGAC<br>ATCGATGTCGAGTGGCAAAGAAACGGACAGCCGGACCCAGAGGGCAAT<br>TACCCCACCAC<br>CCCGCCCCAGCAGGACGTGGACGGGACCTACTTCCTGTACAGCAAGCT<br>CGCGGTGGACA<br>AGGCCAGCTGGCAGCGTGGAGACACATTCCAGTGTGCGGTGATGCACG<br>AGGCTCTGCAC<br>AACCACTACACCC<br>(SEQ ID NO: 107) | AVDKASWQRGDTFQCAVMHEALHNH<br>YT<br>(SEQ ID NO: 106) | | | |
| | IgG5 | GCCCCCAAGACGGCCCCATCGGTCTACCCTCTGGCCCCCTGCAGCAG<br>GGACACGTCTG<br>GCCCTAACGTGGCCTCGGCTGCCTGGTCTCAAGCTACTTCCCCGAGC<br>CAGTGACCGTG<br>ACCTGGAACTCGGGCGCCCTGACCAGTGGCGTGCACACCTTCCCATCC<br>GTCCTGCAGCC<br>CTCAGGGCTCTACTCCCTCAGCAGCATGGTGACCGGCCGGCCCACAGC<br>TTGTCCAGCA<br>AGCGCTATACGTGCAATGTCAACCACCCAGCCACCAAAACCAAGCTGG<br>ACCTGTGTGTT<br>GGACGACCATGTCCCATATGCCCAGGCTGTGAAGTGCCCGGGCCCTCG<br>CTCTTCATCTT<br>CCCTCCAAAACCCAAGGACATCCTCATGATCTCCCGGACCCCCGAGGT<br>CACGTGCGTGG<br>TGGTGGACGTCAGCAAGGAGCACGCCGAGGTCCAGTTCTCCTGGTACG<br>TGGACGGCGAA<br>GAGCTGCACACCGCCGAGACCAGGCCAAAGGACGAGCAGTTCAACACC<br>ACCTACCGCGT<br>GGTCAGCGTCCTGCCCATCCAGCACGAGGACTGGCTGAAGGGGAAGG<br>AGTTCGAGTGCA<br>AGGTCAACAACGAAGACCTCCCAGGCCCCATCACGAGGACCATCTCCA<br>AGCCCAAACCC<br>GTGGTACGGAGCCGGGAGGTGTACACCCTGCCGCCACCCGCCGAGGA<br>GCTGTCCAAGA<br>GCATAGTCACGCTAACCTGCCTGGTCAAAAGCATCTTCCCGTCTTTCA<br>TCCATGTTGAGT | APKTAPSVYPLAPCSRDTSGPNVALG<br>CLVSSYFPEPVTVTWNSGALTSGHVT<br>FPSVLQPSGLYSLSSMVTVPAHSLSS<br>KRYTCNVNHPATKTKVDLCVGRPCPI<br>CPGCEVAGPSVFIFPPKPKDILMISRTP<br>EVTCVVVDVSKEHAEVQFSWYVDGEE<br>VHTAETRPKEEQFNSTYRVVSVLPIQH<br>EDWLKGKEFECKVNNEDLPGPITRTIS<br>KAKGVVRSPEVYTLPPPAEELSKSIVT<br>LTCLVKSIFPIFIHVEWEINGKPEPENA<br>YRTTPPQEDEDRTYFLYSKLAVDKAR<br>WDHGETFECAVMHEALNHNYTQKSIS<br>KTQGK*<br>(SEQ ID NO: 108) | EU372657 | | |

TABLE-continued

| Species | Ig Domain | Nucleotide Sequence | Amino Acid Sequence | GenBank Accession No. | IMGT Database | Reference |
|---|---|---|---|---|---|---|
| | | GGAAAATCAACGGAAAAGGAGAGCCAGAGAACGCATATCGCACCACC | | | | |
| | | GCGGCTCAGGAC | | | | |
| | | CACCAGGACAGGACCTACTCCCTGTACAGCAAGCTCGCCGTGCACAA | | | | |
| | | CGCAAGATGGGA | | | | |
| | | CCATGGAGAAACATTTGAGTGTGCGGTGATGCACGAGGCTCTGCACA | | | | |
| | | ACCACTACACCC | | | | |
| | | AGAAGTCCATCTCGAAGACTCAGGGTAAATGA | | | | |
| | | (SEQ ID NO: 109) | | | | |
| | IgG5 | GCCTACAACACAGCTCGATCGGTCTACCCTCTGGCCCCCTGTGGCAGG | AYNTAPSVYPLAPCGRDVSDHNVALG | EU372686 | | |
| | | GACGTGTCTGA | CLVSSYFPEPVTVTWNWGAQTSGVHT | | | |
| | | TCATAACGTGGCCTTGGGCTGCCTGGTCTCAAGCTACTTCCCCGAGCC | FPSVLQPSGLYSLSSTVTVPAHSLSSK | | | |
| | | AGTGACCGTGA | CFTCNVNHPATTTKVDLCVGKKTKPR | | | |
| | | CCTGGAACTGGGGCGCCCAGACCAGTGGCGTGCACACCTTCCCATCCG | CPICPGCEVAGPSVFIFPPKPKDILMIS | | | |
| | | TCCTGCAGCCG | RTPEVTCVVVDVSKEHAEVQFSWYVD | | | |
| | | TCAGGGCTCTACTGCCTCAGCAGCAGGGTGAGCGTGGCGGCCCACAG | GDDVHTAETRPKEEQFNSTYRVVSVL | | | |
| | | CTTGTCCAGCAA | PIQHEDWLKGKEFECKVNNEDLPGPIT | | | |
| | | CTGCTTCACGTGCAATGTCAACCACCCCGCCACCACCACCAAGGTCGA | RTISKAKGVVRSPEVYTLPPPAEELSK | | | |
| | | CCTCTGTGTTG | SIVTLTCLVKSFFPPFIHVEWKINGKPE | | | |
| | | GAAAAAAGACCAAGCCTCGATGTCCCATATGCCCAGGCTGTGAAGTG | PENAYRTTPPQEDEDGTYFLYSKFSVE | | | |
| | | GCCGGGCCCTCG | KFRWHSGGIHCAVMHEALHNHYT | | | |
| | | GTCTTCATCTTCCCTCCAAAACCCAAGGACATCCTCATGATCTCCCG | (SEQ ID NO: 110) | | | |
| | | GACCCCCGAGGT | | | | |
| | | CACGTGCGTGGTCGTGCACGTCAGCAAGGAGCACGCCGAGGTCCAGTT | | | | |
| | | CTCCTGCTACC | | | | |
| | | TGGACGGCGAAGAGGTGCACACGGCCGAGACGAGACCAAAGGAGGAG | | | | |
| | | CAGTTCAACAGC | | | | |
| | | ACTTACCGCGTGGTCAGCCTCCTGCCCATCCAGCACGAGGACTGGCTG | | | | |
| | | AAGGGGAAGGA | | | | |
| | | CTTCCAGTGCAACGTCAACAACGAACACGTCCCACGCCCCACGACGA | | | | |
| | | GCACCATCTCCA | | | | |
| | | AGCCCAAAGGGGTGGTACGGAGCCCGGAGGTGTACACCCTGCCCCCA | | | | |
| | | CCCGCCGAGGA | | | | |
| | | GCTGTCCAAGAGCATAGTCACGCTAACCTGCCTGGTCAAAAGCTTCTT | | | | |
| | | CCCGCCTTTCAT | | | | |
| | | CGATGTTGAGTGGAAAATCAACGCAAAACCAGAGGCAGAGAACCCATA | | | | |
| | | CCCCACCACCC | | | | |
| | | CGCCCCAGGAGGACGAGGACGGGACCTACTTCCTGTACAGCAAGTTCT | | | | |
| | | CGGTGGAAAAG | | | | |
| | | TTCAGGTGGCACAGTGGAGGCATCCACTGTGCGGTGATGCACGAGGCT | | | | |
| | | CTGCACAACCA | | | | |
| | | CTAGACCC | | | | |
| | | (SEQ ID NO: 111) | | | | |
| | IgG6 | CCCCCCAAGACGCCCCCATTAGTCTACCCTCTGGCCCCCTGCGGCACG | APKTAPSVYPLAPCGRDTSGPNVALG | EU372655 | | |
| | | GACACGTCTG | CLASSYFPEPVTLTWNSGALTSGVHT | | | |
| | | GCCCTAACGTGGCCTTGGGCTGCCTGGCCTCAAGCTACTTCCCCGAGC | FPSVLQPSGLYSLSSMVTVPASSLSS | | | |
| | | CAGTGACCCTG | KSYTCNVNHPATTTKVDLCVGRPCPI | | | |
| | | ACCTGGAACTCGGGCGCCCTGACCAGTGGCGTGCATACCTTCCCATCC | CPACEGPGPSVFIFPPKPKDTLMISRT | | | |
| | | GTCCTGCAGCC | PQVTCVVVDVSQENPEVQFSWYVDG | | | |
| | | GTCAGCCCTGTACTCCCTCAGCAGCATGGTGACCGGCCGGCCAGCAGC | VEVHTAQTRPKEQFNSTYRVVSVLPI | | | |

TABLE-continued

| Species | Ig Domain | Nucleotide Sequence | Amino Acid Sequence | GenBank Accession No. | IMGT Database | Reference |
|---|---|---|---|---|---|---|
| | | CTGTCCAGCA<br>AGAGCTACACCTGCAATGTCAACCACCCGGCCACCACCACCAAGGTGG<br>ACCTGTGTGTT<br>GGACGACCATCTCCCATATGCCCAGCCTGTGAAGGGCCCGGGCCCTCG<br>GTCTTCATCTT<br>CCCTCCAAAACCCAAGGACACCCTCATGATCTCCCGGACACGCCAGGT<br>CACGTGCGTGG<br>TGGTAGATGTGAGCCAGGAAAACCCGGAGGTCCAGTTCTCCTGGTAT<br>GTGGACGGTGTA<br>GAGGTGCACACGGCCCAGACGAGGCCAAAGGAGGCGCAGTTCAACAGC<br>ACCTACCGTGT<br>GGTCAGCGTCCTGCCCATCCAGCACGAGGACTGGCTGAAGGGGAAGGA<br>GTTCGAGTGCA<br>AGGTCAACAACAAAGACCTCCCAGCCCGCATGACAAGGATCATCTGC<br>AAGACCAAAGGG<br>CCGAGCCGGGAGCCACAGGTGTACACCCTGTCCGCATCCGCCGAGGAG<br>CTGTCCAGGA<br>GCAAAGTCAGCATAACCTGCCTGGTCACTGGCTTCTACCCACCTGACA<br>TCGATGTCGAG<br>TGGAACAGCAACGCACAGCCGGAGCCAGAGGGCAATTACCCCACCACC<br>CCGCCCCAGC<br>AGGACGTGGACGGGACCTACTTCCTGTACAGCAAGCTCGCGGTGGAC<br>AAGGCCAGCTGG<br>CAGCGTGTGAGACCCATTCCAGTGTGCGGTGATGCACGAGGCTCTGCA<br>CAACCACTACACCC<br>(SEQ ID NO: 113) | QHEDWLKGKEFECKVNNKDLPAPITRII<br>SKSKGPSREPQVYTLSPSAEELSRSKV<br>SITCLVTGFYPPDIDVEWKSNGQPEPE<br>GNYRTTPPQQDVDGTYFLYSKLAVDK<br>ASWQRGDPFQCAVMHEALHNHT<br>(SEQ ID NO: 112) | | | |
| | IgG6 | CCCCCCAAGACGCCCCCATCGGTCTACCCTCTCGCCCCCTGCCCCAC<br>CCACACCTCTC<br>GCCCTAACGTGCCCTTGGGCTGCCTGGCCTCAAGCTACTTCCCCGAGC<br>CAGTGACCGTG<br>ACCTGGAACTCGGGCGCCCTGACCAGTGGCGTGCACACCTTCCCATGC<br>GTCGTGCAGCC<br>GTCAGCCCTCTACTCCCTCAGCAGCACGGTGACCGTGCCGCCCAGGAG<br>CTCGTCCAGAA<br>ACTGCTTCACGTGCAATGTCAACCACCCGGCCACCACCACCAAGGTGG<br>ACCTGTGTGTT<br>GGACGACCATGTCCCATATGCCCAGCCTGTGAAGGGAACGGGCCCTCG<br>GTCTTCATGTT<br>CCCTCGAAAACCCAAGGACACCCTCATCATCTCCCGGACCCCCGAGCT<br>CACGTGGCTCC<br>TGGTAGATGTGAGCCAGGAAAACCCGGAGGTCCAGTTCTCCTGGTACG<br>TGGACGGCGAA<br>GAGGTGCACACGGCCGAGACGAGGCCAAAGGAGGAGCAGTTCAACAG<br>CACCTACCGTGT<br>GGTCAGCCTCCTGCCCATCCAGCACCAGGACTGGCTGAAGGGAAAGG<br>AGTTCGAGTGCA<br>AGCTCAACAACAAAGACCTCCCAGCCCCCATCACAAGGATCATCTCC<br>AAGGCCAAAGGG<br>CCGAGGCGGGAGCCGCAGGTGTACACCCTGTCCCCATCCGCCGAGGAG | APKTAPSVYPLAPCGRDTSGPNVALG<br>CLASSYFPEPVTVTWNSGALTSGVHT<br>FPSVLQPSGLYSLSSTVTVPARSSSRK<br>CFTCNVNHPATTTKVDLCVGRPCPIC<br>PACEGNGPSVFIFPPKPKTLMISRTP<br>EVTCVVVDVSQENEPEVQFSWYVDGEE<br>VHTAETRPKEEQFNSTRYVVSVLPIQH<br>QDWLKGKEFECKVNNDLPAPITRIISK<br>AKGPSREPQVYTLSPSAEELSRSKVSI<br>TLLVTGFYPPDIDVEWKSNGQPEPEG<br>NYRSTPPQEDEDGTYFLYSKLAVDKA<br>RLQSGGIHCAVMHEALHNHYTQKSISK<br>T<br>(SEQ ID NO: 112) | EU372653 | | |

TABLE-continued

| Species | Ig Domain | Nucleotide Sequence | Amino Acid Sequence | GenBank Accession No. | IMGT Database | Reference |
|---|---|---|---|---|---|---|
| | | CTGTCCAGGA GCAAAGTCAGCATAACCTGCCTGGTCACTGGCTTCTACCCACCTGAC ATCGATGTCGAG TGCAAGAGCAACGGAGACCCGGAGCCAGAGGGCAATTACCGCTCCAC CCCGCCCCAGGA GGACGAGGACGGGACCTACTTCCTGTACAGCAAACTCGCGGTGGACA AGGCGAGGTTGC AGAGTGCAGGCATCCACTGTGCGGTGATGCACGAGGCTCTGCACAACC ACTACACCCAG AAGTCCATCCCAAGACT (SEQ ID NO: 115) | | | | |
| | Porcine Ig light chain constant region: Ig kappa (CK) variant 1 | | | FP312892 | http://www.imgt.org/IMGT reportoire/index.ghp?section=locus Genes&reportoire=genetable&species=*Pig*&group=IGLC | Schwartz J.C. et al Immuno-genetics 84, 303-313 (2012) PMID: 22108543 |
| | Ig kappa (CK) variant 2 | | | CU604948 | | |
| | Ig lambda (CL) variant 1 | | | CU407669 | http://www.imgt.org/IMGT reportoire/index.ghp?section=locus Genes&reportoire=genetable&species=*Pig*&group=IGKC | |
| | Ig lambda (CL) variant 2 | | | CU467599 | | |
| Water buffalo (Scientific Name: *Bubalus bubalis*) | Water buffalo Ig havy chain constant (CJ1 CH3) IgG1? | GAGCGGCGTGCACACCTTCCCGGCCGTCCTTCAGTCC TCCGGGCTCTACTCTCTGAGCAGCACGGTGACCGCGC CCCCCAGCGCCACAAAAAGCCAGACCTTCACCTGCAA CGTAGCCCACCCGGCCAGCAGCACCAAGGTGGACAAG GCTGTTGTTGCCCCATGCAGACCGAAACCCTGTGATTG CTGCCCACCCCCTGAGCTCCCCGGAGGACCCTCTGTC TTCATCTTCCCACCAAAACCCAAGGACACCCTCACAAT CTCTGGAACTCCTGAGGTCACGTGTGTGGTGGTGGAC GTGGGCCAGGATGACCCCGAGGTGAAGTTCTCCTGGT TCGTCGACGATGTGGAGGTAAACACAGCCAGGACGAA GCCAAGAGAGGAGCAGTTCAACAGCACCTACTCGCGTG | SGVHTFPAVLQSSGLYSLSSTVTAPAS ATKSQTFTCNVAHPASSTKVDKAVVP PCRPKPCDCCPPPELPGGPSVFIFPPK PKDTLTISGTPEVTCVVVDVGHDPEV KFSWFVDDVEVNTARTKPREEQFNSTY RVVSALPIQHNDWTGGKEFKCKVYNEG LPAPIVRTISRTKGQAREPQVYVLAPP QDELSKSTVSITCMVTGFYPDYIAVEW QKDGQPESEDKYGTTPPQLDSDGSYF LYSRLRVNKNSWQEGAYICVVMHE (SEQ ID NO: 118) | NW_ 005690903 | Not registered | None |

TABLE-continued

| Species | Ig Domain | Nucleotide Sequence | Amino Acid Sequence | GenBank Accession No. | IMGT Database | Reference |
|---|---|---|---|---|---|---|
| | | GTCAGCGCCCTGCCCATCCAGCACAACGACTGGACTG<br>GAGGAAAGGAGTTCAAGTGCAAGGTCTACAATGAAGGC<br>CTCCCAGCCCCCATCGTGAGGACCATCTCCAGGACCA<br>AAGGGCAGGCCCGGGAGCCGCAGGTGTACGTCCTGGC<br>CCGACCCCAGGACGAGCTCACCAAAAGCACGGTCAGC<br>ATCACTTGCATGGTCACTGGCTTCTACCCAGACTACAT<br>CGCCGTAGAGTGGCAGAAAGATGGGCAGCCTGAGTCA<br>GAGGACAAATATGGCACGACCCCGCCCCAGCTGGACA<br>GCGATGGCTCCTACTTCCTGTACAGCAGGCTCAGGGT<br>GAACAAGAACAGCTGGCAAGAAGGAGGCGCCTACACG<br>TGTGTAGTGATGCATGAGGC<br>(SEQ ID NO: 119) | | | | |
| | IgG2? | GCCTCCATCACAGCCCCGAAAGTCTACCCTCTGACTTC<br>TTGCCGCGCGGAAACGTCCAGCTCCACCGTGACCCTG<br>GGCTGCCTGGTGTCCAGCTACATGCCCGAGCCGGTGA<br>CGGTGACCTGGAACTCGGGTGCCGTGAAGAGCGGCGT<br>GCACACCTTCCCGGCCGTCCTTCAGTCCTCTGGGCTC<br>TACTCTCTCAGCAGCACGGTGACCGCGCCCGCCAGCG<br>CCACAAAAAGCCAGACCTTCACCTGCAACGTAGCCCAC<br>CCGGCCAGCAGCACCAAGGTGGACACGGCTGTTGGGT<br>TCTCGAGTGACTGCTGCAAGTTTCCTAAGCCTTGTGTG<br>AGGGGACCATCTGTCTTCATCTTCCCGCCGAAACCCAA<br>AGACACCCTGATGATCACAGGAAATCCCGAGGTCACAT<br>GTGTGGTGGTGGACGTGGGCCGGGATAACCCCGAGGT<br>GCAGTTCTCCTGGTTCGTGGGTGATGTGGAGGTGCAC<br>ACGGGCAGGTCGAAGCCGAGAGAGGAGCAGTTCAACA<br>GCACCTAGCGCGTGGTCAGCACCCTGCCCATCCAGCA<br>CAATGACTGGACTGGAGGAAAGGAGTTCAAGTGCAAG<br>GTCAACAACAAAGGCCTCCCAGCCCCCATCGTGAGGA<br>CCATCTCCAGGACCAAAGGGCAGGCCCGGGAGCCGCA<br>GGTGTACGTCCTGGCCCCACCCCAGGAAGAGCTCAGC<br>AAAAGCACGGTCAGCGTCACTTCCATGGTCACTGGCTT<br>CTACCCAGACTACATCGCCGTAGAGTCGCATAGAGACC<br>GGCAGGCTGAGTCGGAGGACAAGTACCGCACGACCCC<br>GCCCCAGCTGGACAGCGATGGCTCCTACTTCCTGTAC<br>AGCAGGCTCAAGGTGAACAAGAACAGCTGGCAAGAAG<br>GAGGCGCCTACACGTGTGTAGTGATGCATGAGGC<br>(SEQ ID NO: 121) | ASITAPKVYPLTSCRGETSSSTVTLGC<br>LVSSYMPEPVTVTWNSGALKSGVHTF<br>PAVLQSSGLYSLSSTVTAPASATKSQT<br>FTCNVAHPASSTKVDTAVGFSSDCCK<br>FPKPCVRPGSVFIFPPKPKDTLMITGNP<br>EVTCVVDVGRDNPEVQFSWFVGDVE<br>VHTGRSKPREEQFNSTRYVVSTLPIQH<br>NDWTGGKEFKCKVNKGLPAPIVRTIS<br>RIIKGQAREPQVYLAPPQEELLSKSTVS<br>VTCMVTGFYPDYIAVEWHRDRQAESED<br>KYRTTPPQLDSDGSYFLYSRLKVNKNS<br>WQEGGAYTCVYMHE<br>(SEQ ID NO: 120) | NW_<br>005766143 | | |
| | IgG3? | GCCTCCACCACAGCCCCGAAAGTCTACCCTCTGGCAT<br>CCAGCTGCGGGGACACGTCCAGGTCCACCGTGACCCT<br>GGGCTGCCTGGTCTCCAGCTACATGCCCGAGCCGGTG<br>ACCGTGACCTGGAACTCGGGTGCCCTCAAGAACGGCG<br>TGCACACCTTCCCGGCCGTCGGGCAGTCCTCCGGGCT<br>CTACTCTCTCAGCAGCATGGTGACCATGCCCACCAGCA<br>CCGCAGGAACCCAGACCTTCACCTGCAACGTAGCCCA<br>CCCGGCCAGCAGCACCAAGGTGGACACGGCTGTCACT<br>GCAAGGCATCCGGTCCCGAAGACACCAGAGACACCTA<br>TCCATCCTGTAAAACCCCCAACCCAGGAGCCCAGAGAT<br>GAAAAGACACCCTGCCAGTGTCCCAAATGCCCAGAACC | ASTTAPKVYPLASSCGDTSSSTVTLGC<br>LVSSYMPEPVTVTWNSGALKNGVHTF<br>PAVRQSSGLYSLSSMVTMPTSTAGTQ<br>TFTCNVAHPASSTKVDTAVTARHPVP<br>KTPETPIHPVKPPTQEPRDEKTPCQCP<br>KCPEPLGGLSVFIFPPKPKDTLTISGTP<br>EVTCVVVDVGQDDPEVQFSWFVDDVE<br>VHTARMKPREEQFNSTYRVVSALPIQH<br>QDWLREKEFKCKVNNKGLPAPIVRTISR<br>TKGQAREPQVYVLAPPREELSKSTLSL<br>TCLITGFYPEEVDVEWQRNGQPESEDK | NW_<br>005784206 | | |

TABLE-continued

| Species | Ig Domain | Nucleotide Sequence | Amino Acid Sequence | GenBank Accession No. | IMGT Database | Reference |
|---|---|---|---|---|---|---|
| | | TCTGGGAGGACTGTCTCTCTTCATCTTCCCACCGAAAC<br>CCAAGGACACCCTCACAATCTCTGGAACGCCCGAGGT<br>CACGTGTGTGGTGGTGGACGTGGGCCAGGATGACCCC<br>GAAGTGCAGTTCTCCTGGTTCGTGGATGACGTGGAGG<br>TGCACACAGCCAGGATGAAGCCAAGAGAGGAGCAGTT<br>CAACAGCACCTACCGCGTGGTCAGCGCCCTGCCCATC<br>CAGCACCAGGACTGGCTGCGGGAAAAGGAGTTCAAGT<br>GCAAGGTCAACAACAAAGGCCTCCCGGCCCCCATCGT<br>GAGGACCATCTCCAGGACCAAAGGGCAGGCCCGGGAG<br>CCACAGGTGTATGTCCTGGCCCCACCCCGGGAAGAGC<br>TCAGCAAAAGCACGCTCAGCCTCACCTGCCTAATCACC<br>GGCTTCTACCCAGAAGAGGTAGACGTGGAGTGGCAGA<br>GAAATGGGCAGCCTGAGTCAGAGGACAAGTACCACAC<br>GACCCCACCCCAGCTGGACGCTGACGGCTCCTACTTC<br>CTGTACAGCAGGCTCAGGGTGAACAGGAGCAGCTGGC<br>AGCAAGGAGACCACTACACGTGTGCAGTGATGCATGAA<br>GCTTTACGGAATCACTACAAAGAGAAGCCCATCTCGAG<br>GTCTCCGGCTAAATCA<br>(SEQ ID NO: 123) | YHTTPPQLDADGSYFLYSRLRVKRSSW<br>QEGDHYTCAVMHEALRNHYKEKPISRS<br>PGK*<br>(SEQ ID NO: 122) | | | |
| Water bu-ffalo Ig light chain con-stant region (CL) | Ig lambda? | CAGCCCAAGTCCGCACCCTCAGTCACCCTGTTCCCAC<br>CCTCCACGGAGGAGCTCAGCGCCAACAAGGCCACCCT<br>GGTGTGTCTCATCAGCGACTTCTACCCGGGTAGCATGA<br>CCGTGGCCAGGAAGGCAGACGGCAGCACCATCACCCG<br>GAACGTGGAGACCACCCGGGCCTCCAAACAGAGCAAC<br>AGCAAGTACGCGGCCACCAGCTACCTCAGCCTGACGG<br>GCAGCGAGTGGAAATCGAAAGGCAGTTACAGCTGCGA<br>GGTCACGCACGAGGGGAGCACCGTGACAAAGACAGTG<br>AAGCGCTCAGAGTGTTCTTAG<br>(SEQ ID NO: 117) | QPKSAPSVTLFPPSTEELSANKATLVG<br>LISDFYPGSMTVARKADGSTITRNVETT<br>RASKQSNSKYAASSYLSLTGSEWKSKG<br>SYSCEVTHEGSTVTKTVKPSECS*<br>(SEQ ID NO: 116) | NW_ 005690786 | Not registered | None |

The amino acid sequences as shown in SEQ ID NOS: 8 to 13, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120 and 122 may have deletion(s), substitution(s) or addition(s) of one or several (e.g., up to five, about 10 at the 3 most) amino acids. Even when such mutations have been introduced, the resulting amino acid sequences are capable of having the function as the constant region of Ig heavy chain or light chain.

The anti-PD-L1 antibody of the present invention may have a four-chain structure comprising two light chains and two heavy chains.

The anti-PD-L1 antibody of the present invention may be prepared as described below. Briefly, an artificial gene is synthesized which comprises the light chain sequence (variable region sequence and constant region sequence) and the heavy chain sequence (variable region sequence and constant region sequence) of the anti-PD-L1 antibody of the present invention. The resultant gene is inserted into a vector (e.g., plasmid), which is then introduced into a host cell (e.g., mammal cell such as CHO cell). The host cell is cultured, and the antibody of interest is collected from the resultant culture. In the synthesis of the artificial gene, codons of the nucleotide sequence may be optimized.

The present invention provides a DNA encoding an anti-PD-L1 antibody comprising (a) a light chain comprising CDR1 having the amino acid sequence of KSISKY (SEQ ID NO: 1), CDR2 having the amino acid sequence of SGS and CDR3 having the amino acid sequence of QQHNEYPLT (SEQ ID NO: 2) and (b) a heavy chain comprising CDR1 having the amino acid sequence of GYTFTDYI (SEQ ID NO: 3). CDR2 having the amino acid sequence of INPDSGGN (SEQ ID NO: 4) and CDR3 having the amino acid sequence of ARGITMMVVISHWKFDF (SEQ ID NO: 5). The present invention also provides a DNA encoding a light chain of an anti-PD-L1 antibody comprising CDR1 having the amino acid sequence of KSISKY (SEQ ID NO: 1), CDR2 having the amino acid sequence of SGS and CDR3 having the amino acid sequence of QQHNEYPLT (SEQ ID NO: 2) (the DNA of (a')). Further, the present invention provides a DNA encoding a heavy chain of an anti-PD-L1 antibody comprising CDR1 having the amino acid sequence of GYTFTDYI (SEQ ID NO: 3), CDR2 having the amino acid sequence of INPDSGGN (SEQ ID NO: 4) and CDR3 having the amino acid sequence of ARGITMMVVISHWKFDF (SEQ ID NO: 5) (the DNA of (b')).

For (a) a light chain comprising CDR1 having the amino acid sequence of KSISKY (SEQ ID NO: 1), CDR2 having the amino acid sequence of SGS and CDR3 having the amino acid sequence of QQHNEYPLT (SEQ ID NO: 2) and (b) a heavy chain comprising CDR1 having the amino acid sequence of GYTFTDYI (SEQ ID NO: 3), CDR2 having the amino acid sequence of INPDSGGN (SEQ ID NO: 4) and CDR3 having the amino acid sequence of ARGITMMVVISHWKFDF (SEQ ID NO: 5), reference should be had to the foregoing description. A DNA comprising the DNA of (a') and the DNA of ('b) may be synthesized on commercial synthesizer. Restriction enzyme recognition sites, KOZAK sequences, poly-A addition signal sequences, promoter sequences, intron sequences or the like may be added to this DNA.

The present invention also provides a vector comprising the above-mentioned DNA encoding an anti-PD-L1 antibody.

As the vector, *Escherichia coli*-derived plasmids (e.g., pBR322, pBR325, pUC12 or pUC13); *Bacillus subtilis*-derived plasmids (e.g., pUB110, pTP5 or pC194), yeast-derived plasmids (e.g., pSH19 or pSH15); bacteriophages such as λ phage; animal viruses such as retrovirus or vaccinia virus; or insect pathogen viruses such as baculovirus may be used. In the Examples described later, pDC6 (Japanese Patent No. 5704753, U.S. Pat. No. 9,096,878, EU Patent 2385115, Hong Kong (China) patent HK1163739 and Australia Patent 2009331326) is used.

The vector may also comprise promoters, enhancers, splicing signals, poly-A addition signals, intron sequences, selection markers, SV40 replication origins, and so forth.

The present invention also provides a host cell transformed by the above vector. It is possible to prepare the anti-PD-L1 antibody of the invention by culturing the host cell and collecting the antibody of interest from the resultant culture. Therefore, the present invention also provides a method of preparing an antibody, comprising culturing the above-described host cell and collecting the anti-PD-L1 antibody of the invention from the culture. In the method of the present invention for preparing an antibody, a vector incorporating a DNA comprising a DNA encoding the light chain and a DNA encoding the heavy chain may be transfected into a host cell. Alternatively, a vector incorporating a DNA encoding the light chain and a vector incorporating a DNA encoding the heavy chain may be co-transfected into a host cell.

Examples of the host cell include, but are not limited to, bacterial cells (such as *Escherichia* bacteria, *Bacillus* bacteria or *Bacillus subtilis*), fungal cells (such as yeast or *Aspergillus*), insect cells (such as S2 cells or Sf cells), animal cells (such as CHO cells, COS cells. HeLa cells. C127 cells, 3T3 cells. BHK cells or HEK 293 cells) and plant cells. Among these, CHO-DG44 cell (CHO-DG44 (dfhr$^{-/-}$)) which is a dihydrofolate reductase deficient cell is preferable.

Introduction of a recombinant vector into a host cell may be performed by the methods disclosed in Molecular Cloning 2nd Edition, J. Sambrook et al., Cold Spring Harbor Lab. Press, 1989 (e.g., the calcium phosphate method, the DEAE-dextran method, transfection, microinjection, lipofection, electroporation, transduction, scrape loading, the shotgun method, etc.) or by infection.

The resultant transformant may be cultured in a medium, followed by collection of the anti-PD-L1 antibody of the present invention from the culture. When the antibody is secreted into the medium, the medium may be recovered, followed by isolation and purification of the antibody from the medium. When the antibody is produced within the transformed cells, the cells may be lysed, followed by isolation and purification of the antibody from the cell lysate.

Examples of the medium include, but are not limited to, OptiCHO medium, Dynamis medium, CD CHO medium, ActiCHO medium. FortiCHO medium, Ex-Cell CD CHO medium. BalanCD CHO medium, ProCHO 5 medium and Cellvento CHO-100 medium.

The pH of the medium varies depending on the cell to be cultured. Generally, a pH range from 6.8 to 7.6 is used; mostly, a pH range from 7.0 to 7.4 is appropriate.

When the cell to be cultured is CHO cells, culture may be performed by methods known to those skilled in the art. For example, it is usually possible to perform culturing in a gas-phase atmosphere having a $CO_2$ concentration of 0-40%, preferably 2-10%, at 30-39° C., preferably around 37° C.

The appropriate period of culture is usually from one day to three months, preferably from one day to three weeks.

Isolation and purification of the antibody may be performed by known methods. Known isolation/purification methods which may be used in the present invention include, but are not limited to, methods using difference in solubility (such as salting-out or solvent precipitation); methods using difference in molecular weight (such as dialysis, ultrafiltration, gel filtration or SDS-polyacrylamide gel electrophoresis); methods using difference in electric charge (such as ion exchange chromatography); methods using specific affinity (such as affinity chromatography); methods using difference in hydrophobicity (such as reversed phase high performance liquid chromatography): and methods using difference in isoelectric point (such as isoelectnc focusing).

It is also possible to prepare the anti-PD-L1 antibody of the present invention by culturing a hybridoma which may be prepared by the method disclosed in the literature (Ikebuchi R, Konnai S, Okagawa T, Yokoyama K, Nakajima C, Suzuki Y. Murata S, Ohashi K, Immunology. 2014 August; 142(4):551-61). A hybridoma producing anti-PD-L1 antibody 6C11-3A11 is stored at the laboratory of the present inventors (Laboratory of Infectious Diseases, Department of Disease Control, Faculty of Veterinary Medicine, Hokkaido University).

The PD-L1 antibody of the present invention may be used for detecting PD-L. Therefore, the present invention provides a composition for detecting PD-L1, comprising the PD-L1 antibody as an active ingredient.

Detection of PD-L1 may be performed by such methods including, but are not limited to, immunohistochemical staining, immunocytochemical staining, flow cytometry, enzyme linked immunosorbent assay (ELISA) and Western blotting.

Analytes for detection may be exemplified by samples such as tissues or body fluids taken from organisms (e.g., blood (whole blood, plasma, serum, or specific cell such as erythrocyte, leukocyte or lymphocyte), urine, saliva, etc.); cell culture; and cultured cells (established cell lines, primary cultured cells, subcultured cells, etc.). The source of such analytes is not particularly limited. Examples include rat, canine, ovine, goat, porcine, feline, human, equine, bovine, water buffalo, yak, rabbit, mouse, hamster, and guinea pig.

The PD-L1 antibody of the present invention may be labeled with radioisotopes, enzymes, luminescent substances, fluorescent substances, biotin, or the like. If reaction with a primary antibody (the anti-PD-L1 antibody of the present invention) which specifically binds to a target molecule (PD-L1) is followed by reaction with a secondary antibody which binds to the primary antibody so as to detect the target molecule, it is suitable to label the secondary antibody.

Since PD-L1 is strongly expressed in cancer cells and virus-infected cells, the composition of the present invention may be used for diagnosis of cancers and/or infections. Usually, the amount (concentration) of PD-L in an analyte is determined based on the amount (concentration) of the complex of PD-L1 and anti-PD-L1 antibody. When the amount (concentration) of PD-L1 in the analyte is high compared to negative control (e.g., healthy surrounding tissue (connecting tissue, blood vessels, etc.)), the analyte may be diagnosed as suffering cancer and/or infection. Alternatively, if PD-L1 is detected in the analyte, the analyte may be diagnosed as suffering cancer and/or infection.

Examples of cancers and/or infections include, but are not limited to, neoplastic diseases (e.g., malignant melanoma, lung cancer, gastric cancer, renal cancer, breast cancer, bladder cancer, esophageal cancer, ovarian cancer and the like), leukemia, Johne's disease, anaplasmosis, bacterial mastitis, mycotic mastitis, mycoplasma infections (such as inycoplasma mastitis, mycoplasma pneumonia or the like), tuberculosis, *Theileria orientalis* infection, cryptosporidiosis, coccidiosis, trypanosomiasis and leishmaniasis.

The composition of the present invention can be used to select subject animals suitable for therapy using an anti-PD-L1 antibody. For example, animals satisfying the following two points may be considered as candidate animals.

1. A case diagnosed as suffering cancer (such as melanoma) or infection in pathological examination
2. A case found positive for anti-PD-L1 antibody Negative control may be healthy surrounding tissue (connecting tissue, blood vessels, etc.), and positive control may be a case of cancer (such as melanoma) or infection. Basically, animals with a tumor which is positive in immunohistochemical staining of almost all regions may be subjected to clinical trial.

Subject animals are not particularly limited and may include rat, canine, ovine, goat, porcine, feline, human, equine, bovine, water buffalo, yak, rabbit, mouse, hamster, and guinea pig.

The composition of the present invention may further comprise reagents for detecting labels, diluents, lavage fluids, written instructions describing criteria for diagnosis/selection, and so on.

EXAMPLES

Hereinbelow, the present invention will be described in more detail with reference to the following Examples. However, the present invention is not limited to these Examples.

Example 1

1. Introduction

Programmed cell death 1 (PD-1), an immunoinhibitory receptor, and its ligand programmed cell death ligand 1 (PD-L1) are molecules identified by Prof. Tasuku Honjo et al., Kyoto University, as factors which inhibit excessive immune response and are deeply involved in immunotolerance. Recently, it has been elucidated that these molecules are also involved in immunosuppression in infections and tumors in various animals. In the subject Example, an anti-bovine PD-L1 monoclonal antibody was prepared by immunizing rats, and then a clone (6C11-3A11) capable of detecting canine PD-L1 was selected. Further, the present inventors performed immunohistochemical staining to examine whether or not this anti-bovine PD-L1 antibody 6C11-3A11 would be useful for detecting PD-L1 in canine malignant tumors (such as melanoma) and porcine/ovine infections.

2. Materials and Methods 2.1 Rat Anti-Bovine PD-L1 Monoclonal Antibody Producing Cells The nucleotide sequence of bovine PD-L1 was identified (Ikebuchi R, Konnai S, Shirai T. Sunden Y, Murata S. Onuma M, Ohashi K. Vet Res. 2011 Sep. 26:42:103). Based on the sequence information, a recombinant bovine PD-L1 was prepared. Rat was immunized in the footpad with this recombinant protein, and hybridomas were established by the iliac lymph node method. As a result, a plurality of hybridomas producing rat anti-bovine PD-L1 monoclonal antibodies were obtained (Ikebuchi R, Konnai S, Okagawa T, Yokoyama K, Nakajima C, Suzuki Y, Murata S, Ohashi K. Immunology 2014 August; 142(4):551-561). Rat anti-bovine PD-L1 antibody 6C11-3A11 is one of the monoclonal antibodies established from the above-described immunized rat.

2.2 Identification of Full-Length Canine PD-L1 Gene

To determine the full length of canine PD-L1 cDNA, PCR primers were first designed based on the putative nucleotide sequence of canine PD-L1 already registered at The National Center for Biotechnology Information (NCBI) (GenBank accession number; XM_541302). Briefly, primers to amplify the inner sequence of the open reading frame (ORF) of this gene were designed (cPD-1 inner F and R), and PCR was performed. For the amplified products, nucleotide sequences were determined with a capillary sequencer according to conventional methods. Further, to determine the nucleotide sequence of full-length PD-L1 cDNA, primers (cPD-L1 5' GSP and 3'GSP) were designed based on the canine PD-L1 cDNA sequences determined above. 5'-RACE and 3-RACE were then performed using, respectively, the 5'-RACE system for rapid amplification of cDNA ends and 3'-RACE system for rapid amplification of cDNA ends (Invitrogen). The resultant gene fragments of interest were sequenced as described above (Maekawa N, Konnai S, Ikebuchi R, Okagawa T, Adachi M, Takagi S, Kagawa Y. Nakajima C, Suzuki Y. Murata S, Ohashi K. PLoS One. 2014 Jun. 10; 9(6):e98415).

```
Primer (cPD-L1 inner F):
                                (SEQ ID NO: 22)
ATGAGAATGTTTAGTGTCTT

Primer (cPD-L1 inner R):
                                (SEQ ID NO: 23)
TTATGTCTCTTCAAATTGTATATC

Primer (cPD-L1 5'GSP):
                                (SEQ ID NO: 24)
TTTTAGACAGAAAGTGA

Primer (cPD-L1 3'GSP):
                                (SEQ ID NO: 25)
GACCAGCTCTTCTTGGGGAA
```

2.3 Preparation of Canine PD-L1 Expressing COS-7 Cells

For preparing a canine PD-L1-EGFP expression plasmid, PCR was performed using a synthesized beagle PBMC-derived cDNA as a template and primers designed by adding BglII and EcoRI recognition sites on the 5' side (cPD-L1-EGFP F and R). The resultant PCR products were digested with BglII (New England Biolabs) and EcoRI (Takara), and then purified with FastGene Gel/PCR Extraction Kit (NIPPON Genetics), followed by cloning into pEGFP-N2 vector (Clontech) similarly treated with restriction enzymes. The resultant expression plasmid of interest was extracted with QIAGEN Plasmid Midi kit (Qiagen) and stored at −30° C. until use in experiments. Hereinafter, the thus prepared expression plasmid is designated as pEGFP-N2-cPD-L1.

```
Primer (cPD-L1-EGFP F):
                                (SEQ ID NO: 26)
GAAGATCTATGAGAATGTTTAGTGTC

Primer (cPD-L1-EGFP R):
                                (SEQ ID NO: 27)
GGAATTCTGTCTCTTCAAATTGTATATC
```

COS-7 cells were subcultured at a density of $5\times10^4$ cells/cm in 6-well plates, and then cultured overnight in RPMI 1640 medium containing 10% inactivated fetal bovine serum and 0.01% L-glutamine at 37° C. in the presence of 5% $CO_2$. The pEGFP-N2-cPD-L1 or pEGFP-N2 (negative control) was introduced into COS-7 cells at 0.4 μg/$cm^2$ using Lipofectamine 2000 (Invitrogen). The cells were cultured for 48 hours (canine cPD-L-EGFP expressing cell and EGFP expressing cell). In order to confirm the expression of PD-L1 in the thus prepared expressing cells, intracellular localization of enhanced green fluorescent protein (EGFP) was visualized with an inverted confocal laser microscope LSM700 (ZEISS) (Maekawa N, Konnai S, Ikebuchi R, Okagawa T, Adachi M. Takagi S, Kagawa Y, Nakajima C, Suzuki Y, Murata S, Ohashi K. PLoS One. 2014 Jun. 10; 9(6):e98415).

2.4 Cross-Reactivity of Rat Anti-Bovine PD-L1 Antibody 6C11-3A11 with Canine PD-L1

Figure 1:
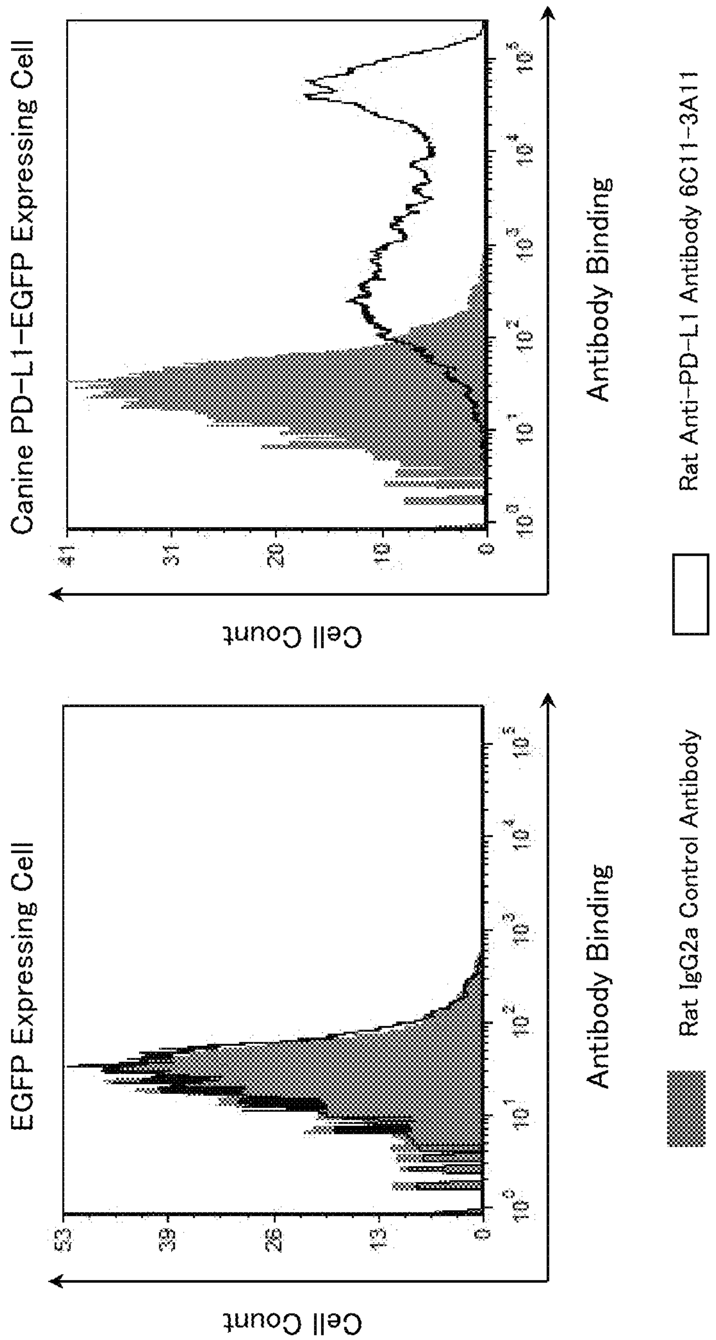
FIG. 1 Binding specificity of rat anti-bovine PD-L1 antibody 6C11-3A11. Rat anti-bovine PD-L1 antibody 6C11-3A11 did not bind to EGFP expressing cells, but specifically bound to canine PD-L1-EGFP expressing cells.

In order to confirm that rat anti-bovine PD-L1 antibody 6C1-3A11 specifically binds to canine PD-L1, flow cytometry was performed using the canine cPD-L1-EGFP expressing cell or the EGFP expressing cell prepared in 2.3 above. To $2\times10^5$-$1\times10^6$ cells, 10 μg/ml of anti-bovine PD-L1 antibody 6C11-3A11 was added and reacted for 30 min at room temperature. After washing, the antibody binding to cell surfaces was detected with Allophycocyanine-labeled goat anti-rat Ig antibody (Beckman Coulter). For the analysis, FACS Verse (Becton. Dickinson and Company) was used. As a negative control antibody, rat IgG2a (κ) isotype control (BD Bioscience) was used. For every washing operation and dilution of antibodies, 10% inactivated goat serum-supplemented PBS was used. The results are shown in FIG. 1.

2.5 CDR Analysis of Rat Anti-Bovine PD-L1 Antibody 6C1-3A11

The heavy chain and the light chain genes of rat anti-bovine PD-L1 antibody 6C11-3A11 were identified from a hybridoma producing the antibody by RACE method. The complementarity-determining regions (CDRs) of rat anti-bovine PD-L1 antibody 6C11-3A11 were determined using NCBI IGBLAST (http://www.ncbi.nlm.nih.gov/igblast/). The results are shown in FIG. 2.

2.6 Immunohistochemical Staining of Canine Tumor Tissues and Ovine/Porcine Infected Tissues In order to confirm that rat anti-bovine PD-L1 antibody 6C11-3A1 is applicable to PD-L1 immunohistochemical staining of canine tumors, formalin-fixed and paraffin-embedded canine tumor samples were immunohistochemically stained. According to conventional methods, the resultant samples were deparaffinized and then subjected to microwave treatment (5 min, twice) in citrate buffer. Subsequently, the samples were reacted with PD-L1 antibody 6C11-3A11 (400-fold dilution) for 30 min and then with Simple Stain Mouse MAX-PO (Rat) (Nichirei Bioscience) for 30 mm. For coloring, diaminobenzidine (DAB) was reacted for 10 min.

The results are shown in FIGS. 3, 4, 5-1, 5-2, 6 and 7.

Figure 3:
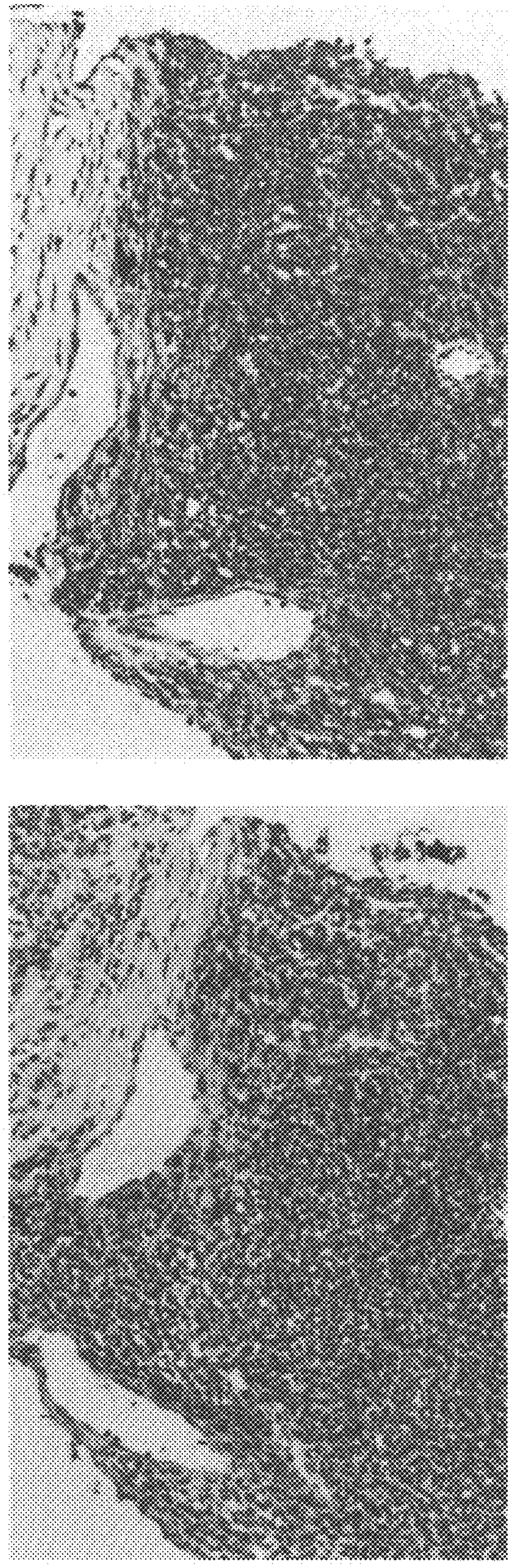
FIG. 3 Comparative immunohistochemical staining images of canine melanoma. Left: stained with a commercial antibody (MelanA antibody). Tumor cells were stained very weakly. Right: stained with the PD-L1 antibody 6C11-3A11 established by the present inventors. Tumor cells were stained very strongly.
Figure 4:
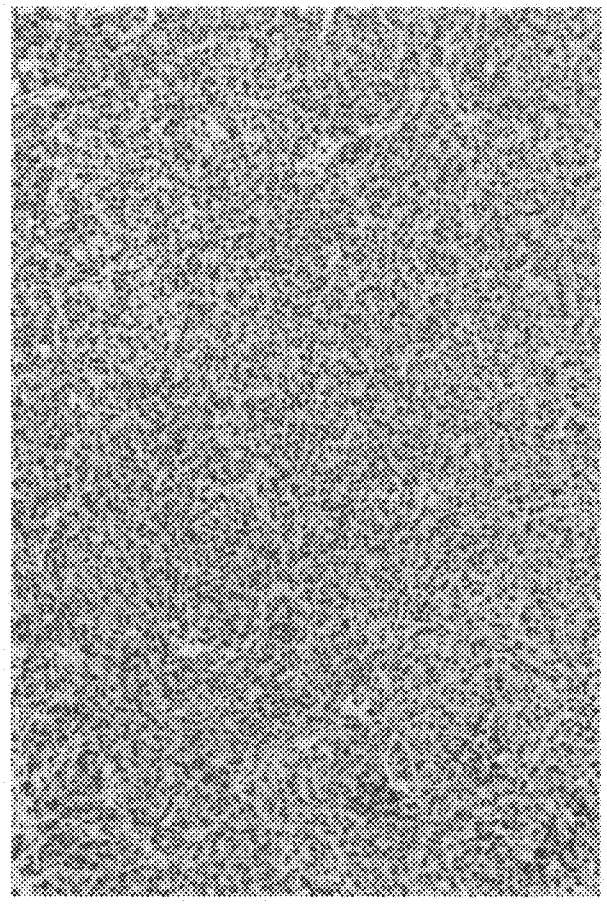
FIG. 4 Immunohistochemical staining image of canine melanoma.

Anti-MelanA antibody, the only commercially available antibody specific to melanoma, stained tumor cells very weakly (FIG. 3, left). On the other hand, the PD-L1 antibody (6C11-3A11) established by the present inventors stained tumor cells very strongly (FIG. 3. Right). The PD-L1 antibody (6C11-3A11) was capable of staining almost all cases of melanoma.

In canine melanoma, tumor cells were found diffusely positive for the PD-L1 antibody (6C1-3A11). (Positive number/tested number=12/12: positive rate 100%)

In canine lymphoma, tumor cells were found diffusely positive for the PD-L1 antibody (6C11-3A11). In canine osteosarcoma, some tumor cells were stained intracellularly.

In canine renal cell carcinoma, tumor cells were found diffusely positive in various tissue types.

Figure 6:
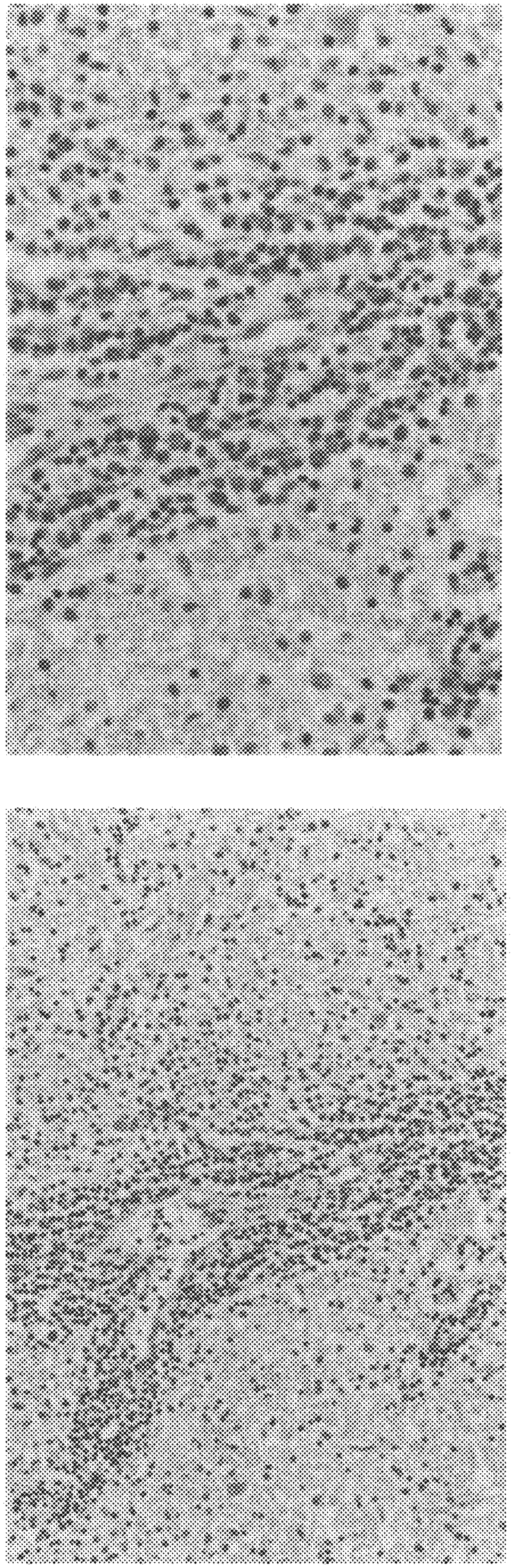
FIG. 6 Immunohistochemical staining image of a case of ovine listeriosis. Left: PD-L1 staining image of a brain lesion of ovine listeriosis exhibiting neurologic symptoms. Right: enlarged photograph of the left image.

In a case of ovine listeriosis, a PD-L1 staining image of a brain lesion of ovine listeriosis showing neurologic symptoms is shown in FIG. 6, left panel. In an enlarged photograph of this image, expression of PD-L1 was observed in macrophages infiltrating into brain lesions (FIG. 6, Right).

Figure 7:
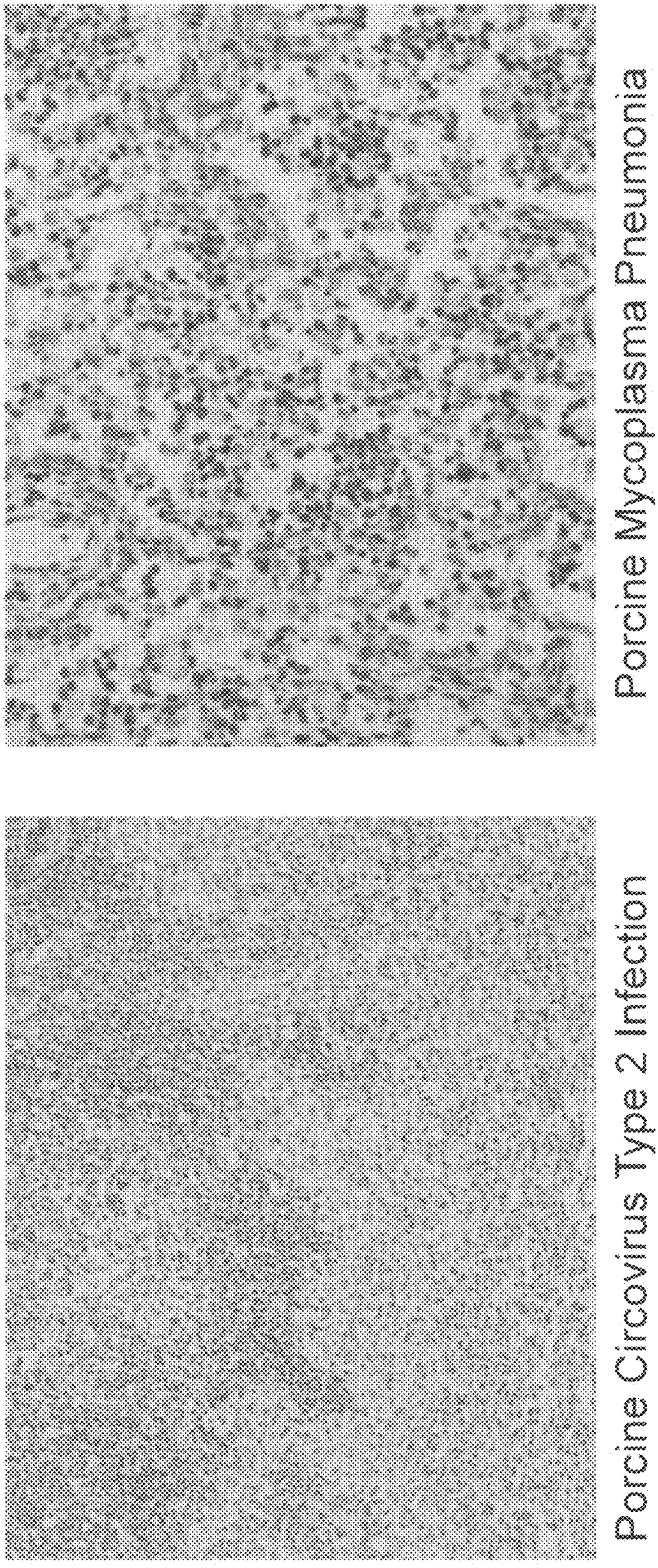
FIG. 7 Immunohistochemical staining images of porcine infections. Left: case of porcine circovirus type 2 infection. Right: case of porcine mycoplasma pneumonia.

In a case of porcine circovirus type 2 infection, PD-L1 was stained with lymphoid follicles, and virus was stained in these cells (FIG. 7, Left).

In a case of porcine mycoplasma pneumonia, a great number of macrophages infiltrated pulmonary lesions, and PD-L1 was stained in these infiltrating cells (FIG. 7, Right).

As described so far, anti-bovine PD-L1 antibody 6C11-3A11 may be used for detecting PD-L1 in various canine tumors (such as malignant melanoma) and ovine/porcine infections by immunohistochemical staining. This suggests the possibility of using anti-bovine PD-L1 antibody 6C11-3A11 for diagnosis in a multiple-animal and a multiple-disease manner.

Example 2J

1. Introduction

Monoclonal antibodies may be produced by culturing hybridomas and purifying antibodies from the resultant culture supernatants. Alternatively, when the nucleotide sequence of an antibody of interest has been identified, a cell expressing the antibody may be prepared by transfecting cultured cells with a vector for expressing the nucleotide sequence; the thus prepared antibody expressing cell may be used as a substitute for hybridoma. In the subject Example, a method will be illustrated below in which an antibody is produced by a protein expression system using an expression vector and a mammalian cell.

2. Materials and Methods 2.1 Preparation of Rat Anti-Bovine PD-L1 Antibody 6C11-3A1 Expression Vector Based on the nucleotide sequence of rat anti-bovine PD-L1 antibody 6C1-3A11 identified in 2.5 of Example 1 above, gene synthesis is performed so that NotI restriction enzyme recognition site, KOZAK sequence, antibody's light chain sequence, poly-A addition signal sequence (PABGH), promoter sequence (PCMV), SacI restriction enzyme recognition site, intron sequence (INRBG), KOZAK sequence, antibody's heavy chain sequence and XbaI restriction enzyme recognition site will be located in this order. In this case, codons of the antibody gene may have been optimized in advance depending on the type of the cell that is to express the gene. The synthesized gene strand is incorporated into an expression vector pDC6 (kindly provided by Prof. S. Suzuki, Research Center for Zoonosis Control, Hokkaido University) at the cloning site (NotI and XbaI restriction enzyme recognition sequences located downstream of PCMV and between INRBG and PABGH) using restriction enzyme recognition sequences so that the above-listed sequences will be located in the above-mentioned order to thereby construct a rat anti-bovine PD-L1 antibody expressing vector pDC6.

2.2 Expression of Rat Anti-Bovine PD-L1 Antibody 6C11-3A11

The rat anti-bovine PD-L1 antibody expressing vector pDC6 as prepared in 2.1 above is transfected into CHO-DG44 cells (CHO-DG44($dfhr^{-/-}$)) which are dihydrofolate reductase deficient cells, and high expression clones are selected by dot blotting. For increased expression, gene amplification treatment may be performed by adding load on cells in a medium containing 60 nM, 250 nM or 1000 nM methotrexate (Mtx). The thus prepared cells stably expressing rat anti-bovine PD-L1 antibody 6C11-3A11 are transferred to Mtx-free Opti-CHO medium. By culturing those cells under shaking for 14 days (125 rpm, 37° C., 5% $CO_2$), a culture supernatant containing the antibody of interest can be obtained. The antibody in the culture supernatant may be purified by known methods such as affinity chromatography or ion exchange chromatography for use in various experiments.

Example 3

1. Introduction

For the purpose of establishing a novel diagnosis method for tumor diseases, a rat-human chimeric anti-PD-L1 antibody is obtained in the subject Example by culturing Chinese hamster ovary cells (CHO cells) that will express a chimeric antibody gene in which the variable region gene of rat anti-bovine PD-L antibody 6C11-3A11 is combined with the constant region gene of human immunoglobulin (IgG4).

Figure 10:
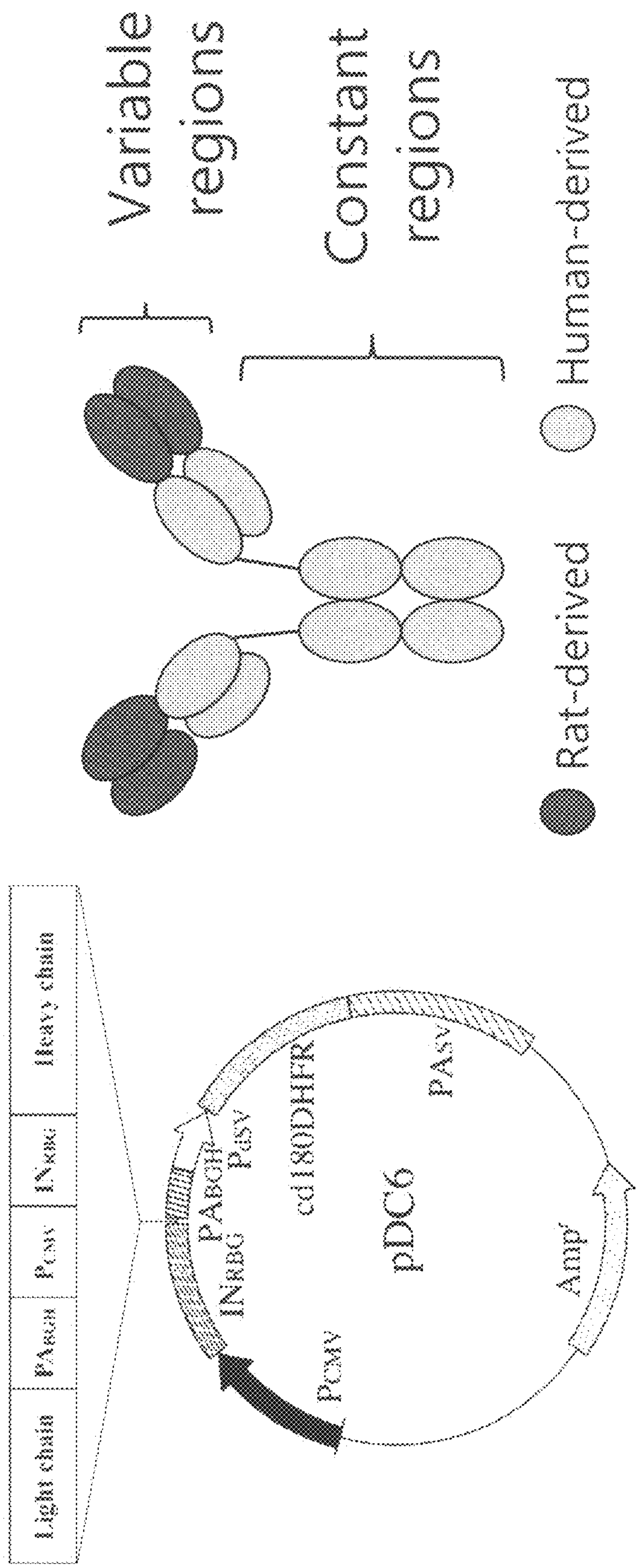
FIG. 10 Schematic drawing of pDC6 vector and a rat-human chimeric anti-PD-L1 antibody.

2. Materials and Methods 2.1 Preparation of Rat-Human Chimeric Anti-PD-L1 Expression Vector (FIG. 10)

Hereinbelow, a rat-human chimeric anti-PD-L1 antibody is established using rat anti-bovine PD-L1 monoclonal antibody 6C1-3A11 as its variable region.

Briefly, heavy chain and light chain variable region genes were identified from a hybridoma producing the rat anti-bovine PD-L1 antibody 6C11-3A11. Further, a nucleotide sequence was prepared by linking the heavy chain and light chain variable region genes of the above rat antibody to the constant region of heavy chain IgG4 and the constant region of light chain Kappa of a known human antibody, respectively. After codon optimization, gene synthesis is performed so that NotI restriction enzyme recognition site, KOZAK sequence, chimeric antibody's light chain sequence, poly-A addition signal sequence (PABGH), promoter sequence (PCMV), SacI restriction enzyme recognition site, intron sequence (INRBG), KOZAK sequence, chimeric antibody's heavy chain sequence and XbaI restriction enzyme recognition site will be located in this order. The synthesized gene strand is incorporated into the expression vector pDC6 (kindly provided by Prof. S. Suzuki, Research Center for Zoonosis Control, Hokkaido University) at the cloning site (NotI and XbaI restriction enzyme recognition sequences located downstream of PCMV and between INRBG and PABGH) using restriction enzyme recognition sequences so that the above-listed sequences will be located in the above-mentioned order (FIG. 10). Thus, a rat-human chimeric anti-PD-L1 antibody expressing vector is constructed. This expression vector is transfected into CHO-DG44 cells (CHO-DG44($dfhr^{-/-}$)) which are dihydrofolate reductase deficient cells, and high expression clones are selected by dot blotting. For increased expression, gene amplification treatment may be performed by adding load on cells in a medium containing 60 nM, 250 nM or 1000 nM methotrexate (Mtx). The thus prepared cells stably expressing rat-human chimeric anti-PD-L1 antibody 6C11-3A11 are transferred to Mtx-free Opti-CHO medium. By culturing those cells under shaking for 14 days (123 rpm, 37° C., 5% $CO_2$), a culture supernatant containing the antibody of interest can be obtained. The antibody in the culture supernatant may be purified by known methods such as affinity chromatography or ion exchange chromatography for use in various experiments.

Example 41

1. Introduction

With respect to PD-L1 in canine tumors, a detection method by immunohistochemical staining with rat anti-bovine PD-L1 antibody 6G7-E1 was previously established, and the expression profiles in various tumors have been reported (Maekawa N, Konnai S, Okagawa T, Ikebuchi R, Izumi Y, Takagi S, Kagawa Y, Nakajima C, Suzuki Y, Kato Y, Murata S. Ohashi K. PLoS One. 2016 Jun. 11(6): e0157176). In the subject Example, in order to examine whether rat anti-bovine PD-L1 antibody 6C11-3A11 is more useful than existing anti-PD-L1 antibody 6G7-E1 in expression analysis of PD-L1 in canine tumors, immunohistochemical staining of various canine tumors was performed to thereby directly compare the PD-L1 detection sensitivities of 6G7-E1 and 6C11-3A11.

2. Materials and Methods 2.1 Comparison by Flow Cytometry Using Canine PD-L-EGFP Stably Expressing CHO-DG44 Cells (FIG. 11)

First, in order to prepare canine PD-L1 membrane expressing cells, 2.5 μg of canine PD-L1-EGFP expression plasmid (pEGFP-N2-cPD-L1) prepared in 2.3 of Example 1 or pEGFP-N2 (negative control) was introduced into $4\times10^6$ CHO-DG44 cells using Lipofectamine LTX (Invitrogen). Forty-eight hours later, the medium was exchanged with CD DG44 medium (Life Technologies) containing G418 (Enzo Life Science) 800 μg/ml, GlutaMAX supplement (Life Technologies) 20 ml-L, and 10% Pluronic F-68 (Life Technologies) 18 ml/L, followed by selection of stably expressing cells and cloning by limiting dilution. The thus prepared canine PD-L1 membrane expressing cell or EGFP expressing cell was reacted with rat anti-bovine PD-L1 antibody 6C11-3A11 or 6G7-E1 at room temperature for 30 min. After washing, antibodies binding to cell surfaces were detected with Allophycocyanine-labeled goat anti-rat Ig antibody (Beckman Coulter). For analysis, FACS Verse (Becton. Dickinson and Company) was used. As a negative control, rat IgG2a (κ) or IgM (κ) isotype control (BD Bioscience) was used. For every washing operation and dilution of antibodies, 10% inactivated goat serum-supplemented PBS was used.

Figure 11:
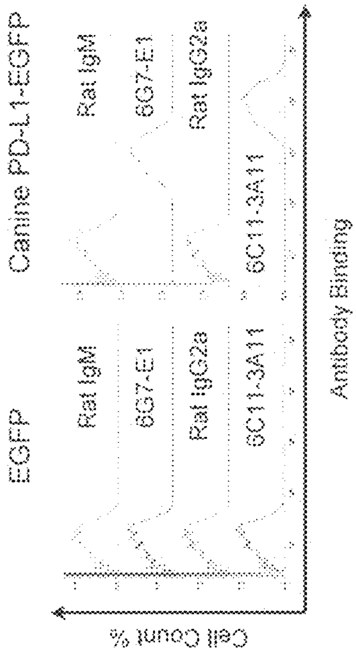
FIG. 11 Binding of rat anti-bovine PD-L1 antibodies 6C11-3A11 and 6G7-E1 to canine PD-L1-EGFP expressing cells. 6C11-3A11 specifically bound to canine PD-L1-EGFP expressing cells.

The results are shown in FIG. 11. Rat anti-bovine PD-L1 antibodies 6C11-3A11 and 6G7-E1 bound specifically to canine PD-L1 membrane expressing cells. The resultant fluorescence intensity was higher with 6C11-3A11 than with 6G7-E1, suggesting that 6C11-3A11 is an antibody with higher affinity.

2.2 Comparison of the Detection Sensitivities of Both Antibodies in PD-L1 Expression Analysis of Various Canine Tumors (Immunohistochemical Staining)

Using samples of canine skin squamous cell carcinoma (n=5), nasal adenocarcinoma (n=5), transitional cell carcinoma (n=5), anal sac gland carcinoma (n=5), soft tissue sarcoma (n=5) and osteosarcoma (n=5), immunohistochemical staining with rat anti-bovine PD-L1 antibody 6C11-3A11 was performed according to the method described in 2.6 of Example 1. With rat anti-bovine PD-L1 antibody 6G7-E1, immunohistochemical staining was performed in the same manner using sections derived from the same analytes. The final concentration of 6G7-E1 used on this occasion was 10 μg/ml, and biotin-labeled goat anti-rat IgM antibody (Jackson ImmunoResearch Laboratories) was used as a secondary antibody.

Figure 12:
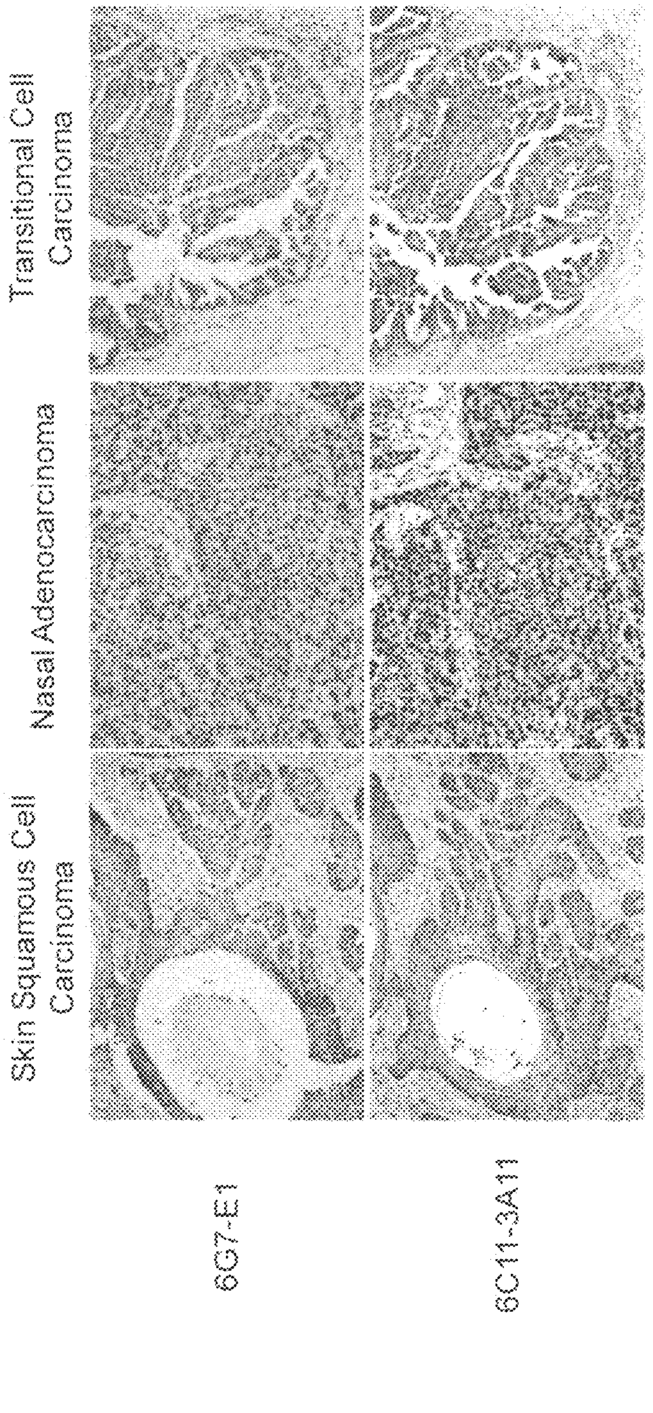
FIG. 12 Immunohistochemical staining images of skin squamous cell carcinoma, nasal adenocarcinoma and transitional cell carcinoma in dogs. No specific signals were detected with 6G7-E1. Tumor cells were stained with 6C11-3A11.
Figure 13:
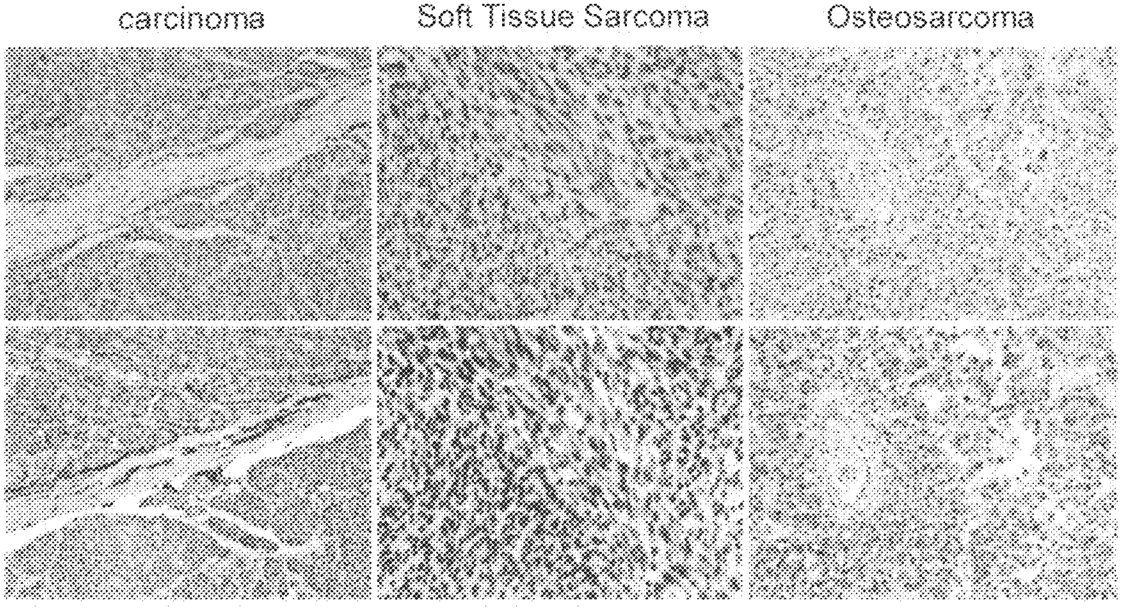
FIG. 13 Immunohistochemical staining images of anal sac gland carcinoma, soft tissue sarcoma and osteosarcoma in dogs. In anal sac gland carcinoma and soft tissue sarcoma, no specific signals were detected with 6G7-E1, but tumor cells were stained with 6C11-3A11. In osteosarcoma, both antibodies stained tumor cells, but stronger signals were obtained with 6C11-3A11.

The results are shown in FIGS. 12 and 13. While specific signals were not observed in squamous cell carcinoma, nasal adenocarcinoma, transitional cell carcinoma, anal sac gland carcinoma and soft tissue sarcoma upon staining with 6G7-E1, satisfactory positive reactions were obtained upon staining with 6C11-3A11. On the other hand, specific signals were also obtained with 6G7-E1 in osteosarcoma but staining with 6C11-3A11 provided higher signal intensities. The PD-L1 positive rate of these tumors obtained by 6C11-3A11 staining was 100% (5 out of 5 cases) in all of the above-listed tumor species excepting soft tissue sarcoma which turned out to be PD-L1 positive at a rate of 80% (4 out of 5 cases).

Subsequently, samples of oral malignant melanoma (n=17), mammary adenocarcinoma (n=10), histiocytic sarcoma (n=10), diffuse large B-cell lymphoma (n=10) and transmissible venereal tumor (n=4) were immunohistochemically stained with 6C11-3A11 to analyze PD-L1 expression therein.

Figure 14:
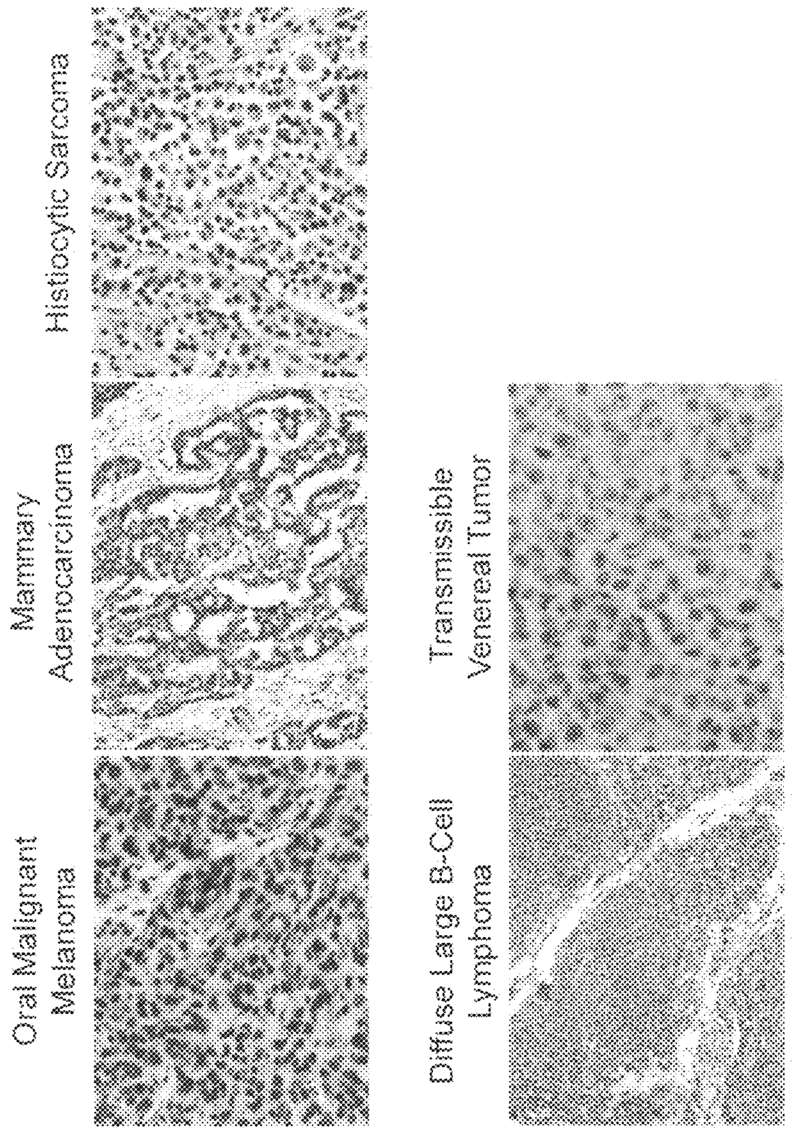
FIG. 14 Immunohistochemical staining images of oral malignant melanoma, mammary adenocarcinoma, histiocytic sarcoma, diffuse large B-cell lymphoma and transmissible venereal tumor in dogs using 6C11-3A11. In the tumor species other than transmissible venereal tumor, PD-L1 on tumor cells was stained.

The results are shown in FIG. 14. The PD-L1 positive rate was 100% in oral malignant melanoma (17 out of 17 cases), 100% in mammary adenocarcinoma (10 out of 10 cases), 20% in histiocytic sarcoma (2 out of 10 cases), 20% in diffuse large B-cell lymphoma (2 out of 10 cases) and 0% in transmissible venereal tumor (0 out of 4 cases).

The above-described results revealed that 6C11-3A1 is superior to the existing anti-PD-L1 antibody 6G7-E1 in the detection of canine PD-L1.

Example 5

1. Introduction

Johne's disease is a bovine chronic infection caused by *Mycobacterium avium* subsp. *paratuberculosis*. In cattle affected with Johne's disease. PD-L1 expression has been confirmed in *M. avium* subsp. *paratuberculosis*-infected cells in ileal lesions which are a localized site of infection with this bacterium (Okagawa T, Konnai S, Nishimori A, Ikebuchi R, Mizorogi S. Nagata R, Kawaji S. Tanaka S, Kagawa Y. Murata S, Mori Y and Ohashi K. Infect Immun, 84:77-89, 2016). In the subject Example, immunohistochemical staining of ileai lesions of cattle with Johne's disease was performed in order to examine whether rat anti-bovine PD-L1 antibody 6C11-3A11 could be used for detecting bovine PD-L1 or not.

2. Materials and Methods 2.1. Construction of Bovine PD-L1 Expressing Cells

The nucleotide sequence of the full-length cDNA of bovine PD-L1 gene (GenBank accession number ABS10902; Ikebuchi R. Konnai S. Shirai T, Sunden Y, Murata S, Onuma M, Ohashi K Vet. Res. 2011 Sep. 26: 42:103) was determined. Based on the resultant nucleotide sequence, bovine PD-L1 membrane expressing cells were prepared. First, for preparing a bovine PD-L1 expressing plasmid, PCR was performed using a synthesized bovine PBMC-derived cDNA as a template and primers having NheI and XhoI recognition sites added on the 5' side (boPD-L1-EGFP F and R). The PCR products were digested with NheI (Takara) and XhoI (Takara), purified with FastGene Gel/PCR Extraction Kit (NIPPON Genetics) and cloned into pEGFP-N2 vector (Clontech) that had been subjected to similar restriction enzyme treatments. The resultant expression plasmid of interest was extracted with QIAGEN Plasmid Midi kit (Qiagen) and stored at −30° C. until use in experiments. Hereinafter, the thus prepared expression plasmid is designated as pEGFP-N2-boPD-L1.

```
Primer (boPD-L1-EGFP F):
                                    (SEQ ID NO: 124)
CTAGCTAGCACCATGAGGATATATAGTGTCTTAAC

Primer (boPD-L1-EGFP R)
                                    (SEQ ID NO: 125)
CAATCTCGAGTTACAGACAGAAGATGACTGC
```

Bovine PD-L1 membrane expressing cells were prepared by the procedures described below. First, 2.5 μg of pEGFP-N2-boPD-L1 or pEGFP-N2 (negative control) was introduced into $4\times10^6$ CHO-DG44 cells using Lipofectamine LTX (Invitrogen). Forty-eight hours later, the medium was exchanged with CD DG44 medium (Life Technologies) containing G418 (Enzo Life Science) 800 μg/ml, GlutaMAX supplement (Life Technologies) 20 ml/L, and 10% Pluronic F-68 (Life Technologies) 18 ml/L; thereafter, selection was performed simultaneously with cloning by limiting dilution (bovine PD-L1 expressing cell and EGFP expressing cell). In order to confirm the expression of bovine PD-L1 in the thus prepared bovine PD-L1 expressing cell, intracellular localization of EGFP was visualized with an inverted confocal laser microscope LSM700 (ZEISS).

2.2. Binding Specificity of Rat Anti-Bovine PD-L1 Antibody 6C11-3A11 to Bovine PD-L1

It was confirmed by flow cytometry that rat anti-bovine PD-L1 antibody 6C11-3A11 specifically binds to the bovine PD-L1 expressing cell (described above). First, rat anti-bovine PD-L1 antibody 6C11-3A11 or rat IgG2a (κ) isotype control (BD Biosciences) as a negative control was reacted with the bovine PD-L1 expressing cell or the EGFP expressing cell (negative control) at room temperature for 30 min. After washing, APC-labeled anti-rat 1 g goat antibody (Southern Biotech) was reacted at room temperature for 30 min. After washing, antibodies bound to cell surfaces were detected by FACS Verse (BD Biosciences). For every washing operation and dilution of antibody. PBS supplemented with 1% bovine serum albumin (Sigma-Aldrich) was used.

Figure 15:
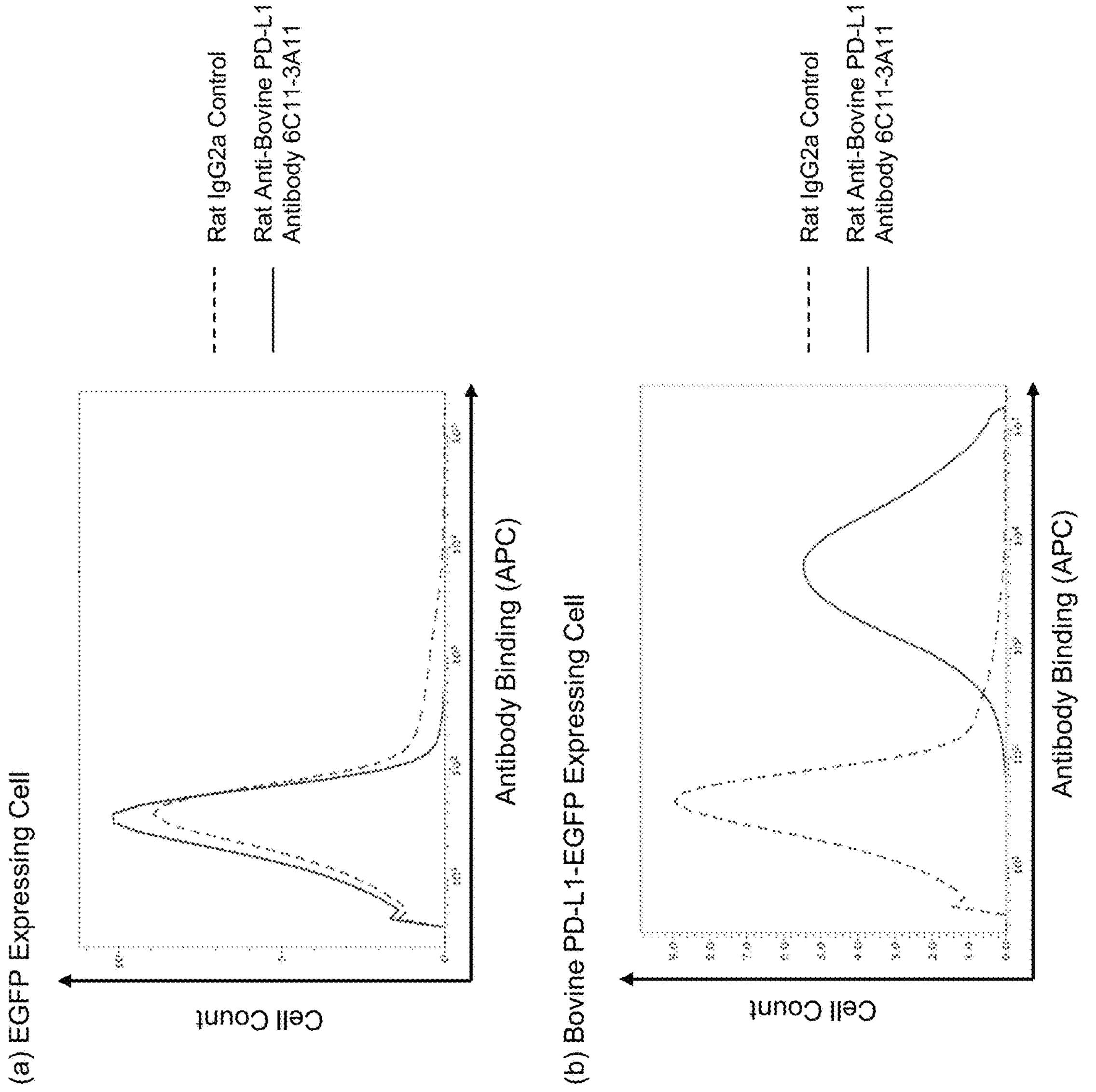
FIG. 15 Binding of rat anti-bovine PD-L1 antibody 6C11-3A11 to bovine PD-L1-EGFP expressing cells. 6C11-3A11 specifically bound to bovine PD-L1-EGFP expressing cells.

The results are shown in FIG. 15. It was revealed that rat anti-bovine PD-L1 antibody 6C11-3A11 binds specifically to the bovine PD-L1 expressing cell.

2.3. Immunohistochemical Staining Using Tissue Samples from Infected Cattle

In order to confirm that rat anti-bovine PD-L1 antibody 6C11-3A11 is applicable to PD-L1 immunohistochemical staining of bovine tissues, immunohistociemical staining was performed with formalin-fixed, paraffin-embedded bovine tissue samples. Briefly, ilium tissue blocks from cattle which naturally developed Johne's disease (#1, presenting clinical symptoms of Johne's disease such as diarrhea and severe emaciation), cattle experimentally infected with *M. avium* subsp. *paratuberculosis* (#65, clinical symptoms such as shedding of *M. avium* subsp. *paratuberculosis* and diarrhea were observed; Okagawa T. Konnai S, Nishimori A, Ikebuchi R, Mizorogi S, Nagata R, Kawaji S. Tanaka S, Kagawa Y, Murata S, Mori Y and Ohashi K. Infect Immun, 84:77-89, 2016) and uninfected control cattle (C #6) (the blocks kindly provided by Dr. Yasuyuki Mori, National Institute of Animal Health, National Agriculture and Food Research Organization) were used for staining. According to conventional methods, the stained samples were deparaffinized and then subjected to microwave treatment (5 min, twice) in citrate buffer. Subsequently, the samples were reacted with rat anti-bovine PD-L1 antibody 6C11-3A11 (400-fold dilution) for 30 min and then with Simple Stain Mouse MAX-PO (Rat) (Nichirei Bioscience) for 30 min. Finally, the samples were reacted with diarninobenzidine (DAB) for 10 min for coloring, followed by observation with an optical microscope.

Figure 16:
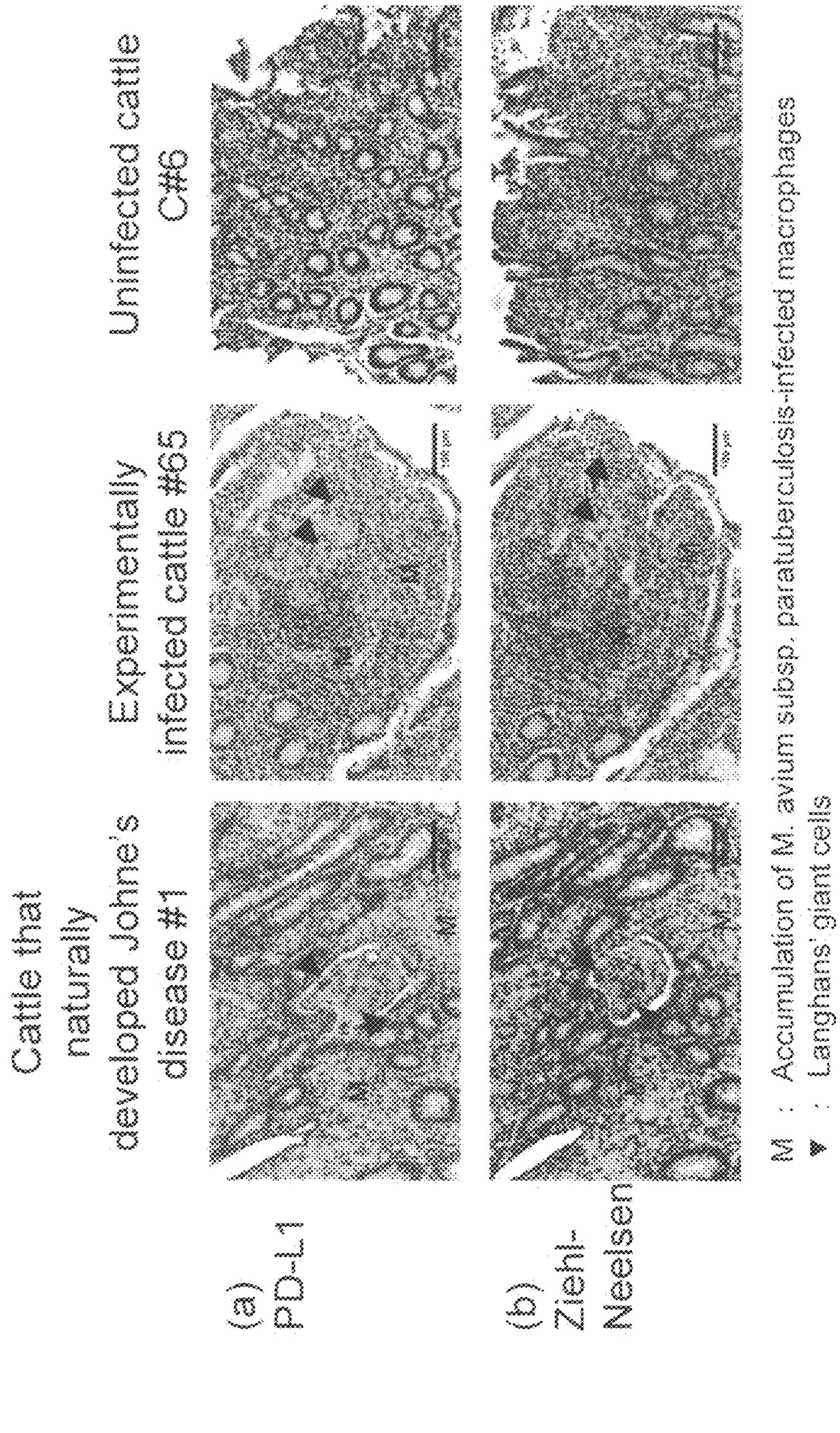
FIG. 16 Immunohistochemical staining images of ileal lesions of cattle naturally and experimentally infected with *Mycobacterium avium* subsp. *paratuberculosis*, using (a) 6C11-3A11 and (b) Ziehl-Neelsen staining. 6C11-3A11 detected PD-L1 expression in cells infected with *M. avium* subsp. *paratuberculosis* (positive in Ziehl-Neelsen staining).

The results are shown in FIG. 16. Rat anti-bovine PD-L1 antibody 6C11-3A11 detected expression of PD-L in *M. avium* subsp. *paratuberculosis*-infected cells (confirmed by Ziehl-Neelsen staining) in ileal lesions of cattle #1 that naturally developed Johne's disease and experimentally infected cattle #65 (FIG. 16*a, b*). On the other hand, PD-L1 was not expressed in the ileum of uninfected cattle (C #6), so reaction of rat anti-bovine PD-L1 antibody 6C11-3A11 (non-specific reaction) was not recognized (FIG. 16*a*).

As described above, it was shown that rat anti-bovine PD-L1 antibody 6C11-3A11 can be used for detecting PD-L1 in bovine tissues by immunohistochemical staining.

All publications, patents and patent applications cited herein are incorporated herein by reference in their entirety.

INDUSTRIAL APPLICABILITY

The anti-PD-L1 antibody of the present invention is applicable to diagnosis of cancers and/or infections. Further, the anti-PD-L1 antibody of the present invention is also applicable to selection of subject animals suitable for therapy with anti-PD-L1 antibodies.

SEQUENCE LISTING FREE TEXT

<SEQ ID NO: 1>

SEQ ID NO: 1 shows the amino acid sequence of CDR1 of the light chain variable region (VL) of anti-PD-L1 antibody 6C11-3A11 (IgG2a).

KSISKY

<SEQ ID NO: 2>

SEQ ID NO: 2 shows the amino acid sequence of CDR3 of the VL of anti-PD-L1 antibody 6C11-3A11 (IgG2a).

QQHNEYPLT

<SEQ ID NO: 3>

SEQ ID NO: 3 shows the amino acid sequence of CDR1 of the heavy chain variable region (VH) of anti-PD-L1 antibody 6C11-3A11

-continued (IgG2a).

GYTFTDYI

<SEQ ID NO: 4>
SEQ ID NO: 4 shows the amino acid sequence of CDR2 of the VH of anti-PD-L1 antibody 6C11-3A11 (IgG2a).

INPDSGGN

<SEQ ID NO: 5>
SEQ ID NO: 5 shows the amino acid sequence of CDR3 of the VH of anti-PD-L1 antibody 6C11-3A11 (IgG2a).

ARGITMMVVISHWKFDF

<SEQ ID NO: 6>
SEQ ID NO: 6 shows the amino acid sequence of the VL of anti-PD-L1 antibody 6C11-3A11 (IgG2a).

MRVQIQFWGLLLLWTSGIQCDVQMTQSPSNLAASPGESVSINCKASKSISKYLAWYQQKPGKANK
LLIYSGSTLQSGTPSRFSGSGSGTDFTLTIRNLEPEDFGLYYCQQHNEYPLTFGSGTKLEIK

<SEQ ID NO: 7>
SEQ ID NO: 7 shows the amino acid sequence of the VH of anti-PD-L1 antibody 6C11-3A11 (IgG2a).

MGWICIIFLVAIATGAHSQVKLLQSGAALVKPGDSVKMSCKASGYFTFDYIIHWVKQSHGKSLEW
IGYINDPSGGNNYNEKFKSKATLTVDKSSSTAYMEFSRLTSEDSAIYYCARGITMMVVISHWKFD
FWGPGTMVTVSS

<SEQ ID NO: 8>
SEQ ID NO: 8 shows the amino acid sequence of the light chain (kappa chain) constant region of anti-PD-L1 antibody 6C11-3A11 (IgG2a).

RADAAPTVSIFPPSTEQLATGGASVVCLMNNFYPRDISVKWKIDGTERRDGVLDSVTDQDSKDST
YSMSSTLSLTKADYESHNLYTCEVVHKTSSSPVVKSFNRNEC*

<SEQ ID NO: 9>
SEQ ID NO: 9 shows the amino acid sequence of the heavy chain constant region (CH) of anti-PD-L1 antibody 6C11-3A11 (IgG2a).

AETTAPSVYPLAPGTALKSNSMVTLGCLVKGYFPEPVTVTWNSGALSSGVHTFPAVLQSGLYTLT
SSVTVPSSTWSSQAVTCNVAHPASSTKVDKKIVPRECNPCGCTGSEVSSVFIFPPKTKDVLTITL
TPKVTCVVVDISQNDPEVRFSWFIDDVEVHTAQTHAPEKQSNSTLRSVSELPIVHRDWLNGKTFK
CKVNSGAFPAPIEKSISKPEGTPRGPQVYTMAPPKEEMTQSQVSITCMVKGFYPPDIYTEWKMNG
QPQENYKNTPPTMDTDGSYFLYSKLNVKKETWQQGNTFTCSVLHEGLHNHHTEKSLSHSPGK*

<SEQ ID NO: 10>
SEQ ID NO: 10 shows the amino acid sequence (GenBank: #V01241.1) of the light chain (kappa chain) constant region of a rat antibody (IgG2a).

-continued

ADAAPTVSIFPPSTEQLATGGASVVCLMNNFYPRDISVKWKIDGTERRDGVLDSVTDQDSKDSTY
SMSSTLSLTKADYESHNLYTCEVVHKTSSSPVVKSFNRNEC*

<SEQ ID NO: 11>

SEQ ID NO: 11 shows the amino acid sequence (GenBank: #X16129.1) of the light chain (kappa chain) constant region of a rat antibody (IgG2a).

RADAAPTVSIFPPSTEQLATGGASVVCLMNNFYPRDISVKWKIDGTERRDGVLDSVTDQDSKDST
YSMSSTLSLSKADYESHNLYTCEVVHKTSSSPVVKSFNRNEC

<SEQ ID NO: 12>

SEQ ID NO: 12 shows the amino acid sequence (GenBank: #DQ402471.1) of the light chain (kappa chain) constant region of a rat antibody (IgG2a).

AAPTVSIFPPSMEQLTSGGATVVCFVNNFYPRDISVKWKIDGSEQRDGVLDSVTDQDSKDSTYSM
SSTLSLTKVEYERHNLYTCEVVHKTSSSPVVKSFNRNEC*

<SEQ ID NO: 13>

SEQ ID NO: 13 shows the amino acid sequence (GenBank: #DQ402472.1) of the CH of a rat antibody (IgG2a).

APSVYPLAPGTALKSNSMVTLGCLVKGYFPEPVTVTWNSGALSSGVHTFPAVLQSGLYTLTSSVT
VPSSTWSSQAVTCNVAHPASSTKVDKKIVPRECNPCGCTGSEVSSVFIFPPKTKDVLTITLTPKV
TCVVVDISQNDPEVRFSWFIDDVEVHTAQTHAPEKQSNSTLRSVSELPIVHRDWLNGKTFKCKVN
SGAFPAPIEKSISKPEGTPRGPQVYTMAPPKEEMTQSQVSITCMVKGFYPPDIYTEWKMNGQPQE
NYKNTPPTMDTDGSYFLYSKLNVKKETWQQGNTFTCSVLHEGLHNHHTEKSLSHSPGK*

<SEQ ID NO: 14>

SEQ ID NO: 14 shows the nucleotide sequence of the VL of anti-PD-L1 antibody 6C11-3A11 (IgG2a).

ATGAGGGTCCAGATTCAGTTTTGGGGGCTTCTTCTGCTCTGGACATCAGGTATACAGTGTGATGT
CCAGATGACCCAGTCTCCATCTAATCTTGCTGCCTCTCCTGGAGAAAGTGTTTCCATCAATTGCA
AGGCAAGTAAGAGCATTAGCAAGTATTTAGCCTGGTATCAACAGAAACCTGGGAAAGCAAATAAG
CTTCTTATCTACTCTGGGTCAACTTTGCAATCTGGAACTCCATCGAGGTTCAGTGGCAGTGGATC
TGGTACAGATTTCACTCTCACCATCAGAAACCTGGAGCCTGAAGATTTTGGACTCTATTACTGTC
AACAGCATAATGAATACCCGCTCACGTTCGGTTCTGGGACCAAGCTGGAGATCAAA

<SEQ ID NO: 15>

SEQ ID NO: 15 shows the nucleotide sequence of the VH of anti-PD-L1 antibody 6C11-3A11 (IgG2a).

ATGGGATGGATCTGTATCATCTTTCTTGTGGCAATAGCTACAGGTGCCCACTCCCAGGTCAAGCT
GCTGCAGTCTGGGGCTGCACTGGTGAAGCCTGGGGACTCTGTGAAGATGTCTTGCAAAGCTTCTG
GTTATACATTCACTGACTACATTATACACTGGGTGAAGCAGAGTCATGGAAAAAGCCTTGAGTGG
ATTGGTTATATTAATCCTGACAGTGGTGGTAATAACTACAATGAAAAGTTCAAGAGCAAGGCCAC
ATTGACTGTAGACAAATCCAGCAGCACAGCCTATATGGAGTTTAGCAGATTGACATCTGAGGATT
CTGCAATCTACTACTGTGCAAGAGGGATTACCATGATGGTAGTTATTAGCCACTGGAAGTTTGAC
TTCTGGGGCCCAGGAACCATGGTCACCGTGTCCTCA

<SEQ ID NO: 16>

-continued

SEQ ID NO: 16 shows the nucleotide sequence of the light chain (kappa chain) constant region of anti-PD-L1 antibody 6C11-3A11 (IgG2a).

CGGGCTGATGCTGCACCAACTGTATCTATCTTCCCACCATCCACGGAACAGTTAGCAACTGGAGG
TGCCTCAGTCGTGTGCCTCATGAACAACTTCTATCCCAGAGACATCAGTGTCAAGTGGAAGATTG
ATGGCACTGAACGACGAGATGGTGTCCTGGACAGTGTTACTGATCAGGACAGCAAAGACAGCACG
TACAGCATGAGCAGCACCCTCTCGTTGACCAAGGCTGACTATGAAAGTCATAACCTCTATACCTG
TGAGGTTGTTCATAAGACATCATCCTCACCCGTCGTCAAGAGCTTCAACAGGAATGAGTGTTAG

<SEQ ID NO: 17>

SEQ ID NO: 17 shows the nucleotide sequence of the CH of anti-PD-L1 antibody 6C11-3A11 (IgG2a).

GCTGAAACAACAGCCCCATCTGTCTATCCACTGGCTCCTGGAACTGCTCTCAAAAGTAACTCCAT
GGTGACCCTGGGATGCCTGGTCAAGGGCTATTTCCCTGAGCCAGTCACCGTGACCTGGAACTCTG
GAGCCCTGTCCAGCGGTGTGCACACCTTCCCAGCTGTCCTGCAGTCTGGACTCTACACTCTCACC
AGCTCAGTGACTGTACCCTCCAGCACCTGGTCCAGCCAGGCCGTCACCTGCAACGTAGCCCACCC
GGCCAGCAGCACCAAGGTGGACAAGAAAATTGTGCCAAGGGAATGCAATCCTTGTGGATGTACAG
GCTCAGAAGTATCATCTGTCTTCATCTTCCCCCCAAAGACCAAAGATGTGCTCACCATCACTCTG
ACTCCTAAGGTCACGTGTGTTGTGGTAGACATTAGCCAGAATGATCCCGAGGTCCGGTTCAGCTG
GTTTATAGATGACGTGGAAGTCCACACAGCTCAGACTCATGCCCCGGAGAAGCAGTCCAACAGCA
CTTTACGCTCAGTCAGTGAACTCCCCATCGTGCACCGGGACTGGCTCAATGGCAAGACGTTCAAA
TGCAAAGTCAACAGTGGAGCATTCCCTGCCCCCATCGAGAAAAGCATCTCCAAACCCGAAGGCAC
ACCACGAGGTCCACAGGTATACACCATGGCGCCTCCCAAGGAAGAGATGACCCAGAGTCAAGTCA
GTATCACCTGCATGGTAAAAGGCTTCTATCCCCCAGACATTTATACGGAGTGGAAGATGAACGGG
CAGCCACAGGAAAACTACAAGAACACTCCACCTACGATGGACACAGATGGGAGTTACTTCCTCTA
CAGCAAGCTCAATGTAAAGAAAGAAACATGGCAGCAGGGAAACACTTTCACGTGTTCTGTGCTGC
ATGAGGGCCTGCACAACCACCATACTGAGAAGAGTCTCTCCCACTCTCCTGGTAAATGA

<SEQ ID NO: 18>

SEQ ID NO: 18 shows the nucleotide sequence (GenBank: #V01241.1) of the light chain (kappa chain) constant region of a rat antibody (IgG2a).

GGGCTGATGCTGCACCAACTGTATCTATCTTCCCACCATCCACGGAACAGTTAGCAACTGGAGGT
GCCTCAGTCGTGTGCCTCATGAACAACTTCTATCCCAGAGACATCAGTGTCAAGTGGAAGATTGA
TGGCACTGAACGACGAGATGGTGTCCTGGACAGTGTTACTGATCAGGACAGCAAAGACAGCACGT
ACAGCATGAGCAGCACCCTCTCGTTGACCAAGGCTGACTATGAAAGTCATAACCTCTATACCTGT
GAGGTTGTTCATAAGACATCATCCTCACCCGTCGTCAAGAGCTTCAACAGGAATGAGTGTTAG

<SEQ ID NO: 19>

SEQ ID NO: 19 shows the nucleotide sequence (GenBank: #X16129.1) of the light chain (kappa chain) constant region of a rat antibody (IgG2a).

CGGGCTGATGCTGCACCAACTGTATCTATCTTCCCACCATCCACGGAACAGTTAGCAACTGGAGG
TGCCTCAGTCGTGTGCCTCATGAACAACTTCTATCCCAGAGACATCAGTGTCAAGTGGAAGATTG

-continued

```
ATGGCACTGAACGACGAGATGGTGTCCTGGACAGTGTTACTGATCAGGACAGCAAAGACAGCACG

TACAGCATGAGCAGCACCCTCTCGTTGTCCAAGGCTGACTATGAAAGTCATAACCTCTATACCTG

TGAGGTTGTTCATAAGACATCATCCTCACCCGTCGTCAAGAGCTTCAACAGGAATGAGTGTTAG

                                                    <SEQ ID NO: 20>
SEQ ID NO: 20 shows the nucleotide sequence (GenBank: #DQ402471.1)

of the light chain (kappa chain) constant region of a rat

antibody (IgG2a).

GCCGCACCAACTGTATCCATCTTCCCACCATCCATGGAACAGTTAACATCTGGAGGTGCCACAGT

CGTGTGCTTCGTGAACAACTTCTATCCCAGAGACATCAGTGTCAAGTGGAAGATTGATGGCAGTG

AACAACGAGATGGTGTCCTGGACAGTGTTACTGATCAGGACAGCAAAGACAGCACGTACAGCATG

AGCAGCACCCTCTCGTTGACCAAGGTTGAATATGAAAGGCATAACCTCTATACCTGTGAGGTTGT

TCATAAGACATCATCCTCACCCGTCGTCAAGAGCTTCAACAGGAATGAGTGTTAG

                                                    <SEQ ID NO: 21>
SEQ ID NO: 21 shows the nucleotide sequence (GenBank: #DQ402472.1)

of the CH of a rat antibody (IgG2a).

CAGCCCCCTCTGTCTATCCACTGGCTCCTGGAACTGCTCTCAAAAGTAACTCCATGGTGACCCTG

GGATGCCTGGTCAAGGGCTATTTCCCTGAGCCAGTCACCGTGACCTGGAACTCTGGAGCCCTGTC

CAGCGGTGTGCACACCTTCCCAGCTGTCCTGCAGTCTGGACTCTACACTCTCACCAGCTCAGTGA

CTGTACCCTCCAGCACCTGGTCCAGCCAGGCCGTCACCTGCAACGTAGCCCACCCGGCCAGCAGC

ACCAAGGTGGACAAGAAAATTGTGCCAAGGGAATGCAATCCTTGTGGATGTACAGGCTCAGAAGT

ATCATCTGTCTTCATCTTCCCCCCAAAGACCAAAGATGTGCTCACCATCACTCTGACTCCTAAGG

TCACGTGTGTTGTGGTAGACATTAGCCAGAATGATCCCGAGGTCCGGTTCAGCTGGTTTATAGAT

GACGTGGAAGTCCACACAGCTCAGACTCATGCCCCGGAGAAGCAGTCCAACAGCACTTTACGCTC

AGTCAGTGAACTCCCCATCGTGCACCGGGACTGGCTCAATGGCAAGACGTTCAAATGCAAAGTCA

ACAGTGGAGCATTCCCTGCCCCCATCGAGAAAAGCATCTCCAAACCCGAAGGCACACCACGAGGT

CCACAGGTATACACCATGGCGCCTCCCAAGGAAGAGATGACCCAGAGTCAAGTCAGTATCACCTG

CATGGTAAAAGGCTTCTATCCCCCAGACATTTATACGGAGTGGAAGATGAACGGGCAGCCACAGG

AAAACTACAAGAACACTCCACCTACGATGGACACAGATGGGAGTTACTTCCTCTACAGCAAGCTC

AATGTAAAGAAAGAAACATGGCAGCAGGGAAACACTTTCACGTGTTCTGTGCTGCATGAGGGCCT

GCACAACCACCATACTGAGAAGAGTCTCTCCCACTCTCCTGGTAAATGA
```

<SEQ ID NOS: 22 to 27>

SEQ ID NOS: 22 to 27 show the nucleotide sequences of primers cPD-L1 inner F, cPD-L1 inner R, cPD-L1 5'GSP, cPD-L1 3'GSP, cPD-L1-EGFP F and cPD-L1-EGFP R in this order.

<SEQ ID NO: 28>

SEQ ID NO: 28 shows the amino acid sequence of the light chain (kappa chain) constant region of a human antibody.

<SEQ ID NO: 29>

SEQ ID NO: 29 shows the nucleotide sequence of the light chain (kappa chain) constant region of a human antibody.

<SEQ ID NO: 30>

SEQ ID NO: 30 shows the amino acid sequence of the CH (CH1-CH3) of a human antibody (IgG4 variant 1).

<SEQ ID NO: 31>

SEQ ID NO: 31 shows the nucleotide sequence of the CH (CH1-CH3) of a human antibody (IgG4 variant 1).

<SEQ ID NO: 32>

SEQ ID NO: 32 shows the amino acid sequence of the CH (CH1-CH3) of a human antibody (IgG4 variant 2).

<SEQ ID NO: 33>

SEQ ID NO: 33 shows the nucleotide sequence of the CH (CH1-CH3) of a human antibody (IgG4 variant 2).

<SEQ ID NO: 34>

SEQ ID NO: 34 shows the amino acid sequence of the CH (CH1-CH3) of a human antibody (IgG4 variant 3).

<SEQ ID NO: 35>

SEQ ID NO: 35 shows the nucleotide sequence of the CH (CH1-CH3) of a human antibody (IgG4 variant 3).

<SEQ ID NO: 36>

SEQ ID NO: 36 shows the amino acid sequence of the light chain (kappa chain) constant region of a mouse antibody.

<SEQ ID NO: 37>
SEQ ID NO: 37 shows the nucleotide sequence of the light chain (kappa chain) constant region of a mouse antibody.
<SEQ ID NO: 38>
SEQ ID NO: 38 shows the amino acid sequence of the light chain (kappa chain) constant region of a mouse antibody.
<SEQ ID NO: 39>
SEQ ID NO: 39 shows the nucleotide sequence of the light chain (kappa chain) constant region of a mouse antibody.
<SEQ ID NO: 40>
SEQ ID NO: 40 shows the amino acid sequence of the light chain (kappa chain) constant region of a mouse antibody.
<SEQ ID NO: 41>
SEQ ID NO: 41 shows the nucleotide sequence of the light chain (kappa chain) constant region of a mouse antibody.
<SEQ ID NO: 42>
SEQ ID NO: 42 shows the amino acid sequence of the light chain (kappa chain) constant region of a mouse antibody.
<SEQ ID NO: 43>
SEQ ID NO: 43 shows the nucleotide sequence of the light chain (kappa chain) constant region of a mouse antibody.
<SEQ ID NO: 44>
SEQ ID NO: 44 shows the amino acid sequence of the CH (CH1-CH3) of a mouse antibody (IgG1 variant 1).
<SEQ ID NO: 45>
SEQ ID NO: 45 shows the nucleotide sequence of the CH (CH1-CH3) of a mouse antibody (IgG1 variant 1).
<SEQ ID NO: 46>
SEQ ID NO: 46 shows the amino acid sequence of the CH (CH1-CH3) of a mouse antibody (IgG1 variant 2).
<SEQ ID NO: 47>
SEQ ID NO: 47 shows the nucleotide sequence of the CH (CH1-CH3) of a mouse antibody (IgG1 variant 2).
<SEQ ID NO: 48>
SEQ ID NO: 48 shows the amino acid sequence of the CH (CH1-CH3) of a mouse antibody (IgG2a variant 1).
<SEQ ID NO: 49>
SEQ ID NO: 49 shows the nucleotide sequence of the CH (CH1-CH3) of a mouse antibody (IgG2a variant 1).
<SEQ ID NO: 50>
SEQ ID NO: 50 shows the amino acid sequence of the CH (CH1-CH3) of a mouse antibody (IgG2a variant 2).
<SEQ ID NO: 51>
SEQ ID NO: 51 shows the nucleotide sequence of the CH (CH1-CH3) of a mouse antibody (IgG2a variant 2).
<SEQ ID NO: 52>
SEQ ID NO: 52 shows the amino acid sequence of the CH (CH1-CH3) of a mouse antibody (IgG2b variant 1).
<SEQ ID NO: 53>
SEQ ID NO: 53 shows the nucleotide sequence of the CH (CH1-CH3) of a mouse antibody (IgG2b variant 1).
<SEQ ID NO: 54>
SEQ ID NO: 54 shows the amino acid sequence of the CH (CH1-CH3) of a mouse antibody (IgG2b variant 2).
<SEQ ID NO: 55>
SEQ ID NO: 55 shows the nucleotide sequence of the CH (CH1-CH3) of a mouse antibody (IgG2b variant 2).
<SEQ ID NO: 56>
SEQ ID NO: 56 shows the amino acid sequence of the CH (CH1-CH3) of a mouse antibody (IgG2c variant 1).
<SEQ ID NO: 57>
SEQ ID NO: 57 shows the nucleotide sequence of the CH (CH1-CH3) of a mouse antibody (IgG2c variant 1).
<SEQ ID NO: 58>
SEQ ID NO: 58 shows the amino acid sequence of the CH (CH1-CH3) of a mouse antibody (IgG2c variant 2).
<SEQ ID NO: 59>
SEQ ID NO: 59 shows the nucleotide sequence of the CH (CH1-CH3) of a mouse antibody (IgG2c variant 2).
<SEQ ID NO: 60>
SEQ ID NO: 60 shows the amino acid sequence of the CH (CH1-CH3) of a mouse antibody (IgG2c % variant 3).
<SEQ ID NO: 61>
SEQ ID NO: 61 shows the nucleotide sequence of the CH (CH1-CH3) of a mouse antibody (IgG2c variant 3).
<SEQ ID NO: 62>
SEQ ID NO: 62 shows the amino acid sequence of the CH (CH1-CH3) of a mouse antibody (IgG3).
<SEQ ID NO: 63>
SEQ ID NO: 63 shows the nucleotide sequence of the CH (CH1-CH3) of a mouse antibody (IgG3).
<SEQ ID NO: 64>
SEQ ID NO: 64 shows the amino acid sequence of the light chain (lambda chain) constant region of a bovine antibody.
<SEQ ID NO: 65>
SEQ ID NO: 65 shows the nucleotide sequence of the light chain (lambda chain) constant region of a bovine antibody.
<SEQ ID NO: 66>
SEQ ID NO: 66 shows the amino acid sequence of the CH (CH1-CH3) of a bovine antibody (IgG1 variant 1).
<SEQ ID NO: 67>
SEQ ID NO: 67 shows the nucleotide sequence of the CH (CH1-CH3) of a bovine antibody (IgG1 variant 1).
<SEQ ID NO: 68>
SEQ ID NO: 68 shows the amino acid sequence of the CH (CH1-CH3) of a bovine antibody (IgG1 variant 2).
<SEQ ID NO: 69>
SEQ ID NO: 69 shows the nucleotide sequence of the CH (CH1-CH3) of a bovine antibody (IgG1 variant 2).
<SEQ ID NO: 70>
SEQ ID NO: 70 shows the amino acid sequence of the CH (CH1-CH3) of a bovine antibody (IgG1 variant 3).
<SEQ ID NO: 71>
SEQ ID NO: 71 shows the nucleotide sequence of the CH (CH1-CH3) of a bovine antibody (IgG1 variant 3).
<SEQ ID NO: 72>
SEQ ID NO: 72 shows the amino acid sequence of the CH (CH1-CH3) of a bovine antibody (IgG2 variant 1).
<SEQ ID NO: 73>
SEQ ID NO: 73 shows the nucleotide sequence of the CH (CH1-CH3) of a bovine antibody (IgG2 variant 1).
<SEQ ID NO: 74>
SEQ ID NO: 74 shows the amino acid sequence of the CH (CH1-CH3) of a bovine antibody (IgG2 variant 2).
<SEQ ID NO: 75>
SEQ ID NO: 75 shows the nucleotide sequence of the CH (CH1-CH3) of a bovine antibody (IgG2 variant 2).
<SEQ ID NO: 76>
SEQ ID NO: 76 shows the amino acid sequence of the CH (CH1-CH3) of a bovine antibody (IgG2 variant 3).
<SEQ ID NO: 77>
SEQ ID NO: 77 shows the nucleotide sequence of the CH (CH1-CH3) of a bovine antibody (IgG2 variant 3).
<SEQ ID NO: 78>
SEQ ID NO: 78 shows the amino acid sequence of the CH (CH1-CH3) of a bovine antibody (IgG3 variant 1).
<SEQ ID NO: 79>
SEQ ID NO: 79 shows the nucleotide sequence of the CH (CH1-CH3) of a bovine antibody (IgG3 variant 1).
<SEQ ID NO: 80>
SEQ ID NO: 80 shows the amino acid sequence of the CH (CH1-CH3) of a bovine antibody (IgG3 variant 2).

<SEQ ID NO: 81>
SEQ ID NO: 81 shows the nucleotide sequence of the CH (CH1-CH3) of a bovine antibody (IgG3 variant 2).
<SEQ ID NO: 82>
SEQ ID NO: 82 shows the amino acid sequence of the light chain (lambda chain) constant region of a canine antibody.
<SEQ ID NO: 83>
SEQ ID NO: 83 shows the nucleotide sequence of the light chain (lambda chain) constant region of a canine antibody.
<SEQ ID NO: 84>
SEQ ID NO: 84 shows the amino acid sequence of the CH (CH1-CH3) of a canine antibody (IgG-D).
<SEQ ID NO: 85>
SEQ ID NO: 85 shows the nucleotide sequence of the CH (CH1-CH3) of a canine antibody (IgG-D).
<SEQ ID NO: 86>
SEQ ID NO: 86 shows the amino acid sequence of the light chain (kappa chain) constant region of an ovine antibody.
<SEQ ID NO: 87>
SEQ ID NO: 87 shows the nucleotide sequence of the light chain (kappa chain) constant region of an ovine antibody.
<SEQ ID NO: 88>
SEQ ID NO: 88 shows the amino acid sequence of the light chain (lambda chain) constant region of an ovine antibody.
<SEQ ID NO: 89>
SEQ ID NO: 89 shows the nucleotide sequence of the light chain (lambda chain) constant region of an ovine antibody.
<SEQ ID NO: 90>
SEQ ID NO: 90 shows the amino acid sequence of the CH (CH1-CH3) of an ovine antibody (IgG1).
<SEQ ID NO: 91>
SEQ ID NO: 91 shows the nucleotide sequence of the CH (CH1-CH3) of an ovine antibody (IgG1).
<SEQ ID NO: 92>
SEQ ID NO: 92 shows the amino acid sequence of the CH (CH1-CH3) of an ovine antibody (IgG2).
<SEQ ID NO: 93>
SEQ ID NO: 93 shows the nucleotide sequence of the CH (CH1-CH3) of an ovine antibody (IgG2).
<SEQ ID NO: 94>
SEQ ID NO: 94 shows the amino acid sequence of the CH (CH1-CH3) of a porcine antibody ($IgG1^a$).
<SEQ ID NO: 95>
SEQ ID NO: 95 shows the nucleotide sequence of the CH (CH1-CH3) of a porcine antibody ($IgG1^a$).
<SEQ ID NO: 96>
SEQ ID NO: 96 shows the amino acid sequence of the CH (CH1-CH3) of a porcine antibody ($IgG1^b$).
<SEQ ID NO: 97>
SEQ ID NO: 97 shows the nucleotide sequence of the CH (CH1-CH3) of a porcine antibody ($IgG1^b$).
<SEQ ID NO: 98>
SEQ ID NO: 98 shows the amino acid sequence of the CH (CH1-CH3) of a porcine antibody ($IgG2^a$).
<SEQ ID NO: 99>
SEQ ID NO: 99 shows the nucleotide sequence of the CH (CH1-CH3) of a porcine antibody ($IgG2^a$).
<SEQ ID NO: 100>
SEQ ID NO: 100 shows the amino acid sequence of the CH (CH1-CH3) of a porcine antibody ($IgG2^b$).
<SEQ ID NO: 101>
SEQ ID NO: 101 shows the nucleotide sequence of the CH (CH1-CH3) of a porcine antibody ($IgG2^b$).
<SEQ ID NO: 102>
SEQ ID NO: 102 shows the amino acid sequence of the CH (CH1-CH3) of a porcine antibody (IgG3).
<SEQ ID NO: 103>
SEQ ID NO: 103 shows the nucleotide sequence of the CH (CH1-CH3) of a porcine antibody (IgG3).
<SEQ ID NO: 104>
SEQ ID NO: 104 shows the amino acid sequence of the CH (CH1-CH3) of a porcine antibody ($IgG4^a$).
<SEQ ID NO: 105>
SEQ ID NO: 105 shows the nucleotide sequence of the CH (CH1-CH3) of a porcine antibody ($IgG4^a$).
<SEQ ID NO: 106>
SEQ ID NO: 106 shows the amino acid sequence of the CH (CH1-CH3) of a porcine antibody ($IgG4^b$).
<SEQ ID NO: 107>
SEQ ID NO: 107 shows the nucleotide sequence of the CH (CH1-CH3) of a porcine antibody ($IgG4^b$).
<SEQ ID NO: 108>
SEQ ID NO: 108 shows the amino acid sequence of the CH (CH1-CH3) of a porcine antibody ($IgG5^a$).
<SEQ ID NO: 109>
SEQ ID NO: 109 shows the nucleotide sequence of the CH (CH1-CH3) of a porcine antibody ($IgG5^a$).
<SEQ ID NO: 110>
SEQ ID NO: 110 shows the amino acid sequence of the CH (CH1-CH3) of a porcine antibody ($IgG5^b$).
<SEQ ID NO: 111>
SEQ ID NO: 111 shows the nucleotide sequence of the CH (CH1-CH3) of a porcine antibody ($IgG5^b$).
<SEQ ID NO: 112>
SEQ ID NO: 112 shows the amino acid sequence of the CH (CH1-CH3) of a porcine antibody ($IgG6^a$).
<SEQ ID NO: 113>
SEQ ID NO: 113 shows the nucleotide sequence of the CH (CH1-CH3) of a porcine antibody ($IgG6^a$).
<SEQ ID NO: 114>
SEQ ID NO: 114 shows the amino acid sequence of the CH (CH1-CH3) of a porcine antibody ($IgG6^b$).
<SEQ ID NO: 115>
SEQ ID NO: 115 shows the nucleotide sequence of the CH (CH1-CH3) of a porcine antibody ($IgG6^b$).
<SEQ ID NO: 116>
SEQ ID NO: 116 shows the amino acid sequence of the light chain (estimated to be Ig lambda) constant region (CL) of a water buffalo antibody.
<SEQ ID NO: 117>
SEQ ID NO: 117 shows the nucleotide sequence of the light chain (estimated to be Ig lambda) constant region (CL) of a water buffalo antibody.
<SEQ ID NO: 118>
SEQ ID NO: 118 shows the amino acid sequence of the CH (CH1-CH3) of a water buffalo antibody (estimated to be IgG1).
<SEQ ID NO: 119>
SEQ ID NO: 119 shows the nucleotide sequence of the CH (CH1-CH3) of a water buffalo antibody (estimated to be IgG1).
<SEQ ID NO: 120>
SEQ ID NO: 120 shows the amino acid sequence of the CH (CH1-CH3) of a water buffalo antibody (estimated to be IgG2).
<SEQ ID NO: 121>
SEQ ID NO: 121 shows the nucleotide sequence of the CH (CH1-CH3) of a water buffalo antibody (estimated to be IgG2).
<SEQ ID NO: 122>
SEQ ID NO: 122 shows the amino acid sequence of the CH (CH1-CH3) of a water buffalo antibody (estimated to be IgG3).

<SEQ ID NO: 123>

SEQ ID NO: 123 shows the nucleotide sequence of the CH (CH1-CH3) of a water buffalo antibody (estimated to be IgG3).

<SEQ ID NO: 124>

SEQ ID NO: 124 shows the nucleotide sequence of primer boPD-L1-EGFP F.

<SEQ ID NO: 125>

SEQ ID NO: 125 shows the nucleotide sequence of primer boPD-L1-EGFP R.

The invention claimed is:

1. An anti-PD-L1 antibody comprising (a) a light chain comprising CDR1 having the amino acid sequence of KSISKY (SEQ ID NO: 1), CDR2 having the amino acid sequence of SGS and CDR3 having the amino acid sequence of QQHNEYPLT (SEQ ID NO: 2) and (b) a heavy chain comprising CDR1 having the amino acid sequence of GYTFTDYI (SEQ ID NO: 3), CDR2 having the amino acid sequence of INPDSGGN (SEQ ID NO: 4) and CDR3 having the amino acid sequence of ARGITMMVVISHWKFDF (SEQ ID NO: 5).

2. The antibody of claim 1, which is from rat.

3. The antibody of claim 2, which is a rat anti-bovine PD-L1 antibody.

4. The antibody of claim 3, wherein the light chain variable region has the amino acid sequence as shown in SEQ ID NO. 6 and the heavy chain variable region has the amino acid sequence as shown in SEQ ID NO: 7.

5. The antibody of claim 1, wherein the light chain constant region has the amino acid sequence of the constant region of kappa chain.

6. The antibody of claim 1, wherein the heavy chain constant region has the amino acid sequence of the constant region of IgG2a.

7. The antibody of claim 5, wherein the light chain constant region has the amino acid sequence as shown in any one of SEQ ID NOS: 8, 10 to 12 and the heavy chain constant region has the amino acid sequence as shown in SEQ ID NO: 9 or 13.

8. The antibody of claim 1 which has a four-chain structure comprising two light chains and two heavy chains.

9. A composition comprising the antibody of claim 1 as an active ingredient and a carrier.

10. A method to diagnose malignant melanoma cancer comprising contacting in vitro one or more cells from a subject with the composition of claim 9; determining if said antibodies in said composition binds to said one or more cells, wherein increased binding to cancer cell as compared to a control is indicative of malignant melanoma cancer.

* * * * *

SEQUENCE LISTING

```
<160> NUMBER OF SEQ ID NOS: 125

<210> SEQ ID NO 1
<211> LENGTH: 6
<212> TYPE: PRT
<213> ORGANISM: Bubalus arnee

<400> SEQUENCE: 1

Lys Ser Ile Ser Lys Tyr
1               5


<210> SEQ ID NO 2
<211> LENGTH: 9
<212> TYPE: PRT
<213> ORGANISM: Bubalus arnee

<400> SEQUENCE: 2

Gln Gln His Asn Glu Tyr Pro Leu Thr
1               5


<210> SEQ ID NO 3
<211> LENGTH: 8
<212> TYPE: PRT
<213> ORGANISM: Bubalus arnee

<400> SEQUENCE: 3

Gly Tyr Thr Phe Thr Asp Tyr Ile
1               5


<210> SEQ ID NO 4
<211> LENGTH: 8
<212> TYPE: PRT
<213> ORGANISM: Bubalus arnee

<400> SEQUENCE: 4

Ile Asn Pro Asp Ser Gly Gly Asn
1               5


<210> SEQ ID NO 5
<211> LENGTH: 17
<212> TYPE: PRT
<213> ORGANISM: Bubalus arnee

<400> SEQUENCE: 5

Ala Arg Gly Ile Thr Met Met Val Val Ile Ser His Trp Lys Phe Asp
1               5                   10                  15

Phe


<210> SEQ ID NO 6
<211> LENGTH: 127
<212> TYPE: PRT
<213> ORGANISM: Bubalus arnee

<400> SEQUENCE: 6

Met Arg Val Gln Ile Gln Phe Trp Gly Leu Leu Leu Leu Trp Thr Ser
1               5                   10                  15

Gly Ile Gln Cys Asp Val Gln Met Thr Gln Ser Pro Ser Asn Leu Ala
```

```
            20                  25                  30

Ala Ser Pro Gly Glu Ser Val Ser Ile Asn Cys Lys Ala Ser Lys Ser
        35                  40                  45

Ile Ser Lys Tyr Leu Ala Trp Tyr Gln Gln Lys Pro Gly Lys Ala Asn
    50                  55                  60

Lys Leu Leu Ile Tyr Ser Gly Ser Thr Leu Gln Ser Gly Thr Pro Ser
65                  70                  75                  80

Arg Phe Ser Gly Ser Gly Ser Gly Thr Asp Phe Thr Leu Thr Ile Arg
                85                  90                  95

Asn Leu Glu Pro Glu Asp Phe Gly Leu Tyr Tyr Cys Gln Gln His Asn
            100                 105                 110

Glu Tyr Pro Leu Thr Phe Gly Ser Gly Thr Lys Leu Glu Ile Lys
        115                 120                 125


<210> SEQ ID NO 7
<211> LENGTH: 142
<212> TYPE: PRT
<213> ORGANISM: Bubalus arnee

<400> SEQUENCE: 7

Met Gly Trp Ile Cys Ile Ile Phe Leu Val Ala Ile Ala Thr Gly Ala
1               5                   10                  15

His Ser Gln Val Lys Leu Leu Gln Ser Gly Ala Ala Leu Val Lys Pro
            20                  25                  30

Gly Asp Ser Val Lys Met Ser Cys Lys Ala Ser Gly Tyr Thr Phe Thr
        35                  40                  45

Asp Tyr Ile Ile His Trp Val Lys Gln Ser His Gly Lys Ser Leu Glu
    50                  55                  60

Trp Ile Gly Tyr Ile Asn Pro Asp Ser Gly Gly Asn Asn Tyr Asn Glu
65                  70                  75                  80

Lys Phe Lys Ser Lys Ala Thr Leu Thr Val Asp Lys Ser Ser Ser Thr
                85                  90                  95

Ala Tyr Met Glu Phe Ser Arg Leu Thr Ser Glu Asp Ser Ala Ile Tyr
            100                 105                 110

Tyr Cys Ala Arg Gly Ile Thr Met Met Val Val Ile Ser His Trp Lys
        115                 120                 125

Phe Asp Phe Trp Gly Pro Gly Thr Met Val Thr Val Ser Ser
    130                 135                 140


<210> SEQ ID NO 8
<211> LENGTH: 107
<212> TYPE: PRT
<213> ORGANISM: Bubalus arnee

<400> SEQUENCE: 8

Arg Ala Asp Ala Ala Pro Thr Val Ser Ile Phe Pro Pro Ser Thr Glu
1               5                   10                  15

Gln Leu Ala Thr Gly Gly Ala Ser Val Val Cys Leu Met Asn Asn Phe
            20                  25                  30

Tyr Pro Arg Asp Ile Ser Val Lys Trp Lys Ile Asp Gly Thr Glu Arg
        35                  40                  45

Arg Asp Gly Val Leu Asp Ser Val Thr Asp Gln Asp Ser Lys Asp Ser
    50                  55                  60

Thr Tyr Ser Met Ser Ser Thr Leu Ser Leu Thr Lys Ala Asp Tyr Glu
65                  70                  75                  80

Ser His Asn Leu Tyr Thr Cys Glu Val Val His Lys Thr Ser Ser Ser
```

```
                85                  90                  95

Pro Val Val Lys Ser Phe Asn Arg Asn Glu Cys
            100                 105


<210> SEQ ID NO 9
<211> LENGTH: 322
<212> TYPE: PRT
<213> ORGANISM: Bubalus arnee

<400> SEQUENCE: 9

Ala Glu Thr Thr Ala Pro Ser Val Tyr Pro Leu Ala Pro Gly Thr Ala
1               5                   10                  15

Leu Lys Ser Asn Ser Met Val Thr Leu Gly Cys Leu Val Lys Gly Tyr
            20                  25                  30

Phe Pro Glu Pro Val Thr Val Thr Trp Asn Ser Gly Ala Leu Ser Ser
        35                  40                  45

Gly Val His Thr Phe Pro Ala Val Leu Gln Ser Gly Leu Tyr Thr Leu
    50                  55                  60

Thr Ser Ser Val Thr Val Pro Ser Ser Thr Trp Ser Ser Gln Ala Val
65                  70                  75                  80

Thr Cys Asn Val Ala His Pro Ala Ser Ser Thr Lys Val Asp Lys Lys
                85                  90                  95

Ile Val Pro Arg Glu Cys Asn Pro Cys Gly Cys Thr Gly Ser Glu Val
            100                 105                 110

Ser Ser Val Phe Ile Phe Pro Pro Lys Thr Lys Asp Val Leu Thr Ile
        115                 120                 125

Thr Leu Thr Pro Lys Val Thr Cys Val Val Val Asp Ile Ser Gln Asn
    130                 135                 140

Asp Pro Glu Val Arg Phe Ser Trp Phe Ile Asp Asp Val Glu Val His
145                 150                 155                 160

Thr Ala Gln Thr His Ala Pro Glu Lys Gln Ser Asn Ser Thr Leu Arg
                165                 170                 175

Ser Val Ser Glu Leu Pro Ile Val His Arg Asp Trp Leu Asn Gly Lys
            180                 185                 190

Thr Phe Lys Cys Lys Val Asn Ser Gly Ala Phe Pro Ala Pro Ile Glu
        195                 200                 205

Lys Ser Ile Ser Lys Pro Glu Gly Thr Pro Arg Gly Pro Gln Val Tyr
    210                 215                 220

Thr Met Ala Pro Pro Lys Glu Glu Met Thr Gln Ser Gln Val Ser Ile
225                 230                 235                 240

Thr Cys Met Val Lys Gly Phe Tyr Pro Pro Asp Ile Tyr Thr Glu Trp
                245                 250                 255

Lys Met Asn Gly Gln Pro Gln Glu Asn Tyr Lys Asn Thr Pro Pro Thr
            260                 265                 270

Met Asp Thr Asp Gly Ser Tyr Phe Leu Tyr Ser Lys Leu Asn Val Lys
        275                 280                 285

Lys Glu Thr Trp Gln Gln Gly Asn Thr Phe Thr Cys Ser Val Leu His
    290                 295                 300

Glu Gly Leu His Asn His His Thr Glu Lys Ser Leu Ser His Ser Pro
305                 310                 315                 320

Gly Lys


<210> SEQ ID NO 10
<211> LENGTH: 106
<212> TYPE: PRT
```

<213> ORGANISM: Bubalus arnee

<400> SEQUENCE: 10

```
Ala Asp Ala Ala Pro Thr Val Ser Ile Phe Pro Pro Ser Thr Glu Gln
1               5                   10                  15

Leu Ala Thr Gly Gly Ala Ser Val Val Cys Leu Met Asn Asn Phe Tyr
            20                  25                  30

Pro Arg Asp Ile Ser Val Lys Trp Lys Ile Asp Gly Thr Glu Arg Arg
        35                  40                  45

Asp Gly Val Leu Asp Ser Val Thr Asp Gln Asp Ser Lys Asp Ser Thr
    50                  55                  60

Tyr Ser Met Ser Ser Thr Leu Ser Leu Thr Lys Ala Asp Tyr Glu Ser
65                  70                  75                  80

His Asn Leu Tyr Thr Cys Glu Val Val His Lys Thr Ser Ser Ser Pro
                85                  90                  95

Val Val Lys Ser Phe Asn Arg Asn Glu Cys
            100                 105
```

<210> SEQ ID NO 11
<211> LENGTH: 107
<212> TYPE: PRT
<213> ORGANISM: Bubalus arnee

<400> SEQUENCE: 11

```
Arg Ala Asp Ala Ala Pro Thr Val Ser Ile Phe Pro Pro Ser Thr Glu
1               5                   10                  15

Gln Leu Ala Thr Gly Gly Ala Ser Val Val Cys Leu Met Asn Asn Phe
            20                  25                  30

Tyr Pro Arg Asp Ile Ser Val Lys Trp Lys Ile Asp Gly Thr Glu Arg
        35                  40                  45

Arg Asp Gly Val Leu Asp Ser Val Thr Asp Gln Asp Ser Lys Asp Ser
    50                  55                  60

Thr Tyr Ser Met Ser Ser Thr Leu Ser Leu Ser Lys Ala Asp Tyr Glu
65                  70                  75                  80

Ser His Asn Leu Tyr Thr Cys Glu Val Val His Lys Thr Ser Ser Ser
                85                  90                  95

Pro Val Val Lys Ser Phe Asn Arg Asn Glu Cys
            100                 105
```

<210> SEQ ID NO 12
<211> LENGTH: 104
<212> TYPE: PRT
<213> ORGANISM: Bubalus arnee

<400> SEQUENCE: 12

```
Ala Ala Pro Thr Val Ser Ile Phe Pro Pro Ser Met Glu Gln Leu Thr
1               5                   10                  15

Ser Gly Gly Ala Thr Val Val Cys Phe Val Asn Asn Phe Tyr Pro Arg
            20                  25                  30

Asp Ile Ser Val Lys Trp Lys Ile Asp Gly Ser Glu Gln Arg Asp Gly
        35                  40                  45

Val Leu Asp Ser Val Thr Asp Gln Asp Ser Lys Asp Ser Thr Tyr Ser
    50                  55                  60

Met Ser Ser Thr Leu Ser Leu Thr Lys Val Glu Tyr Glu Arg His Asn
65                  70                  75                  80

Leu Tyr Thr Cys Glu Val Val His Lys Thr Ser Ser Ser Pro Val Val
                85                  90                  95
```

```
Lys Ser Phe Asn Arg Asn Glu Cys
            100


<210> SEQ ID NO 13
<211> LENGTH: 318
<212> TYPE: PRT
<213> ORGANISM: Bubalus arnee

<400> SEQUENCE: 13

Ala Pro Ser Val Tyr Pro Leu Ala Pro Gly Thr Ala Leu Lys Ser Asn
1               5                   10                  15

Ser Met Val Thr Leu Gly Cys Leu Val Lys Gly Tyr Phe Pro Glu Pro
            20                  25                  30

Val Thr Val Thr Trp Asn Ser Gly Ala Leu Ser Ser Gly Val His Thr
        35                  40                  45

Phe Pro Ala Val Leu Gln Ser Gly Leu Tyr Thr Leu Thr Ser Ser Val
    50                  55                  60

Thr Val Pro Ser Ser Thr Trp Ser Ser Gln Ala Val Thr Cys Asn Val
65                  70                  75                  80

Ala His Pro Ala Ser Ser Thr Lys Val Asp Lys Lys Ile Val Pro Arg
                85                  90                  95

Glu Cys Asn Pro Cys Gly Cys Thr Gly Ser Glu Val Ser Ser Val Phe
            100                 105                 110

Ile Phe Pro Pro Lys Thr Lys Asp Val Leu Thr Ile Thr Leu Thr Pro
        115                 120                 125

Lys Val Thr Cys Val Val Val Asp Ile Ser Gln Asn Asp Pro Glu Val
    130                 135                 140

Arg Phe Ser Trp Phe Ile Asp Asp Val Glu Val His Thr Ala Gln Thr
145                 150                 155                 160

His Ala Pro Glu Lys Gln Ser Asn Ser Thr Leu Arg Ser Val Ser Glu
                165                 170                 175

Leu Pro Ile Val His Arg Asp Trp Leu Asn Gly Lys Thr Phe Lys Cys
            180                 185                 190

Lys Val Asn Ser Gly Ala Phe Pro Ala Pro Ile Glu Lys Ser Ile Ser
        195                 200                 205

Lys Pro Glu Gly Thr Pro Arg Gly Pro Gln Val Tyr Thr Met Ala Pro
    210                 215                 220

Pro Lys Glu Glu Met Thr Gln Ser Gln Val Ser Ile Thr Cys Met Val
225                 230                 235                 240

Lys Gly Phe Tyr Pro Pro Asp Ile Tyr Thr Glu Trp Lys Met Asn Gly
                245                 250                 255

Gln Pro Gln Glu Asn Tyr Lys Asn Thr Pro Pro Thr Met Asp Thr Asp
            260                 265                 270

Gly Ser Tyr Phe Leu Tyr Ser Lys Leu Asn Val Lys Lys Glu Thr Trp
        275                 280                 285

Gln Gln Gly Asn Thr Phe Thr Cys Ser Val Leu His Glu Gly Leu His
    290                 295                 300

Asn His His Thr Glu Lys Ser Leu Ser His Ser Pro Gly Lys
305                 310                 315


<210> SEQ ID NO 14
<211> LENGTH: 381
<212> TYPE: DNA
<213> ORGANISM: Bubalus arnee

<400> SEQUENCE: 14
```

atgagggtcc agattcagtt ttgggggctt cttctgctct ggacatcagg tatacagtgt 60
gatgtccaga tgacccagtc tccatctaat cttgctgcct ctcctggaga aagtgtttcc 120
atcaattgca aggcaagtaa gagcattagc aagtatttag cctggtatca acagaaacct 180
gggaaagcaa ataagcttct tatctactct gggtcaactt tgcaatctgg aactccatcg 240
aggttcagtg gcagtggatc tggtacagat ttcactctca ccatcagaaa cctggagcct 300
gaagattttg gactctatta ctgtcaacag cataatgaat acccgctcac gttcggttct 360
gggaccaagc tggagatcaa a 381

<210> SEQ ID NO 15
<211> LENGTH: 426
<212> TYPE: DNA
<213> ORGANISM: Bubalus arnee

<400> SEQUENCE: 15
atgggatgga tctgtatcat ctttcttgtg gcaatagcta caggtgccca ctcccaggtc 60
aagctgctgc agtctggggc tgcactggtg aagcctgggg actctgtgaa gatgtcttgc 120
aaagcttctg gttatacatt cactgactac attatacact gggtgaagca gagtcatgga 180
aaaagccttg agtggattgg ttatattaat cctgacagtg gtggtaataa ctacaatgaa 240
aagttcaaga gcaaggccac attgactgta gacaaatcca gcagcacagc ctatatggag 300
tttagcagat tgacatctga ggattctgca atctactact gtgcaagagg gattaccatg 360
atggtagtta ttagccactg gaagtttgac ttctggggcc caggaaccat ggtcaccgtg 420
tcctca 426

<210> SEQ ID NO 16
<211> LENGTH: 324
<212> TYPE: DNA
<213> ORGANISM: Bubalus arnee

<400> SEQUENCE: 16
cgggctgatg ctgcaccaac tgtatctatc ttcccaccat ccacggaaca gttagcaact 60
ggaggtgcct cagtcgtgtg cctcatgaac aacttctatc ccagagacat cagtgtcaag 120
tggaagattg atggcactga acgacgagat ggtgtcctgg acagtgttac tgatcaggac 180
agcaaagaca gcacgtacag catgagcagc accctctcgt tgaccaaggc tgactatgaa 240
agtcataacc tctatacctg tgaggttgtt cataagacat catcctcacc cgtcgtcaag 300
agcttcaaca ggaatgagtg ttag 324

<210> SEQ ID NO 17
<211> LENGTH: 969
<212> TYPE: DNA
<213> ORGANISM: Bubalus arnee

<400> SEQUENCE: 17
gctgaaacaa cagccccatc tgtctatcca ctggctcctg gaactgctct caaaagtaac 60
tccatggtga ccctgggatg cctggtcaag ggctatttcc ctgagccagt caccgtgacc 120
tggaactctg gagccctgtc cagcggtgtg cacaccttcc cagctgtcct gcagtctgga 180
ctctacactc tcaccagctc agtgactgta ccctccagca cctggtccag ccaggccgtc 240
acctgcaacg tagcccaccc ggccagcagc accaaggtgg acaagaaaat tgtgccaagg 300
gaatgcaatc cttgtggatg tacaggctca gaagtatcat ctgtcttcat cttcccccca 360
aagaccaaag atgtgctcac catcactctg actcctaagg tcacgtgtgt tgtggtagac 420
attagccaga atgatcccga ggtccggttc agctggttta tagatgacgt ggaagtccac 480
acagctcaga ctcatgcccc ggagaagcag tccaacagca ctttacgctc agtcagtgaa 540
ctccccatcg tgcaccggga ctggctcaat ggcaagacgt tcaaatgcaa agtcaacagt 600
ggagcattcc ctgcccccat cgagaaaagc atctccaaac ccgaaggcac accacgaggt 660
ccacaggtat acaccatggc gcctcccaag gaagagatga cccagagtca agtcagtatc 720
acctgcatgg taaaaggctt ctatccccca gacatttata cggagtggaa gatgaacggg 780
cagccacagg aaaactacaa gaacactcca cctacgatgg acacagatgg gagttacttc 840
ctctacagca agctcaatgt aaagaaagaa acatggcagc agggaaacac tttcacgtgt 900
tctgtgctgc atgagggcct gcacaaccac catactgaga agagtctctc ccactctcct 960
ggtaaatga 969

<210> SEQ ID NO 18
<211> LENGTH: 323
<212> TYPE: DNA
<213> ORGANISM: Bubalus arnee

<400> SEQUENCE: 18
gggctgatgc tgcaccaact gtatctatct tcccaccatc cacggaacag ttagcaactg 60
gaggtgcctc agtcgtgtgc ctcatgaaca acttctatcc cagagacatc agtgtcaagt 120
ggaagattga tggcactgaa cgacgagatg gtgtcctgga cagtgttact gatcaggaca 180
gcaaagacag cacgtacagc atgagcagca ccctctcgtt gaccaaggct gactatgaaa 240
gtcataacct ctatacctgt gaggttgttc ataagacatc atcctcaccc gtcgtcaaga 300
gcttcaacag gaatgagtgt tag 323

<210> SEQ ID NO 19
<211> LENGTH: 324
<212> TYPE: DNA
<213> ORGANISM: Bubalus arnee

<400> SEQUENCE: 19
cgggctgatg ctgcaccaac tgtatctatc ttcccaccat ccacggaaca gttagcaact 60
ggaggtgcct cagtcgtgtg cctcatgaac aacttctatc ccagagacat cagtgtcaag 120
tggaagattg atggcactga acgacgagat ggtgtcctgg acagtgttac tgatcaggac 180
agcaaagaca gcacgtacag catgagcagc accctctcgt tgtccaaggc tgactatgaa 240
agtcataacc tctatacctg tgaggttgtt cataagacat catcctcacc cgtcgtcaag 300
agcttcaaca ggaatgagtg ttag 324

<210> SEQ ID NO 20
<211> LENGTH: 315
<212> TYPE: DNA
<213> ORGANISM: Bubalus arnee

<400> SEQUENCE: 20
gccgcaccaa ctgtatccat cttcccacca tccatggaac agttaacatc tggaggtgcc 60
acagtcgtgt gcttcgtgaa caacttctat cccagagaca tcagtgtcaa gtggaagatt 120
gatggcagtg aacaacgaga tggtgtcctg gacagtgtta ctgatcagga cagcaaagac 180
agcacgtaca gcatgagcag caccctctcg ttgaccaagg ttgaatatga aaggcataac 240
ctctatacct gtgaggttgt tcataagaca tcatcctcac ccgtcgtcaa gagcttcaac 300
aggaatgagt gttag 315

<210> SEQ ID NO 21
<211> LENGTH: 959
<212> TYPE: DNA
<213> ORGANISM: Bubalus arnee

<400> SEQUENCE: 21
cagccccctc tgtctatcca ctggctcctg gaactgctct caaaagtaac tccatggtga 60
ccctgggatg cctggtcaag ggctatttcc ctgagccagt caccgtgacc tggaactctg 120
gagccctgtc cagcggtgtg cacaccttcc cagctgtcct gcagtctgga ctctacactc 180
tcaccagctc agtgactgta ccctccagca cctggtccag ccaggccgtc acctgcaacg 240
tagcccaccc ggccagcagc accaaggtgg acaagaaaat tgtgccaagg gaatgcaatc 300
cttgtggatg tacaggctca gaagtatcat ctgtcttcat cttcccccca aagaccaaag 360
atgtgctcac catcactctg actcctaagg tcacgtgtgt tgtggtagac attagccaga 420
atgatcccga ggtccggttc agctggttta tagatgacgt ggaagtccac acagctcaga 480
ctcatgcccc ggagaagcag tccaacagca ctttacgctc agtcagtgaa ctccccatcg 540
tgcaccggga ctggctcaat ggcaagacgt tcaaatgcaa agtcaacagt ggagcattcc 600
ctgcccccat cgagaaaagc atctccaaac ccgaaggcac accacgaggt ccacaggtat 660
acaccatggc gcctcccaag gaagagatga cccagagtca agtcagtatc acctgcatgg 720
taaaaggctt ctatccccca gacatttata cggagtggaa gatgaacggg cagccacagg 780
aaaactacaa gaacactcca cctacgatgg acacagatgg gagttacttc ctctacagca 840
agctcaatgt aaagaaagaa acatggcagc agggaaacac tttcacgtgt tctgtgctgc 900
atgagggcct gcacaaccac catactgaga agagtctctc ccactctcct ggtaaatga 959

<210> SEQ ID NO 22
<211> LENGTH: 20
<212> TYPE: DNA
<213> ORGANISM: Bubalus arnee

<400> SEQUENCE: 22
atgagaatgt ttagtgtctt 20

<210> SEQ ID NO 23
<211> LENGTH: 24
<212> TYPE: DNA
<213> ORGANISM: Bubalus arnee

<400> SEQUENCE: 23
ttatgtctct tcaaattgta tatc 24

<210> SEQ ID NO 24
<211> LENGTH: 17
<212> TYPE: DNA
<213> ORGANISM: Bubalus arnee

<400> SEQUENCE: 24
ttttagacag aaagtga 17

<210> SEQ ID NO 25
<211> LENGTH: 20
<212> TYPE: DNA
<213> ORGANISM: Bubalus arnee

<400> SEQUENCE: 25
gaccagctct tcttggggaa 20

<210> SEQ ID NO 26
<211> LENGTH: 26
<212> TYPE: DNA
<213> ORGANISM: Bubalus arnee

<400> SEQUENCE: 26
gaagatctat gagaatgttt agtgtc 26

<210> SEQ ID NO 27
<211> LENGTH: 28
<212> TYPE: DNA
<213> ORGANISM: Bubalus arnee

<400> SEQUENCE: 27
ggaattctgt ctcttcaaat tgtatatc 28

<210> SEQ ID NO 28
<211> LENGTH: 106
<212> TYPE: PRT
<213> ORGANISM: Bubalus arnee

<400> SEQUENCE: 28

Thr Val Ala Ala Pro Ser Val Phe Ile Phe Pro Pro Ser Asp Glu Gln
1 5 10 15

Leu Lys Ser Gly Thr Ala Ser Val Val Cys Leu Leu Asn Asn Phe Tyr
20 25 30

Pro Arg Glu Ala Lys Val Gln Trp Lys Val Asp Asn Ala Leu Gln Ser
35 40 45

Gly Asn Ser Gln Glu Ser Val Thr Glu Gln Asp Ser Lys Asp Ser Thr
50 55 60

Tyr Ser Leu Ser Ser Thr Leu Thr Leu Ser Lys Ala Asp Tyr Glu Lys
65 70 75 80

His Lys Val Tyr Ala Cys Glu Val Thr His Gln Gly Leu Ser Ser Pro
85 90 95

Val Thr Lys Ser Phe Asn Arg Gly Glu Cys
100 105

<210> SEQ ID NO 29
<211> LENGTH: 321
<212> TYPE: DNA
<213> ORGANISM: Bubalus arnee

<400> SEQUENCE: 29
actgtggctg caccatctgt cttcatcttc ccgccatctg atgagcagtt gaaatctgga 60
actgcctctg ttgtgtgcct gctgaataac ttctatccca gagaggccaa agtacagtgg 120
aaggtggata acgccctcca atcgggtaac tcccaggaga gtgtcacaga gcaggacagc 180
aaggacagca cctacagcct cagcagcacc ctgacgctga gcaaagcaga ctacgagaaa 240
cacaaagtct acgcctgcga agtcacccat cagggcctga gctcgcccgt cacaaagagc 300
ttcaacaggg gagagtgtta g 321

<210> SEQ ID NO 30
<211> LENGTH: 229
<212> TYPE: PRT
<213> ORGANISM: Bubalus arnee -continued

<400> SEQUENCE: 30

```
Glu Ser Lys Tyr Gly Pro Pro Cys Pro Ser Cys Pro Ala Pro Glu Phe
1               5                   10                  15

Leu Gly Gly Pro Ser Val Phe Leu Phe Pro Pro Lys Pro Lys Asp Thr
            20                  25                  30

Leu Met Ile Ser Arg Thr Pro Glu Val Thr Cys Val Val Val Asp Val
        35                  40                  45

Ser Gln Glu Asp Pro Glu Val Gln Phe Asn Trp Tyr Val Asp Gly Val
    50                  55                  60

Glu Val His Asn Ala Lys Thr Lys Pro Arg Glu Glu Gln Phe Asn Ser
65                  70                  75                  80

Thr Tyr Arg Val Val Ser Val Leu Thr Val Leu His Gln Asp Trp Leu
                85                  90                  95

Asn Gly Lys Glu Tyr Lys Cys Lys Val Ser Asn Lys Gly Leu Pro Ser
            100                 105                 110

Ser Ile Glu Lys Thr Ile Ser Lys Ala Lys Gly Gln Pro Arg Glu Pro
        115                 120                 125

Gln Val Tyr Thr Leu Pro Pro Ser Gln Glu Glu Met Thr Lys Asn Gln
    130                 135                 140

Val Ser Leu Thr Cys Leu Val Lys Gly Phe Tyr Pro Ser Asp Ile Ala
145                 150                 155                 160

Val Glu Trp Glu Ser Asn Gly Gln Pro Glu Asn Asn Tyr Lys Thr Thr
                165                 170                 175

Pro Pro Val Leu Asp Ser Asp Gly Ser Phe Phe Leu Tyr Ser Arg Leu
            180                 185                 190

Thr Val Asp Lys Ser Arg Trp Gln Glu Gly Asn Val Phe Ser Cys Ser
        195                 200                 205

Val Met His Glu Ala Leu His Asn His Tyr Thr Gln Lys Ser Leu Ser
    210                 215                 220

Leu Ser Leu Gly Lys
225
```

<210> SEQ ID NO 31
<211> LENGTH: 690
<212> TYPE: DNA
<213> ORGANISM: Bubalus arnee

<400> SEQUENCE: 31

```
gagtccaaat atggtccccc atgcccatca tgcccagcac ctgagttcct ggggggacca     60

tcagtcttcc tgttcccccc aaaacccaag gacactctca tgatctcccg gacccctgag    120

gtcacgtgcg tggtggtgga cgtgagccag gaagaccccg aggtccagtt caactggtac    180

gtggatggcg tggaggtgca taatgccaag acaaagccgc gggaggagca gttcaacagc    240

acgtaccgtg tggtcagcgt cctcaccgtc ctgcaccagg actggctgaa cggcaaggag    300

tacaagtgca aggtctccaa caaaggcctc ccgtcctcca tcgagaaaac catctccaaa    360

gccaaagggc agccccgaga gccacaggtg tacaccctgc ccccatccca ggaggagatg    420

accaagaacc aggtcagcct gacctgcctg gtcaaaggct tctaccccag cgacatcgcc    480

gtggagtggg agagcaatgg gcagccggag aacaactaca agaccacgcc tcccgtgctg    540

gactccgacg gctccttctt cctctacagc aggctaaccg tggacaagag caggtggcag    600

gaggggaatg tcttctcatg ctccgtgatg catgaggctc tgcacaacca ctacacacag    660

aagagcctct ccctgtctct gggtaaatga                                     690
```

<210> SEQ ID NO 32
<211> LENGTH: 229
<212> TYPE: PRT
<213> ORGANISM: Bubalus arnee

<400> SEQUENCE: 32

Glu Ser Lys Tyr Gly Pro Pro Cys Pro Ser Cys Pro Ala Pro Glu Phe
1               5                   10                  15

Leu Gly Gly Pro Ser Val Phe Leu Phe Pro Pro Lys Pro Lys Asp Thr
            20                  25                  30

Leu Met Ile Ser Arg Thr Pro Glu Val Thr Cys Val Val Val Asp Val
        35                  40                  45

Ser Gln Glu Asp Pro Glu Val Gln Phe Asn Trp Tyr Val Asp Gly Val
    50                  55                  60

Glu Val His Asn Ala Lys Thr Lys Pro Arg Glu Glu Gln Phe Asn Ser
65                  70                  75                  80

Thr Tyr Arg Val Val Ser Val Leu Thr Val Val His Gln Asp Trp Leu
                85                  90                  95

Asn Gly Lys Glu Tyr Lys Cys Lys Val Ser Asn Lys Gly Leu Pro Ser
            100                 105                 110

Ser Ile Glu Lys Thr Ile Ser Lys Ala Lys Gly Gln Pro Arg Glu Pro
        115                 120                 125

Gln Val Tyr Thr Leu Pro Pro Ser Gln Glu Glu Met Thr Lys Asn Gln
    130                 135                 140

Val Ser Leu Thr Cys Leu Val Lys Gly Phe Tyr Pro Ser Asp Ile Ala
145                 150                 155                 160

Val Glu Trp Glu Ser Asn Gly Gln Pro Glu Asn Asn Tyr Lys Thr Thr
                165                 170                 175

Pro Pro Val Leu Asp Ser Asp Gly Ser Phe Phe Leu Tyr Ser Arg Leu
            180                 185                 190

Thr Val Asp Lys Ser Arg Trp Gln Glu Gly Asn Val Phe Ser Cys Ser
        195                 200                 205

Val Met His Glu Ala Leu His Asn His Tyr Thr Gln Lys Ser Leu Ser
    210                 215                 220

Leu Ser Leu Gly Lys
225

<210> SEQ ID NO 33
<211> LENGTH: 690
<212> TYPE: DNA
<213> ORGANISM: Bubalus arnee

<400> SEQUENCE: 33
gagtccaaat atggtccccc gtgcccatca tgcccagcac ctgagttcct gggggggacca 60 tcagtcttcc tgttcccccc aaaacccaag gacactctca tgatctcccg gacccctgag 120
gtcacgtgcg tggtggtgga cgtgagccag gaagaccccg aggtccagtt caactggtac 180
gtggatggcg tggaggtgca taatgccaag acaaagccgc gggaggagca gttcaacagc 240
acgtaccgtg tggtcagcgt cctcaccgtc gtgcaccagg actggctgaa cggcaaggag 300
tacaagtgca aggtctccaa caaaggcctc ccgtcctcca tcgagaaaac catctccaaa 360
gccaaagggc agccccgaga gccacaggtg tacaccctgc ccccatccca ggaggagatg 420
accaagaacc aggtcagcct gacctgcctg gtcaaaggct tctaccccag cgacatcgcc 480
gtggagtggg agagcaatgg gcagccggag aacaactaca agaccacgcc tcccgtgctg 540

```
gactccgacg gctccttctt cctctacagc aggctaaccg tggacaagag caggtggcag    600

gaggggaatg tcttctcatg ctccgtgatg catgaggctc tgcacaacca ctacacgcag    660

aagagcctct ccctgtctct gggtaaatga                                     690


<210> SEQ ID NO 34
<211> LENGTH: 217
<212> TYPE: PRT
<213> ORGANISM: Bubalus arnee

<400> SEQUENCE: 34

Ala Pro Glu Phe Leu Gly Gly Pro Ser Val Phe Leu Phe Pro Pro Lys
1               5                   10                  15

Pro Lys Asp Thr Leu Met Ile Ser Arg Thr Pro Glu Val Thr Cys Val
            20                  25                  30

Val Val Asp Val Ser Gln Glu Asp Pro Glu Val Gln Phe Asn Trp Tyr
        35                  40                  45

Val Asp Gly Val Glu Val His Asn Ala Lys Thr Lys Pro Arg Glu Glu
    50                  55                  60

Gln Phe Asn Ser Thr Tyr Arg Val Val Ser Val Leu Thr Val Leu His
65                  70                  75                  80

Gln Asp Trp Leu Asn Gly Lys Glu Tyr Lys Cys Lys Val Ser Asn Lys
                85                  90                  95

Gly Leu Pro Ser Ser Ile Glu Lys Thr Ile Ser Lys Ala Lys Gly Gln
            100                 105                 110

Pro Arg Glu Pro Gln Val Tyr Thr Leu Pro Pro Ser Gln Glu Glu Met
        115                 120                 125

Thr Lys Asn Gln Val Ser Leu Thr Cys Leu Val Lys Gly Phe Tyr Pro
    130                 135                 140

Ser Asp Ile Ala Val Glu Trp Glu Ser Asn Gly Gln Pro Glu Asn Asn
145                 150                 155                 160

Tyr Lys Thr Thr Pro Pro Val Leu Asp Ser Asp Gly Ser Phe Phe Leu
                165                 170                 175

Tyr Ser Lys Leu Thr Val Asp Lys Ser Arg Trp Gln Glu Gly Asn Val
            180                 185                 190

Phe Ser Cys Ser Val Met His Glu Ala Leu His Asn His Tyr Thr Gln
        195                 200                 205

Lys Ser Leu Ser Leu Ser Leu Gly Lys
    210                 215


<210> SEQ ID NO 35
<211> LENGTH: 654
<212> TYPE: DNA
<213> ORGANISM: Bubalus arnee

<400> SEQUENCE: 35

gcacctgagt tcctgggggg accatcagtc ttcctgttcc ccccaaaacc caaggacact     60

ctcatgatct cccggacccc tgaggtcacg tgcgtggtgg tggacgtgag ccaggaagac    120

cccgaggtcc agttcaactg gtacgtggat ggcgtggagg tgcataatgc caagacaaag    180

ccgcgggagg agcagttcaa cagcacgtac cgtgtggtca gcgtcctcac cgtcctgcac    240

caggactggc tgaacggcaa ggagtacaag tgcaaggtct ccaacaaagg cctcccgtcc    300

tccatcgaga aaaccatctc caaagccaaa gggcagcccc gagagccaca ggtgtacacc    360

ctgcccccat cccaggagga gatgaccaag aaccaggtca gcctgacctg cctggtcaaa    420

ggcttctacc ccagcgacat cgccgtggag tgggagagca atgggcagcc ggagaacaac    480
```

```
tacaagacca cgcctcccgt gctggactcc gacggctcct tcttcctcta cagcaagctc    540

accgtggaca agagcaggtg gcaggagggg aacgtcttct catgctccgt gatgcatgag    600

gctctgcaca accactacac gcagaagagc ctctccctgt ctctgggtaa atga          654


<210> SEQ ID NO 36
<211> LENGTH: 106
<212> TYPE: PRT
<213> ORGANISM: Bubalus arnee

<400> SEQUENCE: 36

Ala Asp Ala Ala Pro Thr Val Ser Ile Phe Pro Pro Ser Ser Glu Gln
1               5                   10                  15

Leu Thr Ser Gly Gly Ala Ser Val Val Cys Phe Leu Asn Asn Phe Tyr
            20                  25                  30

Pro Lys Asp Ile Asn Val Lys Trp Lys Ile Asp Gly Ser Glu Arg Gln
        35                  40                  45

Asn Gly Val Leu Asn Ser Trp Thr Asp Gln Asp Ser Lys Asp Ser Thr
    50                  55                  60

Tyr Ser Met Ser Ser Thr Leu Thr Leu Thr Lys Asp Glu Tyr Glu Arg
65                  70                  75                  80

His Asn Ser Tyr Thr Cys Glu Ala Thr His Lys Thr Ser Thr Ser Pro
                85                  90                  95

Ile Val Lys Ser Phe Asn Arg Asn Glu Cys
            100                 105


<210> SEQ ID NO 37
<211> LENGTH: 321
<212> TYPE: DNA
<213> ORGANISM: Bubalus arnee

<400> SEQUENCE: 37

gctgatgctg caccaactgt atccatcttc ccaccatcca gtgagcagtt aacatctgga     60

ggtgcctcag tcgtgtgctt cttgaacaac ttctacccca aagacatcaa tgtcaagtgg    120

aagattgatg gcagtgaacg acaaaatggc gtcctgaaca gttggactga tcaggacagc    180

aaagacagca cctacagcat gagcagcacc ctcacgttga ccaaggacga gtatgaacga    240

cataacagct atacctgtga ggccactcac aagacatcaa cttcacccat tgtcaagagc    300

ttcaacagga atgagtgtta g                                              321


<210> SEQ ID NO 38
<211> LENGTH: 106
<212> TYPE: PRT
<213> ORGANISM: Bubalus arnee

<400> SEQUENCE: 38

Gly Gln Pro Lys Ser Ser Pro Ser Val Thr Leu Phe Pro Pro Ser Ser
1               5                   10                  15

Glu Glu Leu Glu Thr Asn Lys Ala Thr Leu Val Cys Thr Ile Thr Asp
            20                  25                  30

Phe Tyr Pro Gly Val Val Thr Val Asp Trp Lys Val Asp Gly Thr Pro
        35                  40                  45

Val Thr Gln Gly Met Glu Thr Thr Gln Pro Ser Lys Gln Ser Asn Asn
    50                  55                  60

Lys Tyr Met Ala Ser Ser Tyr Leu Thr Leu Thr Ala Arg Ala Trp Glu
65                  70                  75                  80
```

```
Arg His Ser Ser Tyr Ser Cys Gln Val Thr His Glu Gly His Thr Val
                85                  90                  95

Glu Lys Ser Leu Ser Arg Ala Asp Cys Ser
            100                 105


<210> SEQ ID NO 39
<211> LENGTH: 321
<212> TYPE: DNA
<213> ORGANISM: Bubalus arnee

<400> SEQUENCE: 39

ggccagccca agtcttcgcc atcagtcacc ctgtttccac cttcctctga agagctcgag     60

actaacaagg ccacactggt gtgtacgatc actgatttct acccaggtgt ggtgacagtg    120

gactggaagg tagatggtac ccctgtcact cagggtatgg agacaaccca gccttccaaa    180

cagagcaaca acaagtacat ggctagcagc tacctgaccc tgacagcaag agcatgggaa    240

aggcatagca gttacagctg ccaggtcact catgaaggtc acactgtgga gaagagtttg    300

tcccgtgctg actgttccta g                                              321


<210> SEQ ID NO 40
<211> LENGTH: 105
<212> TYPE: PRT
<213> ORGANISM: Bubalus arnee

<400> SEQUENCE: 40

Gly Gln Pro Lys Ser Thr Pro Thr Leu Thr Val Phe Pro Pro Ser Ser
1               5                   10                  15

Glu Glu Leu Lys Glu Asn Lys Ala Thr Leu Val Cys Leu Ile Ser Asn
            20                  25                  30

Phe Ser Pro Ser Gly Val Thr Val Ala Trp Lys Ala Asn Gly Thr Pro
        35                  40                  45

Ile Thr Gln Gly Val Asp Thr Ser Asn Pro Thr Lys Glu Gly Asn Lys
    50                  55                  60

Phe Met Ala Ser Ser Phe Leu His Leu Thr Ser Asp Gln Trp Arg Ser
65                  70                  75                  80

His Asn Ser Phe Thr Cys Gln Val Thr His Glu Gly Asp Thr Val Glu
                85                  90                  95

Lys Ser Leu Ser Pro Ala Glu Cys Leu
            100                 105


<210> SEQ ID NO 41
<211> LENGTH: 318
<212> TYPE: DNA
<213> ORGANISM: Bubalus arnee

<400> SEQUENCE: 41

ggtcagccca agtccactcc cactctcacc gtgtttccac cttcctctga ggagctcaag     60

gaaaacaaag ccacactggt gtgtctgatt tccaactttt ccccgagtgg tgtgacagtg    120

gcctggaagg caaatggtac acctatcacc cagggtgtgg acacttcaaa tcccaccaaa    180

gagggcaaca agttcatggc cagcagcttc ctacatttga catcggacca gtggagatct    240

cacaacagtt ttacctgtca agttacacat gaaggggaca ctgtggagaa gagtctgtct    300

cctgcagaat gtctctaa                                                  318


<210> SEQ ID NO 42
<211> LENGTH: 105
<212> TYPE: PRT
```

<213> ORGANISM: Bubalus arnee

<400> SEQUENCE: 42

Gly Gln Pro Lys Ser Thr Pro Thr Leu Thr Met Phe Pro Pro Ser Pro
1               5                   10                  15

Glu Glu Leu Gln Glu Asn Lys Ala Thr Leu Val Cys Leu Ile Ser Asn
            20                  25                  30

Phe Ser Pro Ser Gly Val Thr Val Ala Trp Lys Ala Asn Gly Thr Pro
        35                  40                  45

Ile Thr Gln Gly Val Asp Thr Ser Asn Pro Thr Lys Glu Asp Asn Lys
    50                  55                  60

Tyr Met Ala Ser Ser Phe Leu His Leu Thr Ser Asp Gln Trp Arg Ser
65                  70                  75                  80

His Asn Ser Phe Thr Cys Gln Val Thr His Glu Gly Asp Thr Val Glu
                85                  90                  95

Lys Ser Leu Ser Pro Ala Glu Cys Leu
            100                 105

<210> SEQ ID NO 43
<211> LENGTH: 318
<212> TYPE: DNA
<213> ORGANISM: Bubalus arnee

<400> SEQUENCE: 43
ggtcagccca agtccactcc cacactcacc atgtttccac cttcccctga ggagctccag      60
gaaaacaaag ccacactcgt gtgtctgatt tccaattttt ccccaagtgg tgtgacagtg     120
gcctggaagg caaatggtac acctatcacc cagggtgtgg acacttcaaa tcccaccaaa     180
gaggacaaca agtacatggc cagcagcttc ttacatttga catcggacca gtggagatct     240
cacaacagtt ttacctgcca agttacacat gaaggggaca ctgtggagaa gagtctgtct     300
cctgcagaat gtctctaa                                                   318

<210> SEQ ID NO 44
<211> LENGTH: 324
<212> TYPE: PRT
<213> ORGANISM: Bubalus arnee

<400> SEQUENCE: 44

Ala Lys Thr Thr Pro Pro Ser Val Tyr Pro Leu Ala Pro Gly Ser Ala
1               5                   10                  15

Ala Gln Thr Asn Ser Met Val Thr Leu Gly Cys Leu Val Lys Gly Tyr
            20                  25                  30

Phe Pro Glu Pro Val Thr Val Thr Trp Asn Ser Gly Ser Leu Ser Ser
        35                  40                  45

Gly Val His Thr Phe Pro Ala Val Leu Glu Ser Asp Leu Tyr Thr Leu
    50                  55                  60

Ser Ser Ser Val Thr Val Pro Ser Ser Pro Arg Pro Ser Glu Thr Val
65                  70                  75                  80

Thr Cys Asn Val Ala His Pro Ala Ser Ser Thr Lys Val Asp Lys Lys
                85                  90                  95

Ile Val Pro Arg Asp Cys Gly Cys Lys Pro Cys Ile Cys Thr Val Pro
            100                 105                 110

Glu Val Ser Ser Val Phe Ile Phe Pro Pro Lys Pro Lys Asp Val Leu
        115                 120                 125

Thr Ile Thr Leu Thr Pro Lys Val Thr Cys Val Val Val Asp Ile Ser
    130                 135                 140

-continued

```
Lys Asp Asp Pro Glu Val Gln Phe Ser Trp Phe Val Asp Asp Val Glu
145                 150                 155                 160

Val His Thr Ala Gln Thr Gln Pro Arg Glu Glu Gln Phe Asn Ser Thr
                165                 170                 175

Phe Arg Ser Val Ser Glu Leu Pro Ile Met His Gln Asp Trp Leu Asn
            180                 185                 190

Gly Lys Glu Phe Lys Cys Arg Val Asn Ser Ala Ala Phe Pro Ala Pro
        195                 200                 205

Ile Glu Lys Thr Ile Ser Lys Thr Lys Gly Arg Pro Lys Ala Pro Gln
    210                 215                 220

Val Tyr Thr Ile Pro Pro Pro Lys Glu Gln Met Ala Lys Asp Lys Val
225                 230                 235                 240

Ser Leu Thr Cys Met Ile Thr Asp Phe Phe Pro Glu Asp Ile Thr Val
                245                 250                 255

Glu Trp Gln Trp Asn Gly Gln Pro Ala Glu Asn Tyr Lys Asn Thr Gln
            260                 265                 270

Pro Ile Met Asn Thr Asn Gly Ser Tyr Phe Val Tyr Ser Lys Leu Asn
        275                 280                 285

Val Gln Lys Ser Asn Trp Glu Ala Gly Asn Thr Phe Thr Cys Ser Val
    290                 295                 300

Leu His Glu Gly Leu His Asn His His Thr Glu Lys Ser Leu Ser His
305                 310                 315                 320

Ser Pro Gly Lys


<210> SEQ ID NO 45
<211> LENGTH: 975
<212> TYPE: DNA
<213> ORGANISM: Bubalus arnee

<400> SEQUENCE: 45

gccaaaacga cacccccatc tgtctatcca ctggcccctg gatctgctgc ccaaactaac     60

tccatggtga ccctgggatg cctggtcaag ggctatttcc ctgagccagt gacagtgacc    120

tggaactctg gatccctgtc cagcggtgtg cacaccttcc cagctgtcct ggagtctgac    180

ctctacactc tgagcagctc agtgactgtc ccctccagcc ctcggcccag cgagaccgtc    240

acctgcaacg ttgcccaccc ggccagcagc accaaggtgg acaagaaaat tgtgcccagg    300

gattgtggtt gtaagccttg catatgtaca gtcccagaag tatcatctgt cttcatcttc    360

cccccaaagc ccaaggatgt gctcaccatt actctgactc ctaaggtcac gtgtgttgtg    420

gtagacatca gcaaggatga tcccgaggtc cagttcagct ggtttgtaga tgatgtggag    480

gtgcacacag ctcagacgca accccgggag gagcagttca acagcacttt ccgctcagtc    540

agtgaacttc ccatcatgca ccaggactgg ctcaatggca aggagttcaa atgcagggtc    600

aacagtgcag ctttccctgc ccccatcgag aaaaccatct ccaaaaccaa aggcagaccg    660

aaggctccac aggtgtacac cattccacct cccaaggagc agatggccaa ggataaagtc    720

agtctgacct gcatgataac agacttcttc cctgaagaca ttactgtgga gtggcagtgg    780

aatgggcagc cagcggagaa ctacaagaac actcagccca tcatgaacac gaatggctct    840

tacttcgtct acagcaagct caatgtgcag aagagcaact gggaggcagg aaatactttc    900

acctgctctg tgttacatga gggcctgcac aaccaccata ctgagaagag cctctcccac    960

tctcctggta aatga                                                     975
```

<210> SEQ ID NO 46
<211> LENGTH: 324
<212> TYPE: PRT
<213> ORGANISM: Bubalus arnee

<400> SEQUENCE: 46

```
Ala Lys Thr Thr Pro Pro Ser Val Tyr Pro Leu Ala Pro Gly Ser Ala
1               5                   10                  15

Ala Gln Thr Asn Ser Met Val Thr Leu Gly Cys Leu Val Lys Gly Tyr
            20                  25                  30

Phe Pro Glu Pro Val Thr Val Thr Trp Asn Ser Gly Ser Leu Ser Ser
        35                  40                  45

Gly Val His Thr Phe Pro Ala Val Leu Gln Ser Asp Leu Tyr Thr Leu
    50                  55                  60

Ser Ser Ser Val Thr Val Pro Ser Ser Thr Trp Pro Ser Gln Thr Val
65                  70                  75                  80

Thr Cys Asn Val Ala His Pro Ala Ser Ser Thr Lys Val Asp Lys Lys
                85                  90                  95

Ile Val Pro Arg Asp Cys Gly Cys Lys Pro Cys Ile Cys Thr Val Pro
            100                 105                 110

Glu Val Ser Ser Val Phe Ile Phe Pro Pro Lys Pro Lys Asp Val Leu
        115                 120                 125

Thr Ile Thr Leu Thr Pro Lys Val Thr Cys Val Val Val Asp Ile Ser
    130                 135                 140

Lys Asp Asp Pro Glu Val Gln Phe Ser Trp Phe Val Asp Asp Val Glu
145                 150                 155                 160

Val His Thr Ala Gln Thr Lys Pro Arg Glu Glu Gln Ile Asn Ser Thr
                165                 170                 175

Phe Arg Ser Val Ser Glu Leu Pro Ile Met His Gln Asp Trp Leu Asn
            180                 185                 190

Gly Lys Glu Phe Lys Cys Arg Val Asn Ser Ala Ala Phe Pro Ala Pro
        195                 200                 205

Ile Glu Lys Thr Ile Ser Lys Thr Lys Gly Arg Pro Lys Ala Pro Gln
    210                 215                 220

Val Tyr Thr Ile Pro Pro Pro Lys Glu Gln Met Ala Lys Asp Lys Val
225                 230                 235                 240

Ser Leu Thr Cys Met Ile Thr Asn Phe Phe Pro Glu Asp Ile Thr Val
                245                 250                 255

Glu Trp Gln Trp Asn Gly Gln Pro Ala Glu Asn Tyr Lys Asn Thr Gln
            260                 265                 270

Pro Ile Met Asp Thr Asp Gly Ser Tyr Phe Val Tyr Ser Lys Leu Asn
        275                 280                 285

Val Gln Lys Ser Asn Trp Glu Ala Gly Asn Thr Phe Thr Cys Ser Val
    290                 295                 300

Leu His Glu Gly Leu His Asn His His Thr Glu Lys Ser Leu Ser His
305                 310                 315                 320

Ser Pro Gly Lys
```

<210> SEQ ID NO 47
<211> LENGTH: 975
<212> TYPE: DNA
<213> ORGANISM: Bubalus arnee

<400> SEQUENCE: 47

```
gccaaaacga cacccccatc tgtctatcca ctggcccctg gatctgctgc ccaaactaac     60
```

-continued

```
tccatggtga ccctgggatg cctggtcaag ggctatttcc ctgagccagt gacagtgacc    120

tggaactctg gatccctgtc cagcggtgtg cacaccttcc cagctgtcct gcagtctgac    180

ctctacactc tgagcagctc agtgactgtc ccctccagca cctggcccag ccagaccgtc    240

acctgcaacg ttgcccaccc ggccagcagc accaaggtgg acaagaaaat tgtgcccagg    300

gattgtggtt gtaagccttg catatgtaca gtcccagaag tatcatctgt cttcatcttc    360

cccccaaagc ccaaggatgt gctcaccatt actctgactc ctaaggtcac gtgtgttgtg    420

gtagacatca gcaaggatga tcccgaggtc cagttcagct ggtttgtaga tgatgtggag    480

gtgcacacag ctcagacgaa accccgggag gagcagatca acagcacttt ccgttcagtc    540

agtgaacttc ccatcatgca ccaggactgg ctcaatggca aggagttcaa atgcagggtc    600

aacagtgcag ctttccctgc ccccatcgag aaaaccatct ccaaaaccaa aggcagaccg    660

aaggctccac aggtgtacac cattccacct cccaaggagc agatggccaa ggataaagtc    720

agtctgacct gcatgataac aaacttcttc cctgaagaca ttactgtgga gtggcagtgg    780

aatgggcagc cagcggagaa ctacaagaac actcagccca tcatggacac agatggctct    840

tacttcgtct acagcaagct caatgtgcag aagagcaact gggaggcagg aaatactttc    900

acctgctctg tgttacatga gggcctgcac aaccaccata ctgagaagag cctctcccac    960

tctcctggta aatga                                                      975
```

<210> SEQ ID NO 48
<211> LENGTH: 330
<212> TYPE: PRT
<213> ORGANISM: Bubalus arnee

<400> SEQUENCE: 48

```
Ala Lys Thr Thr Ala Pro Ser Val Tyr Pro Leu Ala Pro Val Cys Gly
1               5                   10                  15

Asp Thr Thr Gly Ser Ser Val Thr Leu Gly Cys Leu Val Lys Gly Tyr
            20                  25                  30

Phe Pro Glu Pro Val Thr Leu Thr Trp Asn Ser Gly Ser Leu Ser Ser
        35                  40                  45

Gly Val His Thr Phe Pro Ala Val Leu Gln Ser Asp Leu Tyr Thr Leu
    50                  55                  60

Ser Ser Ser Val Thr Val Thr Ser Ser Thr Trp Pro Ser Gln Ser Ile
65                  70                  75                  80

Thr Cys Asn Val Ala His Pro Ala Ser Ser Thr Lys Val Asp Lys Lys
                85                  90                  95

Ile Glu Pro Arg Gly Pro Thr Ile Lys Pro Cys Pro Pro Cys Lys Cys
            100                 105                 110

Pro Ala Pro Asn Leu Leu Gly Gly Pro Ser Val Phe Ile Phe Pro Pro
        115                 120                 125

Lys Ile Lys Asp Val Leu Met Ile Ser Leu Ser Pro Ile Val Thr Cys
    130                 135                 140

Val Val Val Asp Val Ser Glu Asp Asp Pro Asp Val Gln Ile Ser Trp
145                 150                 155                 160

Phe Val Asn Asn Val Glu Val His Thr Ala Gln Thr Gln Thr His Arg
                165                 170                 175

Glu Asp Tyr Asn Ser Thr Leu Arg Val Val Ser Ala Leu Pro Ile Gln
            180                 185                 190

His Gln Asp Trp Met Ser Gly Lys Glu Phe Lys Cys Lys Val Asn Asn
        195                 200                 205
```

-continued

```
Lys Asp Leu Pro Ala Pro Ile Glu Arg Thr Ile Ser Lys Pro Lys Gly
    210                 215                 220

Ser Val Arg Ala Pro Gln Val Tyr Val Leu Pro Pro Pro Glu Glu Glu
225                 230                 235                 240

Met Thr Lys Lys Gln Val Thr Leu Thr Cys Met Val Thr Asp Phe Met
                245                 250                 255

Pro Glu Asp Ile Tyr Val Glu Trp Thr Asn Asn Gly Lys Thr Glu Leu
            260                 265                 270

Asn Tyr Lys Asn Thr Glu Pro Val Leu Asp Ser Asp Gly Ser Tyr Phe
        275                 280                 285

Met Tyr Ser Lys Leu Arg Val Glu Lys Lys Asn Trp Val Glu Arg Asn
    290                 295                 300

Ser Tyr Ser Cys Ser Val Val His Glu Gly Leu His Asn His His Thr
305                 310                 315                 320

Thr Lys Ser Phe Ser Arg Thr Pro Gly Lys
                325                 330
```

<210> SEQ ID NO 49
<211> LENGTH: 993
<212> TYPE: DNA
<213> ORGANISM: Bubalus arnee

<400> SEQUENCE: 49

```
gccaaaacaa cagccccatc ggtctatcca ctggcccctg tgtgtggaga tacaactggc      60

tcctcggtga ctctaggatg cctggtcaag ggttatttcc ctgagccagt gaccttgacc     120

tggaactctg gatccctgtc cagtggtgtg cacaccttcc cagctgtcct gcagtctgac     180

ctctacaccc tcagcagctc agtgactgta acctcgagca cctggcccag ccagtccatc     240

acctgcaatg tggcccaccc ggcaagcagc accaaggtgg acaagaaaat tgagcccaga     300

gggcccacaa tcaagccctg tcctccatgc aaatgcccag cacctaacct cttgggtgga     360

ccatccgtct tcatcttccc tccaaagatc aaggatgtac tcatgatctc cctgagcccc     420

atagtcacat gtgtggtggt ggatgtgagc gaggatgacc cagatgtcca gatcagctgg     480

tttgtgaaca acgtggaagt acacacagct cagacacaaa cccatagaga ggattacaac     540

agtactctcc gggtggtcag tgccctcccc atccagcacc aggactggat gagtggcaag     600

gagttcaaat gcaaggtcaa caacaaagac ctcccagcgc ccatcgagag aaccatctca     660

aaacccaaag ggtcagtaag agctccacag gtatatgtct tgcctccacc agaagaagag     720

atgactaaga aacaggtcac tctgacctgc atggtcacag acttcatgcc tgaagacatt     780

tacgtggagt ggaccaacaa cgggaaaaca gagctaaact acaagaacac tgaaccagtc     840

ctggactctg atggttctta cttcatgtac agcaagctga gagtggaaaa gaagaactgg     900

gtggaaagaa atagctactc ctgttcagtg gtccacgagg gtctgcacaa tcaccacacg     960

actaagagct tctcccggac tccgggtaaa tga                                  993
```

<210> SEQ ID NO 50
<211> LENGTH: 330
<212> TYPE: PRT
<213> ORGANISM: Bubalus arnee

<400> SEQUENCE: 50

```
Ala Lys Thr Thr Ala Pro Ser Val Tyr Pro Leu Ala Pro Val Cys Gly
1               5                   10                  15

Asp Thr Thr Gly Ser Ser Val Thr Leu Gly Cys Leu Val Lys Gly Tyr
            20                  25                  30
```

```
Phe Pro Glu Pro Val Thr Leu Thr Trp Asn Ser Gly Ser Leu Ser Ser
        35                  40                  45

Gly Val His Thr Phe Pro Ala Val Leu Gln Ser Asp Leu Tyr Thr Leu
    50                  55                  60

Ser Ser Ser Val Thr Val Thr Ser Ser Thr Trp Pro Ser Gln Ser Ile
65                  70                  75                  80

Thr Cys Asn Val Ala His Pro Ala Ser Ser Thr Lys Val Asp Lys Lys
                85                  90                  95

Ile Glu Pro Arg Gly Pro Thr Ile Lys Pro Cys Pro Pro Cys Lys Cys
            100                 105                 110

Pro Ala Pro Asn Leu Leu Gly Gly Pro Ser Val Phe Ile Phe Pro Pro
        115                 120                 125

Lys Ile Lys Asp Val Leu Met Ile Ser Leu Ser Pro Met Val Thr Cys
    130                 135                 140

Val Val Val Asp Val Ser Glu Asp Asp Pro Asp Val Gln Ile Ser Trp
145                 150                 155                 160

Phe Val Asn Asn Val Glu Val Leu Thr Ala Gln Thr Gln Thr His Arg
                165                 170                 175

Glu Asp Tyr Asn Ser Thr Leu Arg Val Val Ser Ala Leu Pro Ile Gln
            180                 185                 190

His Gln Asp Trp Met Ser Gly Lys Glu Phe Lys Cys Lys Val Asn Asn
        195                 200                 205

Lys Ala Leu Pro Ala Pro Ile Glu Arg Thr Ile Ser Lys Pro Lys Gly
    210                 215                 220

Ser Val Arg Ala Pro Gln Val Tyr Val Leu Pro Pro Pro Glu Glu Glu
225                 230                 235                 240

Met Thr Lys Lys Gln Val Thr Leu Thr Cys Met Val Thr Asp Phe Met
                245                 250                 255

Pro Glu Asp Ile Tyr Val Glu Trp Thr Asn Asn Gly Lys Thr Glu Leu
            260                 265                 270

Asn Tyr Lys Asn Thr Glu Pro Val Leu Asp Ser Asp Gly Ser Tyr Phe
        275                 280                 285

Met Tyr Ser Lys Leu Arg Val Glu Lys Lys Asn Trp Val Glu Arg Asn
    290                 295                 300

Ser Tyr Ser Cys Ser Val Val His Glu Gly Leu His Asn His His Thr
305                 310                 315                 320

Thr Lys Ser Phe Ser Arg Thr Pro Gly Lys
                325                 330


<210> SEQ ID NO 51
<211> LENGTH: 993
<212> TYPE: DNA
<213> ORGANISM: Bubalus arnee

<400> SEQUENCE: 51

gccaaaacaa cagccccatc ggtctatcca ctggcccctg tgtgtggaga tacaactggc      60

tcctcggtga ctctaggatg cctggtcaag ggttatttcc ctgagccagt gaccttgacc     120

tggaactctg gatccctgtc cagtggtgtg cacaccttcc cagctgtcct gcagtctgac     180

ctctacaccc tcagcagctc agtgactgta acctcgagca cctggcccag ccagtccatc     240

acctgcaatg tggcccaccc ggcaagcagc accaaggtgg acaagaaaat tgagcccaga     300

gggcccacaa tcaagccctg tcctccatgc aaatgcccag cacctaacct cttgggtgga     360

ccatccgtct tcatcttccc tccaaagatc aaggatgtac tcatgatctc cctgagtccc     420
```

-continued

```
atggtcacat gtgtggtggt ggatgtgagc gaggatgacc cagatgtcca gatcagctgg    480

ttcgtgaaca acgtggaagt actcacagct cagacacaaa cccatagaga ggattacaac    540

agtactctcc gggtggtcag tgccctcccc atccagcacc aggactggat gagtggcaag    600

gagttcaaat gcaaggtcaa caacaaagcc ctcccagcgc ccatcgagag aaccatctca    660

aaacccaaag ggtcagtaag agctccacag gtatatgtct tgcctccacc agaagaagag    720

atgactaaga aacaggtcac tctgacctgc atggtcacag acttcatgcc tgaagacatt    780

tacgtggagt ggaccaacaa cgggaaaaca gagctaaact acaagaacac tgaaccagtc    840

ctggactctg atggttctta cttcatgtac agcaagctga gagtggaaaa gaagaactgg    900

gtggaaagaa atagctactc ctgttcagtg gtccacgagg gtctgcacaa tcaccacacg    960

actaagagct tctcccggac tccgggtaaa tga                                 993
```

<210> SEQ ID NO 52
<211> LENGTH: 336
<212> TYPE: PRT
<213> ORGANISM: Bubalus arnee

<400> SEQUENCE: 52

```
Ala Lys Thr Thr Pro Pro Ser Val Tyr Pro Leu Ala Pro Gly Cys Gly
1               5                   10                  15

Asp Thr Thr Gly Ser Ser Val Thr Leu Gly Cys Leu Val Lys Gly Tyr
            20                  25                  30

Phe Pro Glu Ser Val Thr Val Thr Trp Asn Ser Gly Ser Leu Ser Ser
        35                  40                  45

Ser Val His Thr Phe Pro Ala Leu Leu Gln Ser Gly Leu Tyr Thr Met
    50                  55                  60

Ser Ser Ser Val Thr Val Pro Ser Ser Thr Trp Pro Ser Gln Thr Val
65                  70                  75                  80

Thr Cys Ser Val Ala His Pro Ala Ser Ser Thr Thr Val Asp Lys Lys
                85                  90                  95

Leu Glu Pro Ser Gly Pro Ile Ser Thr Ile Asn Pro Cys Pro Pro Cys
            100                 105                 110

Lys Glu Cys His Lys Cys Pro Ala Pro Asn Leu Glu Gly Gly Pro Ser
        115                 120                 125

Val Phe Ile Phe Pro Pro Asn Ile Lys Asp Val Leu Met Ile Ser Leu
    130                 135                 140

Thr Pro Lys Val Thr Cys Val Val Val Asp Val Ser Glu Asp Asp Pro
145                 150                 155                 160

Asp Val Gln Ile Ser Trp Phe Val Asn Asn Val Glu Val His Thr Ala
                165                 170                 175

Gln Thr Gln Thr His Arg Glu Asp Tyr Asn Ser Thr Ile Arg Val Val
            180                 185                 190

Ser Thr Leu Pro Ile Gln His Gln Asp Trp Met Ser Gly Lys Glu Phe
        195                 200                 205

Lys Cys Lys Val Asn Asn Lys Asp Leu Pro Ser Pro Ile Glu Arg Thr
    210                 215                 220

Ile Ser Lys Ile Lys Gly Leu Val Arg Ala Pro Gln Val Tyr Ile Leu
225                 230                 235                 240

Pro Pro Pro Ala Glu Gln Leu Ser Arg Lys Asp Val Ser Leu Thr Cys
                245                 250                 255

Leu Val Val Gly Phe Asn Pro Gly Asp Ile Ser Val Glu Trp Thr Ser
            260                 265                 270
```

```
Asn Gly His Thr Glu Glu Asn Tyr Lys Asp Thr Ala Pro Val Leu Asp
        275                 280                 285

Ser Asp Gly Ser Tyr Phe Ile Tyr Ser Lys Leu Asn Met Lys Thr Ser
    290                 295                 300

Lys Trp Glu Lys Thr Asp Ser Phe Ser Cys Asn Val Arg His Glu Gly
305                 310                 315                 320

Leu Lys Asn Tyr Tyr Leu Lys Lys Thr Ile Ser Arg Ser Pro Gly Lys
                325                 330                 335


<210> SEQ ID NO 53
<211> LENGTH: 1011
<212> TYPE: DNA
<213> ORGANISM: Bubalus arnee

<400> SEQUENCE: 53

gccaaaacaa cacccccatc agtctatcca ctggcccctg ggtgtggaga tacaactggt      60

tcctccgtga ctctgggatg cctggtcaag ggctacttcc ctgagtcagt gactgtgact     120

tggaactctg gatccctgtc cagcagtgtg cacaccttcc cagctctcct gcagtctgga     180

ctctacacta tgagcagctc agtgactgtc ccctccagca cttggccaag tcagaccgtc     240

acctgcagcg ttgctcaccc agccagcagc accacggtgg acaaaaaact tgagcccagc     300

gggcccattt caacaatcaa cccctgtcct ccatgcaagg agtgtcacaa atgcccagct     360

cctaacctcg agggtggacc atccgtcttc atcttccctc caaatatcaa ggatgtactc     420

atgatctccc tgacacccaa ggtcacgtgt gtggtggtgg atgtgagcga ggatgaccca     480

gacgtccaga tcagctggtt tgtgaacaac gtggaagtac acacagctca gacacaaacc     540

catagagagg attacaacag tactatccgg gtggtcagca ccctccccat ccagcaccag     600

gactggatga gtggcaagga gttcaaatgc aaggtcaaca acaaagacct cccatcaccc     660

atcgagagaa ccatctcaaa aattaaaggg ctagtcagag ctccacaagt atacatcttg     720

ccgccaccag cagagcagtt gtccaggaaa gatgtcagtc tcacttgcct ggtcgtgggc     780

ttcaaccctg gagacatcag tgtggagtgg accagcaatg ggcatacaga ggagaactac     840

aaggacaccg caccagtcct agactctgac ggttcttact tcatatatag caagctcaat     900

atgaaaacaa gcaagtggga gaaaacagat tccttctcat gcaacgtgag acacgagggt     960

ctgaaaaatt actacctgaa gaagaccatc tcccggtctc cgggtaaatg a            1011


<210> SEQ ID NO 54
<211> LENGTH: 336
<212> TYPE: PRT
<213> ORGANISM: Bubalus arnee

<400> SEQUENCE: 54

Ala Lys Thr Thr Pro Pro Ser Val Tyr Pro Leu Ala Pro Gly Cys Gly
1               5                   10                  15

Asp Thr Thr Gly Ser Ser Val Thr Ser Gly Cys Leu Val Lys Gly Tyr
            20                  25                  30

Phe Pro Glu Pro Val Thr Val Thr Trp Asn Ser Gly Ser Leu Ser Ser
        35                  40                  45

Ser Val His Thr Phe Pro Ala Leu Leu Gln Ser Gly Leu Tyr Thr Met
    50                  55                  60

Ser Ser Ser Val Thr Val Pro Ser Ser Thr Trp Pro Ser Gln Thr Val
65                  70                  75                  80

Thr Cys Ser Val Ala His Pro Ala Ser Ser Thr Thr Val Asp Lys Lys
```

|  |  |  | 85 |  |  |  | 90 |  |  |  | 95 |  |
|---|---|---|---|---|---|---|---|---|---|---|---|---|

Leu Glu Pro Ser Gly Pro Ile Ser Thr Ile Asn Pro Cys Pro Pro Cys
    100     105     110

Lys Glu Cys His Lys Cys Pro Ala Pro Asn Leu Glu Gly Gly Pro Ser
    115     120     125

Val Phe Ile Phe Pro Pro Asn Ile Lys Asp Val Leu Met Ile Ser Leu
130     135     140

Thr Pro Lys Val Thr Cys Val Val Val Asp Val Ser Glu Asp Asp Pro
145     150     155     160

Asp Val Gln Ile Ser Trp Phe Val Asn Asn Val Glu Val His Thr Ala
    165     170     175

Gln Thr Gln Thr His Arg Glu Asp Tyr Asn Ser Thr Ile Arg Val Val
    180     185     190

Ser Thr Leu Pro Ile Gln His Gln Asp Trp Met Ser Gly Lys Glu Phe
    195     200     205

Lys Cys Lys Val Asn Asn Lys Asp Leu Pro Ser Pro Ile Glu Arg Thr
210     215     220

Ile Ser Lys Ile Lys Gly Leu Val Arg Ala Pro Gln Val Tyr Thr Leu
225     230     235     240

Pro Pro Pro Ala Glu Gln Leu Ser Arg Lys Asp Val Ser Leu Thr Cys
    245     250     255

Leu Val Val Gly Phe Asn Pro Gly Asp Ile Ser Val Glu Trp Thr Ser
    260     265     270

Asn Gly His Thr Glu Glu Asn Tyr Lys Asp Thr Ala Pro Val Leu Asp
    275     280     285

Ser Asp Gly Ser Tyr Phe Ile Tyr Ser Lys Leu Asn Met Lys Thr Ser
    290     295     300

Lys Trp Glu Lys Thr Asp Ser Phe Ser Cys Asn Val Arg His Glu Gly
305     310     315     320

Leu Lys Asn Tyr Tyr Leu Lys Lys Thr Ile Ser Arg Ser Pro Gly Lys
    325     330     335

<210> SEQ ID NO 55
<211> LENGTH: 1011
<212> TYPE: DNA
<213> ORGANISM: Bubalus arnee

<400> SEQUENCE: 55

```
gccaaaacaa cacccccatc agtctatcca ctggcccctg ggtgtggaga tacaactggt      60
tcctccgtga cctctgggtg cctggtcaag gggtacttcc ctgagccagt gactgtgact     120
tggaactctg gatccctgtc cagcagtgtg cacaccttcc cagctctcct gcagtctgga     180
ctctacacta tgagcagctc agtgactgtc ccctccagca cctggccaag tcagaccgtc     240
acctgcagcg ttgctcaccc agccagcagc accacggtgg acaaaaaact tgagcccagc     300
gggcccattt caacaatcaa cccctgtcct ccatgcaagg agtgtcacaa atgcccagct     360
cctaacctcg agggtggacc atccgtcttc atcttccctc caaatatcaa ggatgtactc     420
atgatctccc tgacacccaa ggtcacgtgt gtggtggtgg atgtgagcga ggatgaccca     480
gacgtccaga tcagctggtt tgtgaacaac gtggaagtac acacagctca gacacaaacc     540
catagagagg attacaacag tactatccgg gtggtcagca ccctccccat ccagcaccag     600
gactggatga gtggcaagga gttcaaatgc aaggtgaaca acaaagacct cccatcaccc     660
atcgagagaa ccatctcaaa aattaaaggg ctagtcagag ctccacaagt atacactttg     720
```

ccgccaccag cagagcagtt gtccaggaaa gatgtcagtc tcacttgcct ggtcgtgggc 780
ttcaaccctg gagacatcag tgtggagtgg accagcaatg ggcatacaga ggagaactac 840
aaggacaccg caccagttct tgactctgac ggttcttact tcatatatag caagctcaat 900
atgaaaacaa gcaagtggga gaaaacagat tccttctcat gcaacgtgag acacgagggt 960
ctgaaaaatt actacctgaa gaagaccatc tcccggtctc cgggtaaatg a 1011

<210> SEQ ID NO 56
<211> LENGTH: 335
<212> TYPE: PRT
<213> ORGANISM: Bubalus arnee

<400> SEQUENCE: 56

```
Ala Lys Thr Thr Ala Pro Ser Val Tyr Pro Leu Ala Pro Val Cys Gly
1               5                   10                  15

Gly Thr Thr Gly Ser Ser Val Thr Leu Gly Cys Leu Val Lys Gly Tyr
            20                  25                  30

Phe Pro Glu Pro Val Thr Leu Thr Trp Asn Ser Gly Ser Leu Ser Ser
        35                  40                  45

Gly Val His Thr Phe Pro Ala Leu Leu Gln Ser Gly Leu Tyr Thr Leu
    50                  55                  60

Ser Ser Ser Val Thr Val Thr Ser Asn Thr Trp Pro Ser Gln Thr Ile
65                  70                  75                  80

Thr Cys Asn Val Ala His Pro Ala Ser Ser Thr Lys Val Asp Lys Lys
                85                  90                  95

Ile Glu Pro Arg Val Pro Ile Thr Gln Asn Pro Cys Pro Pro Leu Lys
            100                 105                 110

Glu Cys Pro Pro Cys Ala Ala Pro Asp Leu Leu Gly Gly Pro Ser Val
        115                 120                 125

Phe Ile Phe Pro Pro Lys Ile Lys Asp Val Leu Met Ile Ser Leu Ser
    130                 135                 140

Pro Met Val Thr Cys Val Val Val Asp Val Ser Glu Asp Asp Pro Asp
145                 150                 155                 160

Val Gln Ile Ser Trp Phe Val Asn Asn Val Glu Val His Thr Ala Gln
                165                 170                 175

Thr Gln Thr His Arg Glu Asp Tyr Asn Ser Thr Leu Arg Val Val Ser
            180                 185                 190

Ala Leu Pro Ile Gln His Gln Asp Trp Met Ser Gly Lys Glu Phe Lys
        195                 200                 205

Cys Lys Val Asn Asn Arg Ala Leu Pro Ser Pro Ile Glu Lys Thr Ile
    210                 215                 220

Ser Lys Pro Arg Gly Pro Val Arg Ala Pro Gln Val Tyr Val Leu Pro
225                 230                 235                 240

Pro Pro Ala Glu Glu Met Thr Lys Lys Glu Phe Ser Leu Thr Cys Met
                245                 250                 255

Ile Thr Gly Phe Leu Pro Ala Glu Ile Ala Val Asp Trp Thr Ser Asn
            260                 265                 270

Gly Arg Thr Glu Gln Asn Tyr Lys Asn Thr Ala Thr Val Leu Asp Ser
        275                 280                 285

Asp Gly Ser Tyr Phe Met Tyr Ser Lys Leu Arg Val Gln Lys Ser Thr
    290                 295                 300

Trp Glu Arg Gly Ser Leu Phe Ala Cys Ser Val Val His Glu Val Leu
305                 310                 315                 320

His Asn His Leu Thr Thr Lys Thr Ile Ser Arg Ser Leu Gly Lys
```

325 330 335

<210> SEQ ID NO 57
<211> LENGTH: 1008
<212> TYPE: DNA
<213> ORGANISM: Bubalus arnee

<400> SEQUENCE: 57

```
gccaaaacaa cagccccatc ggtctatcca ctggcccctg tgtgtggagg tacaactggc     60
tcctcggtga ctctaggatg cctggtcaag ggttatttcc ctgagccagt gaccttgacc    120
tggaactctg gatccctgtc cagtggtgtg cacaccttcc cagctctcct gcagtctggc    180
ctctacaccc tcagcagctc agtgactgta acctcgaaca cctggcccag ccagaccatc    240
acctgcaatg tggcccaccc ggcaagcagc accaaagtgg acaagaaaat tgagcccaga    300
gtgcccataa cacagaaccc ctgtcctcca ctcaaagagt gtcccccatg cgcagctcca    360
gacctcttgg gtggaccatc cgtcttcatc ttccctccaa agatcaagga tgtactcatg    420
atctccctga gccccatggt cacatgtgtg gtggtggatg tgagcgagga tgacccagac    480
gtccagatca gctggtttgt gaacaacgtg gaagtacaca cagctcagac acaaacccat    540
agagaggatt acaacagtac tctccgggtg gtcagtgccc tccccatcca gcaccaggac    600
tggatgagtg gcaaggagtt caaatgcaag gtcaacaaca gagccctccc atcccccatc    660
gagaaaacca tctcaaaacc cagagggcca gtaagagctc cacaggtata tgtcttgcct    720
ccaccagcag aagagatgac taagaaagag ttcagtctga cctgcatgat cacaggcttc    780
ttacctgccg aaattgctgt ggactggacc agcaatgggc gtacagagca aaactacaag    840
aacaccgcaa cagtcctgga ctctgatggt tcttacttca tgtacagcaa gctcagagta    900
caaaagagca cttgggaaag aggaagtctt ttcgcctgct cagtggtcca cgaggtgctg    960
cacaatcacc ttacgactaa gaccatctcc cggtctctgg gtaaatga                1008
```

<210> SEQ ID NO 58
<211> LENGTH: 335
<212> TYPE: PRT
<213> ORGANISM: Bubalus arnee

<400> SEQUENCE: 58

```
Ala Lys Thr Thr Ala Pro Ser Val Tyr Pro Leu Ala Pro Val Cys Gly
1               5                   10                  15

Gly Thr Thr Gly Ser Ser Val Thr Leu Gly Cys Leu Val Lys Gly Tyr
            20                  25                  30

Phe Pro Glu Pro Val Thr Leu Thr Trp Asn Ser Gly Ser Leu Ser Ser
        35                  40                  45

Gly Val His Thr Phe Pro Ala Leu Leu Gln Ser Gly Leu Tyr Thr Leu
    50                  55                  60

Ser Ser Ser Val Thr Val Thr Ser Asn Thr Trp Pro Ser Gln Thr Ile
65                  70                  75                  80

Thr Cys Asn Val Ala His Pro Ala Ser Ser Thr Lys Val Asp Lys Lys
                85                  90                  95

Ile Glu Ser Arg Arg Pro Ile Pro Pro Asn Ser Cys Pro Pro Cys Lys
            100                 105                 110

Glu Cys Ser Ile Phe Pro Ala Pro Asp Leu Leu Gly Gly Pro Ser Val
        115                 120                 125

Phe Ile Phe Pro Pro Lys Ile Lys Asp Val Leu Met Ile Ser Leu Ser
    130                 135                 140
```

-continued

```
Pro Ile Val Thr Cys Val Val Val Asp Val Ser Glu Asp Asp Pro Asp
145                 150                 155                 160

Val Gln Ile Ser Trp Phe Val Asn Asn Val Glu Val His Thr Ala Gln
                165                 170                 175

Thr Gln Thr His Arg Glu Asp Tyr Asn Ser Thr Leu Arg Val Val Ser
            180                 185                 190

Ala Leu Pro Ile Gln His Gln Asp Trp Met Ser Gly Lys Glu Phe Lys
        195                 200                 205

Cys Lys Val Asn Asn Arg Ala Leu Pro Ser Pro Ile Glu Lys Thr Ile
    210                 215                 220

Ser Lys Pro Arg Gly Pro Val Arg Ala Pro Gln Val Tyr Val Leu Pro
225                 230                 235                 240

Pro Pro Ala Glu Glu Met Thr Lys Lys Glu Phe Ser Leu Thr Cys Met
                245                 250                 255

Ile Thr Asp Phe Leu Pro Ala Glu Ile Ala Val Asp Trp Thr Ser Asn
            260                 265                 270

Gly His Lys Glu Leu Asn Tyr Lys Asn Thr Ala Pro Val Leu Asp Thr
        275                 280                 285

Asp Gly Ser Tyr Phe Met Tyr Ser Lys Leu Arg Val Gln Lys Ser Thr
    290                 295                 300

Trp Glu Lys Gly Ser Leu Phe Ala Cys Ser Val Val His Glu Gly Leu
305                 310                 315                 320

His Asn His His Thr Thr Lys Thr Ile Ser Arg Ser Leu Gly Lys
                325                 330                 335


<210> SEQ ID NO 59
<211> LENGTH: 1008
<212> TYPE: DNA
<213> ORGANISM: Bubalus arnee

<400> SEQUENCE: 59

gccaaaacaa cagccccatc ggtctatcca ctggcccctg tgtgtggagg tacaactggc      60

tcctcggtga ctctaggatg cctggtcaag ggttatttcc ctgagccagt gaccttgacc     120

tggaactctg gatccctgtc cagtggtgtg cacaccttcc cagctctcct gcagtctggc     180

ctctacaccc tcagcagctc agtgactgta acctcgaaca cctggcccag ccagaccatc     240

acctgcaatg tggcccaccc ggcaagcagc accaaagtgg acaagaaaat tgaatccaga     300

aggcccatac cacccaactc ctgtcctcca tgcaaagagt gttccatatt cccagctcct     360

gacctcttgg gtggaccatc cgtcttcatc ttccctccaa agatcaagga tgtactcatg     420

atctccctga gccccatagt cacatgtgtg gtggtggatg tgagcgagga tgacccagat     480

gtccagatca gctggtttgt gaacaacgtg gaagtacaca cagctcagac acaaacccat     540

agagaggatt acaacagtac tctccgggtg gtcagtgccc tccccatcca gcaccaggac     600

tggatgagtg gcaaggagtt caaatgcaag gtcaacaaca gagccctccc atcccccatc     660

gagaaaacca tctcaaaacc cagagggcca gtaagagctc cacaggtata tgtcttgcct     720

ccaccagcag aagagatgac taagaaagag ttcagtctga cctgcatgat cacagacttc     780

ttacctgccg aaattgctgt ggactggacc agcaatgggc ataaagagct gaactacaag     840

aacaccgcac cagtcctgga cactgatggt tcttacttca tgtacagcaa gctcagagtg     900

caaaagagca cttgggaaaa aggaagtctt ttcgcctgct cagtggtcca cgagggtctg     960

cacaatcacc atacgactaa gaccatctcc cggtctctgg gtaaatga                 1008
```

<210> SEQ ID NO 60
<211> LENGTH: 335
<212> TYPE: PRT
<213> ORGANISM: Bubalus arnee

<400> SEQUENCE: 60

```
Ala Lys Thr Thr Ala Pro Ser Val Tyr Pro Leu Ala Pro Val Cys Gly
1               5                   10                  15

Gly Thr Thr Gly Ser Ser Val Thr Leu Gly Cys Leu Val Lys Gly Tyr
            20                  25                  30

Phe Pro Glu Pro Val Thr Leu Thr Trp Asn Ser Gly Ser Leu Ser Ser
        35                  40                  45

Gly Val His Thr Phe Pro Ala Leu Leu Gln Ser Gly Leu Tyr Thr Leu
    50                  55                  60

Ser Ser Ser Val Thr Val Thr Ser Asn Thr Trp Pro Ser Gln Thr Ile
65                  70                  75                  80

Thr Cys Asn Val Ala His Pro Ala Ser Ser Thr Lys Val Asp Lys Lys
                85                  90                  95

Ile Glu Pro Arg Val Pro Ile Thr Gln Asn Pro Cys Pro Pro Leu Lys
            100                 105                 110

Glu Cys Pro Pro Cys Ala Ala Pro Asp Leu Leu Gly Gly Pro Ser Val
        115                 120                 125

Phe Ile Phe Pro Pro Lys Ile Lys Asp Val Leu Met Ile Ser Leu Ser
    130                 135                 140

Pro Met Val Thr Cys Val Val Val Asp Val Ser Glu Asp Asp Pro Asp
145                 150                 155                 160

Val Gln Ile Ser Trp Phe Val Asn Asn Val Glu Val His Thr Ala Gln
                165                 170                 175

Thr Gln Thr His Arg Glu Asp Tyr Asn Ser Thr Leu Arg Val Val Ser
            180                 185                 190

Ala Leu Pro Ile Gln His Gln Asp Trp Met Ser Gly Lys Glu Phe Lys
        195                 200                 205

Cys Lys Val Asn Asn Arg Ala Leu Pro Ser Pro Ile Glu Lys Thr Ile
    210                 215                 220

Ser Lys Pro Arg Gly Pro Val Arg Ala Pro Gln Val Tyr Val Leu Pro
225                 230                 235                 240

Pro Pro Ala Glu Glu Met Thr Lys Lys Glu Phe Ser Leu Thr Cys Met
                245                 250                 255

Ile Thr Gly Phe Leu Pro Ala Glu Ile Ala Val Asp Trp Thr Ser Asn
            260                 265                 270

Gly Arg Thr Glu Gln Asn Tyr Lys Asn Thr Ala Thr Val Leu Asp Ser
        275                 280                 285

Asp Gly Ser Tyr Phe Met Tyr Ser Lys Leu Arg Val Gln Lys Ser Thr
    290                 295                 300

Trp Glu Arg Gly Ser Leu Phe Ala Cys Ser Val Val His Glu Gly Leu
305                 310                 315                 320

His Asn His Leu Thr Thr Lys Thr Ile Ser Arg Ser Leu Gly Lys
                325                 330                 335
```

<210> SEQ ID NO 61
<211> LENGTH: 1008
<212> TYPE: DNA
<213> ORGANISM: Bubalus arnee

<400> SEQUENCE: 61

```
gccaaaacaa cagccccatc ggtctatcca ctggcccctg tgtgtggagg tacaactggc     60
```

-continued

```
tcctcggtga ctctaggatg cctggtcaag ggttatttcc ctgagccagt gaccttgacc    120

tggaactctg gatccctgtc cagtggtgtg cacaccttcc cagctctcct gcagtctggc    180

ctctacaccc tcagcagctc agtgactgta acctcgaaca cctggcccag ccagaccatc    240

acctgcaatg tggcccaccc ggcaagcagc accaaagtgg acaagaaaat tgagcccaga    300

gtgcccataa cacagaaccc ctgtcctcca ctcaaagagt gtcccccatg cgcagctcca    360

gacctcttgg gtggaccatc cgtcttcatc ttccctccaa agatcaagga tgtactcatg    420

atctccctga gccccatggt cacatgtgtg gtggtggatg tgagcgagga tgacccagac    480

gtccagatca gctggtttgt gaacaacgtg gaagtacaca cagctcagac acaaacccat    540

agagaggatt acaacagtac tctccgggtg gtcagtgccc tccccatcca gcaccaggac    600

tggatgagtg gcaaggagtt caaatgcaag gtcaacaaca gagccctccc atcccccatc    660

gagaaaacca tctcaaaacc cagagggcca gtaagagctc cacaggtata tgtcttgcct    720

ccaccagcag aagagatgac taagaaagag ttcagtctga cctgcatgat cacaggcttc    780

ttacctgccg aaattgctgt ggactggacc agcaatgggc gtacagagca aaactacaag    840

aacaccgcaa cagtcctgga ctctgatggt tcttacttca tgtacagcaa gctcagagta    900

caaaagagca cttgggaaag aggaagtctt ttcgcctgct cagtggtcca cgagggtctg    960

cacaatcacc ttacgactaa gaccatctcc cggtctctgg gtaaatga                1008


<210> SEQ ID NO 62
<211> LENGTH: 330
<212> TYPE: PRT
<213> ORGANISM: Bubalus arnee

<400> SEQUENCE: 62

Ala Thr Thr Thr Ala Pro Ser Val Tyr Pro Leu Val Pro Gly Cys Ser
1               5                   10                  15

Asp Thr Ser Gly Ser Ser Val Thr Leu Gly Cys Leu Val Lys Gly Tyr
            20                  25                  30

Phe Pro Glu Pro Val Thr Val Lys Trp Asn Tyr Gly Ala Leu Ser Ser
        35                  40                  45

Gly Val Arg Thr Val Ser Ser Val Leu Gln Ser Gly Phe Tyr Ser Leu
    50                  55                  60

Ser Ser Leu Val Thr Val Pro Ser Ser Thr Trp Pro Ser Gln Thr Val
65                  70                  75                  80

Ile Cys Asn Val Ala His Pro Ala Ser Lys Thr Glu Leu Ile Lys Arg
                85                  90                  95

Ile Glu Pro Arg Ile Pro Lys Pro Ser Thr Pro Pro Gly Ser Ser Cys
            100                 105                 110

Pro Pro Gly Asn Ile Leu Gly Gly Pro Ser Val Phe Ile Phe Pro Pro
        115                 120                 125

Lys Pro Lys Asp Ala Leu Met Ile Ser Leu Thr Pro Lys Val Thr Cys
    130                 135                 140

Val Val Val Asp Val Ser Glu Asp Asp Pro Asp Val His Val Ser Trp
145                 150                 155                 160

Phe Val Asp Asn Lys Glu Val His Thr Ala Trp Thr Gln Pro Arg Glu
                165                 170                 175

Ala Gln Tyr Asn Ser Thr Phe Arg Val Val Ser Ala Leu Pro Ile Gln
            180                 185                 190

His Gln Asp Trp Met Arg Gly Lys Glu Phe Lys Cys Lys Val Asn Asn
        195                 200                 205
```

```
Lys Ala Leu Pro Ala Pro Ile Glu Arg Thr Ile Ser Lys Pro Lys Gly
    210                 215                 220

Arg Ala Gln Thr Pro Gln Val Tyr Thr Ile Pro Pro Pro Arg Glu Gln
225                 230                 235                 240

Met Ser Lys Lys Lys Val Ser Leu Thr Cys Leu Val Thr Asn Phe Phe
                245                 250                 255

Ser Glu Ala Ile Ser Val Glu Trp Glu Arg Asn Gly Glu Leu Glu Gln
            260                 265                 270

Asp Tyr Lys Asn Thr Pro Pro Ile Leu Asp Ser Asp Gly Thr Tyr Phe
        275                 280                 285

Leu Tyr Ser Lys Leu Thr Val Asp Thr Asp Ser Trp Leu Gln Gly Glu
    290                 295                 300

Ile Phe Thr Cys Ser Val Val His Glu Ala Leu His Asn His His Thr
305                 310                 315                 320

Gln Lys Asn Leu Ser Arg Ser Pro Gly Lys
                325                 330


<210> SEQ ID NO 63
<211> LENGTH: 993
<212> TYPE: DNA
<213> ORGANISM: Bubalus arnee

<400> SEQUENCE: 63

gctacaacaa cagccccatc tgtctatccc ttggtccctg gctgcagtga cacatctgga      60

tcctcggtga cactgggatg ccttgtcaaa ggctacttcc ctgagccggt aactgtaaaa     120

tggaactatg gagccctgtc cagcggtgtg cgcacagtct catctgtcct gcagtctggg     180

ttctattccc tcagcagctt ggtgactgta ccctccagca cctggcccag ccagactgtc     240

atctgcaacg tagcccaccc agccagcaag actgagttga tcaagagaat cgagcctaga     300

atacccaagc ccagtacccc cccaggttct tcatgcccac ctggtaacat cttgggtgga     360

ccatccgtct tcatcttccc cccaaagccc aaggatgcac tcatgatctc cctaaccccc     420

aaggttacgt gtgtggtggt ggatgtgagc gaggatgacc cagatgtcca tgtcagctgg     480

tttgtggaca acaaagaagt acacacagcc tggacacagc cccgtgaagc tcagtacaac     540

agtaccttcc gagtggtcag tgccctcccc atccagcacc aggactggat gaggggcaag     600

gagttcaaat gcaaggtcaa caacaaagcc ctcccagccc ccatcgagag aaccatctca     660

aaacccaaag gaagagccca gacacctcaa gtatacacca tacccccacc tcgtgaacaa     720

atgtccaaga agaaggttag tctgacctgc ctggtcacca acttcttctc tgaagccatc     780

agtgtggagt gggaaaggaa cggagaactg gagcaggatt acaagaacac tccacccatc     840

ctggactcag atgggaccta cttcctctac agcaagctca ctgtggatac agacagttgg     900

ttgcaaggag aaatttttac ctgctccgtg gtgcatgagg ctctccataa ccaccacaca     960

cagaagaacc tgtctcgctc ccctggtaaa tga                                  993


<210> SEQ ID NO 64
<211> LENGTH: 105
<212> TYPE: PRT
<213> ORGANISM: Bubalus arnee

<400> SEQUENCE: 64

Gln Pro Lys Ser Pro Pro Ser Val Thr Leu Phe Pro Pro Ser Thr Glu
1               5                   10                  15

Glu Leu Asn Gly Asn Lys Ala Thr Leu Val Cys Leu Ile Ser Asp Phe
```

-continued

```
            20                  25                  30

Tyr Pro Gly Ser Val Thr Val Val Trp Lys Ala Asp Gly Ser Thr Ile
        35                  40                  45

Thr Arg Asn Val Glu Thr Thr Arg Ala Ser Lys Gln Ser Asn Ser Lys
    50                  55                  60

Tyr Ala Ala Ser Ser Tyr Leu Ser Leu Thr Ser Ser Asp Trp Lys Ser
65                  70                  75                  80

Lys Gly Ser Tyr Ser Cys Glu Val Thr His Glu Gly Ser Thr Val Thr
                85                  90                  95

Lys Thr Val Lys Pro Ser Glu Cys Ser
            100                 105


<210> SEQ ID NO 65
<211> LENGTH: 318
<212> TYPE: DNA
<213> ORGANISM: Bubalus arnee

<400> SEQUENCE: 65

cagcccaagt ccccaccctc ggtcaccctg ttcccgccct ccacggagga gctcaacggc      60

aacaaggcca ccctggtgtg tctcatcagc gacttctacc cgggtagcgt gaccgtggtc     120

tggaaggcag acggcagcac catcacccgc aacgtggaga ccacccgggc ctccaaacag     180

agcaacagca agtacgcggc cagcagctac ctgagcctga cgagcagcga ctggaaatcg     240

aaaggcagtt acagctgcga ggtcacgcac gaggggagca ccgtgacgaa gacagtgaag     300

ccctcagagt gttcttag                                                   318


<210> SEQ ID NO 66
<211> LENGTH: 329
<212> TYPE: PRT
<213> ORGANISM: Bubalus arnee

<400> SEQUENCE: 66

Ala Ser Thr Thr Ala Pro Lys Val Tyr Pro Leu Ser Ser Cys Cys Gly
1               5                   10                  15

Asp Lys Ser Ser Ser Thr Val Thr Leu Gly Cys Leu Val Ser Ser Tyr
            20                  25                  30

Met Pro Glu Pro Val Thr Val Thr Trp Asn Ser Gly Ala Leu Lys Ser
        35                  40                  45

Gly Val His Thr Phe Pro Ala Val Leu Gln Ser Ser Gly Leu Tyr Ser
    50                  55                  60

Leu Ser Ser Met Val Thr Val Pro Gly Ser Thr Ser Gly Gln Thr Phe
65                  70                  75                  80

Thr Cys Asn Val Ala His Pro Ala Ser Ser Thr Lys Val Asp Lys Ala
                85                  90                  95

Val Asp Pro Thr Cys Lys Pro Ser Pro Cys Asp Cys Cys Pro Pro Pro
            100                 105                 110

Glu Leu Pro Gly Gly Pro Ser Val Phe Ile Phe Pro Pro Lys Pro Lys
        115                 120                 125

Asp Thr Leu Thr Ile Ser Gly Thr Pro Glu Val Thr Cys Val Val Val
    130                 135                 140

Asp Val Gly His Asp Asp Pro Glu Val Lys Phe Ser Trp Phe Val Asp
145                 150                 155                 160

Asp Val Glu Val Asn Thr Ala Thr Thr Lys Pro Arg Glu Glu Gln Phe
                165                 170                 175

Asn Ser Thr Tyr Arg Val Val Ser Ala Leu Arg Ile Gln His Gln Asp
```

```
            180                 185                 190

Trp Thr Gly Gly Lys Glu Phe Lys Cys Lys Val His Asn Glu Gly Leu
        195                 200                 205

Pro Ala Pro Ile Val Arg Thr Ile Ser Arg Thr Lys Gly Pro Ala Arg
    210                 215                 220

Glu Pro Gln Val Tyr Val Leu Ala Pro Pro Gln Glu Glu Leu Ser Lys
225                 230                 235                 240

Ser Thr Val Ser Leu Thr Cys Met Val Thr Ser Phe Tyr Pro Asp Tyr
                245                 250                 255

Ile Ala Val Glu Trp Gln Arg Asn Gly Gln Pro Glu Ser Glu Asp Lys
            260                 265                 270

Tyr Gly Thr Thr Pro Pro Gln Leu Asp Ala Asp Ser Ser Tyr Phe Leu
        275                 280                 285

Tyr Ser Lys Leu Arg Val Asp Arg Asn Ser Trp Gln Glu Gly Asp Thr
    290                 295                 300

Tyr Thr Cys Val Val Met His Glu Ala Leu His Asn His Tyr Thr Gln
305                 310                 315                 320

Lys Ser Thr Ser Lys Ser Ala Gly Lys
                325


<210> SEQ ID NO 67
<211> LENGTH: 990
<212> TYPE: DNA
<213> ORGANISM: Bubalus arnee

<400> SEQUENCE: 67

gcctccacca cagccccgaa agtctaccct ctgagttctt gctgcgggga caagtccagc      60

tccaccgtga ccctgggctg cctggtctcc agctacatgc ccgagccggt gaccgtgacc     120

tggaactcgg gtgccctgaa gagcggcgtg cacaccttcc cggctgtcct tcagtcctcc     180

gggctgtact ctctcagcag catggtgacc gtgcccggca gcacctcagg acagaccttc     240

acctgcaacg tagcccaccc ggccagcagc accaaggtgg acaaggctgt tgatcccaca     300

tgcaaaccat caccctgtga ctgttgccca ccccctgagc tccccggagg accctctgtc     360

ttcatcttcc caccgaaacc caaggacacc ctcacaatct cgggaacgcc cgaggtcacg     420

tgtgtggtgg tggacgtggg ccacgatgac cccgaggtga agttctcctg gttcgtggac     480

gacgtggagg taaacacagc cacgacgaag ccgagagagg agcagttcaa cagcacctac     540

cgcgtggtca gcgccctgcg catccagcac caggactgga ctggaggaaa ggagttcaag     600

tgcaaggtcc acaacgaagg cctcccggcc cccatcgtga ggaccatctc caggaccaaa     660

gggccggccc gggagccgca ggtgtatgtc ctggccccac cccaggaaga gctcagcaaa     720

agcacggtca gcctcacctg catggtcacc agcttctacc cagactacat cgccgtggag     780

tggcagagaa acgggcagcc tgagtcggag gacaagtacg gcacgacccc gccccagctg     840

gacgccgaca gctcctactt cctgtacagc aagctcaggg tggacaggaa cagctggcag     900

gaaggagaca cctacacgtg tgtggtgatg cacgaggccc tgcacaatca ctacacgcag     960

aagtccacct ctaagtctgc gggtaaatga                                      990


<210> SEQ ID NO 68
<211> LENGTH: 329
<212> TYPE: PRT
<213> ORGANISM: Bubalus arnee

<400> SEQUENCE: 68
```

```
Ala Ser Thr Thr Ala Pro Lys Val Tyr Pro Leu Ser Ser Cys Cys Gly
1               5                   10                  15

Asp Lys Ser Ser Ser Thr Val Thr Leu Gly Cys Leu Val Ser Ser Tyr
            20                  25                  30

Met Pro Glu Pro Val Thr Val Thr Trp Asn Ser Gly Ala Leu Lys Ser
        35                  40                  45

Gly Val His Thr Phe Pro Ala Val Leu Gln Ser Ser Gly Leu Tyr Ser
    50                  55                  60

Leu Ser Ser Met Val Thr Val Pro Gly Ser Thr Ser Gly Gln Thr Phe
65                  70                  75                  80

Thr Cys Asn Val Ala His Pro Ala Ser Ser Thr Lys Val Asp Lys Ala
                85                  90                  95

Val Asp Pro Thr Cys Lys Pro Ser Pro Cys Asp Cys Cys Pro Pro Pro
            100                 105                 110

Glu Leu Pro Gly Gly Pro Ser Val Phe Ile Phe Pro Pro Lys Pro Lys
        115                 120                 125

Asp Thr Leu Thr Ile Ser Gly Thr Pro Glu Val Thr Cys Val Val Val
    130                 135                 140

Asp Val Gly His Asp Asp Pro Glu Val Lys Phe Ser Trp Phe Val Asp
145                 150                 155                 160

Asp Val Glu Val Asn Thr Ala Thr Thr Lys Pro Arg Glu Glu Gln Phe
                165                 170                 175

Asn Ser Thr Tyr Arg Val Val Ser Ala Leu Arg Ile Gln His Gln Asp
            180                 185                 190

Trp Thr Gly Gly Lys Glu Phe Lys Cys Lys Val His Asn Glu Gly Leu
        195                 200                 205

Pro Ala Pro Ile Val Arg Thr Ile Ser Arg Thr Lys Gly Pro Ala Arg
    210                 215                 220

Glu Pro Gln Val Tyr Val Leu Ala Pro Pro Gln Glu Glu Leu Ser Lys
225                 230                 235                 240

Ser Thr Val Ser Leu Thr Cys Met Val Thr Ser Phe Tyr Pro Asp Tyr
                245                 250                 255

Ile Ala Val Glu Trp Gln Arg Asn Gly Gln Pro Glu Ser Glu Asp Lys
            260                 265                 270

Tyr Gly Thr Thr Pro Pro Gln Leu Asp Ala Asp Ser Ser Tyr Phe Leu
        275                 280                 285

Tyr Ser Lys Leu Arg Val Asp Arg Asn Ser Trp Gln Glu Gly Asp Thr
    290                 295                 300

Tyr Thr Cys Val Val Met His Glu Ala Leu His Asn His Tyr Thr Gln
305                 310                 315                 320

Lys Ser Thr Ser Lys Ser Ala Gly Lys
                325
```

<210> SEQ ID NO 69
<211> LENGTH: 990
<212> TYPE: DNA
<213> ORGANISM: Bubalus arnee

<400> SEQUENCE: 69

```
gcctccacca cagccccgaa agtctaccct ctgagttctt gctgcgggga caagtccagc      60

tccaccgtga ccctgggctg cctggtctcc agctacatgc ccgagccggt gaccgtgacc     120

tggaactcgg gtgccctgaa gagcggcgtg cacaccttcc cggccgtcct tcagtcctcc     180

gggctgtact ctctcagcag catggtgacc gtgcccggca gcacctcagg acagaccttc     240
```

```
acctgcaacg tagcccaccc ggccagcagc accaaggtgg acaaggctgt tgatcccaca    300

tgcaaaccat caccctgtga ctgttgccca ccccctgagc tccccggagg accctctgtc    360

ttcatcttcc caccgaaacc caaggacacc ctcacaatct cgggaacgcc cgaggtcacg    420

tgtgtggtgg tggacgtggg ccacgatgac cccgaggtga agttctcctg gttcgtggac    480

gacgtggagg taaacacagc cacgacgaag ccgagagagg agcagttcaa cagcacctac    540

cgcgtggtca gcgccctgcg catccagcac caggactgga ctggaggaaa ggagttcaag    600

tgcaaggtcc acaacgaagg cctcccggcc cccatcgtga ggaccatctc caggaccaaa    660

gggccggccc gggagccgca ggtgtatgtc ctggccccac cccaggaaga gctcagcaaa    720

agcacggtca gcctcacctg catggtcacc agcttctacc cagactacat cgccgtggag    780

tggcagagaa acgggcagcc tgagtcggag gacaagtacg gcacgacccc gccccagctg    840

gacgccgaca gctcctactt cctgtacagc aagctcaggg tggacaggaa cagctggcag    900

gaaggagaca cctacacgtg tgtggtgatg cacgaggccc tgcacaatca ctacacgcag    960

aagtccacct ctaagtctgc gggtaaatga                                    990
```

```
<210> SEQ ID NO 70
<211> LENGTH: 329
<212> TYPE: PRT
<213> ORGANISM: Bubalus arnee

<400> SEQUENCE: 70

Ala Ser Thr Thr Ala Pro Lys Val Tyr Pro Leu Ser Ser Cys Cys Gly
1               5                   10                  15

Asp Lys Ser Ser Ser Thr Val Thr Leu Gly Cys Leu Val Ser Ser Tyr
            20                  25                  30

Met Pro Glu Pro Val Thr Val Thr Trp Asn Ser Gly Ala Leu Lys Ser
        35                  40                  45

Gly Val His Thr Phe Pro Ala Val Leu Gln Ser Ser Gly Leu Tyr Ser
    50                  55                  60

Leu Ser Ser Met Val Thr Val Pro Gly Ser Thr Ser Gly Thr Gln Thr
65                  70                  75                  80

Phe Thr Cys Asn Val Ala His Pro Ala Ser Ser Thr Lys Val Asp Lys
                85                  90                  95

Ala Val Asp Pro Arg Cys Lys Thr Thr Cys Asp Cys Cys Pro Pro Pro
            100                 105                 110

Glu Leu Pro Gly Gly Pro Ser Val Phe Ile Phe Pro Pro Lys Pro Lys
        115                 120                 125

Asp Thr Leu Thr Ile Ser Gly Thr Pro Glu Val Thr Cys Val Val Val
    130                 135                 140

Asp Val Gly His Asp Asp Pro Glu Val Lys Phe Ser Trp Phe Val Asp
145                 150                 155                 160

Asp Val Glu Val Asn Thr Ala Thr Thr Lys Pro Arg Glu Glu Gln Phe
                165                 170                 175

Asn Ser Thr Tyr Arg Val Val Ser Ala Leu Arg Ile Gln His Gln Asp
            180                 185                 190

Trp Thr Gly Gly Lys Glu Phe Lys Cys Lys Val His Asn Glu Gly Leu
        195                 200                 205

Pro Ala Pro Ile Val Arg Thr Ile Ser Arg Thr Lys Gly Pro Ala Arg
    210                 215                 220

Glu Pro Gln Val Tyr Val Leu Ala Pro Pro Gln Glu Glu Leu Ser Lys
225                 230                 235                 240
```

```
Ser Thr Val Ser Leu Thr Cys Met Val Thr Ser Phe Tyr Pro Asp Tyr
                245                 250                 255

Ile Ala Val Glu Trp Gln Arg Asn Gly Gln Pro Glu Ser Glu Asp Lys
            260                 265                 270

Tyr Gly Thr Thr Pro Pro Gln Leu Asp Ala Asp Gly Ser Tyr Phe Leu
        275                 280                 285

Tyr Ser Arg Leu Arg Val Asp Arg Asn Ser Trp Gln Glu Gly Asp Thr
    290                 295                 300

Tyr Thr Cys Val Val Met His Glu Ala Leu His Asn His Tyr Thr Gln
305                 310                 315                 320

Lys Ser Thr Ser Lys Ser Ala Gly Lys
                325
```

<210> SEQ ID NO 71
<211> LENGTH: 990
<212> TYPE: DNA
<213> ORGANISM: Bubalus arnee

<400> SEQUENCE: 71

```
gcctccacca cagccccgaa agtctaccct ctgagttctt gctgcgggga caagtccagc     60

tccaccgtga ccctgggctg cctggtctcc agctacatgc ccgagccggt gaccgtgacc    120

tggaactcgg gtgccctgaa gagcggcgtg cacaccttcc cggccgtcct tcagtcctcc    180

gggctctact ctctcagcag catggtgacc gtgcccggca gcacctcagg aacccagacc    240

ttcacctgca acgtagccca cccggccagc agcaccaagg tggacaaggc tgttgatccc    300

agatgcaaaa caacctgtga ctgttgccca ccgcctgagc tccctggagg accctctgtc    360

ttcatcttcc caccgaaacc caaggacacc ctcacaatct cgggaacgcc cgaggtcacg    420

tgtgtggtgg tggacgtggg ccacgatgac cccgaggtga agttctcctg gttcgtggac    480

gacgtggagg taaacacagc cacgacgaag ccgagagagg agcagttcaa cagcacctac    540

cgcgtggtca gcgccctgcg catccagcac caggactgga ctggaggaaa ggagttcaag    600

tgcaaggtcc acaacgaagg cctcccagcc cccatcgtga ggaccatctc caggaccaaa    660

gggccggccc gggagccgca ggtgtatgtc ctggccccac cccaggaaga gctcagcaaa    720

agcacggtca gcctcacctg catggtcacc agcttctacc cagactacat cgccgtggag    780

tggcagagaa atgggcagcc tgagtcagag gacaagtacg gcacgacccc tccccagctg    840

gacgccgacg gctcctactt cctgtacagc aggctcaggg tggacaggaa cagctggcag    900

gaaggagaca cctacacgtg tgtggtgatg cacgaggccc tgcacaatca ctacacgcag    960

aagtccacct ctaagtctgc gggtaaatga                                     990
```

<210> SEQ ID NO 72
<211> LENGTH: 326
<212> TYPE: PRT
<213> ORGANISM: Bubalus arnee

<400> SEQUENCE: 72

```
Ala Ser Thr Thr Ala Pro Lys Val Tyr Pro Leu Ala Ser Ser Cys Gly
1               5                   10                  15

Asp Thr Ser Ser Ser Thr Val Thr Leu Gly Cys Leu Val Ser Ser Tyr
            20                  25                  30

Met Pro Glu Pro Val Thr Val Thr Trp Asn Ser Gly Ala Leu Lys Ser
        35                  40                  45

Gly Val His Thr Phe Pro Ala Val Leu Gln Ser Ser Gly Leu Tyr Ser
    50                  55                  60
```

Leu Ser Ser Met Val Thr Val Pro Ala Ser Ser Ser Gly Gln Thr Phe
65 70 75 80

Thr Cys Asn Val Ala His Pro Ala Ser Ser Thr Lys Val Asp Lys Ala
85 90 95

Val Gly Val Ser Ile Asp Cys Ser Lys Cys His Asn Gln Pro Cys Val
100 105 110

Arg Glu Pro Ser Val Phe Ile Phe Pro Pro Lys Pro Lys Asp Thr Leu
115 120 125

Met Ile Thr Gly Thr Pro Glu Val Thr Cys Val Val Val Asn Val Gly
130 135 140

His Asp Asn Pro Glu Val Gln Phe Ser Trp Phe Val Asp Asp Val Glu
145 150 155 160

Val His Thr Ala Arg Ser Lys Pro Arg Glu Glu Gln Phe Asn Ser Thr
165 170 175

Tyr Arg Val Val Ser Ala Leu Pro Ile Gln His Gln Asp Trp Thr Gly
180 185 190

Gly Lys Glu Phe Lys Cys Lys Val Asn Asn Lys Gly Leu Ser Ala Pro
195 200 205

Ile Val Arg Ile Ile Ser Arg Ser Lys Gly Pro Ala Arg Glu Pro Gln
210 215 220

Val Tyr Val Leu Asp Pro Pro Lys Glu Glu Leu Ser Lys Ser Thr Leu
225 230 235 240

Ser Val Thr Cys Met Val Thr Gly Phe Tyr Pro Glu Asp Val Ala Val
245 250 255

Glu Trp Gln Arg Asn Arg Gln Thr Glu Ser Glu Asp Lys Tyr Arg Thr
260 265 270

Thr Pro Pro Gln Leu Asp Thr Asp Arg Ser Tyr Phe Leu Tyr Ser Lys
275 280 285

Leu Arg Val Asp Arg Asn Ser Trp Gln Glu Gly Asp Ala Tyr Thr Cys
290 295 300

Val Val Met His Glu Ala Leu His Asn His Tyr Met Gln Lys Ser Thr
305 310 315 320

Ser Lys Ser Ala Gly Lys
325

<210> SEQ ID NO 73
<211> LENGTH: 981
<212> TYPE: DNA
<213> ORGANISM: Bubalus arnee

<400> SEQUENCE: 73
gcctccacca cagccccgaa agtctaccct ctggcatcca gctgcggaga cacatccagc 60
tccaccgtga ccctgggctg cctggtgtcc agctacatgc ccgagccggt gaccgtgacc 120
tggaactcgg gtgccctgaa gagcggcgtg cacaccttcc cggctgtcct tcagtcctcc 180
gggctctact ctctcagcag catggtgacc gtgcccgcca gcagctcagg acagaccttc 240
acctgcaacg tagcccaccc ggccagcagc accaaggtgg acaaggctgt tggggtctcc 300
attgactgct ccaagtgtca taaccagcct tgcgtgaggg aaccatctgt cttcatcttc 360
ccaccgaaac ccaaagacac cctgatgatc acaggaacgc ccgaggtcac gtgtgtggtg 420
gtgaacgtgg gccacgataa ccccgaggtg cagttctcct ggttcgtgga tgacgtggag 480
gtgcacacgg ccaggtcgaa gccaagagag gagcagttca acagcacgta ccgcgtggtc 540
agcgccctgc ccatccagca ccaggactgg actggaggaa aggagttcaa gtgcaaggtc 600

-continued

```
aacaacaaag gcctctcggc ccccatcgtg aggatcatct ccaggagcaa agggccggcc    660

cgggagccgc aggtgtatgt cctggaccca cccaaggaag agctcagcaa aagcacgctc    720

agcgtcacct gcatggtcac cggcttctac ccagaagatg tagccgtgga gtggcagaga    780

aaccggcaga ctgagtcgga ggacaagtac cgcacgaccc cgccccagct ggacaccgac    840

cgctcctact tcctgtacag caagctcagg gtggacagga acagctggca ggaaggagac    900

gcctacacgt gtgtggtgat gcacgaggcc ctgcacaatc actacatgca gaagtccacc    960

tctaagtctg cgggtaaatg a                                              981


<210> SEQ ID NO 74
<211> LENGTH: 326
<212> TYPE: PRT
<213> ORGANISM: Bubalus arnee

<400> SEQUENCE: 74

Ala Ser Thr Thr Ala Pro Lys Val Tyr Pro Leu Ser Ser Cys Cys Gly
1               5                   10                  15

Asp Lys Ser Ser Ser Thr Val Thr Leu Gly Cys Leu Val Ser Ser Tyr
            20                  25                  30

Met Pro Glu Pro Val Thr Val Thr Trp Asn Ser Gly Ala Leu Lys Ser
        35                  40                  45

Gly Val His Thr Phe Pro Ala Val Leu Gln Ser Ser Gly Leu Tyr Ser
    50                  55                  60

Leu Ser Ser Met Val Thr Val Pro Gly Ser Thr Ser Gly Gln Thr Phe
65                  70                  75                  80

Thr Cys Asn Val Ala His Pro Ala Ser Ser Thr Lys Val Asp Lys Ala
                85                  90                  95

Val Gly Val Ser Ser Asp Cys Ser Lys Pro Asn Asn Gln His Cys Val
            100                 105                 110

Arg Glu Pro Ser Val Phe Ile Phe Pro Pro Lys Pro Lys Asp Thr Leu
        115                 120                 125

Met Ile Thr Gly Thr Pro Glu Val Thr Cys Val Val Val Asn Val Gly
    130                 135                 140

His Asp Asn Pro Glu Val Gln Phe Ser Trp Phe Val Asp Asp Val Glu
145                 150                 155                 160

Val His Thr Ala Arg Thr Lys Pro Arg Glu Glu Gln Phe Asn Ser Thr
                165                 170                 175

Tyr Arg Val Val Ser Ala Leu Pro Ile Gln His Gln Asp Trp Thr Gly
            180                 185                 190

Gly Lys Glu Phe Lys Cys Lys Val Asn Ile Lys Gly Leu Ser Ala Ser
        195                 200                 205

Ile Val Arg Ile Ile Ser Arg Ser Lys Gly Pro Ala Arg Glu Pro Gln
    210                 215                 220

Val Tyr Val Leu Asp Pro Pro Lys Glu Glu Leu Ser Lys Ser Thr Val
225                 230                 235                 240

Ser Val Thr Cys Met Val Ile Gly Phe Tyr Pro Glu Asp Val Asp Val
                245                 250                 255

Glu Trp Gln Arg Asp Arg Gln Thr Glu Ser Glu Asp Lys Tyr Arg Thr
            260                 265                 270

Thr Pro Pro Gln Leu Asp Ala Asp Arg Ser Tyr Phe Leu Tyr Ser Lys
        275                 280                 285

Leu Arg Val Asp Arg Asn Ser Trp Gln Arg Gly Asp Thr Tyr Thr Cys
    290                 295                 300
```

```
Val Val Met His Glu Ala Leu His Asn His Tyr Met Gln Lys Ser Thr
305                 310                 315                 320

Ser Lys Ser Ala Gly Lys
                325


<210> SEQ ID NO 75
<211> LENGTH: 981
<212> TYPE: DNA
<213> ORGANISM: Bubalus arnee

<400> SEQUENCE: 75

gcctccacca cagccccgaa agtctaccct ctgagttctt gctgcgggga caagtccagc      60

tccaccgtga ccctgggctg cctggtgtcc agctacatgc ccgagccggt gaccgtgacc     120

tggaactcgg gtgccctgaa gagcggcgtg cacaccttcc cggccgtcct tcagtcctcc     180

gggctctact ctctcagcag catggtgacc gtgcccggca gcacctcagg acagaccttc     240

acctgcaacg tagcccaccc ggccagcagc accaaggtgg acaaggctgt tggggtctcc     300

agtgactgct ccaagcctaa taaccagcat tgcgtgaggg aaccatctgt cttcatcttc     360

ccaccgaaac ccaaagacac cctgatgatc acaggaacgc ccgaggtcac gtgtgtggtg     420

gtgaacgtgg gccacgataa ccccgaggtg cagttctcct ggttcgtgga cgacgtggag     480

gtgcacacgg ccaggacgaa gccgagagag gagcagttca acagcacgta ccgcgtggtc     540

agcgccctgc ccatccagca ccaggactgg actggaggaa aggagttcaa gtgcaaggtc     600

aacatcaaag gcctctcggc ctccatcgtg aggatcatct ccaggagcaa agggccggcc     660

cgggagccgc aggtgtatgt cctggaccca cccaaggaag agctcagcaa aagcacggtc     720

agcgtcacct gcatggtcat cggcttctac ccagaagatg tagacgtgga gtggcagaga     780

gaccggcaga ctgagtcgga ggacaagtac cgcacgaccc cgccccagct ggacgccgac     840

cgctcctact tcctgtacag caagctcagg gtggacagga acagctggca gagaggagac     900

acctacacgt gtgtggtgat gcacgaggcc ctgcacaatc actacatgca gaagtccacc     960

tctaagtctg cgggtaaatg a                                               981


<210> SEQ ID NO 76
<211> LENGTH: 327
<212> TYPE: PRT
<213> ORGANISM: Bubalus arnee

<400> SEQUENCE: 76

Ala Ser Thr Thr Ala Pro Lys Val Tyr Pro Leu Ser Ser Cys Cys Gly
1               5                   10                  15

Asp Lys Ser Ser Ser Gly Val Thr Leu Gly Cys Leu Val Ser Ser Tyr
            20                  25                  30

Met Pro Glu Pro Val Thr Val Thr Trp Asn Ser Gly Ala Leu Lys Ser
        35                  40                  45

Gly Val His Thr Phe Pro Ala Val Leu Gln Ser Ser Gly Leu Tyr Ser
    50                  55                  60

Leu Ser Ser Met Val Thr Val Pro Ala Ser Ser Ser Gly Thr Gln Thr
65                  70                  75                  80

Phe Thr Cys Asn Val Ala His Pro Ala Ser Ser Thr Lys Val Asp Lys
                85                  90                  95

Ala Val Gly Val Ser Ser Asp Cys Ser Lys Pro Asn Asn Gln His Cys
            100                 105                 110

Val Arg Glu Pro Ser Val Phe Ile Phe Pro Pro Lys Pro Lys Asp Thr
```

-continued

```
        115                 120                 125

Leu Met Ile Thr Gly Thr Pro Glu Val Thr Cys Val Val Val Asn Val
    130                 135                 140

Gly His Asp Asn Pro Glu Val Gln Phe Ser Trp Phe Val Asp Asp Val
145                 150                 155                 160

Glu Val His Thr Ala Arg Thr Lys Pro Arg Glu Glu Gln Phe Asn Ser
                165                 170                 175

Thr Tyr Arg Val Val Ser Ala Leu Pro Ile Gln His Gln Asp Trp Thr
            180                 185                 190

Gly Gly Lys Glu Phe Lys Cys Lys Val Asn Ile Lys Gly Leu Ser Ala
        195                 200                 205

Ser Ile Val Arg Ile Ile Ser Arg Ser Lys Gly Pro Ala Arg Glu Pro
    210                 215                 220

Gln Val Tyr Val Leu Asp Pro Pro Lys Glu Glu Leu Ser Lys Ser Thr
225                 230                 235                 240

Val Ser Leu Thr Cys Met Val Ile Gly Phe Tyr Pro Glu Asp Val Asp
                245                 250                 255

Val Glu Trp Gln Arg Asp Arg Gln Thr Glu Ser Glu Asp Lys Tyr Arg
            260                 265                 270

Thr Thr Pro Pro Gln Leu Asp Ala Asp Arg Ser Tyr Phe Leu Tyr Ser
        275                 280                 285

Lys Leu Arg Val Asp Arg Asn Ser Trp Gln Arg Gly Asp Thr Tyr Thr
    290                 295                 300

Cys Val Val Met His Glu Ala Leu His Asn His Tyr Met Gln Lys Ser
305                 310                 315                 320

Thr Ser Lys Ser Ala Gly Lys
                325


<210> SEQ ID NO 77
<211> LENGTH: 984
<212> TYPE: DNA
<213> ORGANISM: Bubalus arnee

<400> SEQUENCE: 77

gcctccacca cagccccgaa agtctaccct ctgagttctt gctgcgggga caagtccagc      60

tcgggggtga ccctgggctg cctggtctcc agctacatgc ccgagccggt gaccgtgacc     120

tggaactcgg gtgccctgaa gagcggcgtg cacaccttcc cggccgtcct tcagtcctcc     180

gggctctact ctctcagcag catggtgacc gtgcccgcca gcagctcagg aacccagacc     240

ttcacctgca acgtagccca cccggccagc agcaccaagg tggacaaggc tgttggggtc     300

tccagtgact gctccaagcc taataaccag cattgcgtga gggaaccatc tgtcttcatc     360

ttcccaccga aacccaaaga caccctgatg atcacaggaa cgcccgaggt cacgtgtgtg     420

gtggtgaacg tgggccacga taaccccgag gtgcagttct cctggttcgt ggacgacgtg     480

gaggtgcaca cggccaggac gaagccgaga gaggagcagt tcaacagcac gtaccgcgtg     540

gtcagcgccc tgcccatcca gcaccaggac tggactggag gaaaggagtt caagtgcaag     600

gtcaacatca aaggcctctc ggcctccatc gtgaggatca tctccaggag caaagggccg     660

gcccgggagc cgcaggtgta tgtcctggac ccacccaagg aagagctcag caaaagcacg     720

gtcagcctca cctgcatggt catcggcttc tacccagaag atgtagacgt ggagtggcag     780

agagaccggc agactgagtc ggaggacaag taccgcacga ccccgcccca gctggacgcc     840

gaccgctcct acttcctgta cagcaagctc agggtggaca ggaacagctg gcagagagga     900
```

```
gacacctaca cgtgtgtggt gatgcacgag gccctgcaca atcactacat gcagaagtcc     960

acctctaagt ctgcgggtaa atga                                            984


<210> SEQ ID NO 78
<211> LENGTH: 352
<212> TYPE: PRT
<213> ORGANISM: Bubalus arnee

<400> SEQUENCE: 78

Ala Ser Thr Thr Ala Pro Lys Val Tyr Pro Leu Ala Ser Ser Cys Gly
1               5                   10                  15

Asp Thr Ser Ser Ser Thr Val Thr Leu Gly Cys Leu Val Ser Ser Tyr
            20                  25                  30

Met Pro Glu Pro Val Thr Val Thr Trp Asn Ser Gly Ala Leu Lys Ser
        35                  40                  45

Gly Val His Thr Phe Pro Ala Val Arg Gln Ser Ser Gly Leu Tyr Ser
    50                  55                  60

Leu Ser Ser Met Val Thr Val Pro Ala Ser Ser Ser Glu Thr Gln Thr
65                  70                  75                  80

Phe Thr Cys Asn Val Ala His Pro Ala Ser Ser Thr Lys Val Asp Lys
                85                  90                  95

Ala Val Thr Ala Arg Arg Pro Val Pro Thr Thr Pro Lys Thr Thr Ile
            100                 105                 110

Pro Pro Gly Lys Pro Thr Thr Pro Lys Ser Glu Val Glu Lys Thr Pro
        115                 120                 125

Cys Gln Cys Ser Lys Cys Pro Glu Pro Leu Gly Gly Leu Ser Val Phe
    130                 135                 140

Ile Phe Pro Pro Lys Pro Lys Asp Thr Leu Thr Ile Ser Gly Thr Pro
145                 150                 155                 160

Glu Val Thr Cys Val Val Val Asp Val Gly Gln Asp Asp Pro Glu Val
                165                 170                 175

Gln Phe Ser Trp Phe Val Asp Asp Val Glu Val His Thr Ala Arg Thr
            180                 185                 190

Lys Pro Arg Glu Glu Gln Phe Asn Ser Thr Tyr Arg Val Val Ser Ala
        195                 200                 205

Leu Arg Ile Gln His Gln Asp Trp Leu Gln Gly Lys Glu Phe Lys Cys
    210                 215                 220

Lys Val Asn Asn Lys Gly Leu Pro Ala Pro Ile Val Arg Thr Ile Ser
225                 230                 235                 240

Arg Thr Lys Gly Gln Ala Arg Glu Pro Gln Val Tyr Val Leu Ala Pro
                245                 250                 255

Pro Arg Glu Glu Leu Ser Lys Ser Thr Leu Ser Leu Thr Cys Leu Ile
            260                 265                 270

Thr Gly Phe Tyr Pro Glu Glu Ile Asp Val Glu Trp Gln Arg Asn Gly
        275                 280                 285

Gln Pro Glu Ser Glu Asp Lys Tyr His Thr Thr Ala Pro Gln Leu Asp
    290                 295                 300

Ala Asp Gly Ser Tyr Phe Leu Tyr Ser Lys Leu Arg Val Asn Lys Ser
305                 310                 315                 320

Ser Trp Gln Glu Gly Asp His Tyr Thr Cys Ala Val Met His Glu Ala
                325                 330                 335

Leu Arg Asn His Tyr Lys Glu Lys Ser Ile Ser Arg Ser Pro Gly Lys
            340                 345                 350
```

-continued

<210> SEQ ID NO 79
<211> LENGTH: 1059
<212> TYPE: DNA
<213> ORGANISM: Bubalus arnee

<400> SEQUENCE: 79
gcctccacca cagccccgaa agtctaccct ctggcatcca gctgcggaga cacatccagc 60
tccaccgtga ccctgggctg cctggtctcc agctacatgc ccgagccggt gaccgtgacc 120
tggaactcgg gtgccctgaa gagcggcgtg cacaccttcc cggccgtccg gcagtcctct 180
gggctgtact ctctcagcag catggtgact gtgcccgcca gcagctcaga aacccagacc 240
ttcacctgca acgtagccca cccggccagc agcaccaagg tggacaaggc tgtcactgca 300
aggcgtccag tcccgacgac gccaaagaca actatccctc ctggaaaacc cacaacccca 360
aagtctgaag ttgaaaagac accctgccag tgttccaaat gcccagaacc tctgggagga 420
ctgtctgtct tcatcttccc accgaaaccc aaggacaccc tcacaatctc gggaacgccc 480
gaggtcacgt gtgtggtggt ggacgtgggc caggatgacc ccgaggtgca gttctcctgg 540
ttcgtggacg acgtggaggt gcacacggcc aggacgaagc cgagagagga gcagttcaac 600
agcacctacc gcgtggtcag cgccctgcgc atccagcacc aggactggct gcagggaaag 660
gagttcaagt gcaaggtcaa caacaaaggc ctcccggccc ccattgtgag gaccatctcc 720
aggaccaaag ggcaggcccg ggagccgcag gtgtatgtcc tggccccacc ccgggaagag 780
ctcagcaaaa gcacgctcag cctcacctgc ctgatcaccg gtttctaccc agaagagata 840
gacgtggagt ggcagagaaa tgggcagcct gagtcggagg acaagtacca cacgaccgca 900
ccccagctgg atgctgacgg ctcctacttc ctgtacagca agctcagggt gaacaagagc 960
agctggcagg aaggagacca ctacacgtgt gcagtgatgc acgaagcttt acggaatcac 1020
tacaaagaga agtccatctc gaggtctccg ggtaaatga 1059

<210> SEQ ID NO 80
<211> LENGTH: 352
<212> TYPE: PRT
<213> ORGANISM: Bubalus arnee

<400> SEQUENCE: 80

Ala Ser Thr Thr Ala Pro Lys Val Tyr Pro Leu Ala Ser Arg Cys Gly
1               5                   10                  15

Asp Thr Ser Ser Ser Thr Val Thr Leu Gly Cys Leu Val Ser Ser Tyr
            20                  25                  30

Met Pro Glu Pro Val Thr Val Thr Trp Asn Ser Gly Ala Leu Lys Ser
        35                  40                  45

Gly Val His Thr Phe Pro Ala Val Leu Gln Ser Ser Gly Leu Tyr Ser
    50                  55                  60

Leu Ser Ser Met Val Thr Val Pro Ala Ser Thr Ser Glu Thr Gln Thr
65                  70                  75                  80

Phe Thr Cys Asn Val Ala His Pro Ala Ser Ser Thr Lys Val Asp Lys
                85                  90                  95

Ala Val Thr Ala Arg Arg Pro Val Pro Thr Thr Pro Lys Thr Thr Ile
            100                 105                 110

Pro Pro Gly Lys Pro Thr Thr Gln Glu Ser Glu Val Glu Lys Thr Pro
        115                 120                 125

Cys Gln Cys Ser Lys Cys Pro Glu Pro Leu Gly Gly Leu Ser Val Phe
    130                 135                 140

Ile Phe Pro Pro Lys Pro Lys Asp Thr Leu Thr Ile Ser Gly Thr Pro

-continued

```
145                 150                 155                 160

Glu Val Thr Cys Val Val Val Asp Val Gly Gln Asp Asp Pro Glu Val
                165                 170                 175

Gln Phe Ser Trp Phe Val Asp Asp Val Glu Val His Thr Ala Arg Thr
            180                 185                 190

Lys Pro Arg Glu Glu Gln Phe Asn Ser Thr Tyr Arg Val Val Ser Ala
        195                 200                 205

Leu Arg Ile Gln His Gln Asp Trp Leu Gln Gly Lys Glu Phe Lys Cys
    210                 215                 220

Lys Val Asn Asn Lys Gly Leu Pro Ala Pro Ile Val Arg Thr Ile Ser
225                 230                 235                 240

Arg Thr Lys Gly Gln Ala Arg Glu Pro Gln Val Tyr Val Leu Ala Pro
                245                 250                 255

Pro Arg Glu Glu Leu Ser Lys Ser Thr Leu Ser Leu Thr Cys Leu Ile
            260                 265                 270

Thr Gly Phe Tyr Pro Glu Glu Ile Asp Val Glu Trp Gln Arg Asn Gly
        275                 280                 285

Gln Pro Glu Ser Glu Asp Lys Tyr His Thr Thr Ala Pro Gln Leu Asp
    290                 295                 300

Ala Asp Gly Ser Tyr Phe Leu Tyr Ser Arg Leu Arg Val Asn Lys Ser
305                 310                 315                 320

Ser Trp Gln Glu Gly Asp His Tyr Thr Cys Ala Val Met His Glu Ala
                325                 330                 335

Leu Arg Asn His Tyr Lys Glu Lys Ser Ile Ser Arg Ser Pro Gly Lys
            340                 345                 350
```

<210> SEQ ID NO 81
<211> LENGTH: 1059
<212> TYPE: DNA
<213> ORGANISM: Bubalus arnee

<400> SEQUENCE: 81

```
gcctccacca cagccccgaa agtctaccct ctggcatccc gctgcggaga cacatccagc      60

tccaccgtga ccctgggctg cctggtctcc agctacatgc ccgagccggt gaccgtgacc     120

tggaactcgg gtgccctgaa gagtggcgtg cacaccttcc cggccgtcct tcagtcctcc     180

gggctgtact ctctcagcag catggtgacc gtgcccgcca gcacctcaga aacccagacc     240

ttcacctgca acgtagccca cccggccagc agcaccaagg tggacaaggc tgtcactgca     300

aggcgtccag tcccgacgac gccaaagaca accatccctc ctggaaaacc cacaacccag     360

gagtctgaag ttgaaaagac accctgccag tgttccaaat gcccagaacc tctgggagga     420

ctgtctgtct tcatcttccc accgaaaccc aaggacaccc tcacaatctc gggaacgccc     480

gaggtcacgt gtgtggtggt ggacgtgggc caggatgacc ccgaggtgca gttctcctgg     540

ttcgtggacg acgtggaggt gcacacggcc aggacgaagc cgagagagga gcagttcaac     600

agcacctacc gcgtggtcag cgccctgcgc atccagcacc aggactggct gcagggaaag     660

gagttcaagt gcaaggtcaa caacaaaggc ctcccggccc ccattgtgag gaccatctcc     720

aggaccaaag ggcaggcccg ggagccgcag gtgtatgtcc tggccccacc ccgggaagag     780

ctcagcaaaa gcacgctcag cctcacctgc ctgatcaccg gtttctaccc agaagagata     840

gacgtggagt ggcagagaaa tgggcagcct gagtcggagg acaagtacca cacgaccgca     900

ccccagctgg atgctgacgg ctcctacttc ctgtacagca ggctcagggt gaacaagagc     960

agctggcagg aaggagacca ctacacgtgt gcagtgatgc atgaagcttt acggaatcac    1020
```

-continued

```
tacaaagaga agtccatctc gaggtctccg ggtaaatga                          1059


<210> SEQ ID NO 82
<211> LENGTH: 105
<212> TYPE: PRT
<213> ORGANISM: Bubalus arnee

<400> SEQUENCE: 82

Gln Pro Lys Ala Ser Pro Ser Val Thr Leu Phe Pro Pro Ser Ser Glu
1               5                   10                  15

Glu Leu Gly Ala Asn Lys Ala Thr Leu Val Cys Leu Ile Ser Asp Phe
            20                  25                  30

Tyr Pro Ser Gly Val Thr Val Ala Trp Lys Ala Ser Gly Ser Pro Val
        35                  40                  45

Thr Gln Gly Val Glu Thr Thr Lys Pro Ser Lys Gln Ser Asn Asn Lys
    50                  55                  60

Tyr Ala Ala Ser Ser Tyr Leu Ser Leu Thr Pro Asp Lys Trp Lys Ser
65                  70                  75                  80

His Ser Ser Phe Ser Cys Leu Val Thr His Glu Gly Ser Thr Val Glu
                85                  90                  95

Lys Lys Val Ala Pro Ala Glu Cys Ser
            100                 105


<210> SEQ ID NO 83
<211> LENGTH: 318
<212> TYPE: DNA
<213> ORGANISM: Bubalus arnee

<400> SEQUENCE: 83

cagcccaagg cctccccctc ggtcacactc ttcccgccct cctctgagga gctcggcgcc      60

aacaaggcca ccctggtgtg cctcatcagc gacttctacc ccagcggcgt gacggtggcc     120

tggaaggcaa gcggcagccc cgtcacccag ggcgtggaga ccaccaagcc ctccaagcag     180

agcaacaaca agtacgcggc cagcagctac ctgagcctga cgcctgacaa gtggaaatct     240

cacagcagct tcagctgcct ggtcacgcac gaggggagca ccgtggagaa gaaggtggcc     300

cccgcagagt gctcttag                                                   318


<210> SEQ ID NO 84
<211> LENGTH: 331
<212> TYPE: PRT
<213> ORGANISM: Bubalus arnee

<400> SEQUENCE: 84

Ala Ser Thr Thr Ala Pro Ser Val Phe Pro Leu Ala Pro Ser Cys Gly
1               5                   10                  15

Ser Thr Ser Gly Ser Thr Val Ala Leu Ala Cys Leu Val Ser Gly Tyr
            20                  25                  30

Phe Pro Glu Pro Val Thr Val Ser Trp Asn Ser Gly Ser Leu Thr Ser
        35                  40                  45

Gly Val His Thr Phe Pro Ser Val Leu Gln Ser Ser Gly Leu Tyr Ser
    50                  55                  60

Leu Ser Ser Thr Val Thr Val Pro Ser Ser Arg Trp Pro Ser Glu Thr
65                  70                  75                  80

Phe Thr Cys Asn Val Val His Pro Ala Ser Asn Thr Lys Val Asp Lys
                85                  90                  95

Pro Val Pro Lys Glu Ser Thr Cys Lys Cys Ile Ser Pro Cys Pro Val
```

```
            100                 105                 110

Pro Glu Ser Leu Gly Gly Pro Ser Val Phe Ile Phe Pro Pro Lys Pro
        115                 120                 125

Lys Asp Ile Leu Arg Ile Thr Arg Thr Pro Glu Ile Thr Cys Val Val
    130                 135                 140

Leu Asp Leu Gly Arg Glu Asp Pro Glu Val Gln Ile Ser Trp Phe Val
145                 150                 155                 160

Asp Gly Lys Glu Val His Thr Ala Lys Thr Gln Pro Arg Glu Gln Gln
                165                 170                 175

Phe Asn Ser Thr Tyr Arg Val Val Ser Val Leu Pro Ile Glu His Gln
            180                 185                 190

Asp Trp Leu Thr Gly Lys Glu Phe Lys Cys Arg Val Asn His Ile Gly
        195                 200                 205

Leu Pro Ser Pro Ile Glu Arg Thr Ile Ser Lys Ala Arg Gly Gln Ala
    210                 215                 220

His Gln Pro Ser Val Tyr Val Leu Pro Pro Ser Pro Lys Glu Leu Ser
225                 230                 235                 240

Ser Ser Asp Thr Val Thr Leu Thr Cys Leu Ile Lys Asp Phe Phe Pro
                245                 250                 255

Pro Glu Ile Asp Val Glu Trp Gln Ser Asn Gly Gln Pro Glu Pro Glu
            260                 265                 270

Ser Lys Tyr His Thr Thr Ala Pro Gln Leu Asp Glu Asp Gly Ser Tyr
        275                 280                 285

Phe Leu Tyr Ser Lys Leu Ser Val Asp Lys Ser Arg Trp Gln Gln Gly
    290                 295                 300

Asp Thr Phe Thr Cys Ala Val Met His Glu Ala Leu Gln Asn His Tyr
305                 310                 315                 320

Thr Asp Leu Ser Leu Ser His Ser Pro Gly Lys
                325                 330


<210> SEQ ID NO 85
<211> LENGTH: 996
<212> TYPE: DNA
<213> ORGANISM: Bubalus arnee

<400> SEQUENCE: 85

gcctccacca cggccccctc ggttttccca ctggccccca gctgcgggtc cacttccggc      60

tccacggtgg ccctggcctg cctggtgtca ggctacttcc ccgagcctgt aactgtgtcc     120

tggaattccg gctccttgac cagcggtgtg cacaccttcc cgtccgtcct gcagtcctca     180

gggctctact ccctcagcag cacggtgaca gtgccctcca gcaggtggcc cagcgagacc     240

ttcacctgca acgtggtcca cccggccagc aacactaaag tagacaagcc agtgcccaaa     300

gagtccacct gcaagtgtat atccccatgc ccagtccctg aatcactggg agggccttcg     360

gtcttcatct ttcccccgaa acccaaggac atcctcagga ttacccgaac acccgagatc     420

acctgtgtgg tgttagatct gggccgtgag gaccctgagg tgcagatcag ctggttcgtg     480

gatggtaagg aggtgcacac agccaagacg cagcctcgtg agcagcagtt caacagcacc     540

taccgtgtgg tcagcgtcct ccccattgag caccaggact ggctcaccgg aaaggagttc     600

aagtgcagag tcaaccacat aggcctcccg tcccccatcg agaggactat ctccaaagcc     660

agagggcaag cccatcagcc cagtgtgtat gtcctgccac catccccaaa ggagttgtca     720

tccagtgaca cggtcaccct gacctgcctg atcaaagact tcttcccacc tgagattgat     780

gtggagtggc agagcaatgg acagccggag cccgagagca agtaccacac gactgcgccc     840
```

```
cagctggacg aggacgggtc ctacttcctg tacagcaagc tctctgtgga caagagccgc    900

tggcagcagg gagacacctt cacatgtgcg gtgatgcatg aagctctaca gaaccactac    960

acagatctat ccctctccca ttctccgggt aaatga                              996


<210> SEQ ID NO 86
<211> LENGTH: 102
<212> TYPE: PRT
<213> ORGANISM: Bubalus arnee

<400> SEQUENCE: 86

Pro Ser Val Phe Leu Phe Lys Pro Ser Glu Glu Gln Leu Arg Thr Gly
1               5                   10                  15

Thr Val Ser Val Val Cys Leu Val Asn Asp Phe Tyr Pro Lys Asp Ile
            20                  25                  30

Asn Val Lys Val Lys Val Asp Gly Val Thr Gln Asn Ser Asn Phe Gln
        35                  40                  45

Asn Ser Phe Thr Asp Gln Asp Ser Lys Lys Ser Thr Tyr Ser Leu Ser
    50                  55                  60

Ser Thr Leu Thr Leu Ser Ser Ser Glu Tyr Gln Ser His Asn Ala Tyr
65                  70                  75                  80

Ala Cys Glu Val Ser His Lys Ser Leu Pro Thr Ala Leu Val Lys Ser
                85                  90                  95

Phe Asn Lys Asn Glu Cys
            100


<210> SEQ ID NO 87
<211> LENGTH: 309
<212> TYPE: DNA
<213> ORGANISM: Bubalus arnee

<400> SEQUENCE: 87

ccatccgtct tcctcttcaa accatctgag gaacagctga ggaccggaac tgtctctgtc     60

gtgtgcttgg tgaatgattt ctaccccaaa gatatcaatg tcaaggtgaa agtggatggg    120

gttacccaga acagcaactt ccagaacagc ttcacagacc aggacagcaa gaaaagcacc    180

tacagcctca gcagcaccct gacactgtcc agctcagagt accagagcca taacgcctat    240

gcgtgtgagg tcagccacaa gagcctgccc accgccctcg tcaagagctt caataagaat    300

gaatgttag                                                            309


<210> SEQ ID NO 88
<211> LENGTH: 106
<212> TYPE: PRT
<213> ORGANISM: Bubalus arnee

<400> SEQUENCE: 88

Gly Gln Pro Lys Ser Ala Pro Ser Val Thr Leu Phe Pro Pro Ser Thr
1               5                   10                  15

Glu Glu Leu Ser Thr Asn Lys Ala Thr Val Val Cys Leu Ile Asn Asp
            20                  25                  30

Phe Tyr Pro Gly Ser Val Asn Val Val Trp Lys Ala Asp Gly Ser Thr
        35                  40                  45

Ile Asn Gln Asn Val Lys Thr Thr Gln Ala Ser Lys Gln Ser Asn Ser
    50                  55                  60

Lys Tyr Ala Ala Ser Ser Tyr Leu Thr Leu Thr Gly Ser Glu Trp Lys
65                  70                  75                  80
```

```
Ser Lys Ser Ser Tyr Thr Cys Glu Val Thr His Glu Gly Ser Thr Val
                85                  90                  95

Thr Lys Thr Val Lys Pro Ser Glu Cys Ser
            100                 105


<210> SEQ ID NO 89
<211> LENGTH: 321
<212> TYPE: DNA
<213> ORGANISM: Bubalus arnee

<400> SEQUENCE: 89

ggtcagccca agtccgcacc ctcggtcacc ctgttcccgc cttccacgga ggagctcagt      60

accaacaagg ccaccgtggt gtgtctcatc aacgacttct acccgggtag cgtgaacgtg     120

gtctggaagg cagatggcag caccatcaat cagaacgtga agaccaccca ggcctccaaa     180

cagagcaaca gcaagtacgc ggccagcagc tacctgaccc tgacgggcag cgagtggaag     240

tctaagagca gttacacctg cgaggtcacg cacgagggga gcaccgtgac gaagacagtg     300

aagccctcag agtgttctta g                                               321


<210> SEQ ID NO 90
<211> LENGTH: 331
<212> TYPE: PRT
<213> ORGANISM: Bubalus arnee

<400> SEQUENCE: 90

Ala Ser Thr Thr Pro Pro Lys Val Tyr Pro Leu Thr Ser Cys Cys Gly
1               5                   10                  15

Asp Thr Ser Ser Ser Ile Val Thr Leu Gly Cys Leu Val Ser Ser Tyr
            20                  25                  30

Met Pro Glu Pro Val Thr Val Thr Trp Asn Ser Gly Ala Leu Thr Ser
        35                  40                  45

Gly Val His Thr Phe Pro Ala Ile Leu Gln Ser Ser Gly Leu Tyr Ser
    50                  55                  60

Leu Ser Ser Val Val Thr Val Pro Ala Ser Thr Ser Gly Ala Gln Thr
65                  70                  75                  80

Phe Ile Cys Asn Val Ala His Pro Ala Ser Ser Thr Lys Val Asp Lys
                85                  90                  95

Arg Val Glu Pro Gly Cys Pro Asp Pro Cys Lys His Cys Arg Cys Pro
            100                 105                 110

Pro Pro Glu Leu Pro Gly Gly Pro Ser Val Phe Ile Phe Pro Pro Lys
        115                 120                 125

Pro Lys Asp Thr Leu Thr Ile Ser Gly Thr Pro Glu Val Thr Cys Val
    130                 135                 140

Val Val Asp Val Gly Gln Asp Asp Pro Glu Val Gln Phe Ser Trp Phe
145                 150                 155                 160

Val Asp Asn Val Glu Val Arg Thr Ala Arg Thr Lys Pro Arg Glu Glu
                165                 170                 175

Gln Phe Asn Ser Thr Phe Arg Val Val Ser Ala Leu Pro Ile Gln His
            180                 185                 190

Gln Asp Trp Thr Gly Gly Lys Glu Phe Lys Cys Lys Val His Asn Glu
        195                 200                 205

Ala Leu Pro Ala Pro Ile Val Arg Thr Ile Ser Arg Thr Lys Gly Gln
    210                 215                 220

Ala Arg Glu Pro Gln Val Tyr Val Leu Ala Pro Pro Gln Glu Glu Leu
225                 230                 235                 240
```

```
Ser Lys Ser Thr Leu Ser Val Thr Cys Leu Val Thr Gly Phe Tyr Pro
                245                 250                 255

Asp Tyr Ile Ala Val Glu Trp Gln Lys Asn Gly Gln Pro Glu Ser Glu
            260                 265                 270

Asp Lys Tyr Gly Thr Thr Thr Ser Gln Leu Asp Ala Asp Gly Ser Tyr
        275                 280                 285

Phe Leu Tyr Ser Arg Leu Arg Val Asp Lys Asn Ser Trp Gln Glu Gly
    290                 295                 300

Asp Thr Tyr Ala Cys Val Val Met His Glu Ala Leu His Asn His Tyr
305                 310                 315                 320

Thr Gln Lys Ser Ile Ser Lys Pro Pro Gly Lys
                325                 330


<210> SEQ ID NO 91
<211> LENGTH: 996
<212> TYPE: DNA
<213> ORGANISM: Bubalus arnee

<400> SEQUENCE: 91

gcctcaacaa cacccccgaa agtctaccct ctgacttctt gctgcgggga cacgtccagc      60

tccatcgtga ccctgggctg cctggtctcc agctatatgc ccgagccggt gaccgtgacc     120

tggaactctg gtgccctgac cagcggcgtg cacaccttcc cggccatcct gcagtcctcc     180

gggctctact ctctcagcag cgtggtgacc gtgccggcca gcacctcagg agcccagacc     240

ttcatctgca acgtagccca cccggccagc agcaccaagg tggacaagcg tgttgagccc     300

ggatgcccgg acccatgcaa acattgccga tgcccacccc ctgagctccc cggaggaccg     360

tctgtcttca tcttcccacc gaaacccaag gacaccctta caatctctgg aacgcccgag     420

gtcacgtgtg tggtggtgga cgtgggccag gatgaccccg aggtgcagtt ctcctggttc     480

gtggacaacg tggaggtgcg cacggccagg acaaagccga gagaggagca gttcaacagc     540

accttccgcg tggtcagcgc cctgcccatc cagcaccaag actggactgg aggaaaggag     600

ttcaagtgca aggtccacaa cgaagccctc ccggccccca tcgtgaggac catctccagg     660

accaaagggc aggcccggga gccgcaggtg tacgtcctgg ccccaccccca ggaagagctc     720

agcaaaagca cgctcagcgt cacctgcctg gtcaccggct tctacccaga ctacatcgcc     780

gtggagtggc agaaaaatgg gcagcctgag tcggaggaca agtacggcac gaccacatcc     840

cagctggacg ccgacggctc ctacttcctg tacagcaggc tcagggtgga caagaacagc     900

tggcaagaag gagacaccta cgcgtgtgtg gtgatgcacg aggctctgca caaccactac     960

acacagaagt cgatctctaa gcctccgggt aaatga                               996


<210> SEQ ID NO 92
<211> LENGTH: 329
<212> TYPE: PRT
<213> ORGANISM: Bubalus arnee

<400> SEQUENCE: 92

Ala Ser Thr Thr Ala Pro Lys Val Tyr Pro Leu Thr Ser Cys Cys Gly
1               5                   10                  15

Asp Thr Ser Ser Ser Ser Ser Ile Val Thr Leu Gly Cys Leu Val Ser
            20                  25                  30

Ser Tyr Met Pro Glu Pro Val Thr Val Thr Trp Asn Ser Gly Ala Leu
        35                  40                  45

Thr Ser Gly Val His Thr Phe Pro Ala Ile Leu Gln Ser Ser Gly Leu
    50                  55                  60
```

-continued

Tyr Ser Leu Ser Ser Val Val Thr Val Pro Ala Ser Thr Ser Gly Ala
65 70 75 80

Gln Thr Phe Ile Cys Asn Val Ala His Pro Ala Ser Ser Ala Lys Val
85 90 95

Asp Lys Arg Val Gly Ile Ser Ser Asp Tyr Ser Lys Cys Ser Lys Pro
100 105 110

Pro Cys Val Ser Arg Pro Ser Val Phe Ile Phe Pro Pro Lys Pro Lys
115 120 125

Asp Ser Leu Met Ile Thr Gly Thr Pro Glu Val Thr Cys Val Val Val
130 135 140

Asp Val Gly Gln Gly Asp Pro Glu Val Gln Phe Ser Trp Phe Val Asp
145 150 155 160

Asn Val Glu Val Arg Thr Ala Arg Thr Lys Pro Arg Glu Glu Gln Phe
165 170 175

Asn Ser Thr Phe Arg Val Val Ser Ala Leu Pro Ile Gln His Asp His
180 185 190

Trp Thr Gly Gly Lys Glu Phe Lys Cys Lys Val His Ser Lys Gly Leu
195 200 205

Pro Ala Pro Ile Val Arg Thr Ile Ser Arg Ala Lys Gly Gln Ala Arg
210 215 220

Glu Pro Gln Val Tyr Val Leu Ala Pro Pro Gln Glu Glu Leu Ser Lys
225 230 235 240

Ser Thr Leu Ser Val Thr Cys Leu Val Thr Gly Phe Tyr Pro Asp Tyr
245 250 255

Ile Ala Val Glu Trp Gln Arg Ala Arg Gln Pro Glu Ser Glu Asp Lys
260 265 270

Tyr Gly Thr Thr Thr Ser Gln Leu Asp Ala Asp Gly Ser Tyr Phe Leu
275 280 285

Tyr Ser Arg Leu Arg Val Asp Lys Ser Ser Trp Gln Arg Gly Asp Thr
290 295 300

Tyr Ala Cys Val Val Met His Glu Ala Leu His Asn His Tyr Thr Gln
305 310 315 320

Lys Ser Ile Ser Lys Pro Pro Gly Lys
325

<210> SEQ ID NO 93
<211> LENGTH: 990
<212> TYPE: DNA
<213> ORGANISM: Bubalus arnee

<400> SEQUENCE: 93
gcctccacca cagccccgaa agtctaccct ctgacttctt gctgcgggga cacgtccagc 60
tccagctcca tcgtgaccct gggctgcctg gtctccagct atatgcccga gccggtgacc 120
gtgacctgga actctggtgc cctgaccagc ggcgtgcaca ccttcccggc catcctgcag 180
tcctccgggc tctactctct cagcagcgtg gtgaccgtgc cggccagcac ctcaggagcc 240
cagaccttca tctgcaacgt agcccacccg gccagcagcg ccaaggtgga caagcgtgtt 300
gggatctcca gtgactactc caagtgttct aaaccgcctt gcgtgagccg accgtctgtc 360
ttcatcttcc ccccgaaacc caaggacagc ctcatgatca caggaacgcc cgaggtcacg 420
tgtgtggtgg tggacgtggg ccagggtgac cccgaggtgc agttctcctg gttcgtggac 480
aacgtggagg tgcgcacggc caggacaaag ccgagagagg agcagttcaa cagcaccttc 540
cgcgtggtca gcgccctgcc catccagcac gaccactgga ctggaggaaa ggagttcaag 600

-continued

```
tgcaaggtcc acagcaaagg cctcccggcc cccatcgtga ggaccatctc cagggccaaa    660

gggcaggccc gggagccgca ggtgtacgtc ctggccccac cccaggaaga gctcagcaaa    720

agcacgctca gcgtcacctg cctggtcacc ggcttctacc cagactacat cgccgtggag    780

tggcagagag cgcggcagcc tgagtcggag gacaagtacg gcacgaccac atcccagctg    840

gacgccgacg gctcctactt cctgtacagc aggctcaggg tggacaagag cagctggcaa    900

agaggagaca cctacgcgtg tgtggtgatg cacgaggctc tgcacaacca ctacacacag    960

aagtcgatct ctaagcctcc gggtaaatga                                     990
```

```
<210> SEQ ID NO 94
<211> LENGTH: 328
<212> TYPE: PRT
<213> ORGANISM: Bubalus arnee

<400> SEQUENCE: 94

Ala Pro Lys Thr Ala Pro Ser Val Tyr Pro Leu Ala Pro Cys Gly Arg
1               5                   10                  15

Asp Thr Ser Gly Pro Asn Val Ala Leu Gly Cys Leu Ala Ser Ser Tyr
            20                  25                  30

Phe Pro Glu Pro Val Thr Met Thr Trp Asn Ser Gly Ala Leu Thr Ser
        35                  40                  45

Gly Val His Thr Phe Pro Ser Val Leu Gln Pro Ser Gly Leu Tyr Ser
    50                  55                  60

Leu Ser Ser Met Val Thr Val Pro Ala Ser Ser Leu Ser Ser Lys Ser
65                  70                  75                  80

Tyr Thr Cys Asn Val Asn His Pro Ala Thr Thr Thr Lys Val Asp Lys
                85                  90                  95

Arg Val Gly Thr Lys Thr Lys Pro Pro Cys Pro Ile Cys Pro Gly Cys
            100                 105                 110

Glu Val Ala Gly Pro Ser Val Phe Ile Phe Pro Pro Lys Pro Lys Asp
        115                 120                 125

Thr Leu Met Ile Ser Gln Thr Pro Glu Val Thr Cys Val Val Val Asp
    130                 135                 140

Val Ser Lys Glu His Ala Glu Val Gln Phe Ser Trp Tyr Val Asp Gly
145                 150                 155                 160

Val Glu Val His Thr Ala Glu Thr Arg Pro Lys Glu Glu Gln Phe Asn
                165                 170                 175

Ser Thr Tyr Arg Val Val Ser Val Leu Pro Ile Gln His Gln Asp Trp
            180                 185                 190

Leu Lys Gly Lys Glu Phe Lys Cys Lys Val Asn Asn Val Asp Leu Pro
        195                 200                 205

Ala Pro Ile Thr Arg Thr Ile Ser Lys Ala Ile Gly Gln Ser Arg Glu
    210                 215                 220

Pro Gln Val Tyr Thr Leu Pro Pro Pro Ala Glu Glu Leu Ser Arg Ser
225                 230                 235                 240

Lys Val Thr Val Thr Cys Leu Val Ile Gly Phe Tyr Pro Pro Asp Ile
                245                 250                 255

His Val Glu Trp Lys Ser Asn Gly Gln Pro Glu Pro Glu Gly Asn Tyr
            260                 265                 270

Arg Thr Thr Pro Pro Gln Gln Asp Val Asp Gly Thr Phe Phe Leu Tyr
        275                 280                 285

Ser Lys Leu Ala Val Asp Lys Ala Arg Trp Asp His Gly Glu Thr Phe
    290                 295                 300
```

```
Glu Cys Ala Val Met His Glu Ala Leu His Asn His Tyr Thr Gln Lys
305                 310                 315                 320

Ser Ile Ser Lys Thr Gln Gly Lys
                325


<210> SEQ ID NO 95
<211> LENGTH: 987
<212> TYPE: DNA
<213> ORGANISM: Bubalus arnee

<400> SEQUENCE: 95

gcccccaaga cggccccatc ggtctaccct ctggcccccct gcggcaggga cacgtctggc     60

cctaacgtgg ccttgggctg cctggcctca agctacttcc ccgagccagt gaccatgacc    120

tggaactcgg gcgccctgac cagtggcgtg cataccttcc catccgtcct gcagccgtca    180

gggctctact ccctcagcag catggtgacc gtgccggcca gcagcctgtc cagcaagagc    240

tacacctgca atgtcaacca cccggccacc accaccaagg tggacaagcg tgttggaaca    300

aagaccaaac caccatgtcc catatgccca ggctgtgaag tggccgggcc ctcggtcttc    360

atcttccctc caaaacccaa ggacaccctc atgatctccc agacccccga ggtcacgtgc    420

gtggtggtgg acgtcagcaa ggagcacgcc gaggtccagt tctcctggta cgtggacggc    480

gtagaggtgc acacggccga gacgagacca aaggaggagc agttcaacag cacctaccgt    540

gtggtcagcg tcctgcccat ccagcaccag gactggctga aggggaagga gttcaagtgc    600

aaggtcaaca acgtagacct cccagccccc atcacgagga ccatctccaa ggctataggg    660

cagagccggg agccgcaggt gtacaccctg cccccacccg ccgaggagct gtccaggagc    720

aaagtcaccg taacctgcct ggtcattggc ttctacccac ctgacatcca tgttgagtgg    780

aagagcaacg gacagccgga gccagagggc aattaccgca ccacccccgcc ccagcaggac    840

gtggacggga ccttcttcct gtacagcaag ctcgcggtgg acaaggcaag atgggaccat    900

ggagaaacat ttgagtgtgc ggtgatgcac gaggctctgc acaaccacta cacccagaag    960

tccatctcca agactcaggg taaatga                                        987


<210> SEQ ID NO 96
<211> LENGTH: 328
<212> TYPE: PRT
<213> ORGANISM: Bubalus arnee

<400> SEQUENCE: 96

Ala Pro Lys Thr Ala Pro Ser Val Tyr Pro Leu Ala Pro Cys Gly Arg
1               5                   10                  15

Asp Val Ser Gly Pro Asn Val Ala Leu Gly Cys Leu Ala Ser Ser Tyr
            20                  25                  30

Phe Pro Glu Pro Val Thr Val Thr Trp Asn Ser Gly Ala Leu Thr Ser
        35                  40                  45

Gly Val His Thr Phe Pro Ser Val Leu Gln Pro Ser Gly Leu Tyr Ser
    50                  55                  60

Leu Ser Ser Met Val Thr Val Pro Ala Ser Ser Leu Ser Ser Lys Ser
65                  70                  75                  80

Tyr Thr Cys Asn Val Asn His Pro Ala Thr Thr Thr Lys Val Asp Lys
                85                  90                  95

Arg Val Gly Ile His Gln Pro Gln Thr Cys Pro Ile Cys Pro Gly Cys
            100                 105                 110

Glu Val Ala Gly Pro Ser Val Phe Ile Phe Pro Pro Lys Pro Lys Asp
```

```
        115                 120                 125

Thr Leu Met Ile Ser Gln Thr Pro Glu Val Thr Cys Val Val Val Asp
    130                 135                 140

Val Ser Lys Glu His Ala Glu Val Gln Phe Ser Trp Tyr Val Asp Gly
145                 150                 155                 160

Val Glu Val His Thr Ala Glu Thr Arg Pro Lys Glu Glu Gln Phe Asn
                165                 170                 175

Ser Thr Tyr Arg Val Val Ser Val Leu Pro Ile Gln His Gln Asp Trp
            180                 185                 190

Leu Lys Gly Lys Glu Phe Lys Cys Lys Val Asn Asn Val Asp Leu Pro
        195                 200                 205

Ala Pro Ile Thr Arg Thr Ile Ser Lys Ala Ile Gly Gln Ser Arg Glu
    210                 215                 220

Pro Gln Val Tyr Thr Leu Pro Pro Pro Ala Glu Glu Leu Ser Arg Ser
225                 230                 235                 240

Lys Val Thr Leu Thr Cys Leu Val Ile Gly Phe Tyr Pro Pro Asp Ile
                245                 250                 255

His Val Glu Trp Lys Ser Asn Gly Gln Pro Glu Pro Glu Asn Thr Tyr
            260                 265                 270

Arg Thr Thr Pro Pro Gln Gln Asp Val Asp Gly Thr Phe Phe Leu Tyr
        275                 280                 285

Ser Lys Leu Ala Val Asp Lys Ala Arg Trp Asp His Gly Asp Lys Phe
    290                 295                 300

Glu Cys Ala Val Met His Glu Ala Leu His Asn His Tyr Thr Gln Lys
305                 310                 315                 320

Ser Ile Ser Lys Thr Gln Gly Lys
                325


<210> SEQ ID NO 97
<211> LENGTH: 987
<212> TYPE: DNA
<213> ORGANISM: Bubalus arnee

<400> SEQUENCE: 97

gcccccaaga cggccccatc ggtctaccct ctggcccccct gcggcaggga cgtgtctggc     60

cctaacgtgg ccttgggctg cctggcctca agctacttcc ccgagccagt gaccgtgacc    120

tggaactcgg gcgccctgac cagtggcgtg cacaccttcc catccgtcct gcagccgtca    180

gggctctact ccctcagcag catggtgacc gtgccggcca gcagcctgtc cagcaagagc    240

tacacctgca atgtcaacca cccggccacc accaccaagg tggacaagcg tgttggaata    300

caccagccgc aaacatgtcc catatgccca ggctgtgaag tggccgggcc ctcggtcttc    360

atcttccctc caaaacccaa ggacaccctc atgatctccc agacccccga ggtcacgtgc    420

gtggtggtgg acgtcagcaa ggagcacgcc gaggtccagt tctcctggta cgtggacggc    480

gtagaggtgc acacggccga gacgagacca aaggaggagc agttcaacag cacctaccgt    540

gtggtcagcg tcctgcccat ccagcaccag gactggctga aggggaagga gttcaagtgc    600

aaggtcaaca acgtagacct cccagccccc atcacgagga ccatctccaa ggctataggg    660

cagagccggg agccgcaggt gtacaccctg cccccacccg ccgaggagct gtccaggagc    720

aaagtcacgc taacctgcct ggtcattggc ttctacccac ctgacatcca tgttgagtgg    780

aagagcaacg gacagccgga gccagagaac acataccgca ccaccccgcc ccagcaggac    840

gtggacggga ccttcttcct gtacagcaaa ctcgcggtgg acaaggcaag atgggaccat    900
```

```
ggagacaaat ttgagtgtgc ggtgatgcac gaggctctgc acaaccacta cacccagaag    960

tccatctcca agactcaggg taaatga                                        987


<210> SEQ ID NO 98
<211> LENGTH: 328
<212> TYPE: PRT
<213> ORGANISM: Bubalus arnee

<400> SEQUENCE: 98

Ala Pro Lys Thr Ala Pro Ser Val Tyr Pro Leu Ala Pro Cys Ser Arg
1               5                   10                  15

Asp Thr Ser Gly Pro Asn Val Ala Leu Gly Cys Leu Ala Ser Ser Tyr
            20                  25                  30

Phe Pro Glu Pro Val Thr Val Thr Trp Asn Ser Gly Ala Leu Ser Ser
        35                  40                  45

Gly Val His Thr Phe Pro Ser Val Leu Gln Pro Ser Gly Leu Tyr Ser
    50                  55                  60

Leu Ser Ser Met Val Thr Val Pro Ala Ser Ser Leu Ser Ser Lys Ser
65                  70                  75                  80

Tyr Thr Cys Asn Val Asn His Pro Ala Thr Thr Thr Lys Val Asp Lys
                85                  90                  95

Arg Val Gly Thr Lys Thr Lys Pro Pro Cys Pro Ile Cys Pro Ala Cys
            100                 105                 110

Glu Ser Pro Gly Pro Ser Val Phe Ile Phe Pro Pro Lys Pro Lys Asp
        115                 120                 125

Thr Leu Met Ile Ser Arg Thr Pro Gln Val Thr Cys Val Val Val Asp
    130                 135                 140

Val Ser Gln Glu Asn Pro Glu Val Gln Phe Ser Trp Tyr Val Asp Gly
145                 150                 155                 160

Val Glu Val His Thr Ala Gln Thr Arg Pro Lys Glu Glu Gln Phe Asn
                165                 170                 175

Ser Thr Tyr Arg Val Val Ser Val Leu Pro Ile Gln His Gln Asp Trp
            180                 185                 190

Leu Asn Gly Lys Glu Phe Lys Cys Lys Val Asn Asn Lys Asp Leu Pro
        195                 200                 205

Ala Pro Ile Thr Arg Ile Ile Ser Lys Ala Lys Gly Gln Thr Arg Glu
    210                 215                 220

Pro Gln Val Tyr Thr Leu Pro Pro His Ala Glu Glu Leu Ser Arg Ser
225                 230                 235                 240

Lys Val Ser Ile Thr Cys Leu Val Ile Gly Phe Tyr Pro Pro Asp Ile
                245                 250                 255

Asp Val Glu Trp Gln Arg Asn Gly Gln Pro Glu Pro Glu Gly Asn Tyr
            260                 265                 270

Arg Thr Thr Pro Pro Gln Gln Asp Val Asp Gly Thr Tyr Phe Leu Tyr
        275                 280                 285

Ser Lys Phe Ser Val Asp Lys Ala Ser Trp Gln Gly Gly Gly Ile Phe
    290                 295                 300

Gln Cys Ala Val Met His Glu Ala Leu His Asn His Tyr Thr Gln Lys
305                 310                 315                 320

Ser Ile Ser Lys Thr Pro Gly Lys
                325


<210> SEQ ID NO 99
<211> LENGTH: 987
<212> TYPE: DNA
```

<213> ORGANISM: Bubalus arnee

<400> SEQUENCE: 99

```
gcccccaaga cggccccatc ggtctaccct ctggcccccct gcagcaggga cacgtctggc     60
cctaacgtgg ccttgggctg cctggcctca agctacttcc ccgagccagt gaccgtgacc    120
tggaactcgg gcgccctgtc cagtggcgtg catacttcc catccgtcct gcagccgtca    180
gggctctact ccctcagcag catggtgacc gtgccggcca gcagcctgtc cagcaagagc    240
tacacctgca atgtcaacca cccggccacc accaccaagg tggacaagcg tgttggaaca    300
aagaccaaac caccatgtcc catatgccca gcctgtgaat caccagggcc ctcggtcttc    360
atcttccctc caaaacccaa ggacaccctc atgatctccc ggacaccccca ggtcacgtgc    420
gtggtggttg atgtgagcca ggagaacccg gaggtccagt tctcctggta cgtggacggc    480
gtagaggtgc acacggccca gacgaggcca aaggaggagc agttcaacag cacctaccgc    540
gtggtcagcg tcctacccat ccagcaccag gactggctga acgggaagga gttcaagtgc    600
aaggtcaaca acaaagacct cccagccccc atcacaagga tcatctccaa ggccaaaggg    660
cagacccggg agccgcaggt gtacaccctg cccccacacg ccgaggagct gtccaggagc    720
aaagtcagca taacctgcct ggtcattggc ttctacccac ctgacatcga tgtcgagtgg    780
caaagaaacg gacagccgga gccagagggc aattaccgca ccaccccgcc ccagcaggac    840
gtggacggga cctacttcct gtacagcaag ttctcggtgg acaaggccag ctggcagggt    900
ggaggcatat tccagtgtgc ggtgatgcac gaggctctgc acaaccacta cacccagaag    960
tctatctcca agactccggg taaatga                                         987
```

<210> SEQ ID NO 100
<211> LENGTH: 328
<212> TYPE: PRT
<213> ORGANISM: Bubalus arnee

<400> SEQUENCE: 100

```
Ala Pro Lys Thr Ala Pro Leu Val Tyr Pro Leu Ala Pro Cys Gly Arg
1               5                   10                  15

Asp Thr Ser Gly Pro Asn Val Ala Leu Gly Cys Leu Ala Ser Ser Tyr
            20                  25                  30

Phe Pro Glu Pro Val Thr Val Thr Trp Asn Ser Gly Ala Leu Thr Ser
        35                  40                  45

Gly Val His Thr Phe Pro Ser Val Leu Gln Pro Ser Gly Leu Tyr Ser
    50                  55                  60

Leu Ser Ser Met Val Thr Val Pro Ala Ser Ser Leu Ser Ser Lys Ser
65                  70                  75                  80

Tyr Thr Cys Asn Val Asn His Pro Ala Thr Thr Thr Lys Val Asp Lys
                85                  90                  95

Arg Val Gly Thr Lys Thr Lys Pro Pro Cys Pro Ile Cys Pro Ala Cys
            100                 105                 110

Glu Ser Pro Gly Pro Ser Val Phe Ile Phe Pro Pro Lys Pro Lys Asp
        115                 120                 125

Thr Leu Met Ile Ser Arg Thr Pro Gln Val Thr Cys Val Val Val Asp
    130                 135                 140

Val Ser Gln Glu Asn Pro Glu Val Gln Phe Ser Trp Tyr Val Asp Gly
145                 150                 155                 160

Val Glu Val His Thr Ala Gln Thr Arg Pro Lys Glu Glu Gln Phe Asn
                165                 170                 175
```

```
Ser Thr Tyr Arg Val Val Ser Val Leu Pro Ile Gln His Gln Asp Trp
            180                 185                 190

Leu Asn Gly Lys Glu Phe Lys Cys Lys Val Asn Asn Lys Asp Leu Pro
        195                 200                 205

Ala Pro Ile Thr Arg Ile Ile Ser Lys Ala Lys Gly Gln Thr Arg Glu
    210                 215                 220

Pro Gln Val Tyr Thr Leu Pro Pro His Ala Glu Glu Leu Ser Arg Ser
225                 230                 235                 240

Lys Val Ser Ile Thr Cys Leu Val Ile Gly Phe Tyr Pro Pro Asp Ile
                245                 250                 255

Asp Val Glu Trp Gln Arg Asn Gly Gln Pro Glu Pro Glu Gly Asn Tyr
            260                 265                 270

Arg Thr Thr Pro Pro Gln Gln Asp Val Asp Gly Thr Tyr Phe Leu Tyr
        275                 280                 285

Ser Lys Phe Ser Val Asp Lys Ala Ser Trp Gln Gly Gly Gly Ile Phe
    290                 295                 300

Gln Cys Ala Val Met His Glu Ala Leu His Asn His Tyr Thr Gln Lys
305                 310                 315                 320

Ser Ile Ser Lys Thr Pro Gly Lys
                325


<210> SEQ ID NO 101
<211> LENGTH: 987
<212> TYPE: DNA
<213> ORGANISM: Bubalus arnee

<400> SEQUENCE: 101

gcccccaaga cggccccatt ggtctaccct ctggccccct gcggcaggga cacgtctggc      60

cctaacgtgg ccttgggctg cctggcctca agctacttcc ccgagccagt gaccgtgacc     120

tggaactcgg gcgccctgac cagtggcgtg cataccttcc catccgtcct gcagccgtca     180

gggctctact ccctcagcag catggtgacc gtgccggcca gcagcctgtc cagcaagagc     240

tacacctgca atgtcaacca cccggccacc accaccaagg tggacaagcg tgttggaaca     300

aagaccaaac caccatgtcc catatgccca gcctgtgaat cgccagggcc ctcggtcttc     360

atcttccctc caaaacccaa ggacaccctc atgatctccc ggacacccca ggtcacgtgc     420

gtggtagttg atgtgagcca ggagaacccg gaggtccagt tctcctggta cgtggacggc     480

gtagaggtgc acacggccca gacgaggcca aaggaggagc agttcaacag cacctaccgc     540

gtggtcagcg tcctgcccat ccagcaccag gactggctga acgggaagga gttcaagtgc     600

aaggtcaaca acaaagacct cccagccccc atcacaagga tcatctccaa ggccaaaggg     660

cagacccggg agccgcaggt gtacaccctg cccccacacg ccgaggagct gtccaggagc     720

aaagtcagca taacctgcct ggtcattggc ttctacccac ctgacatcga tgtcgagtgg     780

caaagaaacg gacagccgga gccagagggc aattaccgca ccaccccgcc ccagcaggac     840

gtggacggga cctacttcct gtacagcaag ttctcggtgg acaaggccag ctggcagggt     900

ggaggcatat tccagtgtgc ggtgatgcac gaggctctgc acaaccacta cacccagaag     960

tctatctcca agactccggg taaatga                                         987


<210> SEQ ID NO 102
<211> LENGTH: 333
<212> TYPE: PRT
<213> ORGANISM: Bubalus arnee

<400> SEQUENCE: 102
```

```
Ala Tyr Asn Thr Ala Pro Ser Val Tyr Pro Leu Ala Pro Cys Gly Arg
1               5                   10                  15

Asp Val Ser Asp His Asn Val Ala Leu Gly Cys Leu Val Ser Ser Tyr
            20                  25                  30

Phe Pro Glu Pro Val Thr Val Thr Trp Asn Ser Gly Ala Leu Ser Arg
        35                  40                  45

Val Val His Thr Phe Pro Ser Val Leu Gln Pro Ser Gly Leu Tyr Ser
    50                  55                  60

Leu Ser Ser Met Val Ile Val Ala Ala Ser Ser Leu Ser Thr Leu Ser
65                  70                  75                  80

Tyr Thr Cys Asn Val Tyr His Pro Ala Thr Asn Thr Lys Val Asp Lys
                85                  90                  95

Arg Val Asp Ile Glu Pro Pro Thr Pro Ile Cys Pro Glu Ile Cys Ser
            100                 105                 110

Cys Pro Ala Ala Glu Val Leu Gly Ala Pro Ser Val Phe Leu Phe Pro
        115                 120                 125

Pro Lys Pro Lys Asp Ile Leu Met Ile Ser Arg Thr Pro Lys Val Thr
    130                 135                 140

Cys Val Val Val Asp Val Ser Gln Glu Glu Ala Glu Val Gln Phe Ser
145                 150                 155                 160

Trp Tyr Val Asp Gly Val Gln Leu Tyr Thr Ala Gln Thr Arg Pro Met
                165                 170                 175

Glu Glu Gln Phe Asn Ser Thr Tyr Arg Val Val Ser Val Leu Pro Ile
            180                 185                 190

Gln His Gln Asp Trp Leu Lys Gly Lys Glu Phe Lys Cys Lys Val Asn
        195                 200                 205

Asn Lys Asp Leu Leu Ser Pro Ile Thr Arg Thr Ile Ser Lys Ala Thr
    210                 215                 220

Gly Pro Ser Arg Val Pro Gln Val Tyr Thr Leu Pro Pro Ala Trp Glu
225                 230                 235                 240

Glu Leu Ser Lys Ser Lys Val Ser Ile Thr Cys Leu Val Thr Gly Phe
                245                 250                 255

Tyr Pro Pro Asp Ile Asp Val Glu Trp Gln Ser Asn Gly Gln Gln Glu
            260                 265                 270

Pro Glu Gly Asn Tyr Arg Thr Thr Pro Pro Gln Gln Asp Val Asp Gly
        275                 280                 285

Thr Tyr Phe Leu Tyr Ser Lys Leu Ala Val Asp Lys Val Arg Trp Gln
    290                 295                 300

Arg Gly Asp Leu Phe Gln Cys Ala Val Met His Glu Ala Leu His Asn
305                 310                 315                 320

His Tyr Thr Gln Lys Ser Ile Ser Lys Thr Gln Gly Lys
                325                 330
```

<210> SEQ ID NO 103
<211> LENGTH: 1002
<212> TYPE: DNA
<213> ORGANISM: Bubalus arnee

<400> SEQUENCE: 103

```
gcctacaaca cagctccatc ggtctaccct ctggccccct gtggcaggga cgtgtctgat      60

cataacgtgg ccttgggctg ccttgtctca agctacttcc ccgagccagt gaccgtgacc     120

tggaactcgg gtgccctgtc cagagtcgtg catacottcc catccgtcct gcagccgtca     180

gggctctact ccctcagcag catggtgatc gtggcggcca gcagcctgtc caccctgagc     240
```

-continued

```
tacacgtgca acgtctacca cccggccacc aacaccaagg tggacaagcg tgttgacatc    300

gaacccccca cacccatctg tcccgaaatt tgctcatgcc cagctgcaga ggtcctggga    360

gcaccgtcgg tcttcctctt ccctccaaaa cccaaggaca tcctcatgat ctcccggaca    420

cccaaggtca cgtgcgtggt ggtggacgtg agccaggagg aggctgaagt ccagttctcc    480

tggtacgtgg acggcgtaca gttgtacacg gcccagacga ggccaatgga ggagcagttc    540

aacagcacct accgcgtggt cagcgtcctg cccatccagc accaggactg gctgaagggg    600

aaggagttca agtgcaaggt caacaacaaa gacctccttt cccccatcac gaggaccatc    660

tccaaggcta cagggccgag ccgggtgccg caggtgtaca ccctgccccc agcctgggaa    720

gagctgtcca agagcaaagt cagcataacc tgcctggtca ctggcttcta cccacctgac    780

atcgatgtcg agtggcagag caacggacaa caagagccag agggcaatta ccgcaccacc    840

ccgccccagc aggacgtgga tgggacctac ttcctgtaca gcaagctcgc ggtggacaag    900

gtcaggtggc agcgtggaga cctattccag tgtgcggtga tgcacgaggc tctgcacaac    960

cactacaccc agaagtccat ctccaagact cagggtaaat ga                      1002


<210> SEQ ID NO 104
<211> LENGTH: 277
<212> TYPE: PRT
<213> ORGANISM: Bubalus arnee

<400> SEQUENCE: 104

Thr Phe Pro Ser Val Leu Gln Pro Ser Gly Leu Tyr Ser Leu Ser Ser
1               5                   10                  15

Met Val Thr Val Pro Ala Ser Ser Leu Ser Ser Lys Ser Tyr Thr Cys
            20                  25                  30

Asn Val Asn His Pro Ala Thr Thr Thr Lys Val Asp Lys Arg Val Gly
        35                  40                  45

Thr Lys Thr Lys Pro Pro Cys Pro Ile Cys Pro Ala Cys Glu Gly Pro
    50                  55                  60

Gly Pro Ser Ala Phe Ile Phe Pro Pro Lys Pro Lys Asp Thr Leu Met
65                  70                  75                  80

Ile Ser Arg Thr Pro Lys Val Thr Cys Val Val Val Asp Val Ser Gln
                85                  90                  95

Glu Asn Pro Glu Val Gln Phe Ser Trp Tyr Val Asp Gly Val Glu Val
            100                 105                 110

His Thr Ala Gln Thr Arg Pro Lys Glu Glu Gln Phe Asn Ser Thr Tyr
        115                 120                 125

Arg Val Val Ser Val Leu Pro Ile Gln His Gln Asp Trp Leu Asn Gly
    130                 135                 140

Lys Glu Phe Lys Cys Lys Val Asn Asn Lys Asp Leu Pro Ala Pro Ile
145                 150                 155                 160

Thr Arg Ile Ile Ser Lys Ala Lys Gly Gln Thr Arg Glu Pro Gln Val
                165                 170                 175

Tyr Thr Leu Pro Pro Pro Thr Glu Glu Leu Ser Arg Ser Lys Val Thr
            180                 185                 190

Leu Thr Cys Leu Val Thr Gly Phe Tyr Pro Pro Asp Ile Asp Val Glu
        195                 200                 205

Trp Gln Arg Asn Gly Gln Pro Glu Pro Glu Gly Asn Tyr Arg Thr Thr
    210                 215                 220

Pro Pro Gln Gln Asp Val Asp Gly Thr Tyr Phe Leu Tyr Ser Lys Leu
225                 230                 235                 240
```

```
Ala Val Asp Lys Ala Ser Trp Gln Arg Gly Asp Thr Phe Gln Cys Ala
                245                 250                 255

Val Met His Glu Ala Leu His Asn His Tyr Thr Gln Lys Ser Ile Phe
            260                 265                 270

Lys Thr Pro Gly Lys
        275
```

<210> SEQ ID NO 105
<211> LENGTH: 834
<212> TYPE: DNA
<213> ORGANISM: Bubalus arnee

<400> SEQUENCE: 105

```
accttcccat ccgtcctgca gccgtcaggg ctctactccc tcagcagcat ggtgaccgtg      60

ccggccagca gcctgtccag caagagctac acctgcaatg tcaaccaccc ggccaccacc     120

accaaggtgg acaagcgtgt tggaacaaag accaaaccac catgtcccat atgcccagcc     180

tgtgaagggc ccgggccctc ggccttcatc ttccctccaa aacccaagga caccctcatg     240

atctcccgga cccccaaggt cacgtgcgtg gtggtagatg tgagccagga gaacccggag     300

gtccagttct cctggtacgt ggacggcgta gaggtgcaca cggcccagac gaggccaaag     360

gaggagcagt tcaacagcac ctaccgcgtg gtcagcgtcc tgcccatcca gcaccaggac     420

tggctgaacg ggaaggagtt caagtgcaag gtcaacaaca aagacctccc agcccccatc     480

acaaggatca tctccaaggc caaagggcag acccgggagc cgcaggtgta caccctgccc     540

ccacccaccg aggagctgtc caggagcaaa gtcacgctaa cctgcctggt cactggcttc     600

tacccacctg acatcgatgt cgagtggcaa agaaacggac agccggagcc agagggcaat     660

taccgcacca ccccgcccca gcaggacgtg gacgggacct acttcctgta cagcaagctc     720

gcggtggaca aggccagctg gcagcgtgga gacacattcc agtgtgcggt gatgcacgag     780

gctctgcaca accactacac ccagaagtcc atcttcaaga ctccgggtaa atga           834
```

<210> SEQ ID NO 106
<211> LENGTH: 318
<212> TYPE: PRT
<213> ORGANISM: Bubalus arnee

<400> SEQUENCE: 106

```
Ala Pro Lys Thr Ala Pro Ser Val Tyr Pro Leu Ala Pro Cys Gly Arg
1               5                   10                  15

Asp Val Ser Gly Pro Asn Val Ala Leu Gly Cys Leu Ala Ser Ser Tyr
            20                  25                  30

Phe Pro Glu Pro Val Thr Val Thr Trp Asn Ser Gly Ala Leu Thr Ser
        35                  40                  45

Gly Val His Thr Phe Pro Ser Val Leu Gln Pro Ser Gly Leu Tyr Ser
    50                  55                  60

Leu Ser Ser Met Val Thr Val Pro Ala Ser Ser Leu Ser Ser Lys Ser
65                  70                  75                  80

Tyr Thr Cys Asn Val Asn His Pro Ala Thr Thr Thr Lys Val Asp Lys
                85                  90                  95

Arg Val Gly Ile His Gln Pro Gln Thr Cys Pro Ile Cys Pro Ala Cys
            100                 105                 110

Glu Gly Pro Gly Pro Ser Ala Phe Ile Phe Pro Pro Lys Pro Lys Asp
        115                 120                 125

Thr Leu Met Ile Ser Arg Thr Pro Lys Val Thr Cys Val Val Val Asp
```

```
    130                 135                 140

Val Ser Gln Glu Asn Pro Glu Val Gln Phe Ser Trp Tyr Val Asp Gly
145                 150                 155                 160

Val Glu Val His Thr Ala Gln Thr Arg Pro Lys Glu Glu Gln Phe Asn
                165                 170                 175

Ser Thr Tyr Arg Val Val Ser Val Leu Leu Ile Gln His Gln Asp Trp
            180                 185                 190

Leu Asn Gly Lys Glu Phe Lys Cys Lys Val Asn Asn Lys Asp Leu Pro
        195                 200                 205

Ala Pro Ile Thr Arg Ile Ile Ser Lys Ala Lys Gly Gln Thr Arg Glu
    210                 215                 220

Pro Gln Val Tyr Thr Leu Pro Pro Pro Thr Glu Glu Leu Ser Arg Ser
225                 230                 235                 240

Lys Val Thr Leu Thr Cys Leu Val Thr Gly Phe Tyr Pro Pro Asp Ile
                245                 250                 255

Asp Val Glu Trp Gln Arg Asn Gly Gln Pro Glu Pro Glu Gly Asn Tyr
            260                 265                 270

Arg Thr Thr Pro Pro Gln Gln Asp Val Asp Gly Thr Tyr Phe Leu Tyr
        275                 280                 285

Ser Lys Leu Ala Val Asp Lys Ala Ser Trp Gln Arg Gly Asp Thr Phe
    290                 295                 300

Gln Cys Ala Val Met His Glu Ala Leu His Asn His Tyr Thr
305                 310                 315


<210> SEQ ID NO 107
<211> LENGTH: 955
<212> TYPE: DNA
<213> ORGANISM: Bubalus arnee

<400> SEQUENCE: 107

gcccccaaga cggccccatc ggtctaccct ctggccccct gcggcaggga cgtgtctggc     60

cctaacgtgg ccttgggctg cctggcctca agctacttcc ccgagccagt gaccgtgacc    120

tggaactcgg gcgccctgac cagtggcgtg cacaccttcc catccgtcct gcagccgtca    180

gggctctact ccctcagcag catggtgacc gtgccggcca gcagcctgtc cagcaagagc    240

tacacctgca atgtcaacca cccggccacc accaccaagg tggacaagcg tgttggaata    300

caccagccgc aaacatgtcc catatgccca gcctgtgaag ggcccgggcc ctcggccttc    360

atcttccctc caaaacccaa ggacaccctc atgatctccc ggacccccaa ggtcacgtgc    420

gtggtggttg atgtgagcca ggagaacccg gaggtccagt tctcctggta cgtggacggc    480

gtagaggtgc acacggccca gacgaggcca aaggaggagc agttcaacag cacctaccgc    540

gtggtcagcg tcctgctcat ccagcaccag gactggctga acgggaagga gttcaagtgc    600

aaggtcaaca acaaagacct cccagccccc atcacaagga tcatctccaa ggccaaaggg    660

cagacccggg agccgcaggt gtacaccctg cccccaccca ccgaggagct gtccaggagc    720

aaagtcacgc taacctgcct ggtcactggc ttctacccac ctgacatcga tgtcgagtgg    780

caaagaaacg gacagccgga gccagagggc aattaccgca ccaccccgcc ccagcaggac    840

gtggacggga cctacttcct gtacagcaag ctcgcggtgg acaaggccag ctggcagcgt    900

ggagacacat tccagtgtgc ggtgatgcac gaggctctgc acaaccacta caccc         955


<210> SEQ ID NO 108
<211> LENGTH: 323
<212> TYPE: PRT
```

-continued

<213> ORGANISM: Bubalus arnee

<400> SEQUENCE: 108

```
Ala Pro Lys Thr Ala Pro Ser Val Tyr Pro Leu Ala Pro Cys Ser Arg
1               5                   10                  15

Asp Thr Ser Gly Pro Asn Val Ala Leu Gly Cys Leu Val Ser Ser Tyr
            20                  25                  30

Phe Pro Glu Pro Val Thr Val Thr Trp Asn Ser Gly Ala Leu Thr Ser
        35                  40                  45

Gly Val His Thr Phe Pro Ser Val Leu Gln Pro Ser Gly Leu Tyr Ser
    50                  55                  60

Leu Ser Ser Met Val Thr Val Pro Ala His Ser Leu Ser Ser Lys Arg
65                  70                  75                  80

Tyr Thr Cys Asn Val Asn His Pro Ala Thr Lys Thr Lys Val Asp Leu
                85                  90                  95

Cys Val Gly Arg Pro Cys Pro Ile Cys Pro Gly Cys Glu Val Ala Gly
            100                 105                 110

Pro Ser Val Phe Ile Phe Pro Pro Lys Pro Lys Asp Ile Leu Met Ile
        115                 120                 125

Ser Arg Thr Pro Glu Val Thr Cys Val Val Val Asp Val Ser Lys Glu
    130                 135                 140

His Ala Glu Val Gln Phe Ser Trp Tyr Val Asp Gly Glu Glu Val His
145                 150                 155                 160

Thr Ala Glu Thr Arg Pro Lys Glu Glu Gln Phe Asn Ser Thr Tyr Arg
                165                 170                 175

Val Val Ser Val Leu Pro Ile Gln His Glu Asp Trp Leu Lys Gly Lys
            180                 185                 190

Glu Phe Glu Cys Lys Val Asn Asn Glu Asp Leu Pro Gly Pro Ile Thr
        195                 200                 205

Arg Thr Ile Ser Lys Ala Lys Gly Val Val Arg Ser Pro Glu Val Tyr
    210                 215                 220

Thr Leu Pro Pro Pro Ala Glu Glu Leu Ser Lys Ser Ile Val Thr Leu
225                 230                 235                 240

Thr Cys Leu Val Lys Ser Ile Phe Pro Phe Ile His Val Glu Trp Lys
                245                 250                 255

Ile Asn Gly Lys Pro Glu Pro Glu Asn Ala Tyr Arg Thr Thr Pro Pro
            260                 265                 270

Gln Glu Asp Glu Asp Arg Thr Tyr Phe Leu Tyr Ser Lys Leu Ala Val
        275                 280                 285

Asp Lys Ala Arg Trp Asp His Gly Glu Thr Phe Glu Cys Ala Val Met
    290                 295                 300

His Glu Ala Leu His Asn His Tyr Thr Gln Lys Ser Ile Ser Lys Thr
305                 310                 315                 320

Gln Gly Lys
```

<210> SEQ ID NO 109
<211> LENGTH: 975
<212> TYPE: DNA
<213> ORGANISM: Bubalus arnee
<220> FEATURE:
<221> NAME/KEY: misc_feature
<222> LOCATION: (748)..(748)
<223> OTHER INFORMATION: n is a, c, g, or t

<400> SEQUENCE: 109

```
gcccccaaga cggccccatc ggtctaccct ctggccccct gcagcaggga cacgtctggc      60
```

```
cctaacgtgg ccttgggctg cctggtctca agctacttcc ccgagccagt gaccgtgacc    120

tggaactcgg gcgccctgac cagtggcgtg cacaccttcc catccgtcct gcagccgtca    180

gggctctact ccctcagcag catggtgacc gtgccggccc acagcttgtc cagcaagcgc    240

tatacgtgca atgtcaacca cccagccacc aaaaccaagg tggacctgtg tgttggacga    300

ccatgtccca tatgcccagg ctgtgaagtg gccgggccct cggtcttcat cttccctcca    360

aaacccaagg acatcctcat gatctcccgg acccccgagg tcacgtgcgt ggtggtggac    420

gtcagcaagg agcacgccga ggtccagttc tcctggtacg tggacggcga agaggtgcac    480

acggccgaga cgaggccaaa ggaggagcag ttcaacagca cctaccgcgt ggtcagcgtc    540

ctgcccatcc agcacgagga ctggctgaag gggaaggagt tcgagtgcaa ggtcaacaac    600

gaagacctcc caggccccat cacgaggacc atctccaagg ccaaaggggt ggtacggagc    660

ccggaggtgt acaccctgcc cccacccgcc gaggagctgt ccaagagcat agtcacgcta    720

acctgcctgg tcaaaagcat cttcccgnct ttcatccatg ttgagtggaa aatcaacgga    780

aaaccagagc cagagaacgc atatcgcacc accccgcctc aggaggacga ggacaggacc    840

tacttcctgt acagcaagct cgcggtggac aaggcaagat gggaccatgg agaaacattt    900

gagtgtgcgg tgatgcacga ggctctgcac aaccactaca cccagaagtc catctccaag    960

actcagggta aatga                                                     975
```

```
<210> SEQ ID NO 110
<211> LENGTH: 317
<212> TYPE: PRT
<213> ORGANISM: Bubalus arnee

<400> SEQUENCE: 110

Ala Tyr Asn Thr Ala Pro Ser Val Tyr Pro Leu Ala Pro Cys Gly Arg
1               5                   10                  15

Asp Val Ser Asp His Asn Val Ala Leu Gly Cys Leu Val Ser Ser Tyr
            20                  25                  30

Phe Pro Glu Pro Val Thr Val Thr Trp Asn Trp Gly Ala Gln Thr Ser
        35                  40                  45

Gly Val His Thr Phe Pro Ser Val Leu Gln Pro Ser Gly Leu Tyr Ser
    50                  55                  60

Leu Ser Ser Thr Val Thr Val Pro Ala His Ser Leu Ser Ser Lys Cys
65                  70                  75                  80

Phe Thr Cys Asn Val Asn His Pro Ala Thr Thr Thr Lys Val Asp Leu
                85                  90                  95

Cys Val Gly Lys Lys Thr Lys Pro Arg Cys Pro Ile Cys Pro Gly Cys
            100                 105                 110

Glu Val Ala Gly Pro Ser Val Phe Ile Phe Pro Pro Lys Pro Lys Asp
        115                 120                 125

Ile Leu Met Ile Ser Arg Thr Pro Glu Val Thr Cys Val Val Val Asp
    130                 135                 140

Val Ser Lys Glu His Ala Glu Val Gln Phe Ser Trp Tyr Val Asp Gly
145                 150                 155                 160

Glu Glu Val His Thr Ala Glu Thr Arg Pro Lys Glu Glu Gln Phe Asn
                165                 170                 175

Ser Thr Tyr Arg Val Val Ser Val Leu Pro Ile Gln His Glu Asp Trp
            180                 185                 190

Leu Lys Gly Lys Glu Phe Glu Cys Lys Val Asn Asn Glu Asp Leu Pro
        195                 200                 205
```

```
Gly Pro Ile Thr Arg Thr Ile Ser Lys Ala Lys Gly Val Val Arg Ser
    210                 215                 220

Pro Glu Val Tyr Thr Leu Pro Pro Pro Ala Glu Glu Leu Ser Lys Ser
225                 230                 235                 240

Ile Val Thr Leu Thr Cys Leu Val Lys Ser Phe Phe Pro Pro Phe Ile
                245                 250                 255

His Val Glu Trp Lys Ile Asn Gly Lys Pro Glu Pro Glu Asn Ala Tyr
            260                 265                 270

Arg Thr Thr Pro Pro Gln Glu Asp Glu Asp Gly Thr Tyr Phe Leu Tyr
        275                 280                 285

Ser Lys Phe Ser Val Glu Lys Phe Arg Trp His Ser Gly Gly Ile His
    290                 295                 300

Cys Ala Val Met His Glu Ala Leu His Asn His Tyr Thr
305                 310                 315


<210> SEQ ID NO 111
<211> LENGTH: 952
<212> TYPE: DNA
<213> ORGANISM: Bubalus arnee

<400> SEQUENCE: 111

gcctacaaca cagctccatc ggtctaccct ctggccccct gtggcaggga cgtgtctgat      60

cataacgtgg ccttgggctg cctggtctca agctacttcc ccgagccagt gaccgtgacc     120

tggaactggg gcgcccagac cagtggcgtg cacaccttcc catccgtcct gcagccgtca     180

gggctctact ccctcagcag cacggtgacc gtgccggccc acagcttgtc cagcaagtgc     240

ttcacgtgca atgtcaacca cccggccacc accaccaagg tggacctgtg tgttggaaaa     300

aagaccaagc ctcgatgtcc catatgccca ggctgtgaag tggccgggcc ctcggtcttc     360

atcttccctc caaaacccaa ggacatcctc atgatctccc ggacccccga ggtcacgtgc     420

gtggtggtgg acgtcagcaa ggagcacgcc gaggtccagt tctcctggta cgtggacggc     480

gaagaggtgc acacggccga gacgagacca aaggaggagc agttcaacag cacttaccgc     540

gtggtcagcg tcctgcccat ccagcacgag gactggctga aggggaagga gttcgagtgc     600

aaggtcaaca acgaagacct cccaggcccc atcacgagga ccatctccaa ggccaaaggg     660

gtggtacgga gcccggaggt gtacaccctg cccccacccg ccgaggagct gtccaagagc     720

atagtcacgc taacctgcct ggtcaaaagc ttcttcccgc ctttcatcca tgttgagtgg     780

aaaatcaacg gaaaaccaga gccagagaac gcataccgca ccaccccgcc ccaggaggac     840

gaggacggga cctacttcct gtacagcaag ttctcggtgg aaaagttcag gtggcacagt     900

ggaggcatcc actgtgcggt gatgcacgag gctctgcaca accactacac cc             952


<210> SEQ ID NO 112
<211> LENGTH: 314
<212> TYPE: PRT
<213> ORGANISM: Bubalus arnee

<400> SEQUENCE: 112

Ala Pro Lys Thr Ala Pro Ser Val Tyr Pro Leu Ala Pro Cys Gly Arg
1               5                   10                  15

Asp Thr Ser Gly Pro Asn Val Ala Leu Gly Cys Leu Ala Ser Ser Tyr
            20                  25                  30

Phe Pro Glu Pro Val Thr Leu Thr Trp Asn Ser Gly Ala Leu Thr Ser
        35                  40                  45
```

Gly Val His Thr Phe Pro Ser Val Leu Gln Pro Ser Gly Leu Tyr Ser
50 55 60

Leu Ser Ser Met Val Thr Val Pro Ala Ser Ser Leu Ser Ser Lys Ser
65 70 75 80

Tyr Thr Cys Asn Val Asn His Pro Ala Thr Thr Thr Lys Val Asp Leu
85 90 95

Cys Val Gly Arg Pro Cys Pro Ile Cys Pro Ala Cys Glu Gly Pro Gly
100 105 110

Pro Ser Val Phe Ile Phe Pro Pro Lys Pro Lys Asp Thr Leu Met Ile
115 120 125

Ser Arg Thr Pro Gln Val Thr Cys Val Val Val Asp Val Ser Gln Glu
130 135 140

Asn Pro Glu Val Gln Phe Ser Trp Tyr Val Asp Gly Val Glu Val His
145 150 155 160

Thr Ala Gln Thr Arg Pro Lys Glu Ala Gln Phe Asn Ser Thr Tyr Arg
165 170 175

Val Val Ser Val Leu Pro Ile Gln His Glu Asp Trp Leu Lys Gly Lys
180 185 190

Glu Phe Glu Cys Lys Val Asn Asn Lys Asp Leu Pro Ala Pro Ile Thr
195 200 205

Arg Ile Ile Ser Lys Ala Lys Gly Pro Ser Arg Glu Pro Gln Val Tyr
210 215 220

Thr Leu Ser Pro Ser Ala Glu Glu Leu Ser Arg Ser Lys Val Ser Ile
225 230 235 240

Thr Cys Leu Val Thr Gly Phe Tyr Pro Pro Asp Ile Asp Val Glu Trp
245 250 255

Lys Ser Asn Gly Gln Pro Glu Pro Glu Gly Asn Tyr Arg Thr Thr Pro
260 265 270

Pro Gln Gln Asp Val Asp Gly Thr Tyr Phe Leu Tyr Ser Lys Leu Ala
275 280 285

Val Asp Lys Ala Ser Trp Gln Arg Gly Asp Pro Phe Gln Cys Ala Val
290 295 300

Met His Glu Ala Leu His Asn His Tyr Thr
305 310

<210> SEQ ID NO 113
<211> LENGTH: 943
<212> TYPE: DNA
<213> ORGANISM: Bubalus arnee

<400> SEQUENCE: 113
gcccccaaga cggccccatc ggtctaccct ctggcccccct gcggcaggga cacgtctggc 60
cctaacgtgg ccttgggctg cctggcctca agctacttcc ccgagccagt gaccctgacc 120
tggaactcgg gcgccctgac cagtggcgtg cataccttcc catccgtcct gcagccgtca 180
gggctctact ccctcagcag catggtgacc gtgccggcca gcagcctgtc cagcaagagc 240
tacacctgca atgtcaacca cccggccacc accaccaagg tggacctgtg tgttggacga 300
ccatgtccca tatgcccagc ctgtgaaggg cccgggccct cggtcttcat cttccctcca 360
aaacccaagg acaccctcat gatctcccgg acaccccagg tcacgtgcgt ggtggtagat 420
gtgagccagg aaaacccgga ggtccagttc tcctggtatg tggacggtgt agaggtgcac 480
acggcccaga cgaggccaaa ggaggcgcag ttcaacagca cctaccgtgt ggtcagcgtc 540
ctgcccatcc agcacgagga ctggctgaag gggaaggagt tcgagtgcaa ggtcaacaac 600

```
aaagacctcc cagcccccat cacaaggatc atctccaagg ccaaagggcc gagccgggag    660

ccgcaggtgt acaccctgtc cccatccgcc gaggagctgt ccaggagcaa agtcagcata    720

acctgcctgg tcactggctt ctacccacct gacatcgatg tcgagtggaa gagcaacgga    780

cagccggagc cagagggcaa ttaccgcacc accccgcccc agcaggacgt ggacgggacc    840

tacttcctgt acagcaagct cgcggtggac aaggccagct ggcagcgtgg agacccattc    900

cagtgtgcgg tgatgcacga ggctctgcac aaccactaca ccc                      943
```

```
<210> SEQ ID NO 114
<211> LENGTH: 320
<212> TYPE: PRT
<213> ORGANISM: Bubalus arnee

<400> SEQUENCE: 114

Ala Pro Lys Thr Ala Pro Ser Val Tyr Pro Leu Ala Pro Cys Gly Arg
1               5                   10                  15

Asp Thr Ser Gly Pro Asn Val Ala Leu Gly Cys Leu Ala Ser Ser Tyr
            20                  25                  30

Phe Pro Glu Pro Val Thr Val Thr Trp Asn Ser Gly Ala Leu Thr Ser
        35                  40                  45

Gly Val His Thr Phe Pro Ser Val Leu Gln Pro Ser Gly Leu Tyr Ser
    50                  55                  60

Leu Ser Ser Thr Val Thr Val Pro Ala Arg Ser Ser Ser Arg Lys Cys
65                  70                  75                  80

Phe Thr Cys Asn Val Asn His Pro Ala Thr Thr Thr Lys Val Asp Leu
                85                  90                  95

Cys Val Gly Arg Pro Cys Pro Ile Cys Pro Ala Cys Glu Gly Asn Gly
            100                 105                 110

Pro Ser Val Phe Ile Phe Pro Pro Lys Pro Lys Asp Thr Leu Met Ile
        115                 120                 125

Ser Arg Thr Pro Glu Val Thr Cys Val Val Val Asp Val Ser Gln Glu
    130                 135                 140

Asn Pro Glu Val Gln Phe Ser Trp Tyr Val Asp Gly Glu Glu Val His
145                 150                 155                 160

Thr Ala Glu Thr Arg Pro Lys Glu Glu Gln Phe Asn Ser Thr Tyr Arg
                165                 170                 175

Val Val Ser Val Leu Pro Ile Gln His Gln Asp Trp Leu Lys Gly Lys
            180                 185                 190

Glu Phe Glu Cys Lys Val Asn Asn Lys Asp Leu Pro Ala Pro Ile Thr
        195                 200                 205

Arg Ile Ile Ser Lys Ala Lys Gly Pro Ser Arg Glu Pro Gln Val Tyr
    210                 215                 220

Thr Leu Ser Pro Ser Ala Glu Glu Leu Ser Arg Ser Lys Val Ser Ile
225                 230                 235                 240

Thr Cys Leu Val Thr Gly Phe Tyr Pro Pro Asp Ile Asp Val Glu Trp
                245                 250                 255

Lys Ser Asn Gly Gln Pro Glu Pro Glu Gly Asn Tyr Arg Ser Thr Pro
            260                 265                 270

Pro Gln Glu Asp Glu Asp Gly Thr Tyr Phe Leu Tyr Ser Lys Leu Ala
        275                 280                 285

Val Asp Lys Ala Arg Leu Gln Ser Gly Gly Ile His Cys Ala Val Met
    290                 295                 300

His Glu Ala Leu His Asn His Tyr Thr Gln Lys Ser Ile Ser Lys Thr
305                 310                 315                 320
```

<210> SEQ ID NO 115
<211> LENGTH: 960
<212> TYPE: DNA
<213> ORGANISM: Bubalus arnee

<400> SEQUENCE: 115
gcccccaaga cggccccatc ggtctaccct ctggccccct gcggcaggga cacgtctggc 60
cctaacgtgg ccttgggctg cctggcctca agctacttcc ccgagccagt gaccgtgacc 120
tggaactcgg gcgccctgac cagtggcgtg cacaccttcc catccgtcct gcagccgtca 180
gggctctact ccctcagcag cacggtgacc gtgccggcca ggagctcgtc cagaaagtgc 240
ttcacgtgca atgtcaacca cccggccacc accaccaagg tggacctgtg tgttggacga 300
ccatgtccca tatgcccagc ctgtgaaggg aacgggccct cggtcttcat cttccctcca 360
aaacccaagg acaccctcat gatctcccgg acccccgagg tcacgtgcgt ggtggtagat 420
gtgagccagg aaaacccgga ggtccagttc tcctggtacg tggacggcga agaggtgcac 480
acggccgaga cgaggccaaa ggaggagcag ttcaacagca cctaccgtgt ggtcagcgtc 540
ctgcccatcc agcaccagga ctggctgaag ggaaaggagt tcgagtgcaa ggtcaacaac 600
aaagacctcc cagcccccat cacaaggatc atctccaagg ccaaagggcc gagccgggag 660
ccgcaggtgt acaccctgtc cccatccgcc gaggagctgt ccaggagcaa agtcagcata 720
acctgcctgg tcactggctt ctacccacct gacatcgatg tcgagtggaa gagcaacgga 780
cagccggagc cagagggcaa ttaccgctcc accccgcccc aggaggacga ggacgggacc 840
tacttcctgt acagcaaact cgcggtggac aaggcgaggt tgcagagtgg aggcatccac 900
tgtgcggtga tgcacgaggc tctgcacaac cactacaccc agaagtccat ctccaagact 960

<210> SEQ ID NO 116
<211> LENGTH: 105
<212> TYPE: PRT
<213> ORGANISM: Bubalus arnee

<400> SEQUENCE: 116

Gln Pro Lys Ser Ala Pro Ser Val Thr Leu Phe Pro Pro Ser Thr Glu
1 5 10 15

Glu Leu Ser Ala Asn Lys Ala Thr Leu Val Cys Leu Ile Ser Asp Phe
20 25 30

Tyr Pro Gly Ser Met Thr Val Ala Arg Lys Ala Asp Gly Ser Thr Ile
35 40 45

Thr Arg Asn Val Glu Thr Thr Arg Ala Ser Lys Gln Ser Asn Ser Lys
50 55 60

Tyr Ala Ala Ser Ser Tyr Leu Ser Leu Thr Gly Ser Glu Trp Lys Ser
65 70 75 80

Lys Gly Ser Tyr Ser Cys Glu Val Thr His Glu Gly Ser Thr Val Thr
85 90 95

Lys Thr Val Lys Pro Ser Glu Cys Ser
100 105

<210> SEQ ID NO 117
<211> LENGTH: 318
<212> TYPE: DNA
<213> ORGANISM: Bubalus arnee

<400> SEQUENCE: 117
cagcccaagt ccgcaccctc agtcaccctg ttcccaccct ccacggagga gctcagcgcc 60

```
aacaaggcca ccctggtgtg tctcatcagc gacttctacc cgggtagcat gaccgtggcc    120

aggaaggcag acggcagcac catcacccgg aacgtggaga ccacccgggc ctccaaacag    180

agcaacagca agtacgcggc cagcagctac ctgagcctga cgggcagcga gtggaaatcg    240

aaaggcagtt acagctgcga ggtcacgcac gaggggagca ccgtgacaaa gacagtgaag    300

ccctcagagt gttcttag                                                  318


<210> SEQ ID NO 118
<211> LENGTH: 266
<212> TYPE: PRT
<213> ORGANISM: Bubalus arnee

<400> SEQUENCE: 118

Ser Gly Val His Thr Phe Pro Ala Val Leu Gln Ser Ser Gly Leu Tyr
1               5                   10                  15

Ser Leu Ser Ser Thr Val Thr Ala Pro Ala Ser Ala Thr Lys Ser Gln
            20                  25                  30

Thr Phe Thr Cys Asn Val Ala His Pro Ala Ser Ser Thr Lys Val Asp
        35                  40                  45

Lys Ala Val Val Pro Pro Cys Arg Pro Lys Pro Cys Asp Cys Cys Pro
    50                  55                  60

Pro Pro Glu Leu Pro Gly Gly Pro Ser Val Phe Ile Phe Pro Pro Lys
65                  70                  75                  80

Pro Lys Asp Thr Leu Thr Ile Ser Gly Thr Pro Glu Val Thr Cys Val
                85                  90                  95

Val Val Asp Val Gly His Asp Asp Pro Glu Val Lys Phe Ser Trp Phe
            100                 105                 110

Val Asp Asp Val Glu Val Asn Thr Ala Arg Thr Lys Pro Arg Glu Glu
        115                 120                 125

Gln Phe Asn Ser Thr Tyr Arg Val Val Ser Ala Leu Pro Ile Gln His
    130                 135                 140

Asn Asp Trp Thr Gly Gly Lys Glu Phe Lys Cys Lys Val Tyr Asn Glu
145                 150                 155                 160

Gly Leu Pro Ala Pro Ile Val Arg Thr Ile Ser Arg Thr Lys Gly Gln
                165                 170                 175

Ala Arg Glu Pro Gln Val Tyr Val Leu Ala Pro Pro Gln Asp Glu Leu
            180                 185                 190

Ser Lys Ser Thr Val Ser Ile Thr Cys Met Val Thr Gly Phe Tyr Pro
        195                 200                 205

Asp Tyr Ile Ala Val Glu Trp Gln Lys Asp Gly Gln Pro Glu Ser Glu
    210                 215                 220

Asp Lys Tyr Gly Thr Thr Pro Pro Gln Leu Asp Ser Asp Gly Ser Tyr
225                 230                 235                 240

Phe Leu Tyr Ser Arg Leu Arg Val Asn Lys Asn Ser Trp Gln Glu Gly
                245                 250                 255

Gly Ala Tyr Thr Cys Val Val Met His Glu
            260                 265


<210> SEQ ID NO 119
<211> LENGTH: 801
<212> TYPE: DNA
<213> ORGANISM: Bubalus arnee

<400> SEQUENCE: 119

gagcggcgtg cacaccttcc cggccgtcct tcagtcctcc gggctctact ctctcagcag     60
```

```
cacggtgacc gcgcccgcca gcgccacaaa aagccagacc ttcacctgca acgtagccca    120

cccggccagc agcaccaagg tggacaaggc tgttgttccc ccatgcagac cgaaaccctg    180

tgattgctgc ccaccccctg agctccccgg aggaccctct gtcttcatct tcccaccaaa    240

acccaaggac accctcacaa tctctggaac tcctgaggtc acgtgtgtgg tggtggacgt    300

gggccacgat gaccccgagg tgaagttctc ctggttcgtg gacgatgtgg aggtaaacac    360

agccaggacg aagccaagag aggagcagtt caacagcacc taccgcgtgg tcagcgccct    420

gcccatccag cacaacgact ggactggagg aaaggagttc aagtgcaagg tctacaatga    480

aggcctccca gcccccatcg tgaggaccat ctccaggacc aaagggcagg cccgggagcc    540

gcaggtgtac gtcctggccc caccccagga cgagctcagc aaaagcacgg tcagcatcac    600

ttgcatggtc actggcttct acccagacta catcgccgta gagtggcaga aagatgggca    660

gcctgagtca gaggacaaat atggcacgac cccgccccag ctggacagcg atggctccta    720

cttcctgtac agcaggctca gggtgaacaa gaacagctgg caagaaggag gcgcctacac    780

gtgtgtagtg atgcatgagg c                                              801
```

```
<210> SEQ ID NO 120
<211> LENGTH: 309
<212> TYPE: PRT
<213> ORGANISM: Bubalus arnee

<400> SEQUENCE: 120

Ala Ser Ile Thr Ala Pro Lys Val Tyr Pro Leu Thr Ser Cys Arg Gly
1               5                   10                  15

Glu Thr Ser Ser Ser Thr Val Thr Leu Gly Cys Leu Val Ser Ser Tyr
            20                  25                  30

Met Pro Glu Pro Val Thr Val Thr Trp Asn Ser Gly Ala Leu Lys Ser
        35                  40                  45

Gly Val His Thr Phe Pro Ala Val Leu Gln Ser Ser Gly Leu Tyr Ser
    50                  55                  60

Leu Ser Ser Thr Val Thr Ala Pro Ala Ser Ala Thr Lys Ser Gln Thr
65                  70                  75                  80

Phe Thr Cys Asn Val Ala His Pro Ala Ser Ser Thr Lys Val Asp Thr
                85                  90                  95

Ala Val Gly Phe Ser Ser Asp Cys Cys Lys Phe Pro Lys Pro Cys Val
            100                 105                 110

Arg Gly Pro Ser Val Phe Ile Phe Pro Pro Lys Pro Lys Asp Thr Leu
        115                 120                 125

Met Ile Thr Gly Asn Pro Glu Val Thr Cys Val Val Val Asp Val Gly
    130                 135                 140

Arg Asp Asn Pro Glu Val Gln Phe Ser Trp Phe Val Gly Asp Val Glu
145                 150                 155                 160

Val His Thr Gly Arg Ser Lys Pro Arg Glu Glu Gln Phe Asn Ser Thr
                165                 170                 175

Tyr Arg Val Val Ser Thr Leu Pro Ile Gln His Asn Asp Trp Thr Gly
            180                 185                 190

Gly Lys Glu Phe Lys Cys Lys Val Asn Asn Lys Gly Leu Pro Ala Pro
        195                 200                 205

Ile Val Arg Thr Ile Ser Arg Thr Lys Gly Gln Ala Arg Glu Pro Gln
    210                 215                 220

Val Tyr Val Leu Ala Pro Pro Gln Glu Glu Leu Ser Lys Ser Thr Val
225                 230                 235                 240
```

```
Ser Val Thr Cys Met Val Thr Gly Phe Tyr Pro Asp Tyr Ile Ala Val
                245                 250                 255

Glu Trp His Arg Asp Arg Gln Ala Glu Ser Glu Asp Lys Tyr Arg Thr
            260                 265                 270

Thr Pro Pro Gln Leu Asp Ser Asp Gly Ser Tyr Phe Leu Tyr Ser Arg
        275                 280                 285

Leu Lys Val Asn Lys Asn Ser Trp Gln Glu Gly Gly Ala Tyr Thr Cys
    290                 295                 300

Val Val Met His Glu
305


<210> SEQ ID NO 121
<211> LENGTH: 929
<212> TYPE: DNA
<213> ORGANISM: Bubalus arnee

<400> SEQUENCE: 121

gcctccatca cagccccgaa agtctaccct ctgacttctt gccgcgggga aacgtccagc      60

tccaccgtga ccctgggctg cctggtctcc agctacatgc ccgagccggt gaccgtgacc     120

tggaactcgg gtgccctgaa gagcggcgtg cacaccttcc cggccgtcct tcagtcctct     180

gggctctact ctctcagcag cacggtgacc gcgcccgcca gcgccacaaa aagccagacc     240

ttcacctgca acgtagccca cccggccagc agcaccaagg tggacacggc tgttgggttc     300

tccagtgact gctgcaagtt tcctaagcct tgtgtgaggg gaccatctgt cttcatcttc     360

ccgccgaaac ccaaagacac cctgatgatc acaggaaatc ccgaggtcac atgtgtggtg     420

gtggacgtgg gccgggataa ccccgaggtg cagttctcct ggttcgtggg tgatgtggag     480

gtgcacacgg gcaggtcgaa gccgagagag gagcagttca acagcaccta ccgcgtggtc     540

agcaccctgc ccatccagca caatgactgg actggaggaa aggagttcaa gtgcaaggtc     600

aacaacaaag gcctcccagc ccccatcgtg aggaccatct ccaggaccaa agggcaggcc     660

cgggagccgc aggtgtacgt cctggcccca ccccaggaag agctcagcaa aagcacggtc     720

agcgtcactt gcatggtcac tggcttctac ccagactaca tcgccgtaga gtggcataga     780

gaccggcagg ctgagtcgga ggacaagtac cgcacgaccc cgccccagct ggacagcgat     840

ggctcctact tcctgtacag caggctcaag gtgaacaaga acagctggca agaaggaggc     900

gcctacacgt gtgtagtgat gcatgaggc                                       929


<210> SEQ ID NO 122
<211> LENGTH: 352
<212> TYPE: PRT
<213> ORGANISM: Bubalus arnee

<400> SEQUENCE: 122

Ala Ser Thr Thr Ala Pro Lys Val Tyr Pro Leu Ala Ser Ser Cys Gly
1               5                   10                  15

Asp Thr Ser Ser Ser Thr Val Thr Leu Gly Cys Leu Val Ser Ser Tyr
            20                  25                  30

Met Pro Glu Pro Val Thr Val Thr Trp Asn Ser Gly Ala Leu Lys Asn
        35                  40                  45

Gly Val His Thr Phe Pro Ala Val Arg Gln Ser Ser Gly Leu Tyr Ser
    50                  55                  60

Leu Ser Ser Met Val Thr Met Pro Thr Ser Thr Ala Gly Thr Gln Thr
65                  70                  75                  80
```

-continued

```
Phe Thr Cys Asn Val Ala His Pro Ala Ser Ser Thr Lys Val Asp Thr
                85                  90                  95

Ala Val Thr Ala Arg His Pro Val Pro Lys Thr Pro Glu Thr Pro Ile
            100                 105                 110

His Pro Val Lys Pro Pro Thr Gln Glu Pro Arg Asp Glu Lys Thr Pro
        115                 120                 125

Cys Gln Cys Pro Lys Cys Pro Glu Pro Leu Gly Gly Leu Ser Val Phe
    130                 135                 140

Ile Phe Pro Pro Lys Pro Lys Asp Thr Leu Thr Ile Ser Gly Thr Pro
145                 150                 155                 160

Glu Val Thr Cys Val Val Val Asp Val Gly Gln Asp Asp Pro Glu Val
                165                 170                 175

Gln Phe Ser Trp Phe Val Asp Asp Val Glu Val His Thr Ala Arg Met
            180                 185                 190

Lys Pro Arg Glu Glu Gln Phe Asn Ser Thr Tyr Arg Val Val Ser Ala
        195                 200                 205

Leu Pro Ile Gln His Gln Asp Trp Leu Arg Glu Lys Glu Phe Lys Cys
    210                 215                 220

Lys Val Asn Asn Lys Gly Leu Pro Ala Pro Ile Val Arg Thr Ile Ser
225                 230                 235                 240

Arg Thr Lys Gly Gln Ala Arg Glu Pro Gln Val Tyr Val Leu Ala Pro
                245                 250                 255

Pro Arg Glu Glu Leu Ser Lys Ser Thr Leu Ser Leu Thr Cys Leu Ile
            260                 265                 270

Thr Gly Phe Tyr Pro Glu Glu Val Asp Val Glu Trp Gln Arg Asn Gly
        275                 280                 285

Gln Pro Glu Ser Glu Asp Lys Tyr His Thr Thr Pro Pro Gln Leu Asp
    290                 295                 300

Ala Asp Gly Ser Tyr Phe Leu Tyr Ser Arg Leu Arg Val Asn Arg Ser
305                 310                 315                 320

Ser Trp Gln Glu Gly Asp His Tyr Thr Cys Ala Val Met His Glu Ala
                325                 330                 335

Leu Arg Asn His Tyr Lys Glu Lys Pro Ile Ser Arg Ser Pro Gly Lys
            340                 345                 350
```

<210> SEQ ID NO 123
<211> LENGTH: 1059
<212> TYPE: DNA
<213> ORGANISM: Bubalus bubalis

<400> SEQUENCE: 123

```
gcctccacca cagccccgaa agtctaccct ctggcatcca gctgcgggga cacgtccagc      60

tccaccgtga ccctgggctg cctggtctcc agctacatgc ccgagccggt gaccgtgacc     120

tggaactcgg gtgccctgaa gaacggcgtg cacaccttcc cggccgtccg gcagtcctcc     180

gggctctact ctctcagcag catggtgacc atgcccacca gcaccgcagg aacccagacc     240

ttcacctgca acgtagccca cccggccagc agcaccaagg tggacacggc tgtcactgca     300

aggcatccgg tcccgaagac accagagaca cctatccatc ctgtaaaacc cccaacccag     360

gagcccagag atgaaaagac accctgccag tgtcccaaat gcccagaacc tctgggagga     420

ctgtctgtct tcatcttccc accgaaaccc aaggacaccc tcacaatctc tggaacgccc     480

gaggtcacgt gtgtggtggt ggacgtgggc caggatgacc ccgaagtgca gttctcctgg     540

ttcgtggatg acgtggaggt gcacacagcc aggatgaagc caagagagga gcagttcaac     600
```

-continued

```
agcacctacc gcgtggtcag cgccctgccc atccagcacc aggactggct gcgggaaaag    660

gagttcaagt gcaaggtcaa caacaaaggc ctcccggccc ccatcgtgag gaccatctcc    720

aggaccaaag ggcaggcccg ggagccacag gtgtatgtcc tggccccacc ccgggaagag    780

ctcagcaaaa gcacgctcag cctcacctgc ctaatcaccg gcttctaccc agaagaggta    840

gacgtggagt ggcagagaaa tgggcagcct gagtcagagg acaagtacca cacgacccca    900

ccccagctgg acgctgacgg ctcctacttc ctgtacagca ggctcagggt gaacaggagc    960

agctggcagg aaggagacca ctacacgtgt gcagtgatgc atgaagcttt acggaatcac   1020

tacaaagaga agcccatctc gaggtctccg ggtaaatga                          1059


<210> SEQ ID NO 124
<211> LENGTH: 35
<212> TYPE: DNA
<213> ORGANISM: Artificial Sequence
<220> FEATURE:
<223> OTHER INFORMATION: A synthetic primer

<400> SEQUENCE: 124

ctagctagca ccatgaggat atatagtgtc ttaac                                35


<210> SEQ ID NO 125
<211> LENGTH: 31
<212> TYPE: DNA
<213> ORGANISM: Artificial Sequence
<220> FEATURE:
<223> OTHER INFORMATION: A synthetic primer

<400> SEQUENCE: 125

caatctcgag ttacagacag aagatgactg c                                    31
```